(12) United States Patent
Simpson et al.

(10) Patent No.: US 10,791,928 B2
(45) Date of Patent: *Oct. 6, 2020

(54) ANALYTE SENSORS HAVING A SIGNAL-TO-NOISE RATIO SUBSTANTIALLY UNAFFECTED BY NON-CONSTANT NOISE

(71) Applicant: DexCom, Inc., San Diego, CA (US)

(72) Inventors: Peter C. Simpson, Encinitas, CA (US); Robert J. Boock, Carlsbad, CA (US); Mark C. Brister, Cardiff, CA (US); Monica A. Rixman, Medford, MA (US); Kum Ming Woo, San Diego, CA (US); Lisa Nguyen, San Diego, CA (US); Seth R. Brunner, San Diego, CA (US); Arthur Chee, San Diego, CA (US); Melissa A. Nicholas, Monterey, CA (US); Matthew D. Wightlin, San Diego, CA (US); Jack Pryor, San Diego, CA (US); Dubravka Markovic, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/796,830

(22) Filed: Feb. 20, 2020

(65) Prior Publication Data
US 2020/0187776 A1 Jun. 18, 2020

Related U.S. Application Data

(63) Continuation of application No. 16/599,072, filed on Oct. 10, 2019, which is a continuation of application
(Continued)

(51) Int. Cl.
*A61B 5/145* (2006.01)
*A61B 5/00* (2006.01)
(Continued)

(52) U.S. Cl.
CPC .............. *A61B 5/00* (2013.01); *A61B 5/1473* (2013.01); *A61B 5/1486* (2013.01);
(Continued)

(58) Field of Classification Search
None
See application file for complete search history.

(56) References Cited

U.S. PATENT DOCUMENTS 3,220,960 A 11/1965 Wichterle et al.
3,562,352 A 2/1971 Nyilas
(Continued)

FOREIGN PATENT DOCUMENTS

EP 0107634 A2 5/1984
EP 0291130 A2 11/1988
(Continued)

OTHER PUBLICATIONS

Aalders, et al., "Development of a Wearable Glucose Sensor; Studies in Healthy Volunteers and in Diabetic Patients," The International Journal of Artificial Organs, 1991, vol. 14, No. 2, pp. 102-108.

(Continued)

*Primary Examiner* — Eric J Messersmith
(74) *Attorney, Agent, or Firm* — Knobbe Martens Olson & Bear, LLP

(57) ABSTRACT

Systems and methods of use involving sensors having a signal-to-noise ratio that is substantially unaffected by non-constant noise are provided for continuous analyte measurement in a host. In some embodiments, a continuous analyte measurement system is configured to be wholly, transcutaneously, intravascularly or extracorporeally implanted.

9 Claims, 12 Drawing Sheets

Related U.S. Application Data

No. 16/453,925, filed on Jun. 26, 2019, which is a continuation of application No. 14/145,404, filed on Dec. 31, 2013, now Pat. No. 10,376,143, which is a continuation of application No. 13/732,848, filed on Jan. 2, 2013, now Pat. No. 9,763,609, which is a continuation of application No. 11/750,907, filed on May 18, 2007, now Pat. No. 8,364,229.

(51) Int. Cl.
*A61B 5/1486* (2006.01)
*A61B 5/1473* (2006.01)

(52) U.S. Cl.
CPC ...... *A61B 5/14532* (2013.01); *A61B 5/14546* (2013.01); *A61B 5/14735* (2013.01); *A61B 5/14865* (2013.01); *A61B 5/6848* (2013.01); *A61B 5/7203* (2013.01)

(56) References Cited

U.S. PATENT DOCUMENTS

| | | |
|---|---|---|
| 3,746,588 A | 7/1973 | Brunetz et al. |
| 3,837,339 A | 9/1974 | Aisenberg et al. |
| 3,874,850 A | 4/1975 | Sorensen et al. |
| 3,926,760 A | 12/1975 | Allen et al. |
| 3,966,580 A | 6/1976 | Janata et al. |
| 3,979,274 A | 9/1976 | Newman |
| 4,008,717 A | 2/1977 | Kowarski |
| 4,016,866 A | 4/1977 | Lawton |
| 4,024,312 A | 5/1977 | Korpman |
| 4,040,908 A | 8/1977 | Clark, Jr. |
| 4,073,713 A | 2/1978 | Newman |
| 4,076,656 A | 2/1978 | White et al. |
| 4,136,250 A | 1/1979 | Mueller et al. |
| 4,197,840 A | 4/1980 | Beck et al. |
| 4,240,889 A | 12/1980 | Yoda et al. |
| 4,256,561 A | 3/1981 | Schindler et al. |
| 4,260,725 A | 4/1981 | Keogh et al. |
| 4,292,423 A | 9/1981 | Kaufmann et al. |
| 4,327,725 A | 5/1982 | Cortese et al. |
| 4,388,166 A | 6/1983 | Suzuki et al. |
| 4,415,666 A | 11/1983 | D'Orazio et al. |
| 4,418,148 A | 11/1983 | Oberhardt |
| 4,431,507 A | 2/1984 | Nankai et al. |
| 4,453,537 A | 6/1984 | Spitzer |
| 4,484,987 A | 11/1984 | Gough |
| 4,486,290 A | 12/1984 | Cahalan et al. |
| 4,492,575 A | 1/1985 | Mabille |
| 4,493,714 A | 1/1985 | Ueda et al. |
| 4,506,680 A | 3/1985 | Stokes |
| 4,519,973 A | 5/1985 | Cahalan et al. |
| 4,527,999 A | 7/1985 | Lee |
| 4,534,355 A | 8/1985 | Potter |
| 4,538,616 A | 9/1985 | Rogoff |
| 4,545,382 A | 10/1985 | Higgins et al. |
| 4,565,665 A | 1/1986 | Fogt |
| 4,565,666 A | 1/1986 | Cahalan et al. |
| 4,568,444 A | 2/1986 | Nakamura et al. |
| 4,577,642 A | 3/1986 | Stokes |
| 4,592,824 A | 6/1986 | Smith et al. |
| 4,600,495 A | 7/1986 | Fogt |
| 4,602,922 A | 7/1986 | Cabasso et al. |
| 4,632,968 A | 12/1986 | Yokota et al. |
| 4,644,046 A | 2/1987 | Yamada |
| 4,647,643 A | 3/1987 | Zdrahala et al. |
| 4,650,547 A | 3/1987 | Gough |
| 4,663,824 A | 5/1987 | Kenmochi |
| 4,671,288 A | 6/1987 | Gough |
| 4,675,346 A | 6/1987 | Lin et al. |
| 4,680,268 A | 7/1987 | Clark, Jr. |
| 4,684,538 A | 8/1987 | Klemarczyk |
| 4,685,463 A | 8/1987 | Williams |
| 4,686,137 A | 8/1987 | Ward, Jr. et al. |
| 4,689,149 A | 8/1987 | Kanno et al. |
| 4,689,309 A | 8/1987 | Jones |
| 4,694,861 A | 9/1987 | Goodale et al. |
| 4,702,732 A | 10/1987 | Powers et al. |
| 4,703,756 A | 11/1987 | Gough et al. |
| 4,711,245 A | 12/1987 | Higgins et al. |
| 4,711,251 A | 12/1987 | Stokes |
| 4,721,677 A | 1/1988 | Clark, Jr. |
| 4,726,381 A | 2/1988 | Jones |
| 4,753,652 A | 6/1988 | Langer et al. |
| 4,757,022 A | 7/1988 | Shults et al. |
| 4,759,828 A | 7/1988 | Young et al. |
| 4,763,658 A | 8/1988 | Jones |
| 4,776,944 A | 10/1988 | Janata et al. |
| 4,777,953 A | 10/1988 | Ash et al. |
| 4,781,733 A | 11/1988 | Babcock et al. |
| 4,786,657 A | 11/1988 | Hammar et al. |
| 4,793,555 A | 12/1988 | Lee et al. |
| 4,795,542 A | 1/1989 | Ross et al. |
| 4,803,243 A | 2/1989 | Fujimoto et al. |
| 4,809,704 A | 3/1989 | Sogawa et al. |
| 4,810,470 A | 3/1989 | Burkhardt et al. |
| 4,820,281 A | 4/1989 | Lawler, Jr. |
| 4,822,336 A | 4/1989 | Ditraglia |
| 4,828,544 A | 5/1989 | Lane et al. |
| 4,834,101 A | 5/1989 | Collison et al. |
| 4,841,974 A | 6/1989 | Gumbrecht et al. |
| 4,849,458 A | 7/1989 | Reed et al. |
| 4,854,322 A | 8/1989 | Ash et al. |
| 4,861,830 A | 8/1989 | Ward, Jr. |
| 4,867,741 A | 9/1989 | Portnoy |
| 4,880,883 A | 11/1989 | Grasel et al. |
| 4,886,740 A | 12/1989 | Vadgama |
| 4,889,744 A | 12/1989 | Quaid |
| 4,890,620 A | 1/1990 | Gough |
| 4,902,294 A | 2/1990 | Gosserez |
| 4,907,857 A | 3/1990 | Giuliani et al. |
| 4,908,208 A | 3/1990 | Lee et al. |
| 4,909,908 A | 3/1990 | Ross et al. |
| 4,919,141 A | 4/1990 | Zier et al. |
| 4,934,375 A | 6/1990 | Cole et al. |
| 4,935,345 A | 6/1990 | Guilbeau et al. |
| 4,951,657 A | 8/1990 | Pfister et al. |
| 4,963,595 A | 10/1990 | Ward et al. |
| 4,967,940 A | 11/1990 | Blette et al. |
| 4,970,145 A | 11/1990 | Bennetto et al. |
| 4,973,320 A | 11/1990 | Brenner et al. |
| 4,974,929 A | 12/1990 | Curry |
| 4,979,509 A | 12/1990 | Hakky |
| 4,986,671 A | 1/1991 | Sun et al. |
| 4,994,026 A | 2/1991 | Fecondini |
| 4,994,167 A | 2/1991 | Shults et al. |
| 5,002,572 A | 3/1991 | Picha |
| 5,002,590 A | 3/1991 | Friesen et al. |
| 5,006,050 A | 4/1991 | Cooke et al. |
| 5,006,111 A | 4/1991 | Inokuchi et al. |
| 5,007,929 A | 4/1991 | Quaid |
| 5,009,251 A | 4/1991 | Pike et al. |
| 5,030,199 A | 7/1991 | Barwick et al. |
| 5,034,461 A | 7/1991 | Lai et al. |
| 5,035,711 A | 7/1991 | Aoki et al. |
| 5,041,092 A | 8/1991 | Barwick |
| 5,055,198 A | 10/1991 | Shettigar |
| 5,063,081 A | 11/1991 | Cozzette et al. |
| 5,067,491 A | 11/1991 | Taylor, II et al. |
| 5,070,169 A | 12/1991 | Robertson et al. |
| 5,071,452 A | 12/1991 | Avrillon et al. |
| 5,109,850 A | 5/1992 | Blanco et al. |
| 5,112,301 A | 5/1992 | Fenton, Jr. et al. |
| 5,113,871 A | 5/1992 | Viljanto et al. |
| 5,120,813 A | 6/1992 | Ward, Jr. |
| 5,128,408 A | 7/1992 | Tanaka et al. |
| 5,147,725 A | 9/1992 | Pinchuk |
| 5,155,149 A | 10/1992 | Atwater et al. |
| 5,165,407 A | 11/1992 | Wilson et al. |
| 5,169,906 A | 12/1992 | Cray et al. |
| 5,174,291 A | 12/1992 | Schoonen et al. |
| 5,182,004 A | 1/1993 | Kohno |
| 5,183,549 A | 2/1993 | Joseph et al. |
| 5,200,051 A | 4/1993 | Cozzette et al. |

(56) References Cited

U.S. PATENT DOCUMENTS

| | | |
|---|---|---|
| 5,202,261 A | 4/1993 | Musho et al. |
| 5,208,313 A | 5/1993 | Krishnan |
| 5,212,050 A | 5/1993 | Mier et al. |
| 5,220,917 A | 6/1993 | Cammilli et al. |
| 5,221,724 A | 6/1993 | Li et al. |
| 5,235,003 A | 8/1993 | Ward et al. |
| 5,242,835 A | 9/1993 | Jensen |
| 5,249,576 A | 10/1993 | Goldberger et al. |
| 5,250,439 A | 10/1993 | Musho et al. |
| 5,271,736 A | 12/1993 | Picha |
| 5,282,848 A | 2/1994 | Schmitt |
| 5,284,140 A | 2/1994 | Allen et al. |
| 5,286,364 A | 2/1994 | Yacynych et al. |
| 5,296,144 A | 3/1994 | Sternina et al. |
| 5,299,571 A | 4/1994 | Mastrototaro |
| 5,314,471 A | 5/1994 | Brauker et al. |
| 5,316,452 A | 5/1994 | Bogen et al. |
| 5,322,063 A | 6/1994 | Allen et al. |
| 5,326,356 A | 7/1994 | Della Valle et al. |
| 5,326,449 A | 7/1994 | Cunningham |
| 5,330,521 A | 7/1994 | Cohen |
| 5,330,634 A | 7/1994 | Wong et al. |
| 5,337,747 A | 8/1994 | Neftel |
| 5,340,352 A | 8/1994 | Nakanishi et al. |
| 5,342,693 A | 8/1994 | Winters et al. |
| 5,342,789 A | 8/1994 | Chick et al. |
| 5,344,451 A | 9/1994 | Dayton |
| 5,344,454 A | 9/1994 | Clarke et al. |
| 5,348,788 A | 9/1994 | White |
| 5,352,348 A | 10/1994 | Young et al. |
| 5,372,133 A | 12/1994 | Hogen Esch |
| 5,380,665 A | 1/1995 | Cusack et al. |
| 5,387,327 A | 2/1995 | Khan |
| 5,397,848 A | 3/1995 | Yang et al. |
| 5,411,052 A | 5/1995 | Murray |
| 5,423,738 A | 6/1995 | Robinson et al. |
| 5,426,158 A | 6/1995 | Mueller et al. |
| 5,428,123 A | 6/1995 | Ward et al. |
| 5,431,921 A | 7/1995 | Thombre |
| 5,443,508 A | 8/1995 | Giampapa |
| 5,453,278 A | 9/1995 | Chan et al. |
| 5,458,631 A | 10/1995 | Xavier |
| 5,462,064 A | 10/1995 | D'Angelo et al. |
| 5,466,575 A | 11/1995 | Cozzette et al. |
| 5,469,846 A | 11/1995 | Khan |
| 5,476,094 A | 12/1995 | Allen et al. |
| 5,482,446 A | 1/1996 | Williamson et al. |
| 5,482,473 A | 1/1996 | Lord et al. |
| 5,484,404 A | 1/1996 | Schulman et al. |
| 5,494,562 A | 2/1996 | Maley et al. |
| 5,497,772 A | 3/1996 | Schulman et al. |
| 5,505,828 A | 4/1996 | Wong et al. |
| 5,507,288 A | 4/1996 | Bocker et al. |
| 5,509,888 A | 4/1996 | Miller |
| 5,512,055 A | 4/1996 | Domb et al. |
| 5,514,253 A | 5/1996 | Davis et al. |
| 5,520,788 A | 5/1996 | Johnson |
| 5,521,273 A | 5/1996 | Yilgor et al. |
| 5,531,679 A | 7/1996 | Schulman et al. |
| 5,538,511 A | 7/1996 | Van Antwerp |
| 5,541,305 A | 7/1996 | Yokota et al. |
| 5,545,220 A | 8/1996 | Andrews et al. |
| 5,545,223 A | 8/1996 | Neuenfeldt et al. |
| 5,549,651 A | 8/1996 | Lynn |
| 5,549,675 A | 8/1996 | Neuenfeldt et al. |
| 5,551,850 A | 9/1996 | Williamson et al. |
| 5,552,112 A | 9/1996 | Schiffmann et al. |
| 5,554,339 A | 9/1996 | Cozzette et al. |
| 5,564,439 A | 10/1996 | Picha |
| 5,569,219 A | 10/1996 | Hakki et al. |
| 5,575,930 A | 11/1996 | Tietje-Girault et al. |
| 5,584,876 A | 12/1996 | Bruchman et al. |
| 5,586,553 A | 12/1996 | Halili et al. |
| 5,587,273 A | 12/1996 | Yan et al. |
| 5,589,563 A | 12/1996 | Ward et al. |
| 5,593,440 A | 1/1997 | Brauker et al. |
| 5,593,852 A | 1/1997 | Heller et al. |
| 5,605,152 A | 2/1997 | Slate et al. |
| 5,611,900 A | 3/1997 | Worden et al. |
| 5,624,537 A | 4/1997 | Turner et al. |
| 5,626,563 A | 5/1997 | Dodge et al. |
| 5,628,619 A | 5/1997 | Wilson |
| 5,628,890 A | 5/1997 | Carter et al. |
| 5,630,978 A | 5/1997 | Domb |
| 5,637,083 A | 6/1997 | Bertrand et al. |
| 5,637,135 A | 6/1997 | Ottenstein et al. |
| 5,640,470 A | 6/1997 | Iyer et al. |
| 5,651,767 A | 7/1997 | Schulman et al. |
| 5,653,756 A | 8/1997 | Clarke et al. |
| 5,658,330 A | 8/1997 | Carlisle et al. |
| 5,660,163 A | 8/1997 | Schulman et al. |
| 5,665,065 A | 9/1997 | Colman et al. |
| 5,665,222 A | 9/1997 | Heller et al. |
| 5,673,694 A | 10/1997 | Rivers |
| 5,676,651 A | 10/1997 | Larson, Jr. et al. |
| 5,681,572 A | 10/1997 | Seare, Jr. |
| 5,683,562 A | 11/1997 | Schaffar et al. |
| 5,688,239 A | 11/1997 | Walker |
| 5,703,359 A | 12/1997 | Wampler, III |
| 5,704,354 A | 1/1998 | Preidel et al. |
| 5,706,807 A | 1/1998 | Picha |
| 5,711,861 A | 1/1998 | Ward et al. |
| 5,713,888 A | 2/1998 | Neuenfeldt et al. |
| 5,733,336 A | 3/1998 | Neuenfeldt et al. |
| 5,741,330 A | 4/1998 | Brauker et al. |
| 5,746,898 A | 5/1998 | Preidel |
| 5,756,632 A | 5/1998 | Ward et al. |
| 5,760,155 A | 6/1998 | Mowrer et al. |
| 5,772,586 A | 6/1998 | Heinonen et al. |
| 5,773,270 A | 6/1998 | D'Orazio et al. |
| 5,773,286 A | 6/1998 | Dionne et al. |
| 5,777,060 A | 7/1998 | Van Antwerp |
| 5,782,912 A | 7/1998 | Brauker et al. |
| 5,783,054 A | 7/1998 | Raguse et al. |
| 5,787,900 A | 8/1998 | Butler et al. |
| 5,791,344 A | 8/1998 | Schulman et al. |
| 5,791,880 A | 8/1998 | Wilson |
| 5,795,453 A | 8/1998 | Gilmartin |
| 5,795,774 A | 8/1998 | Matsumoto et al. |
| 5,798,065 A | 8/1998 | Picha |
| 5,800,420 A | 9/1998 | Gross et al. |
| 5,800,529 A | 9/1998 | Brauker et al. |
| 5,804,048 A | 9/1998 | Wong et al. |
| 5,807,406 A | 9/1998 | Brauker et al. |
| 5,811,487 A | 9/1998 | Schulz, Jr. et al. |
| 5,820,589 A | 10/1998 | Torgerson et al. |
| 5,833,603 A | 11/1998 | Kovacs et al. |
| 5,836,887 A | 11/1998 | Oka et al. |
| 5,837,454 A | 11/1998 | Cozzette et al. |
| 5,840,026 A | 11/1998 | Uber, III et al. |
| 5,858,296 A | 1/1999 | Domb |
| 5,863,972 A | 1/1999 | Beckelmann et al. |
| 5,871,514 A | 2/1999 | Wiklund et al. |
| 5,873,862 A | 2/1999 | Lopez |
| 5,879,713 A | 3/1999 | Roth et al. |
| 5,882,354 A | 3/1999 | Brauker et al. |
| 5,882,494 A | 3/1999 | Van Antwerp |
| 5,889,855 A | 3/1999 | Davis |
| 5,897,578 A | 4/1999 | Wiklund et al. |
| 5,899,855 A | 5/1999 | Brown |
| 5,913,998 A | 6/1999 | Butler et al. |
| 5,914,026 A | 6/1999 | Blubaugh, Jr. et al. |
| 5,917,346 A | 6/1999 | Gord |
| 5,919,215 A | 7/1999 | Wiklund et al. |
| 5,928,155 A | 7/1999 | Eggers et al. |
| 5,928,182 A | 7/1999 | Kraus et al. |
| 5,928,195 A | 7/1999 | Malamud et al. |
| 5,932,175 A | 8/1999 | Knute et al. |
| 5,935,785 A | 8/1999 | Reber et al. |
| 5,957,854 A | 9/1999 | Besson et al. |
| 5,964,261 A | 10/1999 | Neuenfeldt et al. |
| 5,964,745 A | 10/1999 | Lyles et al. |
| 5,964,804 A | 10/1999 | Brauker et al. |
| 5,964,993 A | 10/1999 | Blubaugh, Jr. et al. |

(56) References Cited

U.S. PATENT DOCUMENTS

| | | | |
|---|---|---|---|
| 5,965,380 A | 10/1999 | Heller et al. |
| 5,972,199 A | 10/1999 | Heller et al. |
| 5,985,129 A | 11/1999 | Gough et al. |
| 5,987,352 A | 11/1999 | Klein et al. |
| 5,995,860 A | 11/1999 | Sun et al. |
| 5,999,848 A | 12/1999 | Gord et al. |
| 6,001,067 A | 12/1999 | Shults et al. |
| 6,001,471 A | 12/1999 | Bries et al. |
| 6,002,954 A | 12/1999 | Van Antwerp et al. |
| 6,011,984 A | 1/2000 | Van Antwerp et al. |
| 6,014,577 A | 1/2000 | Henning et al. |
| 6,015,572 A | 1/2000 | Lin et al. |
| 6,017,435 A | 1/2000 | Hassard et al. |
| 6,018,033 A | 1/2000 | Chen et al. |
| 6,030,827 A | 2/2000 | Davis et al. |
| 6,032,059 A | 2/2000 | Henning et al. |
| 6,043,328 A | 3/2000 | Domschke et al. |
| 6,045,671 A | 4/2000 | Wu et al. |
| 6,048,691 A | 4/2000 | Maracas |
| 6,051,372 A | 4/2000 | Bayerl et al. |
| 6,055,456 A | 4/2000 | Gerber |
| 6,057,377 A | 5/2000 | Sasaki et al. |
| 6,063,637 A | 5/2000 | Arnold et al. |
| 6,066,448 A | 5/2000 | Wohlstadter et al. |
| 6,077,299 A | 6/2000 | Adelberg et al. |
| 6,081,736 A | 6/2000 | Colvin et al. |
| 6,083,523 A | 7/2000 | Dionne et al. |
| 6,083,710 A | 7/2000 | Heller et al. |
| 6,088,608 A | 7/2000 | Schulman et al. |
| 6,103,033 A | 8/2000 | Say et al. |
| 6,119,028 A | 9/2000 | Schulman et al. |
| 6,120,460 A | 9/2000 | Abreu |
| 6,121,009 A | 9/2000 | Heller et al. |
| 6,123,827 A | 9/2000 | Wong et al. |
| 6,127,154 A | 10/2000 | Mosbach et al. |
| 6,134,461 A | 10/2000 | Say et al. |
| 6,139,718 A * | 10/2000 | Kurnik ............... C12Q 1/54 204/403.14 |
| 6,157,860 A | 12/2000 | Hauser et al. |
| 6,162,611 A | 12/2000 | Heller et al. |
| 6,164,921 A | 12/2000 | Moubayed et al. |
| 6,175,752 B1 * | 1/2001 | Say ..................... A61B 5/01 600/345 |
| 6,183,437 B1 | 2/2001 | Walker |
| 6,189,536 B1 | 2/2001 | Martinez et al. |
| 6,201,980 B1 | 3/2001 | Darrow et al. |
| 6,212,416 B1 | 4/2001 | Ward et al. |
| 6,213,739 B1 | 4/2001 | Phallen, IV et al. |
| 6,214,185 B1 | 4/2001 | Offenbacher et al. |
| 6,223,080 B1 | 4/2001 | Thompson |
| 6,231,879 B1 | 5/2001 | Li et al. |
| 6,248,067 B1 | 6/2001 | Causey, III et al. |
| 6,251,280 B1 | 6/2001 | Dai et al. |
| 6,254,586 B1 | 7/2001 | Mann et al. |
| 6,256,522 B1 | 7/2001 | Schultz |
| 6,259,937 B1 | 7/2001 | Schulman et al. |
| 6,264,825 B1 | 7/2001 | Blackburn et al. |
| 6,271,332 B1 | 8/2001 | Lohmann et al. |
| 6,272,382 B1 | 8/2001 | Faltys et al. |
| 6,274,285 B1 | 8/2001 | Gries et al. |
| 6,281,015 B1 | 8/2001 | Mooney et al. |
| 6,284,478 B1 | 9/2001 | Heller et al. |
| 6,293,925 B1 | 9/2001 | Safabash et al. |
| 6,299,583 B1 | 10/2001 | Eggers et al. |
| 6,306,594 B1 | 10/2001 | Cozzette et al. |
| 6,309,384 B1 | 10/2001 | Harrington et al. |
| 6,310,110 B1 | 10/2001 | Markowitz et al. |
| 6,312,706 B1 | 11/2001 | Lai et al. |
| 6,315,738 B1 | 11/2001 | Nishikawa et al. |
| 6,319,566 B1 | 11/2001 | Polanyi et al. |
| 6,325,978 B1 | 12/2001 | Labuda et al. |
| 6,325,979 B1 | 12/2001 | Hahn et al. |
| 6,329,161 B1 | 12/2001 | Heller et al. |
| 6,330,464 B1 | 12/2001 | Colvin, Jr. et al. |
| 6,343,225 B1 | 1/2002 | Clark, Jr. |
| 6,365,670 B1 | 4/2002 | Fry |
| 6,372,244 B1 | 4/2002 | Antanavich et al. |
| 6,379,883 B2 | 4/2002 | Davis et al. |
| 6,391,019 B1 | 5/2002 | Ito |
| 6,396,416 B1 | 5/2002 | Kuusela et al. |
| 6,405,066 B1 | 6/2002 | Essenpreis et al. |
| 6,407,195 B2 | 6/2002 | Sherman et al. |
| 6,413,393 B1 | 7/2002 | Van Antwerp et al. |
| 6,428,475 B1 | 8/2002 | Shen |
| 6,442,413 B1 | 8/2002 | Silver |
| 6,447,448 B1 | 9/2002 | Ishikawa et al. |
| 6,447,542 B1 | 9/2002 | Weadock |
| 6,454,710 B1 | 9/2002 | Ballerstadt et al. |
| 6,459,917 B1 | 10/2002 | Gowda et al. |
| 6,461,496 B1 | 10/2002 | Feldman et al. |
| 6,465,066 B1 | 10/2002 | Rule et al. |
| 6,466,810 B1 | 10/2002 | Ward et al. |
| 6,467,480 B1 | 10/2002 | Meier et al. |
| 6,471,689 B1 | 10/2002 | Joseph et al. |
| 6,477,392 B1 | 11/2002 | Honigs et al. |
| 6,477,395 B2 | 11/2002 | Schulman et al. |
| 6,484,045 B1 | 11/2002 | Holker et al. |
| 6,484,046 B1 | 11/2002 | Say et al. |
| 6,485,449 B2 | 11/2002 | Ito |
| 6,488,652 B1 | 12/2002 | Weijand et al. |
| 6,494,830 B1 | 12/2002 | Wessel |
| 6,494,879 B2 | 12/2002 | Lennox et al. |
| 6,497,729 B1 | 12/2002 | Moussy et al. |
| 6,498,043 B1 | 12/2002 | Schulman et al. |
| 6,498,941 B1 | 12/2002 | Jackson |
| 6,512,939 B1 | 1/2003 | Colvin et al. |
| 6,514,718 B2 | 2/2003 | Heller et al. |
| 6,520,326 B2 | 2/2003 | McIvor et al. |
| 6,520,477 B2 | 2/2003 | Trimmer |
| 6,520,937 B2 | 2/2003 | Hart et al. |
| 6,520,997 B1 | 2/2003 | Pekkarinen et al. |
| 6,526,298 B1 | 2/2003 | Khalil et al. |
| 6,528,584 B2 | 3/2003 | Kennedy et al. |
| 6,537,318 B1 | 3/2003 | Ita et al. |
| 6,541,107 B1 | 4/2003 | Zhong et al. |
| 6,542,765 B1 | 4/2003 | Guy et al. |
| 6,545,085 B2 | 4/2003 | Kilgour et al. |
| 6,546,268 B1 | 4/2003 | Ishikawa et al. |
| 6,547,839 B2 | 4/2003 | Zhang et al. |
| 6,551,496 B1 | 4/2003 | Moles et al. |
| 6,553,244 B2 | 4/2003 | Lesho et al. |
| 6,554,822 B1 | 4/2003 | Holschneider et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,565,509 B1 | 5/2003 | Say et al. |
| 6,565,807 B1 | 5/2003 | Patterson et al. |
| 6,569,521 B1 | 5/2003 | Sheridan et al. |
| 6,571,128 B2 | 5/2003 | Lebel et al. |
| 6,574,490 B2 | 6/2003 | Abbink et al. |
| 6,576,461 B2 | 6/2003 | Heller et al. |
| 6,579,498 B1 | 6/2003 | Eglise |
| 6,579,690 B1 | 6/2003 | Bonnecaze et al. |
| 6,585,763 B1 | 7/2003 | Keilman et al. |
| 6,595,756 B2 | 7/2003 | Gray et al. |
| 6,602,221 B1 | 8/2003 | Saravia et al. |
| 6,607,509 B2 | 8/2003 | Bobroff et al. |
| 6,613,379 B2 | 9/2003 | Ward et al. |
| 6,618,934 B1 | 9/2003 | Feldman et al. |
| 6,633,772 B2 | 10/2003 | Ford et al. |
| 6,641,533 B2 | 11/2003 | Causey, III et al. |
| 6,642,015 B2 | 11/2003 | Vachon et al. |
| 6,654,625 B1 | 11/2003 | Say et al. |
| 6,656,157 B1 | 12/2003 | Duchon et al. |
| 6,663,615 B1 | 12/2003 | Madou et al. |
| 6,666,821 B2 | 12/2003 | Keimel |
| 6,670,115 B1 | 12/2003 | Zhang |
| 6,673,596 B1 | 1/2004 | Sayler et al. |
| 6,689,265 B2 | 2/2004 | Heller et al. |
| 6,699,188 B2 | 3/2004 | Wessel |
| 6,699,218 B2 | 3/2004 | Flaherty et al. |
| 6,702,857 B2 | 3/2004 | Brauker et al. |
| 6,705,833 B2 | 3/2004 | Tam et al. |
| 6,721,587 B2 | 4/2004 | Gough |

(56) References Cited

U.S. PATENT DOCUMENTS

| | | |
|---|---|---|
| 6,741,877 B1 | 5/2004 | Shults et al. |
| 6,749,587 B2 | 6/2004 | Flaherty |
| 6,770,030 B1 | 8/2004 | Schaupp et al. |
| 6,770,067 B2 | 8/2004 | Lorenzen et al. |
| 6,780,297 B2 | 8/2004 | Matsumoto et al. |
| 6,784,274 B2 | 8/2004 | Van Antwerp et al. |
| 6,793,632 B2 | 9/2004 | Sohrab |
| 6,801,041 B2 | 10/2004 | Karinka et al. |
| 6,805,693 B2 | 10/2004 | Gray et al. |
| 6,809,507 B2 | 10/2004 | Morgan et al. |
| 6,809,653 B1 | 10/2004 | Mann et al. |
| 6,814,845 B2 | 11/2004 | Wilson et al. |
| 6,815,186 B2 | 11/2004 | Clark, Jr. |
| 6,862,465 B2 | 3/2005 | Shults et al. |
| 6,875,386 B1 | 4/2005 | Ward et al. |
| 6,881,551 B2 | 4/2005 | Heller et al. |
| 6,891,317 B2 | 5/2005 | Pei et al. |
| 6,892,085 B2 | 5/2005 | McIvor et al. |
| 6,893,552 B1 | 5/2005 | Wang et al. |
| 6,895,265 B2 | 5/2005 | Silver |
| 6,913,626 B2 | 7/2005 | McGhan |
| 6,926,691 B2 | 8/2005 | Miethke |
| 6,932,584 B2 | 8/2005 | Gray et al. |
| 6,932,894 B2 | 8/2005 | Mao et al. |
| 6,936,006 B2 | 8/2005 | Sabra |
| 6,958,705 B2 | 10/2005 | Lebel et al. |
| 6,960,192 B1 | 11/2005 | Flaherty et al. |
| 6,966,325 B2 | 11/2005 | Erickson |
| 6,973,706 B2 | 12/2005 | Say et al. |
| 6,975,893 B2 | 12/2005 | Say et al. |
| 6,989,891 B2 | 1/2006 | Braig et al. |
| 6,997,921 B2 | 2/2006 | Gray et al. |
| 7,008,979 B2 | 3/2006 | Schottman et al. |
| 7,025,727 B2 | 4/2006 | Brockway et al. |
| 7,033,322 B2 | 4/2006 | Silver |
| 7,061,593 B2 | 6/2006 | Braig et al. |
| 7,066,884 B2 | 6/2006 | Custer et al. |
| 7,070,577 B1 | 7/2006 | Haller et al. |
| 7,097,775 B2 | 8/2006 | Greenberg et al. |
| 7,098,803 B2 | 8/2006 | Mann et al. |
| 7,110,803 B2 | 9/2006 | Shults et al. |
| 7,120,483 B2 | 10/2006 | Russell et al. |
| 7,131,967 B2 | 11/2006 | Gray et al. |
| 7,134,999 B2 | 11/2006 | Brauker et al. |
| 7,136,689 B2 | 11/2006 | Shults et al. |
| 7,150,741 B2 | 12/2006 | Erickson et al. |
| 7,192,450 B2 | 3/2007 | Brauker et al. |
| 7,241,586 B2 | 7/2007 | Gulati et al. |
| 7,247,138 B2 | 7/2007 | Reghabi et al. |
| 7,248,906 B2 | 7/2007 | Dirac et al. |
| 7,254,450 B2 | 8/2007 | Christopherson et al. |
| 7,255,690 B2 | 8/2007 | Gray et al. |
| 7,279,174 B2 | 10/2007 | Pacetti et al. |
| 7,288,085 B2 | 10/2007 | Olsen |
| 7,299,082 B2 | 11/2007 | Feldman et al. |
| 7,316,662 B2 | 1/2008 | Delnevo et al. |
| 7,318,814 B2 | 1/2008 | Levine et al. |
| 7,329,234 B2 | 2/2008 | Sansoucy |
| 7,335,195 B2 | 2/2008 | Mehier |
| 7,335,286 B2 | 2/2008 | Abel et al. |
| 7,336,984 B2 | 2/2008 | Gough et al. |
| 7,357,793 B2 | 4/2008 | Pacetti |
| 7,361,155 B2 | 4/2008 | Sage, Jr. et al. |
| 7,364,562 B2 | 4/2008 | Braig et al. |
| 7,366,556 B2 | 4/2008 | Brister et al. |
| 7,379,765 B2 | 5/2008 | Petisce et al. |
| 7,396,353 B2 | 7/2008 | Lorenzen et al. |
| 7,447,596 B2 | 11/2008 | Kawatahara et al. |
| 7,519,408 B2 | 4/2009 | Rasdal et al. |
| 7,587,287 B2 | 9/2009 | Connolly et al. |
| 7,591,801 B2 | 9/2009 | Brauker et al. |
| 7,595,723 B2 | 9/2009 | Heitzmann et al. |
| 7,602,310 B2 | 10/2009 | Mann et al. |
| 7,722,536 B2 | 5/2010 | Goodnow |
| 7,927,274 B2 | 4/2011 | Rasdal et al. |
| 7,976,492 B2 | 7/2011 | Brauker et al. |
| 8,029,459 B2 | 10/2011 | Rush et al. |
| 8,029,460 B2 | 10/2011 | Rush et al. |
| 9,763,609 B2 | 9/2017 | Simpson et al. |
| 2002/0009810 A1 | 1/2002 | O'Connor et al. |
| 2002/0018843 A1 | 2/2002 | Van Antwerp et al. |
| 2002/0019330 A1 | 2/2002 | Murray et al. |
| 2002/0023852 A1 | 2/2002 | McIvor et al. |
| 2002/0042561 A1 | 4/2002 | Schulman et al. |
| 2002/0065453 A1 | 5/2002 | Lesho et al. |
| 2002/0068860 A1 | 6/2002 | Clark, Jr. |
| 2002/0119711 A1 | 8/2002 | VanAntwerp et al. |
| 2002/0123087 A1 | 9/2002 | Vachon et al. |
| 2002/0133224 A1 | 9/2002 | Bajgar et al. |
| 2002/0137193 A1 | 9/2002 | Heller et al. |
| 2002/0151796 A1 | 10/2002 | Koulik |
| 2002/0169369 A1 | 11/2002 | Ward et al. |
| 2002/0182241 A1 | 12/2002 | Borenstein et al. |
| 2002/0188185 A1 | 12/2002 | Sohrab |
| 2003/0004457 A1 | 1/2003 | Andersson |
| 2003/0006669 A1 | 1/2003 | Pei et al. |
| 2003/0009093 A1 | 1/2003 | Silver |
| 2003/0031699 A1 | 2/2003 | Van Antwerp |
| 2003/0032874 A1 | 2/2003 | Rhodes et al. |
| 2003/0036803 A1 | 2/2003 | McGhan |
| 2003/0059631 A1 | 3/2003 | Al-Lamee |
| 2003/0065254 A1 | 4/2003 | Schulman et al. |
| 2003/0069383 A1 | 4/2003 | Van Antwerp et al. |
| 2003/0072741 A1 | 4/2003 | Berglund et al. |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0088166 A1 | 5/2003 | Say et al. |
| 2003/0091433 A1 | 5/2003 | Tam et al. |
| 2003/0099682 A1 | 5/2003 | Moussy et al. |
| 2003/0100040 A1 | 5/2003 | Bonnecaze et al. |
| 2003/0104119 A1 | 6/2003 | Wilson et al. |
| 2003/0125613 A1 | 7/2003 | Enegren et al. |
| 2003/0132227 A1 | 7/2003 | Geisler et al. |
| 2003/0134347 A1 | 7/2003 | Heller et al. |
| 2003/0188427 A1 | 10/2003 | Say et al. |
| 2003/0199744 A1 | 10/2003 | Buse et al. |
| 2003/0199745 A1 | 10/2003 | Burson et al. |
| 2003/0208113 A1 | 11/2003 | Mault et al. |
| 2003/0211050 A1 | 11/2003 | Majeti et al. |
| 2003/0217966 A1 | 11/2003 | Tapsak et al. |
| 2003/0225324 A1 | 12/2003 | Anderson et al. |
| 2003/0228681 A1 | 12/2003 | Ritts et al. |
| 2004/0006263 A1 | 1/2004 | Anderson et al. |
| 2004/0010207 A1 | 1/2004 | Flaherty et al. |
| 2004/0023253 A1 | 2/2004 | Kunwar et al. |
| 2004/0023317 A1 | 2/2004 | Motamedi et al. |
| 2004/0030294 A1 | 2/2004 | Mahurkar |
| 2004/0039406 A1 | 2/2004 | Jessen |
| 2004/0054352 A1 | 3/2004 | Adams et al. |
| 2004/0063167 A1 | 4/2004 | Kaastrup et al. |
| 2004/0074785 A1 | 4/2004 | Holker et al. |
| 2004/0078219 A1 | 4/2004 | Kaylor et al. |
| 2004/0106857 A1 | 6/2004 | Gough |
| 2004/0111017 A1 | 6/2004 | Say et al. |
| 2004/0146909 A1 | 7/2004 | Duong et al. |
| 2004/0152187 A1 | 8/2004 | Haight et al. |
| 2004/0167801 A1 | 8/2004 | Say et al. |
| 2004/0176672 A1 | 9/2004 | Silver et al. |
| 2004/0180391 A1 | 9/2004 | Gratzl et al. |
| 2004/0186362 A1 | 9/2004 | Brauker et al. |
| 2004/0219664 A1 | 11/2004 | Heller et al. |
| 2004/0224001 A1 | 11/2004 | Pacetti et al. |
| 2004/0234575 A1 | 11/2004 | Horres et al. |
| 2004/0248282 A1 | 12/2004 | Sobha M. et al. |
| 2004/0253365 A1 | 12/2004 | Warren et al. |
| 2004/0254433 A1 | 12/2004 | Bandis et al. |
| 2005/0003399 A1 | 1/2005 | Blackburn et al. |
| 2005/0026689 A1 | 2/2005 | Marks |
| 2005/0031689 A1 | 2/2005 | Shults et al. |
| 2005/0033132 A1 | 2/2005 | Shults et al. |
| 2005/0044088 A1 | 2/2005 | Lindsay et al. |
| 2005/0051427 A1 | 3/2005 | Brauker et al. |
| 2005/0051440 A1 | 3/2005 | Simpson et al. |

(56) References Cited

U.S. PATENT DOCUMENTS

| | | |
|---|---|---|
| 2005/0056552 A1 | 3/2005 | Simpson et al. |
| 2005/0070770 A1 | 3/2005 | Dirac et al. |
| 2005/0077584 A1 | 4/2005 | Uhland et al. |
| 2005/0079200 A1 | 4/2005 | Rathenow et al. |
| 2005/0090607 A1 | 4/2005 | Tapsak et al. |
| 2005/0103625 A1 | 5/2005 | Rhodes et al. |
| 2005/0107677 A1 | 5/2005 | Ward et al. |
| 2005/0115832 A1 | 6/2005 | Simpson et al. |
| 2005/0118344 A1 | 6/2005 | Pacetti |
| 2005/0119720 A1 | 6/2005 | Gale et al. |
| 2005/0121322 A1 | 6/2005 | Say et al. |
| 2005/0143635 A1 | 6/2005 | Kamath et al. |
| 2005/0154271 A1 | 7/2005 | Rasdal et al. |
| 2005/0154272 A1 | 7/2005 | Dirac et al. |
| 2005/0161346 A1 | 7/2005 | Simpson et al. |
| 2005/0176136 A1 | 8/2005 | Burd et al. |
| 2005/0176678 A1 | 8/2005 | Horres et al. |
| 2005/0177036 A1 | 8/2005 | Shults et al. |
| 2005/0181012 A1 | 8/2005 | Saint et al. |
| 2005/0182451 A1 | 8/2005 | Griffin et al. |
| 2005/0192557 A1 | 9/2005 | Brauker et al. |
| 2005/0197554 A1 | 9/2005 | Polcha |
| 2005/0203360 A1 | 9/2005 | Brauker et al. |
| 2005/0242479 A1 | 11/2005 | Petisce et al. |
| 2005/0245795 A1 | 11/2005 | Goode, Jr. et al. |
| 2005/0245799 A1* | 11/2005 | Brauker ............ A61B 5/14865 600/347 |
| 2005/0251083 A1 | 11/2005 | Carr-Brendel et al. |
| 2005/0282997 A1 | 12/2005 | Ward et al. |
| 2005/0288596 A1 | 12/2005 | Eigler et al. |
| 2006/0001550 A1 | 1/2006 | Mann et al. |
| 2006/0003398 A1 | 1/2006 | Heller et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1* | 2/2006 | Brister ............... A61B 5/14507 600/345 |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0047095 A1 | 3/2006 | Pacetti |
| 2006/0052745 A1 | 3/2006 | Van Antwerp et al. |
| 2006/0067908 A1 | 3/2006 | Ding |
| 2006/0078908 A1 | 4/2006 | Pitner et al. |
| 2006/0079740 A1 | 4/2006 | Silver et al. |
| 2006/0079809 A1 | 4/2006 | Goldberger et al. |
| 2006/0094946 A1 | 5/2006 | Kellogg et al. |
| 2006/0134165 A1 | 6/2006 | Pacetti |
| 2006/0142651 A1 | 6/2006 | Brister et al. |
| 2006/0155180 A1 | 7/2006 | Brister et al. |
| 2006/0159981 A1 | 7/2006 | Heller |
| 2006/0171980 A1 | 8/2006 | Helmus et al. |
| 2006/0177379 A1 | 8/2006 | Asgari |
| 2006/0183178 A1 | 8/2006 | Gulati et al. |
| 2006/0183871 A1 | 8/2006 | Ward et al. |
| 2006/0189856 A1 | 8/2006 | Petisce et al. |
| 2006/0189863 A1 | 8/2006 | Peyser et al. |
| 2006/0195029 A1 | 8/2006 | Shults et al. |
| 2006/0198864 A1 | 9/2006 | Shults et al. |
| 2006/0200019 A1 | 9/2006 | Petisce et al. |
| 2006/0200970 A1 | 9/2006 | Brister et al. |
| 2006/0204536 A1 | 9/2006 | Shults et al. |
| 2006/0229512 A1 | 10/2006 | Petisce et al. |
| 2006/0253085 A1 | 11/2006 | Geismar et al. |
| 2006/0258761 A1 | 11/2006 | Boock et al. |
| 2006/0263839 A1 | 11/2006 | Ward et al. |
| 2006/0269586 A1 | 11/2006 | Pacetti |
| 2006/0275857 A1 | 12/2006 | Kjaer et al. |
| 2006/0275859 A1 | 12/2006 | Kjaer |
| 2006/0289307 A1 | 12/2006 | Yu et al. |
| 2006/0293487 A1 | 12/2006 | Gaymans et al. |
| 2007/0007133 A1 | 1/2007 | Mang et al. |
| 2007/0032718 A1 | 2/2007 | Shults et al. |
| 2007/0038044 A1 | 2/2007 | Dobbles et al. |
| 2007/0088208 A1 | 4/2007 | Yasuzawa et al. |
| 2007/0129524 A1 | 6/2007 | Sunkara |
| 2007/0135698 A1 | 6/2007 | Shah et al. |
| 2007/0163880 A1 | 7/2007 | Woo et al. |
| 2007/0173709 A1 | 7/2007 | Petisce et al. |
| 2007/0173710 A1 | 7/2007 | Petisce et al. |
| 2007/0197890 A1 | 8/2007 | Boock et al. |
| 2007/0200267 A1 | 8/2007 | Tsai |
| 2007/0203407 A1 | 8/2007 | Hoss et al. |
| 2007/0213611 A1 | 9/2007 | Simpson et al. |
| 2007/0215491 A1 | 9/2007 | Heller et al. |
| 2007/0218097 A1 | 9/2007 | Heller et al. |
| 2007/0227907 A1 | 10/2007 | Shah et al. |
| 2007/0233013 A1 | 10/2007 | Schoenberg |
| 2007/0235331 A1 | 10/2007 | Simpson et al. |
| 2007/0244379 A1 | 10/2007 | Boock et al. |
| 2007/0244383 A1 | 10/2007 | Talbot et al. |
| 2007/0275193 A1 | 11/2007 | Desimone et al. |
| 2007/0299385 A1 | 12/2007 | Santini, Jr. et al. |
| 2007/0299409 A1 | 12/2007 | Whitbourne et al. |
| 2008/0021008 A1 | 1/2008 | Pacetti et al. |
| 2008/0027301 A1 | 1/2008 | Ward et al. |
| 2008/0029391 A1 | 2/2008 | Mao et al. |
| 2008/0033254 A1 | 2/2008 | Kamath et al. |
| 2008/0033269 A1 | 2/2008 | Zhang |
| 2008/0034972 A1 | 2/2008 | Gough et al. |
| 2008/0045824 A1 | 2/2008 | Tapsak et al. |
| 2008/0086040 A1 | 4/2008 | Heller et al. |
| 2008/0086041 A1 | 4/2008 | Heller et al. |
| 2008/0086043 A1 | 4/2008 | Heller et al. |
| 2008/0091094 A1 | 4/2008 | Heller et al. |
| 2008/0091095 A1 | 4/2008 | Heller et al. |
| 2008/0228057 A1 | 9/2008 | Graskov et al. |
| 2008/0287761 A1 | 11/2008 | Hayter et al. |
| 2008/0287765 A1 | 11/2008 | Rasdal et al. |
| 2008/0319295 A1 | 12/2008 | Bernstein et al. |
| 2009/0069655 A1 | 3/2009 | Say et al. |
| 2009/0131860 A1 | 5/2009 | Nielsen |
| 2010/0137698 A1 | 6/2010 | Andrews et al. |
| 2013/0131478 A1 | 5/2013 | Simpson et al. |
| 2014/0128704 A1 | 5/2014 | Simpson et al. |

FOREIGN PATENT DOCUMENTS

| | | |
|---|---|---|
| EP | 0313951 A1 | 5/1989 |
| EP | 0362145 A2 | 4/1990 |
| EP | 0390390 A1 | 10/1990 |
| EP | 0396788 A1 | 11/1990 |
| EP | 0539625 A1 | 5/1993 |
| EP | 0286118 B1 | 1/1995 |
| EP | 0747069 A2 | 12/1996 |
| EP | 0838230 A2 | 4/1998 |
| EP | 0885932 A2 | 12/1998 |
| EP | 1266607 A2 | 12/2002 |
| JP | S57110236 A | 7/1982 |
| JP | S57156004 A | 9/1982 |
| JP | S57156005 A | 9/1982 |
| JP | S58163402 A | 9/1983 |
| JP | S58163403 A | 9/1983 |
| JP | S5929693 A | 2/1984 |
| JP | S5949803 A | 3/1984 |
| JP | S5949805 A | 3/1984 |
| JP | S5959221 A | 4/1984 |
| JP | S5987004 A | 5/1984 |
| JP | S59209608 A | 11/1984 |
| JP | S59209609 A | 11/1984 |
| JP | S59209610 A | 11/1984 |
| JP | S60245623 A | 12/1985 |
| JP | S61238319 A | 10/1986 |

(56) References Cited

FOREIGN PATENT DOCUMENTS

| | | |
|---|---|---|
| JP | S6274406 A | 4/1987 |
| JP | S62102815 A | 5/1987 |
| JP | S62227423 A | 10/1987 |
| JP | S63130661 A | 6/1988 |
| JP | S6418404 A | 1/1989 |
| JP | S6418405 A | 1/1989 |
| JP | H05279447 A | 10/1993 |
| JP | H08196626 A | 8/1996 |
| WO | WO-9000738 A1 | 1/1990 |
| WO | WO-9207525 A1 | 5/1992 |
| WO | WO-9213271 A1 | 8/1992 |
| WO | WO-9319701 A1 | 10/1993 |
| WO | WO-9422367 A1 | 10/1994 |
| WO | WO-9601611 A1 | 1/1996 |
| WO | WO-9603117 A1 | 2/1996 |
| WO | WO-9614026 A1 | 5/1996 |
| WO | WO-9630431 A1 | 10/1996 |
| WO | WO-9632076 A1 | 10/1996 |
| WO | WO-9636296 A1 | 11/1996 |
| WO | WO-9637246 A1 | 11/1996 |
| WO | WO-9701986 A1 | 1/1997 |
| WO | WO-9711067 A1 | 3/1997 |
| WO | WO-9719188 A1 | 5/1997 |
| WO | WO-9913574 A1 | 3/1999 |
| WO | WO-9948419 A1 | 9/1999 |
| WO | WO-9956613 A1 | 11/1999 |
| WO | WO-0013003 A1 | 3/2000 |
| WO | WO-0019887 A1 | 4/2000 |
| WO | WO-0033065 A1 | 6/2000 |
| WO | WO-0112158 A1 | 2/2001 |
| WO | WO-0113102 A1 | 2/2001 |
| WO | WO-0120019 A2 | 3/2001 |
| WO | WO-0143660 A2 | 6/2001 |
| WO | WO-0158348 A2 | 8/2001 |
| WO | WO-0168901 A2 | 9/2001 |
| WO | WO-0169222 A2 | 9/2001 |
| WO | WO-01885244 A1 | 11/2001 |
| WO | WO-02082989 A1 | 10/2002 |
| WO | WO-03022125 A2 | 3/2003 |
| WO | WO-03101862 A1 | 12/2003 |
| WO | WO-2004071294 A1 | 8/2004 |
| WO | WO-2005026689 A2 | 3/2005 |
| WO | WO-2005032400 A2 | 4/2005 |
| WO | WO-2005044088 A2 | 5/2005 |
| WO | WO-2006018425 A2 | 2/2006 |
| WO | WO-2006122553 A1 | 11/2006 |
| WO | WO-2007114943 A2 | 10/2007 |

OTHER PUBLICATIONS

Abe, et al., "Characterization of Glucose Microsensors for Intracellular Measurements," Analytical Chemistry, 1992, vol. 64, No. 18, pp. 2160-2163.
Abel, et al., "Biosensors for in Vivo Glucose Measurements: Can We Cross the Experimental Stage," Biosensors & Bioelectronics, 2002, vol. 17, pp. 1059-1070.
Amin R., et al., "Hypoglycemia Prevalence in Prepubertal Children With Type 1 Diabetes on Standard Insulin Regimen: Use of Continuous Glucose Monitoring System," Diabetes Care, 2003, vol. 26, No. 3, pp. 662-667.
Armour J.C., et al., "Application of Chronic Intravascular Blood Glucose Sensor in Dogs," Diabetes, Dec. 1990, vol. 39, pp. 1519-1526.
Asberg P., et al., "Hydrogels of a Conducting Conjugated Polymer as 3-D Enzyme Electrode," Biosensors Bioelectronics, 2003, vol. 19, pp. 199-207.
Atanasov P., et al., "Biosensor for Continuous Glucose Monitoring," Biotechnology and Bioengineering, John Wiley & sons Inc, 1994, vol. 43, pp. 262-266.
Atanasov P., et al., "Implantation of a Refillable Glucose Monitoring-Telemetry Device," Biosenors and Bioelectronics, vol. 12 (7), 1997, pp. 669-680.
Bailey T.S., et al., "Reduction in Hemoglobin A1C with Real-Time Continuous Glucose Monitoring: Results from a 12-Week Observational Study," Diabetes Technology & Therapeutics, vol. 9 (3), 2007, pp. 203-210.
Beach R.D., et al., "Subminiature Implantable Potentiostat and Modified Commercial Telemetry Device for Remote Glucose Monitoring," IEEE Transactions on Instrumentation and Measurement, vol. 48 (6), Dec. 1999, pp. 1239-1245.
Bindra D.S., et al., "Design and in Vitro Studies of a Needle-Type Glucose Sensor for Subcutaneous Monitoring," Analytical Chemistry, vol. 63, Sep. 1, 1991, pp. 1692-1696.
Bindra D.S., et al., "Pulsed Amperometric Detection of Glucose in Biological Fluids at a Surface-Modified Gold Electrode," Analytical Chemistry, vol. 61 (22), Nov. 15, 1989, pp. 2566-2570.
Bisenberger M., et al., "A Triple-Step Potential Waveform at Enzyme Multisensors with Thick-Film Gold Electrodes for Detection of Glucose and Sucrose," Sensors and Actuators B, vol. 28, 1995, pp. 181-189.
Bland J.M., et al., "A Note on the Use of the Intraclass Correlation Coefficient in the Evaluation of Agreement between Two Methods of Measurement," Computers in Biology and Medicine, vol. 20 (5), 1990, pp. 337-340.
Bode B.W., "Clinical Utility of the Continuous Glucose Monitoring System," Diabetes Technology & Therapeutics, vol. 2, Supplement 1, 2000, pp. S35-S41.
Bode B.W., et al., "Continuous Glucose Monitoring Used to Adjust Diabetes Therapy Improves Glycosylated Hemoglobin: A Pilot Study," Diabetes Research and Clinical Practice, vol. 46, 1999, pp. 183-190.
Bode B.W., et al., "Using the Continuous Glucose Monitoring System to Improve the Management of Type 1 Diabetes," Diabetes Technology & Therapeutics, vol. 2, Supplement 1, 2000, pp. S43-S48.
Boland E., et al., "Limitations of Conventional Methods of Self-Monitoring of Blood Glucose," Diabetes Care, vol. 24 (11), Nov. 2001, pp. 1858-1862.
Bott A.W., "A Comparison of Cyclic Voltammetry and Cyclic Staircase Voltammetry," Current Separations, vol. 16 (1), 1997, pp. 23-26.
Bowman L., et al., "The Packaging of Implantable Integrated Sensors," IEEE Transactions in Biomedical Engineering, vol. BME-33 (2), Feb. 1986, pp. 248-255.
Brauker, et al., "Sustained Expression of High Levels of Human Factor IX from Human Cells Implanted within an Immunoisolation Device into Athymic Rodents," Human Gene Therapy, Apr. 10, 1998, vol. 9, pp. 879-888.
Brauker J., et al., "Local Inflammatory Response Around Diffusion Chambers Containing Xenografts," Transplantation, vol. 61 (12), Jun. 27, 1996, pp. 1671-1677.
Brauker J H., et al., "Neovascularization of Synthetic Membranes Directed by Membrane Microarchitecture," Journal of Biomedical Material Research, 1995, vol. 29, pp. 1517-1524.
Brauker J., "Unraveling Mysteries at the Biointerface: Molecular Mediator of Inhibition of Blood Vessel Formation in the Foreign Body Capsule Revealed," SurFACTS in Biomaterials, vol. 6 (3), 2001, 2 pages.
Bremer T.M., et al., "Benchmark Data from the Literature for Evaluation of New Glucose Sensing Technologies," Diabetes Technology & Therapeutics, vol. 3 (3), 2001, pp. 409-418.
Brooks S.L., et al., "Development of an On-line Glucose Sensor for Fermentation Monitoring," Biosensors, vol. 3, 1987/1988, pp. 45-56.
Bruckel J., et al., "In Vivo Measurement of Subcutaneous Glucose Concentrations with an Enzymatic Glucose Sensor and a Wick Method," Klin Wochenschr, vol. 67, 1989, pp. 491-495.
Brunner G.A., et al., "Validation of Home Blood Glucose Meters with Respect to Clinical and Analytical Approaches," Diabetes Care, vol. 21, No. 4, Apr. 1998, pp. 585-590.
Cai Q., et al., "A Wireless, Remote Query Glucose Biosensor Based on a pH-Sensitive Polymer," Analytical Chemistry, vol. 76 (14), Jul. 15, 2004, pp. 4038-4043.
Campanella L., et al., "Biosensor for Direct Determination of Glucose and Lactate in Undiluted Biological Fluids," Biosensors & Bioelectronics, vol. 8, 1993, pp. 307-314.

(56) References Cited

OTHER PUBLICATIONS

Cass A.E.G., et al., "Ferrocene-Mediated Enzyme Electrodes for Amperometric Determination of Glucose," Analytical Chemistry, vol. 56 (4), Apr. 1984, pp. 667-671.
Chase H.P., et al., "Continuous Subcutaneous Glucose Monitoring in Children with Type 1 Diabetes," Pediatrics, vol. 107 (2), Feb. 2001, pp. 222-226.
Chen C., et al., "A Noninterference Polypyrrole Glucose Biosensor," Biosensors and Bioelectronics, vol. 22, 2006, pp. 639-643.
Ciba Specialty Chemicals, "Ciba® IRGACURE® 2959," Coating Effects Segment, Photoinitiator Product Description, Basel Switzerland, Apr. 2, 1998, 3 pages.
Claremont D.J., et al., "Potentially-Implantable, Ferrocene-Mediated Glucose Sensor," Journal of Biomedical Engineering, vol. 8, Jul. 1986, pp. 272-274.
Claremont D.J., et al., "Subcutaneous Implantation of a Ferrocene-Mediated Glucose Sensor in Pigs," Diabetologia, vol. 29, 1986, pp. 817-821.
Clark L.C., et al., "Long-Term Stability of Electroenzymatic Glucose Sensors Implanted in Mice," vol. XXXIV, Transactions—American Society for Artificial Internal Organs, 1988, vol. 34, pp. 259-265.
Colowick S.P., et al., "Methods in Enzymology," vol. XLIV, Immobilized Enzymes, Edited by Mosbach K, New York Academic Press, 1976, 11 pages.
Cox D.J., et al., "Accuracy of Perceiving Blood Glucose in IDDM," Diabetes Care, vol. 8 (6), Nov.-Dec. 1985, pp. 529-536.
Csoregi E., et al., "Design, Characterization and One-Point in Vivo Calibration of a Subcutaneously Implanted Glucose Electrode," American Chemical Society, Analytical Chemistry, vol. 66 (19), Oct. 1, 1994, pp. 3131-3138.
Dai W.S., et al., "Hydrogel Membranes with Mesh Size Asymmetry based on the Gradient Crosslinking of Poly(Vinyl Alcohol)," Journal of Membrane Science, 1999, vol. 156, pp. 67-79.
D'Arrigo G., et al., "Porous-Si Based Bio Reactors for Glucose Monitoring and Drugs Production," Proceedings of SPIE, 2003, vol. 4982, pp. 178-184.
Dixon B.M., et al., "Characterization in Vitro and in Vivo of the Oxygen Dependence of an Enzyme/Polymer Biosensor for Monitoring Brain Glucose," Journal of Neuroscience Methods, vol. 119, 2002, pp. 135-142.
DuPont, "Dimension® AR Clinical Chemistry System," the Chemistry Analyzer that Makes the most of your Time, Money and Effort, Dade International, Chemistry Systems, Newark, 1998, 18 pages.
Edwards Lifesciences, "Accuracy for You and Your Patients," Marketing materials, 2002, 4 pages.
El Degheidy M.M., et al., "Optimization of an Implantable Coated Wire Glucose Sensor," Journal of Biomedical Engineering, vol. 8, Apr. 1986, pp. 121-129.
ELCO Diagnostics Company, "Direct 30/30® Blood Glucose Sensor," Markwell Medical Catalog, 1990, 1 page.
El-Khatib F.H., et al., "Adaptive Closed-Loop Control Provides Blood-Glucose Regulation Using Dual Subcutaneous Insulin and Glucagon Infusion in Diabetic Swine," Journal of Diabetes Science and Technology, Diabetes Technology Society, vol. 1 (2), 2007, pp. 181-192.
El-Sa'Ad L., et al., "Moisture Absorption by Epoxy Resins: The Reverse Thermal Effect," Journal of Materials Science, vol. 25, 1990, pp. 3577-3582.
Ernst H., et al., "Reliable Glucose Monitoring Through the Use of Microsystem Technology," Analytical Bioanalytical Chemistry, vol. 373, 2002, pp. 758-761.
Fare T.L., et al., "Functional Characterization of a Conducting Polymer-Based Immunoassay System," Biosensors & Bioelectronics, vol. 13 (3-4), 1998, pp. 459-470.
Feldman B., et al., "A Continuous Glucose Sensor Based on Wired EnzymeTM Technology—Results from a 3-Day Trial in Patients with Type 1 Diabetes," Diabetes Technology & Therapeutics, vol. 5 (5), 2003, pp. 769-779.

Fischer U., et al., "Oxygen Tension at the Subcutaneous Implantation Site of Glucose Sensors," Biomed. Biochim. Acta, vol. 48 (11/12), 1989, pp. 965-971.
Frohnauer M.K., et al., "Graphical Human Insulin Time-Activity Profiles Using Standardized Definitions," Diabetes Technology & Therapeutics, vol. 3 (3), 2001, pp. 419-429.
Frost M.C., et al., "Implantable Chemical Sensors for Real-Time Clinical Monitoring: Progress and Challenges," Current Opinion in Chemical Biology, Analytical Techniques, vol. 6, 2002, pp. 633-641.
Garg S.K., et al., "Improved Glucose Excursions Using an Implantable Real-Time Continuous Glucose Sensor in Adults With Type 1 Diabetes," Emerging Treatments and Technologies, Diabetes Care, vol. 27 (3), 2004, pp. 734-738.
Geller R.I., et al., "Use of an Immunoisolation Device for Cell Transplantation and Tumor Immunotherapy," Annals of the New York Academy of Science, 1997, vol. 831, pp. 438-451.
Gerritsen M., et al., "Influence of Inflammatory Cells and Serum on the Performance of Implantable Glucose Sensors," Journal of Biomedical Material Research, 2001, vol. 54, pp. 69-75.
Gerritsen M., et al., "Performance of Subcutaneously Implanted Glucose Sensors for Continuous Monitoring," The Netherlands Journal of Medicine, vol. 54, 1999, pp. 167-179.
Gerritsen M., et al., "Problems Associated with Subcutaneously Implanted Glucose Sensors," Diabetes Care, vol. 23 (2), Feb. 2000, pp. 143-145.
Gilligan B.J., et al., "Evaluation of a Subcutaneous Glucose Sensor Out to 3 Months in a Dog Model" Diabetes Care, vol. 17 (8), Aug. 1994, pp. 882-887.
Gilligan B.J., et al., "Feasibility of Continuous Long-Term Glucose Monitoring from a Subcutaneous Glucose Sensor in Humans," Diabetes Technology & Therapeutics, vol. 6 (3), 2004, pp. 378-386.
Godsland I.F., et al., "Maximizing the Success Rate of Minimal Model Insulin Sensivity Measurement in Humans: The Importance of Basal Glucose Levels," The Biochemical Society and the Medical Research Society, Clinical Science, vol. 101, 2001, pp. 1-9.
Gough D.A., et al., "Frequency Characterization of Blood Glucose Dynamics," Annals of Biomedical Engineering, vol. 31, 2003, pp. 91-97.
Gough D.A., et al., "Immobilized Glucose Oxidase in Implantable Glucose Sensor Technology," Diabetes Technology & Therapeutics, vol. 2 (3), 2000, pp. 377-380.
Gregg B A., et al., "Cross-Linked Redox Gels Containing Glucose Oxidase for Amperometric Biosensor Applications," Anal Chem, 1990, vol. 62, pp. 258-263.
Gross, et al., "Diabetes Technology & Therapeutics," Letters to the Editor, Diabetes Technology & Therapeutics, vol. 3 (1), 2001, pp. 129-131.
Gross T.M., et al., "Efficacy and Reliability of the Continuous Glucose Monitoring System," Diabetes Technology & Therapeutics, vol. 2, Supplement 1, 2000, pp. S19-S26.
Gross T.M., et al., "Performance Evaluation of the Minimed® Continuous Glucose Monitoring System During Patient Home Use," Diabetes Technology & Therapeutics, vol. 2(1), 2000, pp. 49-56.
Hall S.B., et al., "Electrochemical Oxidation of Hydrogen Peroxide at Platinum Electrodes. Part 1. An Adsorption-controlled Mechanism," Electrochimica Acta, vol. 43, Nos. 5/6, 1998, pp. 579-588.
Hall S.B., et al., "Electrochemical Oxidation of Hydrogen Peroxide at Platinum Electrodes. Part II: Effect of potential," Electrochimica Acta, vol. 43 (14-15), 1998, pp. 2015-2024.
Hall S.B., et al., "Electrochemical Oxidation of Hydrogen Peroxide at Platinum Electrodes. Part III: Effect of Temperature," Electrochimica Acta, vol. 44, 1999, pp. 2455-2462.
Hall S.B., et al., "Electrochemical Oxidation of Hydrogen Peroxide at Platinum Electrodes. Part IV: Phosphate Buffer Dependence," Electrochimica Acta, vol. 44, 1999, pp. 4573-4582.
Hall S.B., et al., "Electrochemical Oxidation of Hydrogen Peroxide at Platinum Electrodes. Part V: Inhibition by Chloride," Electrochimica Acta, vol. 45, 2000, pp. 3573-3579.
Heller A., "Electrical Connection of Enzyme Redox Centers to Electrodes," J. Phys. Chem., vol. 96, 1992, pp. 3579-3587.

(56) References Cited

OTHER PUBLICATIONS

Heller A., "Implanted Electrochemical Glucose Sensors for the Management of Diabetes," Annu. Rev., Biomed Eng., vol. 1, 1999, pp. 153-175.

Heller A., "Plugging Metal Connectors into Enzymes," Nature Biotechnology, vol. 21, No. 6, Jun. 2003, pp. 631-632.

Hitchman M.L., "Measurement of Dissolved Oxygen," Edited by Elving P.J et al., Chemical Analysis, New York, John Wiley & Sons, vol. 49, Chapter 3, 1978, pp. 34-49 and 59-123.

Houghton Mifflin Company, "Xenogenic, the American Heritage Stedman's Medical Dictionary," 2002, Answers.Com, retrieved from http://www.answers.com/topic/xenogenic, on Nov. 7, 2006, 2 Pages.

Hrapovic S., et al., "Picoamperometric Detection of Glucose at Ultrasmall Platinum-Based Biosensors Preparation and Characterization," Anal. Chem, vol. 75, 2003, pp. 3308-3315.

Huang C., et al., "Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode," U.S. Department of Commence/NTIS, 1975, 126 pages.

Huang Q., et al., "A 0.5mW Passive Telemetry IC for Biomedical Applications," Proceedings of the 23rd European Solid-State Circuits Conference (ESSCIRC '97), Southampton, UK, Sep. 16-18, 1997, pp. 172-175.

Hunter I., et al., "Minimally Invasive Glucose Sensor and Insulin Delivery System," MIT Home Automation and Healthcare Consortium, Mar. 31, 2000, Progress Report No. 25, 17 pages.

International Preliminary Examination Report for Application No. PCT/US2006/014127 dated Oct. 14, 2008, 5 pages.

International Search Report and Written Opinion for Application No. PCT/US2006/014127, dated Jul. 5, 2007, 7 pages.

Ishikawa M., et al., "Initial Evaluation of a 290-Mm Diameter Subcutaneous Glucose Sensor: Glucose Monitoring With a Biocompatible, Flexible-Wire, Enzyme-Based Amperometric Microsensor in Diabetic and Nondiabetic Humans," Journal of Diabetes and Its Complications, vol. 12, 1998, pp. 295-301.

Jensen M.B., et al., "Fast Wave Forms for Pulsed Electrochemical Detection of Glucose by Incorporation of Reductive Desorption of Oxidation Products," Analytical Chemistry, vol. 69 (9), May 1997, pp. 1776-1781.

Jeutter D.C., "A Transcutaneous Implanted Battery Recharging and Biotelemeter Power Switching System," IEEE Transactions on Biomedical Engineering, vol. BME-29 (5), May 1982, pp. 314-321.

Johnson K.W., et al., "In Vivo Evaluation of an Electroenzymatic Glucose Sensor Implanted in Subcutaneous Tissue," Biosensors and Bioelectronics, 1992, vol. 7, pp. 709-714.

Jovanovic L.M.D., "The Role of Continuous Glucose Monitoring in Gestational Diabetes Mellitus," Diabetes Technology and Therapeutics, vol. 2 (1), 2000, pp. S67-S71.

Kang S.K., et al., "In Vitro and Short-Term in Vivo Characteristics of a Kel-F Thin Film Modified Glucose Sensor," Analytical Sciences, vol. 19, Nov. 2003, pp. 1481-1486.

Kargol M., et al., "Studies on the Structural Properties of Porous Membranes: Measurement of Linear Dimensions of Solutes," Biophysical Chemistry, 2001, vol. 91, pp. 263-271.

Karube I., et al., "Microbiosensors for Acetylcholine and Glucose," Biosensors & Bioelectronics, 1993, vol. 8, pp. 219-228.

Kaufman F.R., et al., "A Pilot Study of the Continuous Glucose Monitoring System," Diabetes Care, vol. 24 (12), Dec. 2001, pp. 2030-2034.

Kaufman F.R., "Role of the Continuous Glucose Monitoring System in Pediatric Patients," Diabetes Technology and Therapeutics, vol. 2 (1), 2000, S49-S52.

Kerner, et al., "A Potentially Implantable Enzyme Electrode for Amperometric Measurement of Glucose," Hormone and Metabolic Research Supplement, vol. 20, 1988, pp. 8-13.

Kerner W., et al., "The Function of a Hydrogen Peroxide-Detecting Electroenzymatic Glucose Electrode is Markedly Impaired in Human Sub-Cutaneous Tissue and Plasma," Biosensors and Bioelectronics, vol. 8, 1993, pp. 473-482.

Kiechle F.L., "The Impact of Continuous Glucose Monitoring on Hospital Point-of-Care Testing Programs," Diabetes Technology and Therapeutics, vol. 3 (4), 2001, pp. 647-650.

Klueh U., et al., "Inflammation and Glucose Sensors: Use of Dexamethasone to Extend Glucose Sensor Function and Life Span in Vivo," Journal of Diabetes Science and Technology, vol. 1 (4), Jul. 2007, pp. 496-504.

Klueh U., et al., "Use of Vascular Endothelial Cell Growth Factor Gene Transfer to Enhance Implantable Sensor Function in Vivo," Biosensor Function and VEGF-Gene Transfer, vol. 67 (4), 2003, pp. 1072-1086.

Kondo T., et al., "A Miniature Glucose Sensor, Implantable in the Blood Stream," Diabetes Care, vol. 5 (3), May-Jun. 1982, 218-221.

Koschinsky T., et al., "Sensors for Glucose Monitoring: Technical and Clinical Aspects," Diabetes Metabolism Research and Reviews, vol. 17, 2001, pp. 113-123.

Koschinsky T., et al., "New Approach to Technical and Clinical Evaluation of Devices for Self-Monitoring of Blood Glucose," Diabetes Care, vol. 11 (8), Sep. 1988, pp. 619-629.

Koudelka M., et al., "In Vivo Response of Microfabricated Glucose Sensors to Glycemia Changes in Normal Rats," Biomed. Biochim. Acta, vol. 48 (11/12), Nov.-Dec. 1989, pp. 953-956.

Koudelka M., et al., "In-Vivo Behaviour of Hypodermically Implanted Microfabricated Glucose Sensors," Biosensors and Bioelectronics, vol. 6, 1991, pp. 31-36.

Kraver., et al., "A Mixed-Signal Sensor Interface Microinstrument," Sensors and Actuators A, Physical 2001, vol. 91, pp. 266-277.

Kruger D., et al., "Psychological Motivation and Patient Education: A Role for Continuous Glucose Monitoring," Diabetes Technology and Therapeutics, vol. 2 (1), 2000, pp. S93-S97.

Kunzler J., et al.,"Hydrogels based on Hydrophilic Side Chain Siloxanes," Poly Mat Sci and Eng, 1993, vol. 69, pp. 226-227.

Kunzler J F., et al., "Contact Lens Materials," Chemistry & Industry, Aug. 21, 1995, pp. 651-655.

Kurtz T.W., et al., "Recommendations for Blood Pressure Measurement in Humans and Experimental Animals, Part 2: Blood Pressure Measurement in Experimental Animals: A Statement for Professionals From the Subcommittee of Professional and Public Education of the American Heart Association Council on High Blood Pressure Research," Hypertension, Feb. 2005, vol. 45, pp. 299-310.

Lee E., et al., "Effects of Pore Size, Void Volume, and Pore Connectivity on Tissue Responses to Porous Silicone Implants," Society for Biomaterials, 25th Annual Meeting, 1999, p. 171.

Lerner., et al., "An Implantable Electrochemical Glucose Sensor," Ann. N. Y. Acad. Sci., vol. 428, May 1984, pp. 263-278.

Lewandowski J.J., et al., "Evaluation of a Miniature Blood Glucose Sensor," Transactions—American Society for Artificial Internal Organs, vol. 34, 1988, pp. 255-258.

Leypoldt J.K., et al., "Model of a Two-Substrate Enzyme Electrode for Glucose," Analytical Chemistry, vol. 56, 1984, pp. 2896-2904.

Linke B., et al., "Amperometric Biosensor for In Vivo Glucose Sensing Based on Glucose Oxidase Immobilized in a Redox Hydrogel," Biosensors and Bioelectronics, vol. 9, 1994, pp. 151-158.

Loffler P., et al., "Separation and Determination of Traces of Ammonia in Air by Means of Chromatomembrane Cells," Fresenius Journal of Analytical Chemistry, 1995, vol. 352, pp. 613-614.

Luong J.H.T., et al., "Solubilization of Multiwall Carbon Nanotubes by 3-Aminopropyltriethoxysilane towards the Fabrication of Electrochemical Biosensors with Promoted Electron Transfer," Electroanalysis, vol. 16 (1-2), 2004, pp. 132-139.

Lyman D J., "Polyurethanes. I. The Solution Polymerization of Diisocyanates with Ethylene Glycol," Journal of Polymer Science, 1960, vol. XLV, pp. 49-59.

Madaras M B., et al., "Microfabricated Amperometric Creatine and Creatinine Biosensors," Analytica Chimica Acta, 1996, vol. 319, pp. 335-345.

Makale M.T., et al., "Tissue Window Chamber System for Validation of Implanted Oxygen Sensors," American Journal of Physiology—Heart and Circulatory Physiology, vol. 284, Feb. 21, 2003, pp. 1-27.

(56) References Cited

OTHER PUBLICATIONS

Malin S.F., et al., "Noninvasive Prediction of Glucose by Near-Infrared Diffuse Reflectance Spectroscopy," Clinical Chemistry, vol. 45 (9), 1999, pp. 1651-1658.
March W.F., "Dealing with the Delay," Diabetes Technology & Therapeutics, vol. 4 (1), 2002, pp. 49-50.
Mastrototaro J.J., et al., "An Electroenzymatic Glucose Sensor Fabricated on a Flexible Substrate," Sensors and Actuators B, vol. 5, 1991, pp. 139-144.
Mastrototaro J.J., et al., "Reproducibility of the Continuous Glucose Monitoring System Matches Previous Reports and the Intended Use of the Product," Diabetes Care, vol. 26 (1), Jan. 2003, pp. 256-257.
Mastrototaro J.J., "The MiniMed Continuous Glucose Monitoring System," Diabetes Technology & Therapeutics, vol. 2, Supplement 1, 2000, pp. S13-S18.
Matsumoto T., et al., "A long-Term Lifetime Amperometric Glucose Sensor with a Perfluorocarbon Polymer Coating," Biosensors & Bioelectronics, vol. 16, 2001, pp. 271-276.
Matsumoto T., et al., "A Micro-Planar Amperometric Glucose Sensor Unsusceptible to Interference Species," Sensors and Actuators B, 49, 1998, pp. 68-72.
Matthews D.R., et al., "An Amperometric Needle-Type Glucose Sensor Testing in Rats and Man," Diabetic Medicine, vol. 5, 1988, pp. 248-252.
McCartney L.J., et al., "Near-Infrared Fluorescence Lifetime Assay for Serum Glucose Based on Allophycocyanin-Labeled Concanavalin A," Analytical Biochemistry, vol. 292, 2001, pp. 216-221.
McGrath M.J., et al., "The Use of Differential Measurements with a Glucose Biosensor for Interference Compensation During Glucose Determinations by Flow Injection Analysis," Biosens Bioelectron, vol. 10, 1995, pp. 937-943.
McKean B.D., et al., "A Telemetry Instrumentation System for Chronically Implanted Glucose and Oxygen Sensors," IEEE Transactions on Biomedical Engineering, vol. 35 (7), Jul. 1988, pp. 526-532.
Memoli A., et al., "A Comparison between Different Immobilised Glucoseoxidase-Based Electrodes," Journal of Pharmaceutical and Biomedical Analysis, vol. 29, 2002, pp. 1045-1052.
Merriam-Webster Online Dictionary, Definition of "Nominal" retrieved from http://www.merriam-webster.com/dictionary/nominal, Apr. 23, 2007, 1 page.
Meyerhoff C., et al., "On Line Continuous Monitoring of Subcutaneous Tissue Glucose in Men by Combining Portable Glucosensor With Microdialysis," Diabetologia, vol. 35 (11), 1992, pp. 1087-1092.
Miller K.M., et al., "Generation of IL-1 like Activity in Response to Biomedical Polymer Implants: a Comparison of in Vitro and in Vivo Models," Journal of Biomedical Materials Research, vol. 23(9), 1989, pp. 1007-1026.
Miller K.M., et al., "Human monocyte/macrophage activation and interleukin 1 generation by biomedical polymers," Journal of Biomedical Materials Research, vol. 22 (8), 1988, pp. 713-731.
Miller K.M., et al., "In Vitro Stimulation of Fibroblast Activity by Factors Generated from Human Monocytes Activated by Biomedical Polymers," Journal of Biomedical Materials Research, vol. 23(8), 1989, pp. 911-930.
Moatti-Sirat D., et al., "Evaluating In Vitro and In Vivo the Interference of Ascorbate and Acetaminophen on Glucose Detection by a Needle-Type Glucose Sensor," Biosensors and Bioelectronics, vol. 7, 1992, pp. 345-352.
Moatti-Sirat., et al., "Towards Continuous Glucose Monitoring: In Vivo Evaluation of a Miniaturized Glucose Sensor Implanted for Several Days in Rat Subcutaneous Tissue," Diabetologia, vol. 35, 1992, pp. 224-230.
Moussy F., et al., "Biomaterials community examines biosensor biocompatibility," Diabetes Technology & Therapeutics, vol. 2(3), 2000, pp. 473-477.
Mowery K.A., et al., "Preparation and Characterization by Hydrophobic Polymeric Films that are Thromboresistant via Nitric Oxide Release," Biomaterials, vol. 21, 2000, pp. 9-21.
Muslu, "Trickling Filter Performance," Applied Biochemistry and Biotechnology, vol. 37, 1992, pp. 211-224.
Myler S., et al., "Ultra-Thin-Polysiloxane-Film-Composite Membranes for the Optimisation of Amperometric Oxidase Enzyme Electrodes," Biosensors & Bioelectronics, vol. 17, 2002, pp. 35-43.
Nakayama Y., et al., "Surface Fixation of Hydrogels: Heparin and Glucose Oxidase Hydrogelated Surfaces" ASAIO Journal, 1992, pp. M421-M424.
Nam Y.S., et al., "A Novel Fabrication Method of Macroporous Biodegradable Polymer Scaffolds Using Gas Foaming Salt as a Porogen Additive," J Biomed Mater Res, 2000, vol. 53, pp. 1-7.
Office Action for U.S. Appl. No. 10/695,636, dated Dec. 6, 2005, 8 pages.
Office Action for U.S. Appl. No. 10/695,636, dated Mar. 14, 2007, 5 pages.
Office Action for U.S. Appl. No. 10/695,636, dated May 22, 2006, 5 pages.
Office Action for U.S. Appl. No. 10/896,639, dated Apr. 6, 2006, 6 pages.
Office Action for U.S. Appl. No. 10/896,639, dated Apr. 11, 2007, 7 pages.
Office Action for U.S. Appl. No. 10/896,639, dated Aug. 22, 2006, 7 pages.
Office Action for U.S. Appl. No. 10/896,639, dated Oct. 5, 2007, 9 pages.
Office Action for U.S. Appl. No. 10/896,639, dated Sep. 23, 2005, 9 pages.
Office Action for U.S. Appl. No. 11/675,063, dated Dec. 3, 2008, 15 pages.
Ohara T.J., et al., ""Wired" Enzyme Electrodes for Amperometric Determination of Glucose or Lactate in the Presence of Interfering Substances," Anal Chem, vol. 66, 1994, pp. 2451-2457.
Okuda, et al., "Mutarotase Effect on Micro Determinations of D-Glucose and its Anomers with β D-Glucose Oxidase," Anal Biochem, vol. 43 (1), 1971, pp. 312-315.
Palmisano F., et al., "Simultaneous Monitoring of Glucose and Lactate by an Interference and Cross-Talk Free Dual Electrode Amperometric Biosensor Based on Electropolymerized Thin Films," Biosensors & Bioelectronics, vol. 15, 2000, pp. 531-539.
Panetti T.S., "Differential Effects of Sphingosine 1-Phosphate and Lysophosphatidic Acid on Endothelial Cells," Biochimica et Biophysica Acta, vol. 1582, 2002, pp. 190-196.
Patel H., et al., "Amperometric Glucose Sensors Based on Ferrocene Containing Polymeric Electron Transfer Systems—A Preliminary Report," Biosensors & Bioelectronics, vol. 18, 2003, pp. 1073-1076.
Pegoraro M., et al., "Gas Transport Properties of Siloxane Polyurethanes," Journal of Applied Polymer Science, vol. 57, 1995, pp. 421-429.
Pfeiffer E.F., et al., "On Line Continuous Monitoring of Subcutaneous Tissue Glucose is Feasible by Combining Portable Glucosensor with Microdialysis," Horm. Metab. Res., vol. 25, 1993, pp. 121-124.
Pfeiffer E.F., "The Glucose Sensor: The Missing Link in Diabetes Therapy," Horm Metab Res Suppl., vol. 24, 1990, pp. 154-164.
Phillips R.E., et al., "Biomedical Applications of Polyurethanes: Implications of Failure Mechanisms," Journal of Biomedical application, vol. 3, Oct. 1988, pp. 206-227.
Pichert J.W., et al., "Issues for the Coming Age of Continuous Glucose Monitoring," Diabetes Educator, vol. 26 (6), Nov.-Dec. 2000, pp. 969-980.
Pickup J.C., et al., "Implantable Glucose Sensors: Choosing the Appropriate Sensor Strategy," Biosensors, vol. 3, (1987/1988), pp. 335-346.
Pickup J.C., et al., "In Vivo Molecular Sensing in Diabetes Mellitus: An Implantable Glucose Sensor with Direct Electron Transfer," Diabetologia, vol. 32, 1989, pp. 213-217.
Pickup J.C., et al., "Potentially-Implantable, Amperometric Glucose Sensors with Mediated Electron Transfer: Improving the Operating Stability," Biosensors, vol. 4, 1989, pp. 109-119.
Pickup J.C., et al., "Progress Towards in Vivo Glucose Sensing with a Ferrocene-Mediated Amperometric Enzyme Electrode," Horm Metab Res Suppl, vol. 20, 1988, pp. 34-36.

(56) References Cited

OTHER PUBLICATIONS

Pineda L.M., et al., "Bone Regeneration with Resorbable Polymeric Membranes. III. Effect of Poly(L-lactide) Membrane Pore Size on the Bone Healing Process in Large Defects," Journal of Biomedical Materials Research, vol. 31, 1996, pp. 385-394.
Pishko M.V., et al., "Amperometric Glucose Microelectrodes Prepared Through Immobilization of Glucose Oxidase in Redox Hydrogels," Analytical Chemistry, vol. 63 (20), 1991, pp. 2268-2272.
Pitzer K.R., et al., "Detection of Hypogylcemia with the Glucowatch Biographer," Diabetes Care, vol. 24 (5), 2001, pp. 881-885.
Poitout V., et al., "A Glucose Monitoring System for on Line Estimation in Man of Blood Glucose Concentration Using a Miniaturized Glucose Sensor Implanted in the Subcutaneous Tissue and a Wearable Control Unit," Diabetologia, vol. 36, 1993, pp. 658-663.
Poitout V., et al., "Development of a Glucose Sensor for Glucose Monitoring in Man: The Disposable Implant Concept," Clinical Materials, vol. 15, 1994, pp. 241-246.
Postlethwaite T.A., et al., "Interdigitated Array Electrode as an Alternative to the Rotated Ring-Disk Electrode for Determination of the Reaction Products of Dioxygen Reduction," Analytical Chemistry, vol. 68 (17), Sep. 1996, pp. 2951-2958.
Quinn C.A.P., et al., "Biocompatible, Glucose-Permeable Hydrogel for In situ Coating of Implantable Biosensors," Biomaterials, vol. 18 (24), 1997, pp. 1665-1670.
Quinn C.P., et al., "Kinetics of Glucose Delivery to Subcutaneous Tissue in Rats Measured with 0.3-mm Amperometric Microsensors," The American Physiological Society, vol. 269, 1995, pp. E155-E161.
Ratner B.D., "Reducing Capsular Thickness and Enhancing Angiogenesis around Implant Drug Release Systems," Journal of Controlled Release, vol. 78, 2002, pp. 211-218.
Reach G., "A Method for Evaluating in vivo the Functional Characteristics of Glucose Sensors," Biosensors, vol. 2, 1986, pp. 211-220.
Reach G., "Which Threshold to Detect Hypoglycemia? Value of Receiver-Operator Curve Analysis to Find a Compromise Between Sensitivity and Specificity," Diabetes Care, vol. 24 (5), May 2001, pp. 803-804.
Rebrin K., et al., "Automated Feedback Control of Subcutaneous Glucose Concentration in Diabetic Dogs," Diabetologia, vol. 32, 1989, pp. 573-576.
Rebrin K., et al., "Subcutaenous Glucose Monitoring by Means of Electrochemical Sensors: Fiction or Reality?," Journal of Biomedical Engineering, vol. 14, Jan. 1992, pp. 33-40.
Rhodes R.K., et al., "Prediction of Pocket-Portable and Implantable Glucose Enzyme Electrode Performance from Combined Species Permeability and Digital Simulation Analysis," Analytical Chemistry, vol. 66 (9), May 1, 1994, pp. 1520-1529.
Sachlos E., et al., "Making Tissue Engineering Scaffolds Work Review on the Application of Sold Freeform Fabrication Technology to the Production of Tissue Engineering Scaffolds," European Cells and Materials, vol. 5, 2003, pp. 29-40.
Sakakida M., et al., "Development of Ferrocene-Mediated Needle-Type Glucose Sensor as a Measure of True Subcutaneous Tissue Glucose Concentrations," Artif. Organs Today, vol. 2 (2), 1992, pp. 145-158.
Sakakida M., et al., "Ferrocene-Mediated Needle Type Glucose Sensor Covered with Newly Designed Biocompatible Membrane," Sensors and Actuators B, vol. 13-14, 1993, pp. 319-322.
Salardi S., et al., "The Glucose Area Under the Profiles Obtained with Continuous Glucose Monitoring System Relationships with HbA1C in Pediatric Type 1 Diabetic Patients," Diabetes Care, vol. 25 (10), Oct. 2002, pp. 1840-1844.
Sanders E., et al., "Fibrous Encapsulation of Single Polymer Microfibers Depends on their Vertical Dimension in Subcutaneous Tissue Polymer Microfibers," Journal of Biomedical Material Research, vol. 67A, 2003, pp. 1181-1187.

Sansen W., et al., "A Smart Sensor for the Voltammetric Measurement of Oxygen or Glucose Concentrations," Sensors and Actuators B1, 1990, pp. 298-302.
Sansen W., et al., "Glucose Sensor with Telemetry System," In Implantable Sensors for Closed Loop Prosthetic Systems edited by Ko W.H, Chapter 12, 1985, pp. 167-175.
Schmidt F.J., et al., "Glucose Concentration in Subcutaneous Extracellular Space," Diabetes Care, vol. 16 (5), May 1993, pp. 695-700.
Schoemaker M., et al., "The SCGMI System: Subcutaneous Continuous Glucose Monitoring Based on Microdialysis Technique," Diabetes Technology & Therapeutics, vol. 5 (4), 2003, pp. 599-608.
Schoonen A.J.M., et al., "Development of a Potentially Wearable Glucose Sensor for Patients with Diabetes Mellitus: Design and In-vitro Evaluation," Biosensors & Bioelectronics, vol. 5, 1990, pp. 37-46.
Schuler, et al., "Modified Gas-Permeable Silicone Rubber Membranes for Covalent Immobilisation of Enzymes and their Use in Biosensor Development," Analyst, 1999, vol. 124, pp. 1181-1184.
Selam J.L., "Management of Diabetes with Glucose Sensors and Implantable Insulin Pumps," From the Dream of the 60s to the Realities of the 90s, ASAIO Journal 1997, vol. 43, pp. 137-141.
Service R.F., "Can Sensors Make a Home in the Body?," Science, Materials Science: Soft Surface, vol. 297, Aug. 9, 2002, pp. 962-963.
Shaw G.W., et al., "In Vitro Testing of a Simply Constructed, Highly Stable Glucose Sensor Suitable for Implantation in Diabetic Patients," Biosensors & Bioelectronics, vol. 6, 1991, pp. 401-406.
Shichiri M., et al., "Glycaemic Control in Pancreatectomized Dogs with a Wearable Artificial Endocrine Pancreas," Diabetologia, vol. 24, 1983, pp. 179-184.
Shichiri M., et al., "Membrane Design for Extending the Long-Life of an Implantable Glucose Sensor," Diabetes Nutrition & Metabolism, vol. 2 (4), 1989, pp. 309-313.
Shichiri M., et al., "Needle Type Glucose Sensor for Wearable Artificial Endocrine Pancreas," in Implantable Sensors for Closed-Loop Prosthetic Systems edited by Ko W.H, Chapter 15, 1985, pp. 197-210.
Shichiri M., et al., "Wearable Artificial Endocrine Pancreas with Needle-Type Glucose Sensor," Preliminary Communication, Lancet, vol. 2, Nov. 20, 1982, pp. 1129-1131.
Shults M.C., et al., "A Telemetry-Instrumentation System for Monitoring Multiple Subcutaneously Implanted Glucose Sensors," IEEE Transactions on Biomedical Engineering, vol. 41 (10), Oct. 1994, pp. 937-942.
Sieminski, et al., "Biomaterial-Microvasculature Interactions," Biomaterials, 2000, vol. 21, pp. 2233-2241.
Sigma-Aldrich Corp., "Cellulose Acetate," Product Description, Product No. 419028, St. Louis, MO, 2005, 1 page.
Sigma-Aldrich Corp "Nafion® 117 Solution Product Description, Product No. 70160," retrieved from https//:www.sigmaaldrich.com/cgi-bin/hsrun/Suite7/Suite/HAHTpage/Suite.HsExternalProd on Apr. 7, 2005, 1 page.
Skyler J.S., "The Economic Burden of Diabetes and the Benefits of Improved Glycemic Control: The Potential Role of a Continuous Glucose Monitoring System," Diabetes Technology & Therapeutics, vol. 2, Supplement 1, 2000, pp. S7-S12.
Sokol L., et al., "Immobilized-Enzyme Rate-Determination Method for Glucose Analysis," Clinical Chemistry, vol. 26 (1), 1980, pp. 89-92.
Sriyudthsak M., et al., "Enzyme-Epoxy Membrane Based Glucose Analyzing System and Medical Applications," Biosensors & Bioelectronics, vol. 11 (8), 1996, pp. 735-742.
Steil G.M., et al., "Determination of Plasma Glucose During Rapid Glucose Excursions with a Subcutaneous Glucose Sensor," Diabetes Technology & Therapeutics, vol. 5 (1), 2003, pp. 27-31.
Sternberg, et al., "Covalent Enzyme Coupling on Cellulose Acetate Membranes for Glucose Sensor Development," Anal Chem, Dec. 1988, vol. 60(24), pp. 2781-2786.
Sternberg R., et al., "Study and Development of Multilayer Needle-type Enzyme Based Glucose Microsensors," Biosensors, vol. 4, 1988, pp. 27-40.
Stokes, "Polyether Polyurethanes: Biostable or Not," Journal of Biomaterials Applications, Oct. 1988, vol. 3, pp. 228-259.

(56) References Cited

OTHER PUBLICATIONS

Suh, et al., "Behavior of Fibroblasts on a Porous Hyaluronic Acid Incorporated Collagen Matrix," Yonsei Medical Journal, 2002, vol. 43 (2), pp. 193-202.
Sumino T., et al., "Preliminary Study of Continuous Glucose Monitoring with a Microdialysis Technique," Proceedings of the 20th Annual International Conference of the IEEE Engineering in Medicine and Biology Society, vol. 20 (4), 1998, pp. 1775-1778.
Takegami S., et al., "Pervaporation of Ethanol/Water Mixtures Using Novel Hydrophobic Membranes Containing Polydimethylsiloxane," Journal of Membrane Science, vol. 75, 1992, pp. 93-105.
Tanenberg R.J., et al., "Continuous Glucose Monitoring System: A New Approach to the Diagnosis of Diabetic Gastroparesis," Diabetes Technology & Therapeutics, vol. 2, Supplement 1, 2000, pp. S73-S80.
Tang, et al., "Inflammatory Responses to Biomaterials," Am J Clin Pathol, 1995, vol. 103, pp. 466-471.
Tang, et al., "Mast Cells Mediate Acute Inflammatory Responses to Implanted Biomaterials," Proceedings of the National Academy of Sciences of the USA, 1998, vol. 95, pp. 8841-8846.
Tang, et al., "Molecular Determinants of Acute Inflammatory Responses to Biomaterials," J Clin Invest, 1996, vol. 97, pp. 1329-1334.
Thome-Duret V., et al., "Continuous Glucose Monitoring in the Free-Moving Rat," Metabolism, vol. 47 (7), Jul. 1998, pp. 799-803.
Thome-Duret V., et al., "Modification of the Sensitivity of Glucose Sensor Implanted into Subcutaneous Tissue," Diabetes & Metabolism, vol. 22, 1996, pp. 174-178.
Thompson M., et al., "In Vivo Probes: Problems and Perspectives," Clinical Biochemistry, vol. 19 (5), Oct. 1986, pp. 255-261.
Tibell, et al., "Survival of Macroencapsulated Allogeneic Parathyroid Tissue One Year after Transplantation in Nonimmunosuppressed Humans," Cell Transplantation, 2001, vol. 10, pp. 591-599.
Tierney M.J., et al., "Effect of Acetaminophen on the Accuracy of Glucose Measurements Obtained with the GlucoWatch Biographer," Diabetes Technology & Therapeutics, vol. 2 (2), 2000, pp. 199-207.
Tierney M.J., et al., "The Gluco Watch® Biographer: A Frequent, Automatic and Noninvasive Glucose Monitor," Annals of Medicine, vol. 32, 2000, pp. 632-641.
Trecroci D., "A Glimpse into the Future-Continuous Monitoring of Glucose with a Microfiber," Diabetes Interview, Jul. 2002, pp. 42-43.
TSE P.S.H., et al., "Time-Dependent Inactivation of Immobilized Glucose Oxidase and Catalase," Biotechnology & Bioengineering, vol. 29, 1987, pp. 705-713.
Turner A.P.F., "Amperometric Biosensor based on Mediator-Modified Electrodes," Methods in Enzymology, 1988, vol. 137, pp. 90-103.
Turner A.P.F., et al., "Diabetes Mellitus: Biosensors for Research and Management," Biosensors, vol. 1, 1985, pp. 85-115.
Unger J., et al., "Glucose Control in the Hospitalized Patient," Emergency Medicine, vol. 36 (9), 2004, pp. 12-18.
Updike S.J., et al., "A Subcutaneous Glucose Sensor with Improved Longevity, Dynamic Range, and Stability of Calibration," Diabetes Care, vol. 23 (2), Feb. 2000, pp. 208-214.
Updike S.J., et al., "Enzymatic Glucose Sensor: Improved Long-Term Performance in Vitro and In Vivo," ASAIO Journal, vol. 40 (2), Apr.-Jun. 1994, pp. 157-163.
Updike S.J., et al., "Laboratory Evaluation of New Reusable Blood Glucose Sensor," Diabetes Care, vol. 11 (10), Nov.-Dec. 1988, pp. 801-807.
Updike S.J., et al., "Principles of Long-Term Fully Implanted Sensors with Emphasis on Radiotelemetric Monitoring of Blood Glucose Form Inside a Subcutaneous Foreign Body Capsule (FBC)," Edited by Fraser D M, Biosensors in the Body: Continuous in vivo Monitoring, John Wiley & Sons Ltd., New York, 1997, Chapter 4, pp. 117-137.
Updike S.J., et al., "The Enzyme Electrode," Nature, vol. 214, Jun. 3, 1967, pp. 986-988.

Utah Medical Products Inc., "Deltran—Disposable Blood Pressure Tranducers," Product Specifications, 2003-2006, 6 pages.
Vadgama P., "Enzyme Electrodes as Practical Biosensors," Journal of Medical Engineering & Technology, vol. 5 (6), Nov. 1981, pp. 293-298.
Van Den Berghe, "Tight Blood Glucose Control with Insulin in "Real-Life" Intensive Care," Mayo Clinic Proceedings, vol. 79 (8), Aug. 2004, pp. 977-978.
Velho G., et al., "In Vitro and In Vivo Stability of Electrode Potentials in Needle-Type Glucose Sensors," Influence of Needle Material, Diabetes, vol. 38, Feb. 1989, pp. 164-171.
Wade L.G., "Reactions of Aromatic Compounds," Organic Chemistry, Chapter 17, 5th edition, 2003, pp. 762-763.
Wagner, et al., "Continuous Amperometric Monitoring of Glucose in a Brittle Diabetic Chimpanzee with a Miniature Subcutaneous Electrode," Proc. Natl. Acad. Sci. USA, vol. 95, May 1998, pp. 6379-6382.
Wang J., et al., "Highly Selective Membrane-Free Mediator-Free Glucose Biosensor," Analytical Chemistry, vol. 66 (21), Nov. 1, 1994, pp. 3600-3603.
Wang X., et al., "Improved Ruggedness for Membrane-Based Amperometric Sensors using a Pulsed Amperometric Method," Analytical Chemistry, vol. 69 (21), Nov. 1, 1997, pp. 4482-4489.
Ward W.K., et al., "A New Amperometric Glucose Microsensor: In Vitro and Short-Term In Vivo Evaluation," Biosensors & Bioelectronics, vol. 17, 2002, pp. 181-189.
Ward W.K., et al., "Rise in Background Current Over Time in a Subcutaneous Glucose Sensor in the Rabbit," Relevance to Calibration and Accuracy, Biosensors & Bioelectronics, vol. 15, 2000, pp. 53-61.
Ward W.K., et al., "Understanding Spontaneous Output Fluctuations of an Amperometric Glucose Sensor: Effect of Inhalation Anesthesia and Use of a Nonenzyme Containing Electrode," ASAIO Journal, 2000, pp. 540-546.
Wientjes K.J.C., "Development of a Glucose Sensor for Diabetic Patients," (Ph.D. Thesis), 2000, 212 pages.
Wilkins E., et al., "Glucose Monitoring: State of the Art and Future Possibilities," Med. Eng. Phys., vol. 18 (4), 1996, pp. 273-288.
Wilkins E., et al., "Integrated Implantable Device for Long-Term Glucose Monitoring," Biosensors & Bioelectronics, vol. 10, 1995, pp. 485-494.
Wilkins E.S., et al., "The Coated Wire Electrode Glucose Sensor," Horm Metab Res Suppl., vol. 20, 1988, pp. 50-55.
Wilson G.S., et al., "Enzyme-Based Biosensors for In Vivo Measurements," Chem. Rev., vol. 100, 2000, pp. 2693-2704.
Wilson G.S., et al., "Progress Toward the Development of an Implantable Sensor for Glucose," Clinical Chemistry, vol. 38 (9), 1992, pp. 1613-1617.
Wood W D., et al., "Hermetic Sealing with Epoxy," Pave Technology-Mechanical Engineering, Mar. 1990, 3 pages.
Wu H., et al., "In Situ Electrochemical Oxygen Generation with an Immunoisolation Device," Annals New York Academy of Sciences, vol. 875, 1999, pp. 105-125.
Yamasaki Y., et al., "Direct Measurement of Whole Blood Glucose by a Needle-Type Sensor," Clinica Chimica Acta. 93, 1989, pp. 93-98.
Yamasaki Y., "The Development of a Needle-Type Glucose Sensor for Wearable Artificial Endocrine Pancreas," Medical Journal of Osaka University, vol. 35 (1-2), Sep. 1984, pp. 25-34.
Yang Q., et al., "Development of Needle-Type Glucose Sensor with High Selectivity," Science and Actuators B, vol. 46, 1998, pp. 249-256.
Yang S., et al., "A Glucose Biosensor Based on an Oxygen Electrode: In-Vitro Performances in a Model Buffer Solution and in Blood Plasma," Biomedical Instrumentation & Technology, vol. 30 (1), 1996, pp. 55-61.
Zamzow K.L., et al., "Development and Evaluation of a Wearable Blood Glucose Monitor," ASAIO Transactions, vol. 36 (3), 1990, pp. M588-M591.

(56) References Cited

OTHER PUBLICATIONS

Zhang, et al., "Elimination of the Acetaminophen Interference in an Implantable Glucose Sensor," Analytical Chemistry, 1994, vol. 66 (7), pp. 1183-1188.

\* cited by examiner

US 10,791,928 B2

ANALYTE SENSORS HAVING A SIGNAL-TO-NOISE RATIO SUBSTANTIALLY UNAFFECTED BY NON-CONSTANT NOISE

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/599,072, filed Oct. 10, 2019, which is a continuation of U.S. application Ser. No. 16/453,925, filed Jun. 26, 2019, which is a continuation of U.S. application Ser. No. 14/145,404, filed Dec. 31, 2013, now U.S. Pat. No. 10,376,143, which is a continuation of Ser. No. 13/732,848, filed Jan. 2, 2013, now U.S. Pat. No. 9,763,609, which is a continuation of U.S. patent application Ser. No. 11/750,907, filed May 18, 2007, now U.S. Pat. No. 8,364,229. Each of the aforementioned applications is incorporated by reference herein in its entirety, and each is hereby expressly made a part of this specification.

FIELD OF THE INVENTION

The preferred embodiments relate generally to implantable devices, such as analyte sensors, and methods for detecting and/or measuring an analyte in a sample, such as a bodily fluid or tissue, as well as devices and methods for reducing or eliminating noise on a signal detected by the device.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which may cause an array of physiological derangements (for example, kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically comprises uncomfortable finger pricking methods. Due to the lack of comfort and convenience, a diabetic will normally only measure his or her glucose level two to four times per day. Unfortunately, these time intervals are so far spread apart that the diabetic will likely find out too late, sometimes incurring dangerous side effects, of a hyperglycemic or hypoglycemic condition. In fact, it is not only unlikely that a diabetic will take a timely SMBG value, but the diabetic will not know if their blood glucose value is going up (higher) or down (lower) based on conventional methods, inhibiting their ability to make educated insulin therapy decisions.

SUMMARY OF THE INVENTION

In a first aspect, an electrochemical analyte sensor for determining a concentration of an analyte in a host, the sensor configured for insertion into a host, wherein the sensor comprises at least one electrode configured to measure an analyte concentration substantially continuously; and electronics configured to provide a signal measured at the electrode; wherein the signal comprises an analyte-related component and a noise component, wherein the noise component comprises a substantially non-constant non-analyte-related component; and wherein the sensor is configured such that the substantially non-constant non-analyte related component does not substantially contribute to the signal, after sensor break-in, for at least about one day.

In an embodiment of the first aspect, the analyte is glucose.

In an embodiment of the first aspect, the signal contribution due to the non-constant non-analyte-related component is less than about 20% of the signal over a time period of at least about one day.

In an embodiment of the first aspect, the signal contribution due to the non-constant non-analyte-related component is less than about 20% of the signal over a time period of at least about three days.

In an embodiment of the first aspect, the signal contribution due to the non-constant non-analyte-related component is less than about 20% of the signal over a time period of at least about five days.

In an embodiment of the first aspect, the analyte sensor comprises a membrane system disposed over the electrode.

In an embodiment of the first aspect, the membrane system comprises glucose oxidase.

In an embodiment of the first aspect, the membrane system is configured to inactivate at least one non-constant noise-causing electroactive species formed in a metabolic process of the host.

In an embodiment of the first aspect, the non-constant noise-causing electroactive species comprises an electroactive species having a redox potential that substantially overlaps with a redox potential of a measured species indicative of the concentration of the analyte.

In an embodiment of the first aspect, the measured species comprises hydrogen peroxide.

In an embodiment of the first aspect, the noise-causing electroactive species comprises at least one species selected from the group consisting of reactive oxygen species, nitrogen species, and hydrogen peroxide formed in a metabolic process of the host.

In an embodiment of the first aspect, the membrane system is configured to substantially block passage therethrough of at least one non-constant noise-causing electroactive species formed in a metabolic process of the host.

In an embodiment of the first aspect, the membrane system is configured to consume at least one non-constant noise-causing electroactive species formed in a metabolic process of the host.

In an embodiment of the first aspect, at least a portion of the membrane system comprises a torturous diffusion path configured to render inactive, at the electrode, at least one non-constant noise-causing electroactive species formed in a metabolic process of the host.

In an embodiment of the first aspect, the membrane system comprises a Heme compound.

In an embodiment of the first aspect, the membrane system comprises a resistance domain configured to restrict flow of the analyte therethrough.

In an embodiment of the first aspect, the resistance domain comprises a polymer comprising hydrophilic components and hydrophobic components.

In an embodiment of the first aspect, the sensor is configured with electronics to detect the analyte with a sensitivity of from about 1 pA/mg/dl to about 500-pA/mg/dl.

In an embodiment of the first aspect, the signal contribution due to the non-constant non-analyte-related component is less than about 10% of the signal over a time period of at least about one day.

In an embodiment of the first aspect, the signal contribution due to the non-constant non-analyte-related component is less than about 5% of the signal over a time period of at least about one day.

In an embodiment of the first aspect, the signal contribution due to the non-constant non-analyte-related component is less than about 1% of the signal over a time period of at least about one day.

In an embodiment of the first aspect, the electrode comprises a dispersed electroactive surface area.

In an embodiment of the first aspect, the dispersed electroactive surface area comprises a plurality of spaced electroactive surface areas.

In an embodiment of the first aspect, the sensor is configured to measure the concentration of the analyte along a substantial length of an in vivo portion of the sensor.

In an embodiment of the first aspect, the sensor comprises an in vivo portion, wherein an area of the electroactive surface covers at least about 50% the in vivo portion.

In an embodiment of the first aspect, the electrode comprises an electroactive surface, wherein the sensor comprises a discontinuous portion, and wherein the electroactive surface is spaced from the discontinuous portion by a distance substantially farther than a diffusion distance of at least one non-constant noise-causing electroactive species formed in a metabolic process of the host In an embodiment of the first aspect, the in vivo portion of the sensor is tapered.

In an embodiment of the first aspect, the analyte-related component of the signal is at least about 80% of the signal over a time period of at least about one day.

In an embodiment of the first aspect, the analyte sensor comprises a membrane system disposed over the electrode and wherein the membrane system comprises an outer domain comprising a discontinuously hydrophilic surface.

In an embodiment of the first aspect, the outer domain comprises at least about 5 wt. % of a hydrophilic component.

In an embodiment of the first aspect, the hydrophilic component comprises polyethylene glycol.

In an embodiment of the first aspect, the outer domain comprises at least about 10 wt. % of a hydrophilic component.

In an embodiment of the first aspect, the outer domain comprises at least about 20 wt. % of a hydrophilic component.

In an embodiment of the first aspect, the outer domain is configured to control a flux of the analyte therethrough.

In an embodiment of the first aspect, the analyte sensor is configured to detect hydrogen peroxide via diffusion to the electrode, wherein the sensor comprises a membrane system disposed over the electrode, wherein the membrane system comprises an electrode domain adjacent to the electrode, wherein the electrode domain is configured to maintain a layer of water at electrochemically reactive surfaces of the sensor, and wherein the electrode domain comprises an enzyme configured for detecting the analyte.

In an embodiment of the first aspect, the analyte sensor is configured for ambulatory wear.

DETAILED DESCRIPTION OF THE PREFERRED EMBODIMENT

Figure 1:
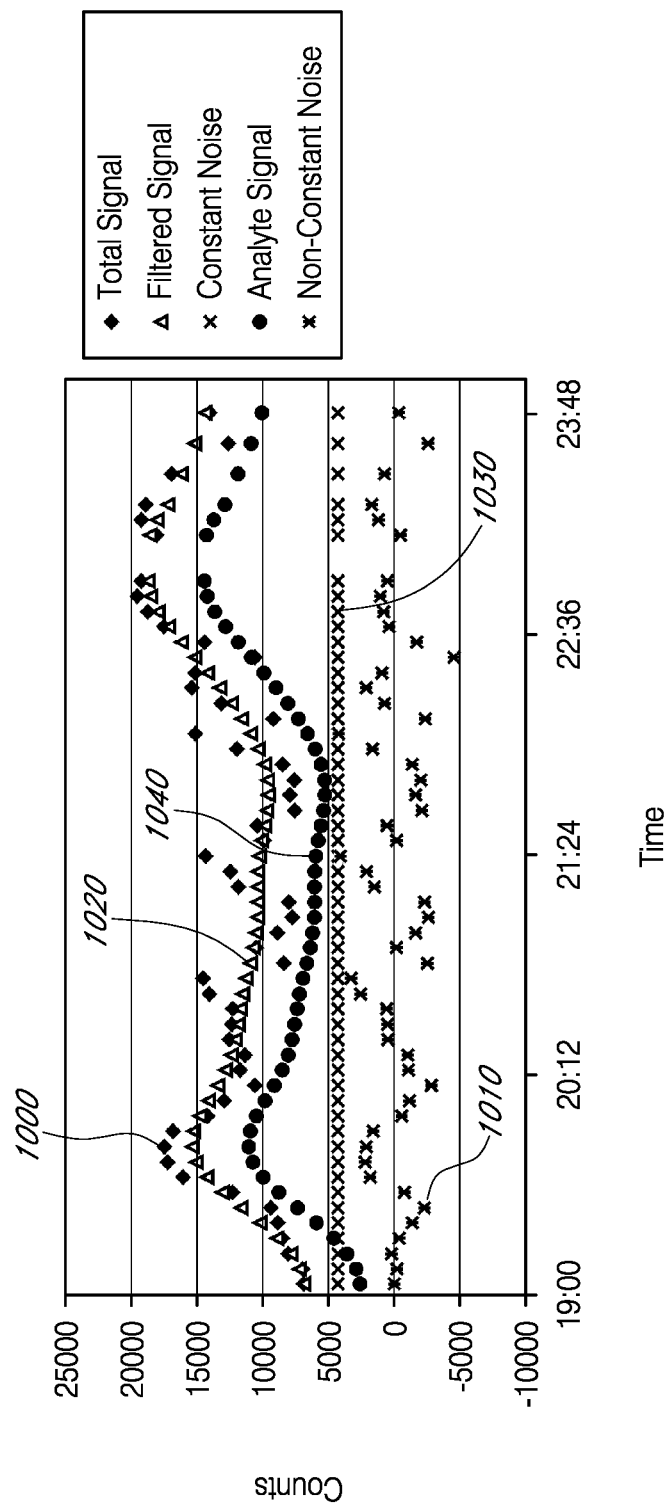
FIG. 1 is a graph illustrating the components of a signal measured by a transcutaneous glucose sensor (after sensor break-in was complete), implanted in a non-diabetic, human volunteer host.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the preferred embodiments.

Definitions

In order to facilitate an understanding of the preferred embodiments, a number of terms are defined below.

The terms "physiological parameters" and "physiological boundaries" as used herein are broad terms, and are to be given their ordinary and customary meaning to a person of ordinary skill in the art (and are not to be limited to a special or customized meaning), and refer without limitation to the parameters obtained from continuous studies of physiological data in humans and/or animals. For example, a maximal sustained rate of change of glucose in humans of about 4 to 6 mg/dL/min and a maximum acceleration of the rate of change of about 0.1 to 0.2 mg/dL/min$^2$ are deemed physiologically feasible limits; values outside of these limits would be considered non-physiological. As another example, the rate of change of glucose is lowest at the maxima and minima of the daily glucose range, which are the areas of greatest risk in patient treatment, thus a physiologically feasible rate of change can be set at the maxima and minima based on continuous studies of glucose data. As a further example, it has been observed that the best solution for the shape of the curve at any point along glucose signal data stream over a certain time period (for example, about 20 to 30 minutes) is a straight line, which can be used to set physiological limits. These terms are broad enough to include physiological parameters for any analyte.

The term "analyte" as used herein is a broad term, and is to be given its ordinary and customary meaning to a person of ordinary skill in the art (and it is not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies A, S, C, and E, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The term "continuous glucose sensor" as used herein is a broad term, and is to be given its ordinary and customary meaning to a person of ordinary skill in the art (and it is not to be limited to a special or customized meaning), and refers without limitation to a device that continuously or continually measures glucose concentration, for example, at time intervals ranging from fractions of a second up to, for example, 1, 2, or 5 minutes, or longer. It should be understood that continuous glucose sensors can continually measure glucose concentration without requiring user initiation and/or interaction for each measurement, such as described with reference to U.S. Pat. No. 6,001,067, for example.

The phrase "continuous glucose sensing" as used herein is a broad term, and is to be given its ordinary and customary meaning to a person of ordinary skill in the art (and it is not to be limited to a special or customized meaning), and refers without limitation to the period in which monitoring of glucose concentration is continuously or continually performed, for example, at time intervals ranging from fractions of a second up to, for example, 1, 2, or 5 minutes, or longer.

The term "biological sample" as used herein is a broad term, and is to be given its ordinary and customary meaning to a person of ordinary skill in the art (and it is not to be limited to a special or customized meaning), and refers without limitation to a sample of a host body, for example, blood, interstitial fluid, spinal fluid, saliva, urine, tears, sweat, tissue, and the like.

The term "host" as used herein is a broad term, and is to be given its ordinary and customary meaning to a person of ordinary skill in the art (and it is not to be limited to a special or customized meaning), and refers without limitation to plants or animals, for example humans.

The term "biointerface membrane" as used herein is a broad term, and is to be given its ordinary and customary meaning to a person of ordinary skill in the art (and it is not to be limited to a special or customized meaning), and refers without limitation to a permeable or semi-permeable membrane that can include one or more domains and is typically constructed of materials of a few microns thickness or more, which can be placed over the sensing region to keep host cells (for example, macrophages) from gaining proximity to, and thereby damaging the membrane system or forming a barrier cell layer and interfering with the transport of glucose across the tissue-device interface.

The term "membrane system" as used herein is a broad term, and is to be given its ordinary and customary meaning to a person of ordinary skill in the art (and it is not to be limited to a special or customized meaning), and refers without limitation to a permeable or semi-permeable membrane that can be comprised of one or more domains and is typically constructed of materials of a few microns thickness or more, which may be permeable to oxygen and are optionally permeable to glucose. In one example, the membrane system comprises an immobilized glucose oxidase enzyme, which enables an electrochemical reaction to occur to measure a concentration of glucose.

The term "domain" as used herein is a broad term, and is to be given its ordinary and customary meaning to a person of ordinary skill in the art (and it is not to be limited to a special or customized meaning), and refers without limitation to regions of a membrane that can be layers, uniform or non-uniform gradients (for example, anisotropic), functional aspects of a material, or provided as portions of the membrane.

The term "copolymer" as used herein is a broad term, and is to be given its ordinary and customary meaning to a person of ordinary skill in the art (and it is not to be limited to a special or customized meaning), and refers without limitation to polymers having two or more different repeat units and includes copolymers, terpolymers, tetrapolymers, and the like.

The term "sensing region" as used herein is a broad term, and is to be given its ordinary and customary meaning to a person of ordinary skill in the art (and it is not to be limited to a special or customized meaning), and refers without limitation to the region of a monitoring device responsible for the detection of a particular analyte. In one embodiment, the sensing region generally comprises a non-conductive body, at least one electrode, a reference electrode and a optionally a counter electrode passing through and secured within the body forming an electrochemically reactive surface at one location on the body and an electronic connection at another location on the body, and a membrane system affixed to the body and covering the electrochemically reactive surface. In another embodiment, the sensing region generally comprises a non-conductive body, a working electrode (anode), a reference electrode (optionally can be remote from the sensing region), an insulator disposed therebetween, and a multi-domain membrane affixed to the body and covering the electrochemically reactive surfaces of the working and optionally reference electrodes.

The term "electrochemically reactive surface" as used herein is a broad term, and is to be given its ordinary and customary meaning to a person of ordinary skill in the art (and it is not to be limited to a special or customized meaning), and refers without limitation to the surface of an electrode where an electrochemical reaction takes place. In one embodiment, a working electrode measures hydrogen peroxide creating a measurable electronic current.

The term "electrochemical cell" as used herein is a broad term, and is to be given its ordinary and customary meaning to a person of ordinary skill in the art (and it is not to be limited to a special or customized meaning), and refers without limitation to a device in which chemical energy is converted to electrical energy. Such a cell typically consists of two or more electrodes held apart from each other and in contact with an electrolyte solution. Connection of the electrodes to a source of direct electric current renders one of them negatively charged and the other positively charged. Positive ions in the electrolyte migrate to the negative electrode (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction.

The term "enzyme" as used herein is a broad term, and is to be given its ordinary and customary meaning to a person of ordinary skill in the art (and it is not to be limited to a special or customized meaning), and refers without limitation to a protein or protein-based molecule that speeds up a chemical reaction occurring in a living thing. Enzymes may act as catalysts for a single reaction, converting a reactant (also called an analyte herein) into a specific product. In one exemplary embodiment of a glucose oxidase-based glucose sensor, an enzyme, glucose oxidase (GOX) is provided to react with glucose (the analyte) and oxygen to form hydrogen peroxide.

The term "co-analyte" as used herein is a broad term, and is to be given its ordinary and customary meaning to a person of ordinary skill in the art (and it is not to be limited to a special or customized meaning), and refers without limitation to a molecule required in an enzymatic reaction to react with the analyte and the enzyme to form the specific product being measured. In one exemplary embodiment of a glucose sensor, an enzyme, glucose oxidase (GOX) is provided to react with glucose and oxygen (the co-analyte) to form hydrogen peroxide.

The term "constant analyte" as used herein is a broad term, and is to be given its ordinary and customary meaning to a person of ordinary skill in the art (and it is not to be limited to a special or customized meaning), and refers without limitation to an analyte that remains relatively constant over a time period, for example over an hour to a day as compared to other variable analytes. For example, in a person with diabetes, oxygen and urea may be relatively constant analytes in particular tissue compartments relative to glucose, which is known to oscillate from about 40 to about 400 mg/dL during a 24-hour cycle. Although analytes such as oxygen and urea are known to oscillate to a lesser degree, for example due to physiological processes in a host, they are substantially constant, relative to glucose, and can be digitally filtered, for example low pass filtered, to minimize or eliminate any relatively low amplitude oscillations. Constant analytes other than oxygen and urea are also contemplated.

The term "proximal" as used herein is a broad term, and is to be given its ordinary and customary meaning to a person of ordinary skill in the art (and it is not to be limited to a special or customized meaning), and refers without limitation to near to a point of reference such as an origin or a point of attachment. For example, in some embodiments of a membrane system that covers an electrochemically reactive surface, the electrolyte domain is located more proximal to the electrochemically reactive surface than the resistance domain.

The term "distal" as used herein is a broad term, and is to be given its ordinary and customary meaning to a person of ordinary skill in the art (and it is not to be limited to a special or customized meaning), and refers without limitation to spaced relatively far from a point of reference, such as an origin or a point of attachment. For example, in some embodiments of a membrane system that covers an electrochemically reactive surface, a resistance domain is located more distal to the electrochemically reactive surfaces than the electrolyte domain.

The terms "computer" or "computer system" as used herein are broad terms, and are to be given their ordinary and customary meanings to a person of ordinary skill in the art (and are not to be limited to a special or customized meaning), and refer without limitation to a machine that can be programmed to manipulate data.

The term "modem" as used herein is a broad term, and is to be given its ordinary and customary meaning to a person of ordinary skill in the art (and it is not to be limited to a special or customized meaning), and refers without limitation to an electronic device for converting between serial data from a computer and an audio signal suitable for transmission over a telecommunications connection to another modem.

The terms "processor module" and "microprocessor" as used herein are broad terms, and are to be given their ordinary and customary meaning to a person of ordinary skill in the art (and they are not to be limited to a special or customized meaning), and refer without limitation to a computer system, state machine, processor, or the like designed to perform arithmetic and logic operations using logic circuitry that responds to and processes the basic instructions that drive a computer.

The term "ROM" as used herein is a broad term, and is to be given its ordinary and customary meaning to a person of ordinary skill in the art (and it is not to be limited to a special or customized meaning), and refers without limitation to read-only memory, which is a type of data storage device manufactured with fixed contents. ROM is broad enough to include EEPROM, for example, which is electrically erasable programmable read-only memory (ROM).

The term "RAM" as used herein is a broad term, and is to be given its ordinary and customary meaning to a person of ordinary skill in the art (and it is not to be limited to a special or customized meaning), and refers without limitation to a data storage device for which the order of access to different locations does not affect the speed of access. RAM is broad enough to include SRAM, for example, which is static random access memory that retains data bits in its memory as long as power is being supplied.

The term "A/D Converter" as used herein is a broad term, and is to be given its ordinary and customary meaning to a person of ordinary skill in the art (and it is not to be limited to a special or customized meaning), and refers without limitation to hardware and/or software that converts analog electrical signals into corresponding digital signals.

The term "RF transceiver" as used herein is a broad term, and is to be given its ordinary and customary meaning to a person of ordinary skill in the art (and it is not to be limited to a special or customized meaning), and refers without limitation to a radio frequency transmitter and/or receiver for transmitting and/or receiving signals.

The terms "raw data stream" and "data stream" as used herein are broad terms, and are to be given their ordinary and customary meaning to a person of ordinary skill in the art (and they are not to be limited to a special or customized meaning), and refer without limitation to an analog or digital signal directly related to the analyte concentration measured by the analyte sensor. In one example, the raw data stream is digital data in "counts" converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer. In some embodiments, raw data includes one or more values (e.g., digital value) representative of the current flow integrated over time (e.g., integrated value), for example, using a charge counting device, or the like.

The term "counts" as used herein is a broad term, and is to be given its ordinary and customary meaning to a person of ordinary skill in the art (and it is not to be limited to a special or customized meaning), and refers without limitation to a unit of measurement of a digital signal. In one example, a raw data stream measured in counts is directly related to a voltage (for example, converted by an A/D converter), which is directly related to current from a working electrode.

The term "electronic circuitry" as used herein is a broad term, and is to be given its ordinary and customary meaning to a person of ordinary skill in the art (and it is not to be limited to a special or customized meaning), and refers without limitation to the components (for example, hardware and/or software) of a device configured to process data. In the case of an analyte sensor, the data includes biological information obtained by a sensor regarding the concentration of the analyte in a biological fluid. U.S. Pat. Nos. 4,757,022, 5,497,772 and 4,787,398, which are hereby incorporated by reference in their entirety, describe suitable electronic circuits that can be utilized with devices of certain embodiments.

The term "potentiostat" as used herein is a broad term, and is to be given its ordinary and customary meaning to a person of ordinary skill in the art (and it is not to be limited to a special or customized meaning), and refers without limitation to an electrical system that applies a potential between the working and reference electrodes of a two- or three-electrode cell at a preset value and measures the current flow through the working electrode. Typically, the potentiostat forces whatever current is necessary to flow between the working and reference or counter electrodes to keep the desired potential, as long as the needed cell voltage and current do not exceed the compliance limits of the potentiostat.

The terms "operably connected" and "operably linked" as used herein are broad terms, and are to be given their ordinary and customary meaning to a person of ordinary skill in the art (and they are not to be limited to a special or customized meaning), and refer without limitation to one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity.

The term "smoothing" and "filtering" as used herein are broad terms, and are to be given their ordinary and customary meaning to a person of ordinary skill in the art (and they are not to be limited to a special or customized meaning), and refer without limitation to modification of a set of data to make it smoother and more continuous and remove or diminish outlying points, for example, by performing a moving average of the raw data stream.

The term "algorithm" as used herein is a broad term, and is to be given its ordinary and customary meaning to a person of ordinary skill in the art (and it is not to be limited to a special or customized meaning), and refers without limitation to the computational processes (for example, programs) involved in transforming information from one state to another, for example using computer processing.

The term "regression" as used herein is a broad term, and is to be given its ordinary and customary meaning to a person of ordinary skill in the art (and it is not to be limited to a special or customized meaning), and refers without limitation to finding a line in which a set of data has a minimal measurement (for example, deviation) from that line. Regression can be linear, non-linear, first order, second order, and so forth. One example of regression is least squares regression.

The term "pulsed amperometric detection" as used herein is a broad term, and is to be given its ordinary and customary meaning to a person of ordinary skill in the art (and it is not to be limited to a special or customized meaning), and refers without limitation to an electrochemical flow cell and a controller, which applies the potentials and monitors current generated by the electrochemical reactions. The cell can include one or multiple working electrodes at different applied potentials. Multiple electrodes can be arranged so that they face the chromatographic flow independently (parallel configuration), or sequentially (series configuration).

The term "calibration" as used herein is a broad term, and is to be given its ordinary and customary meaning to a person of ordinary skill in the art (and it is not to be limited to a special or customized meaning), and refers without limitation to the relationship and/or the process of determining the relationship between the sensor data and corresponding reference data, which may be used to convert sensor data into meaningful values substantially equivalent to the reference. In some embodiments, namely in continuous analyte sensors, calibration may be updated or recalibrated over time if changes in the relationship between the sensor and reference data occur, for example due to changes in sensitivity, baseline, transport, metabolism, or the like.

The term "sensor analyte values" and "sensor data" as used herein are broad terms, and are to be given their ordinary and customary meaning to a person of ordinary skill in the art (and they are not to be limited to a special or customized meaning), and refer without limitation to data received from a continuous analyte sensor, including one or more time-spaced sensor data points.

The term "reference analyte values" and "reference data" as used herein are broad terms, and are to be given their ordinary and customary meaning to a person of ordinary skill in the art (and they are not to be limited to a special or customized meaning), and refer without limitation to data from a reference analyte monitor, such as a blood glucose meter, or the like, including one or more reference data points. In some embodiments, the reference glucose values are obtained from a self-monitored blood glucose (SMBG) test (for example, from a finger or forearm blood test) or an YSI (Yellow Springs Instruments) test, for example.

The term "matched data pairs" as used herein is a broad term, and is to be given its ordinary and customary meaning to a person of ordinary skill in the art (and it is not to be limited to a special or customized meaning), and refers without limitation to reference data (for example, one or more reference analyte data points) matched with substantially time corresponding sensor data (for example, one or more sensor data points).

The terms "interferants" and "interfering species" as used herein are broad terms, and are to be given their ordinary and customary meaning to a person of ordinary skill in the art (and are not to be limited to a special or customized meaning), and refer without limitation to effects and/or species that interfere with the measurement of an analyte of interest in a sensor so as to produce a signal that does not accurately represent the analyte measurement. In one example of an electrochemical sensor, interfering species are compounds with an oxidation potential that overlaps with that of the analyte to be measured, producing a false positive signal. In another example of an electrochemical sensor, interfering species are substantially non-constant compounds (e.g., the concentration of an interfering species fluctuates over time). Interfering species include but are not limited to compounds with electroactive acidic, amine or sulfhydryl groups, urea, lactic acid, phosphates, citrates, peroxides, amino acids, amino acid precursors or breakdown products, nitric oxide (NO), NO-donors, NO-precursors, acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, and uric acid electroactive species produced during cell metabolism and/or wound healing, electroactive species that arise during body pH changes and the like. Electroactive species that cause constant and/or non-constant noise are included in the definitions of "interferants" and "interfering species".

The term "bifunctional" as used herein is a broad term, and is to be given its ordinary and customary meaning to a person of ordinary skill in the art (and it is not to be limited to a special or customized meaning), and refers without limitation to having or serving two functions. For example, in a needle-type analyte sensor, a metal wire is bifunctional because it provides structural support and acts as an electrical conductor.

The term "function" as used herein is a broad term, and is to be given its ordinary and customary meaning to a person of ordinary skill in the art (and it is not to be limited to a special or customized meaning), and refers without limitation to an action or use for which something is suited or designed.

The term "electrical conductor" as used herein is a broad term, and is to be given its ordinary and customary meaning to a person of ordinary skill in the art (and is not to be limited to a special or customized meaning) and refers without limitation to materials that contain movable charges of electricity. When an electric potential difference is impressed across separate points on a conductor, the mobile charges within the conductor are forced to move, and an electric current between those points appears in accordance with Ohm's law.

Accordingly, the term "electrical conductance" as used herein is a broad term, and is to be given its ordinary and customary meaning to a person of ordinary skill in the art (and is not to be limited to a special or customized meaning) and refers without limitation to the propensity of a material to behave as an electrical conductor. In some embodiments, the term refers to a sufficient amount of electrical conductance (e.g., material property) to provide a necessary function (electrical conduction).

The terms "insulative properties," "electrical insulator" and "insulator" as used herein are broad terms, and are to be given their ordinary and customary meaning to a person of ordinary skill in the art (and is not to be limited to a special or customized meaning) and refers without limitation to the tendency of materials that lack mobile charges to prevent movement of electrical charges between two points. In one exemplary embodiment, an electrically insulative material may be placed between two electrically conductive materials, to prevent movement of electricity between the two electrically conductive materials. In some embodiments, the terms refer to a sufficient amount of insulative property (e.g., of a material) to provide a necessary function (electrical insulation). The terms "insulator" and "non-conductive material" can be used interchangeably herein.

The term "structural support" as used herein is a broad term, and is to be given its ordinary and customary meaning to a person of ordinary skill in the art (and is not to be limited to a special or customized meaning) and refers without limitation to the tendency of a material to keep the sensor's structure stable or in place. For example, structural support can include "weight bearing" as well as the tendency to hold the parts or components of a whole structure together. A variety of materials can provide "structural support" to the sensor.

The term "diffusion barrier" as used herein is a broad term, and is to be given its ordinary and customary meaning to a person of ordinary skill in the art (and is not to be limited to a special or customized meaning) and refers without limitation to something that obstructs the random movement of compounds, species, atoms, molecules, or ions from one site in a medium to another. In some embodiments, a diffusion barrier is structural, such as a wall that separates two working electrodes and substantially prevents diffusion of a species from one electrode to the other. In some embodiments, a diffusion barrier is spatial, such as separating working electrodes by a distance sufficiently large enough to substantially prevent a species at a first electrode from affecting a second electrode. In other embodiments, a diffusion barrier can be temporal, such as by turning the first and second working electrodes on and off, such that a reaction at a first electrode will not substantially affect the function of the second electrode.

The terms "integral," "integrally," "integrally formed," integrally incorporated," "unitary" and "composite" as used herein are broad terms, and are to be given their ordinary and customary meaning to a person of ordinary skill in the art (and they are not to be limited to a special or customized meaning), and refer without limitation to the condition of being composed of essential parts or elements that together make a whole. The parts are essential for completeness of the whole. In one exemplary embodiment, at least a portion (e.g., the in vivo portion) of the sensor is formed from at least one platinum wire at least partially covered with an insulative coating, which is at least partially helically wound with at least one additional wire, the exposed electroactive portions of which are covered by a membrane system (see description of FIG. 1B or 9B); in this exemplary embodiment, each element of the sensor is formed as an integral part of the sensor (e.g., both functionally and structurally).

The term "coaxial" as used herein is a broad term, and is to be given its ordinary and customary meaning to a person of ordinary skill in the art (and it is not to be limited to a special or customized meaning), and refers without limitation to having a common axis, having coincident axes or mounted on concentric shafts.

The term "twisted" as used herein is a broad term, and is to be given its ordinary and customary meaning to a person of ordinary skill in the art (and it is not to be limited to a special or customized meaning), and refers without limitation to united by having one part or end turned in the opposite direction to the other, such as, but not limited to the twisted strands of fiber in a string, yarn, or cable.

The term "helix" as used herein is a broad term, and is to be given its ordinary and customary meaning to a person of ordinary skill in the art (and it is not to be limited to a special or customized meaning), and refers without limitation to a spiral or coil, or something in the form of a spiral or coil (e.g. a corkscrew or a coiled spring). In one example, a helix is a mathematical curve that lies on a cylinder or cone and makes a constant angle with the straight lines lying in the cylinder or cone. A "double helix" is a pair of parallel helices intertwined about a common axis, such as but not limited to that in the structure of DNA.

The term "in vivo portion" as used herein is a broad term, and is to be given its ordinary and customary meaning to a person of ordinary skill in the art (and it is not to be limited to a special or customized meaning), and refers without limitation to a portion of a device that is to be implanted or inserted into the host. In one exemplary embodiment, an in vivo portion of a transcutaneous sensor is a portion of the sensor that is inserted through the host's skin and resides within the host.

The term "sensor break-in" as used herein is a broad term, and is to be given its ordinary and customary meaning to a person of ordinary skill in the art (and is not to be limited to a special or customized meaning), and refers without limitation to the time required for the sensor's output signal to provide a substantially linear response to the analyte concentration (e.g., glucose level). In some embodiments, sensor break-in generally includes both electrochemical break-in and membrane break-in.

The term "membrane break-in" as used herein is a broad term, and is to be given its ordinary and customary meaning to a person of ordinary skill in the art (and is not to be limited to a special or customized meaning), and refers without limitation to a time necessary for the membrane to equilibrate to its surrounding environment (e.g., physiological environment in vivo).

The term "electrochemical break-in" as used herein is a broad term, and is to be given its ordinary and customary meaning to a person of ordinary skill in the art (and is not to be limited to a special or customized meaning), and refers without limitation to a time, after sensor insertion in vitro and/or in vivo, at which the current output from the sensor settles to a stable value following the application of the potential to the sensor. Numerous methods of accelerating electrochemical break-in can be used, such as, but not limited to, configuring the sensor electronics to aid in decreasing the break-in time of the sensor by applying different voltage settings (for example, starting with a higher voltage setting and then reducing the voltage setting). Additional methods of accelerating sensor break-in time are described in U.S. Pat. No. 5,411,647, for example, which is incorporated herein by reference in its entirety.

The "noise" as used herein is a broad term, and is to be given its ordinary and customary meaning to a person of ordinary skill in the art (and is not to be limited to a special or customized meaning), and refers without limitation to a component of an analyte sensor signal that is not related to the analyte concentration. In one example of a glucose sensor, the noise is composed substantially of signal contribution due to factors other than glucose (for example, interfering species, non-reaction-related hydrogen peroxide, or other electroactive species with an oxidation potential that overlaps with hydrogen peroxide). In general, noise comprises components related to constant and non-constant factors (e.g., constant noise and non-constant noise), including endogenous and exogenous interfering species.

The term "constant noise" and "constant background" as used herein are broad terms, and are to be given their ordinary and customary meaning to a person of ordinary skill in the art (and it is not to be limited to a special or customized meaning), and refer without limitation to the component of the noise signal that remains relatively constant over time. In some embodiments, constant noise may be referred to as "background" or "baseline." For example, certain electroactive compounds found in the human body are relatively constant factors (e.g., baseline of the host's physiology). In some circumstances, constant background noise can slowly drift over time (e.g., increase or decrease), however this drift need not adversely affect the accuracy of a sensor, for example, because a sensor can be calibrated and re-calibrated and/or the drift measured and compensated for.

The term "non-constant noise" or non-constant background" as used herein are broad terms, and are to be given their ordinary and customary meaning to a person of ordinary skill in the art (and it is not to be limited to a special or customized meaning), and refer without limitation to a component of the background signal that is relatively non-constant, for example, transient and/or intermittent. For example, certain electroactive compounds, are relatively non-constant (e.g., intermittent interferents due to the host's ingestion, metabolism, wound healing, and other mechanical, chemical and/or biochemical factors), which create intermittent (e.g., non-constant) "noise" on the sensor signal that can be difficult to "calibrate out" using a standard calibration equations (e.g., because the background of the signal does not remain constant).

The terms "inactive enzyme" or "inactivated enzyme" as used herein are broad terms, and are to be given their ordinary and customary meaning to a person of ordinary skill in the art (and it is not to be limited to a special or customized meaning), and refer without limitation to an enzyme (e.g., glucose oxidase, GOx) that has been rendered inactive (e.g., "killed" or "dead") and has no enzymatic activity. Enzymes can be inactivated using a variety of techniques known in the art, such as but not limited to heating, freeze-thaw, denaturing in organic solvent, acids or bases, cross-linking, genetically changing enzymatically critical amino acids, and the like. In some embodiments, a solution containing active enzyme can be applied to the sensor, and the applied enzyme subsequently inactivated by heating or treatment with an inactivating solvent.

The term "non-enzymatic" as used herein is a broad term, and is to be given their ordinary and customary meaning to a person of ordinary skill in the art (and it is not to be limited to a special or customized meaning), and refers without limitation to a lack of enzyme activity. In some embodiments, a "non-enzymatic" membrane portion contains no enzyme; while in other embodiments, the "non-enzymatic" membrane portion contains inactive enzyme. In some embodiments, an enzyme solution containing inactive enzyme or no enzyme is applied.

The term "GOX" as used herein is a broad term, and is to be given their ordinary and customary meaning to a person of ordinary skill in the art (and it is not to be limited to a special or customized meaning), and refers without limitation to the enzyme Glucose Oxidase (e.g., GOX or GOx is an abbreviation/acronym).

The term "mechanism" as used herein is a broad term, and is to be given their ordinary and customary meaning to a person of ordinary skill in the art (and it is not to be limited to a special or customized meaning), and refers without limitation to a process, technique, or system for achieving a result. The term is not limited by the processes, techniques or systems described herein, but also includes any process, technique, or system that can achieve a stated result.

The term "redox" as used herein is a broad term, and is to be given their ordinary and customary meaning to a person of ordinary skill in the art (and it is not to be limited to a special or customized meaning), and refers without limitation to "oxidation/reduction," which describes all chemical reactions in which atoms have their oxidation number (oxidation state) changed. The term "oxidation" describes the loss of electrons by a molecule, atom or ion. In contrast, the term "reduction" describes the gain of electrons by a molecule, atom or ion. For example, hydrogen peroxide reduces to hydroxide in the presence of an acid:

$$H_2O_2 + 2e^- \rightarrow 2OH^-$$

The term "redox potential" as used herein is a broad term, and is to be given their ordinary and customary meaning to a person of ordinary skill in the art (and it is not to be limited to a special or customized meaning), and refers without limitation to the tendency of a chemical species to acquire electrons and thereby be reduced. Each species has its own intrinsic reduction potential, the more positive the potential, the greater the species' affinity for electrons and tendency to be reduced.

The term "hydrophilic" as used herein is a broad term, and is to be given its ordinary and customary meaning to a person of ordinary skill in the art (and is not to be limited to a special or customized meaning), and refers without limitation to the property of having affinity for water. For example, a hydrophilic polymer (e.g., having a hydrophilic component) is primarily soluble in water or has a tendency to absorb water. In general, the more hydrophilic a polymer is, the more that polymer tends to dissolve in, mix with, or be wetted by water. In one exemplary embodiment, the hydrophilic component of a hydrophilic polymer promotes the movement of water (e.g., by diffusion or other means) through a membrane formed of the hydrophilic polymer, such as by lowering the thermodynamic barrier to movement of water through the membrane. In some embodiments, a hydrophilic polymer includes a hydrophilic-hydrophobic or hydrophobic-hydrophilic polymer.

The terms "hydrophilic-hydrophobic" and "hydrophobic-hydrophilic" as used herein are broad terms, and are to be given their ordinary and customary meaning to a person of ordinary skill in the art (and are not to be limited to a special or customized meaning), and refer without limitation to the property of having both hydrophilic and hydrophobic substituents and/or characteristics, such as, for example, a polymer. The terms hydrophilic-hydrophobic and hydrophobic-hydrophilic are used interchangeably herein, and are not meant to imply if either the hydrophilic or the hydrophobic substituents are the major component of the polymer.

The term "hydrophobic" as used herein is a broad term, and is to be given its ordinary and customary meaning to a person of ordinary skill in the art (and is not to be limited to a special or customized meaning), and refers without limitation to the property of lacking affinity for, or even repelling, water. For example, the more hydrophobic a polymer, the more that polymer tends to not dissolve in, not mix with, or not be wetted by water. Hydrophilicity and hydrophobicity can be spoken of in relative terms, such as but not limited to a spectrum of hydrophilicity/hydrophobicity within a group of compounds. In some embodiments wherein two or more polymers are being discussed, the term "hydrophobic polymer" can be defined based on the polymer's relative hydrophobicity when compared to another, more hydrophilic polymer. In some embodiments, a hydrophobic polymer includes a hydrophobic-hydrophilic or a hydrophilic-hydrophobic polymer.

The term "clinical acceptability" as used herein is a broad term, and is to be given its ordinary and customary meaning to a person of ordinary skill in the art (and is not to be limited to a special or customized meaning), and refers without limitation to determination of the risk of an inaccuracy to a patient. Clinical acceptability considers a deviation between time corresponding analyte measurements (for example, data from a glucose sensor and data from a reference glucose monitor) and the risk (for example, to the decision making of a person with diabetes) associated with that deviation based on the analyte value indicated by the sensor and/or reference data. An example of clinical acceptability can be 85% of a given set of measured analyte values within the "A" and "B" region of a standard Clarke Error Grid when the sensor measurements are compared to a standard reference measurement.

The term "comprising" as used herein is synonymous with "including," "containing," or "characterized by," and is inclusive or open-ended and does not exclude additional, unrecited elements or method steps.

The terms "substantial" and "substantially" as used herein are broad terms, and are to be given their ordinary and customary meaning to a person of ordinary skill in the art (and are not to be limited to a special or customized meaning), and refer without limitation to a sufficient amount that provides a desired function. For example, the interference domain of some embodiments is configured to resist a sufficient amount of interfering species such that tracking of glucose levels can be achieved, which may include an amount greater than 50 percent, an amount greater than 60 percent, an amount greater than 70 percent, an amount greater than 80 percent, and an amount greater than 90 percent of interfering species. In one exemplary embodiment, two compounds are "substantially blended;" meaning that the two compounds are mixed together and at least more than 50% of the molecules of the two compounds are not chemically linked (e.g., cross-linked). In a more preferred exemplary embodiment, at least 70, 75, 80, 85, 90 or 90%, or more, of the blended compounds are not chemically linked. In an exemplary embodiment of a substantial blend of a silicone polymer and a hydrophilic copolymer, at least 95% or more of the silicone polymer is not chemically cross-linked with the hydrophilic copolymer. In some preferred embodiments, the phrase "substantially accurate" means that the calibrated analyte level is sufficiently accurate to be displayed to the host, for example, due to its clinical acceptability or statistical accuracy. For example, the data meet the ±20% accuracy standard (e.g., wherein the data are compared to a gold standard, such as YSI) for blood glucose meters (BGM) established by the U.S. Food and Drug Administration (FDA). In some exemplary embodiments, the non-constant noise component of the total signal is less than 20% of the total signal for at least one day. In another exemplary embodiment, the analyte component of the total signal is greater than 80% of the total signal for at least one day.

Overview

The preferred embodiments generally relate to implantable devices and methods of use, for detecting an analyte in a host, including a sensor exhibiting a signal-to-noise ratio that is not substantially affected by non-constant noise. For example, the signal-to-noise ratio can be attained by incorporating sensor configurations that reduce and/or eliminate the effects of noise-causing interfering species as well as sensor configurations that increase the analyte component of the total signal detected.

Although the description that follows is primarily directed at glucose monitoring devices, these sensor configurations are not limited to use in devices that measure or monitor glucose. Rather, these sensor configurations can be applied to a variety of devices, including for example, those that detect and quantify other analytes present in biological fluids (including, but not limited to, cholesterol, amino acids and lactate), especially those analytes that are substrates for oxidase enzymes (see, e.g., U.S. Pat. No. 4,703,756), cell transplantation devices (U.S. Pat. Nos. 6,015,572, 5,964,745 and 6,083,523), drug delivery devices (U.S. Pat. Nos. 5,458, 631, 5,820,589, and 5,972,369) and electrical delivery and/or measuring devices such as implantable pulse generation cardiac pacing devices (U.S. Pat. Nos. 6,157,860, 5,782,880, and 5,207,218), electrocardiogram device (U.S. Pat. No. 4,625,730 and U.S. Pat. No. 5,987,352) and electrical nerve stimulating devices (U.S. Pat. Nos. 6,175,767, 6,055,456, and 4,940,065).

Noise

Generally, implantable sensors measure a signal related to an analyte of interest in a host. For example, an electrochemical sensor can measure glucose, creatinine, or urea in a host, such as an animal (e.g., a human). Generally, the signal is converted mathematically to a numeric value indicative of analyte status, such as analyte concentration. The signal detected by the sensor can be broken down into its component parts. For example, in an enzymatic electrochemical analyte sensor, preferably after sensor break-in is complete, the total signal can be divided into an "analyte component," which is representative of analyte (e.g., glucose) concentration, and a "noise component," which is caused by non-analyte-related species that have a redox potential that substantially overlaps with the redox potential of the analyte (or measured species, e.g., $H_2O_2$) at an applied voltage. The noise component can be further divided into its component parts, i.e., constant and non-constant noise. It is not unusual for a sensor to experience a certain level of noise. In general, "constant noise" (sometimes referred to as constant background or baseline) is caused by non-analyte-related factors that are relatively stable over time, including but not limited to electroactive species that arise from generally constant (e.g., daily) metabolic processes. Constant noise can vary widely between hosts. In contrast, "non-constant noise" (sometimes referred to as non-constant background) is caused by non-constant, non-analyte-related species (e.g., non-constant noise-causing electroactive species) that arise during transient events, such as during host metabolic processes (e.g., wound healing or in response to an illness), or due to ingestion of certain compounds (e.g., certain drugs). In some circumstances, noise can be caused by a variety of noise-causing electroactive species, which are discussed in detail elsewhere herein.

FIG. 1 is a graph illustrating the components of a signal measured by a transcutaneous glucose sensor (after sensor break-in was complete), in a non-diabetic volunteer host. The Y-axis indicates the signal amplitude (in counts) detected by the sensor. The term "counts" as used herein is a broad term, and is to be given its ordinary and customary meaning to a person of ordinary skill in the art (and it is not to be limited to a special or customized meaning), and refers without limitation to a unit of measurement of a digital signal. In one example, a raw data stream measured in counts is directly related to a voltage (for example, converted by an A/D converter), which is directly related to current from a working electrode. The X-axis indicates time.

The total signal collected by the sensor is represented by line 1000, which includes components related to glucose, constant noise, and non-constant noise, which are described in more detail elsewhere herein. In some embodiments, the total signal is a raw data stream, which can include an averaged or integrated the signal, for example, using a charge-counting device.

The non-constant noise component of the total signal is represented by line 1010. The non-constant noise component 1010 of the total signal 1000 can be obtained by filtering the total signal 1000 to obtain a filtered signal 1020 using any of a variety of known filtering techniques, and then subtracting the filtered signal 1020 from the total signal 1000. In some embodiments, the total signal can be filtered using linear regression analysis of the n (e.g., 10) most recent sampled sensor values. In some embodiments, the total signal can be filtered using non-linear regression. In some embodiments, the total signal can be filtered using a trimmed regression, which is a linear regression of a trimmed mean (e.g., after rejecting wide excursions of any point from the regression line). In this embodiment, after the sensor records glucose measurements at a predetermined sampling rate (e.g., every 30 seconds), the sensor calculates a trimmed mean (e.g., removes highest and lowest measurements from a data set) and then regresses the remaining measurements to estimate the glucose value. In some embodiments, the total signal can be filtered using a non-recursive filter, such as a finite impulse response (FIR) filter. An FIR filter is a digital signal filter, in which every sample of output is the weighted sum of past and current samples of input, using only some finite number of past samples. In some embodiments, the total signal can be filtered using a recursive filter, such as an infinite impulse response (IIR) filter. An IIR filter is a type of digital signal filter, in which every sample of output is the weighted sum of past and current samples of input. In some embodiments, the total signal can be filtered using a maximum-average (max-average) filtering algorithm, which smoothes data based on the discovery that the substantial majority of signal artifacts observed after implantation of glucose sensors in humans, for example, is not distributed evenly above and below the actual blood glucose levels. It has been observed that many data sets are actually characterized by extended periods in which the noise appears to trend downwardly from maximum values with occasional high spikes. To overcome these downward trending signal artifacts, the max-average calculation tracks with the highest sensor values, and discards the bulk of the lower values. Additionally, the max-average method is designed to reduce the contamination of the data with unphysiologically high data from the high spikes. The max-average calculation smoothes data at a sampling interval (e.g., every 30 seconds) for transmission to the receiver at a less frequent transmission interval (e.g., every 5 minutes), to minimize the effects of low non-physiological data. First, the microprocessor finds and stores a maximum sensor counts value in a first set of sampled data points (e.g., 5 consecutive, accepted, thirty-second data points). A frame shift time window finds a maximum sensor counts value for each set of sampled data (e.g., each 5-point cycle length) and stores each maximum value. The microprocessor then computes a rolling average (e.g., 5-point average) of these maxima for each sampling interval (e.g., every 30 seconds) and stores these data. Periodically (e.g., every $10^{th}$ interval), the sensor outputs to the receiver the current maximum of the rolling average (e.g., over the last 10 thirty-second intervals as a smoothed value for that time period (e.g., 5 minutes)). In some embodiments, the total signal can be filtered using a "Cone of Possibility Replacement Method," which utilizes physiological information along with glucose signal values in order define a "cone" of physiologically feasible glucose signal values within a human. Particularly, physiological information depends upon the physiological parameters obtained from continuous studies in the literature as well as our own observations. A first physiological parameter uses a maximal sustained rate of change of glucose in humans (e.g., about 4 to 5 mg/dl/min) and a maximum sustained acceleration of that rate of change (e.g., about 0.1 to 0.2 mg/min/min). A second physiological parameter uses the knowledge that rate of change of glucose is lowest at the maxima and minima, which are the areas of greatest risk in patient treatment. A third physiological parameter uses the fact that the best solution for the shape of the curve at any point along the curve over a certain time period (e.g., about 20-25 minutes) is a straight line. It is noted that the maximum rate of change can be narrowed in some instances. Therefore, additional physiological data can be used to modify the limits imposed upon the Cone of Possibility Replacement Method for sensor glucose values. For example, the maximum per minute rate change can be lower when the subject is lying down or sleeping; on the other hand, the maximum per minute rate change can be higher when the subject is exercising, for example. In some embodiments, the total signal can be filtered using reference changes in electrode potential to estimate glucose sensor data during positive detection of signal artifacts from an electrochemical glucose sensor, the method hereinafter referred to as reference drift replacement. In this embodiment, the electrochemical glucose sensor comprises working, counter, and reference electrodes. This method exploits the function of the reference electrode as it drifts to compensate for counter electrode limitations during oxygen deficits, pH changes, and/or temperature changes. In alternative implementations of the reference drift method, a variety of algorithms can therefore be implemented based on the changes measured in the reference electrode. Linear algorithms, and the like, are suitable for interpreting the direct relationship between reference electrode drift and the non-glucose rate limiting signal noise such that appropriate conversion to signal noise compensation can be derived. Additional description of signal filtering can be found in U.S. Patent Publication No. US-2005-0043598-A1.

The constant noise signal component 1030 can be obtained by calibrating the sensor signal using reference data, such as one or more blood glucose values obtained from a hand-held blood glucose meter, from which the baseline "b" of a regression can be obtained, representing the constant noise signal component 1030.

The analyte signal component 1040 can be obtained by subtracting the constant noise signal component 1030 from the filtered signal 1020.

Noise is clinically important because it can induce error and can reduce sensor performance, such as by providing a signal that causes the analyte concentration to appear higher or lower than the actual analyte concentration. For example, upward or high noise (e.g., noise that causes the signal to increase) can cause the host's glucose concentration to appear higher than it truly is, which can lead to improper treatment decisions. Similarly, downward or low noise (e.g., noise that causes the signal to decrease) can cause the host's glucose concentration to appear lower than it is, which can also lead to improper treatment decisions. Accordingly, noise reduction is desirable.

Noise can be caused by a variety of factors, ranging from mechanical factors to biological factors. For example, it is known that macro- or micro-motion, ischemia, pH changes, temperature changes, pressure, stress, or even unknown mechanical, electrical, and/or biochemical sources can cause noise, in some embodiments. Interfering species, which are known to cause non-constant noise, can be compounds, such as drugs that have been administered to the host, or intermittently produced products of various host metabolic processes. Exemplary interferents include but are not limited to a variety of drugs (e.g., acetaminophen), $H_2O_2$ from exterior sources (e.g., produced outside the sensor membrane system), and reactive metabolic species (e.g., reactive oxygen and nitrogen species, some hormones, etc.). Some known interfering species for a glucose sensor include but are not limited to acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid. In some embodiments, the interference domain, described elsewhere herein, of the preferred embodiments is less permeable to one or more of the interfering species than to the measured species, e.g., the product of an enzymatic reaction that is measured at the electroactive surface(s), such as but not limited to $H_2O_2$.

In some experiments of implantable glucose sensors, it was observed that noise increased when some hosts were intermittently sedentary, such as during sleep or sitting for extended periods. When the host began moving again, the noise quickly dissipated. Noise that occurs during intermittent, sedentary periods (sometimes referred to as intermittent sedentary noise) can occur during relatively inactive periods, such as sleeping. Non-constant, non-analyte-related factors can cause intermittent sedentary noise, such as was observed in one exemplary study of non-diabetic individuals implanted with enzymatic-type glucose sensors built without enzyme. These sensors (without enzyme) could not react with or measure glucose and therefore provided a signal due to non-glucose effects only (e.g., constant and non-constant noise). During sedentary periods (e.g., during sleep), extensive, sustained signal was observed on the sensors. Then, when the host got up and moved around, the signal rapidly corrected. As a control, in vitro experiments were conducted to determine if a sensor component might have leached into the area surrounding the sensor and caused the noise, but none was detected. From these results, it is believed that a host-produced non-analyte related reactant was diffusing to the electrodes and producing the unexpected non-constant noise signal.

While not wishing to be bound by theory, it is believed that a concentration increase of noise-causing electroactive species, such as electroactive metabolites from cellular metabolism and wound healing, can interfere with sensor function and cause noise observed during host sedentary periods. For example, local lymph pooling, which can occur when a part of the body is compressed or when the body is inactive, can cause, in part, this local build up of interferants (e.g., electroactive metabolites). Similarly, a local accumulation of wound healing metabolic products (e.g., at the site of sensor insertion) likely causes noise on the sensor. Noise-causing electroactive species can include but are not limited to compounds with electroactive acidic, amine or sulfhydryl groups, urea, lactic acid, phosphates, citrates, peroxides, amino acids (e.g., L-arginine), amino acid precursors or break-down products, nitric oxide (NO), NO-donors, NO-precursors or other electroactive species or metabolites produced during cell metabolism and/or wound healing, for example. For a more complete discussion of noise and its sources, see U.S. Patent Publication No. US-2007-0027370-A1.

Noise can be recognized and/or analyzed in a variety of ways. For example, in some circumstances, non-constant noise changes faster than the analyte signal and/or does not follow an expected analyte signal pattern; and lasts for a period of about 10 hours or more, 8 hours, 6 hours, 4 hours, 2 hours, 60 minutes, 30 minutes, or 10 minutes or less. In some embodiments, the sensor data stream can be monitored, signal artifacts detected, and data processing performed based at least in part on whether or not a signal artifact has been detected, such as described in U.S. Patent Publication No. US-2005-0043598-A1. Additional discussion of noise recognition and analysis can also be found in U.S. Patent Publication No. US-2007-0032706-A1.

In some conventional analyte sensors, non-constant noise can be a significant component of the total signal, such as 30%, 40%, 50%, 60% or more of the total signal. Additionally, non-constant noise can occur for durations of minutes or hours, in some circumstances. In some circumstances, non-constant noise can be equivalent to a glucose concentration of about 400-mg/dl or more. Noise can induce error in the sensor reading, which can reduce sensor accuracy and clinically useful data. However, a high level of sensor accuracy is critical for successful patient care and desirable clinical outcomes. In preferred embodiments, as described in greater detail herein, the sensor is configured to reduce the non-constant noise component of the signal to below 20% of the total signal, such that the negative effects of noise are is substantially reduced and clinically useful data are provided to the user.

In preferred embodiments, sensor accuracy is provided by adjusting the ratio of the analyte signal to the non-constant noise signal (e.g., signal-to-noise ratio). In some embodiments, an electrochemical analyte detection system is provided, which includes a sensor configured for substantially continuous analyte detection, such as in an ambulatory host. The sensor includes at least one electrode and electronics configured to provide a signal measured at the electrode; wherein the measured signal can be broken down (e.g., after sensor break-in) into its component parts, a substantially analyte-related component, a substantially constant non-analyte-related component (i.e., constant noise) and a substantially non-constant non-analyte-related component (i.e., non-constant noise), wherein the sensor is configured such that the substantially non-constant non-analyte-related component does not substantially contribute to the signal for at least about one day. In some preferred embodiments, the signal contribution of the non-constant noise is less than about 20% of the signal (e.g., total signal) over a time period of at least about one day; in some preferred embodiments, the time period is at least about two, three, four, five, six, seven days or more, including weeks or months, and the signal contribution of the non-constant noise is less than about 18%, 16%, 14%, 12%, 10%, 8%, 6%, 5%, 4%, 3%, 2%, or 1%. In some preferred embodiments, the sensor is configured such that the signal contribution of the analyte-related component is at least about 80% of the signal (e.g., total signal) over a time period of at least about one day; in some preferred embodiments, the time period is at least about two, three, four, five, six, seven days or more, including weeks or months, and the signal contribution of the analyte-related component is at least about 82%, 84%, 86%, 88%, 90%, 91%, 92%, 93%, 94%, 95%, 96%, 97%, 98%, 99% or more.

A signal component's percentage of the total signal can be determined using a variety of methods of quantifying an amplitude of signal components and total signal, from each components percent contribution can be calculated, as is appreciated by one skilled in the art. In some embodiments, the signal component(s) can be quantified by comparing the peak-to-peak amplitudes of each signal component for a time period, whereby the peak-to-peak amplitudes of each component can be compared to the peak-to-peak amplitude of the total signal to determine it's percentage of the total signal, as is appreciated by one skilled in the art. In some embodiments, the signal component(s) can be quantified by determining the Root Mean Square (RMS) of the signal component for a time period. In one exemplary of Root Mean Square analysis of signal components, the signal component(s) can be quantified using the formula:

$$RMS = \sqrt{\frac{\Sigma(x_1^2 + x_2^2 + x_3^2 + x_n^2)}{n}}$$

wherein there are a number (n) of data values (x) for a signal (e.g., analyte component, non-constant noise component, constant noise component, and/or total signal) during a predetermined time period (e.g., about 1 day, about 2 days, about 3 days, etc). Once the signal components and/or total signal are quantified, the signal components can be compared to the total signal to determine a percentage of each signal component within the total signal.

Analyte Sensor Configurations/Components

The preferred embodiments provide a continuous analyte sensor that measures a concentration of the analyte of interest or a substance indicative of the concentration or presence of the analyte. In some embodiments, the analyte sensor is an invasive, minimally invasive, or non-invasive device, for example a subcutaneous, transdermal, intravascular, or extracorporeal device. In some embodiments, the analyte sensor may analyze a plurality of intermittent biological samples. The analyte sensor may use any method of analyte-measurement, including enzymatic, chemical, physical, electrochemical, spectrophotometric, polarimetric, calorimetric, radiometric, or the like.

In general, analyte sensors provide at least one working electrode and at least one reference electrode, which are configured to measure a signal associated with a concentration of the analyte in the host, such as described in more detail below, and as appreciated by one skilled in the art. The output signal is typically a raw data stream that is used to provide a useful value of the measured analyte concentration in a host to the patient or doctor, for example. However, the analyte sensors of some embodiments comprise at least one additional working electrode configured to measure at least one additional signal, as discussed elsewhere herein. For example, in some embodiments, the additional signal is associated with the baseline and/or sensitivity of the analyte sensor, thereby enabling monitoring of baseline and/or sensitivity changes that may occur in a continuous analyte sensor over time.

In general, continuous analyte sensors define a relationship between sensor-generated measurements (for example, current in pA, nA, or digital counts after A/D conversion) and a reference measurement (for example, glucose concentration mg/dL or mmol/L) that are meaningful to a user (for example, patient or doctor). In the case of an implantable diffusion-based glucose oxidase electrochemical glucose sensor, the sensing mechanism generally depends on phenomena that are linear with glucose concentration, for example: (1) diffusion of glucose through a membrane system (for example, biointerface membrane and membrane system) situated between implantation site and/or the electrode surface, (2) an enzymatic reaction within the membrane system, and (3) diffusion of the $H_2O_2$ to the sensor. Because of this linearity, calibration of the sensor can be understood by solving an equation:

$$y=mx+b$$

where y represents the sensor signal (e.g., counts), x represents the estimated glucose concentration (e.g., mg/dL), m represents the sensor sensitivity to glucose (e.g., counts/mg/dL), and b represents the baseline signal (e.g., counts). When both sensitivity m and baseline (background) b change over time in vivo, calibration has generally requires at least two independent, matched data pairs ($x_1$, $y_1$; $x_2$, $y_2$) to solve for m and b and thus allow glucose estimation when only the sensor signal, y is available. Matched data pairs can be created by matching reference data (for example, one or more reference glucose data points from a blood glucose meter, or the like) with substantially time corresponding sensor data (for example, one or more glucose sensor data points) to provide one or more matched data pairs, such as described in co-pending U.S. Patent Publication No. US-2005-0027463-A1. In some implantable glucose sensors, such as described in more detail in U.S. Pat. No. 6,329,161 to Heller et al., which is incorporated herein by reference in its entirety, the sensing layer utilizes immobilized mediators (e.g., redox compounds) to electrically connect the enzyme to the working electrode, rather than using a diffusional mediator. In some implantable glucose sensors, such as described in more detail in U.S. Pat. No. 4,703,756, the system has two oxygen sensors situated in an oxygen-permeable housing, one sensor being unaltered and the other contacting glucose oxidase allowing for differential measurement of oxygen content in bodily fluids or tissues indicative of glucose levels. A variety of systems and methods of measuring glucose in a host are known, all of which may benefit from some of all of the preferred embodiments to provide a sensor having a signal-to-noise ratio that is not substantially affected by non-constant noise.

Additional description of analyte sensor configurations can be found in co-pending U.S. patent application Ser. No. 11/692,154, filed on Mar. 27, 2007 and entitled "DUAL ELECTRODE SYSTEM FOR A CONTINUOUS ANALYTE SENSOR", U.S. Patent Publication No. US-2007-0027385-A1, and U.S. Patent Publication No. US-2005-0143635-A1

Sensor Components Overview

In some embodiments, an analyte sensor includes a sensing mechanism 34 with a small structure (e.g., small-structured, micro- or small diameter sensor), for example, a needle-type sensor, in at least a portion thereof (see FIG.

2A). As used herein the term "small-structured" preferably refers to an architecture with at least one dimension less than about 1 mm. The small structured sensing mechanism can be wire-based, substrate based, or any other architecture. In some alternative embodiments, the term "small-structured" can also refer to slightly larger structures, such as those having their smallest dimension being greater than about 1 mm, however, the architecture (e.g., mass or size) is designed to minimize the foreign body response (FBR) due to size and/or mass. In some embodiments, a biointerface membrane (e.g., membrane system or sensing membrane) is formed onto the sensing mechanism 34 as described in more detail below. In some alternative embodiments, the sensor is configured to be wholly implanted in a host, such as in the host abdomen; such is described in U.S. Patent Publication No. US-2006-0020187-A1. In still other embodiments, the sensor is configured to be implanted in a host vessel or extracorporeally, such as is described in U.S. Patent Publication No. US-2007-0027385-A1, co-pending U.S. patent application Ser. No. 11/543,396 filed Oct. 4, 2006, co-pending U.S. patent application Ser. No. 11/691,426 Mar. 26, 2007, and co-pending U.S. patent application Ser. No. 11/675,063 filed on Feb. 14, 2007.

In the illustrated embodiments, the sensor is an enzyme-based electrochemical sensor, wherein the working electrode 38 measures the hydrogen peroxide ($H_2O_2$) produced by the enzyme catalyzed reaction of glucose being detected and creates a measurable electronic current (for example, detection of glucose utilizing glucose oxidase produces hydrogen peroxide as a by-product, $H_2O_2$ reacts with the surface of the working electrode producing two protons ($2H^+$), two electrons ($2e^-$) and one molecule of oxygen ($O_2$) which produces the electronic current being detected), such as described in more detail herein and as is appreciated by one skilled in the art. Preferably, one or more potentiostat(s) is employed to monitor the electrochemical reaction at the electroactive surface of the working electrode(s). The potentiostat applies a constant potential to the working electrode and its associated reference electrode to determine the current produced at the working electrode. The current that is produced at the working electrode (and flows through the circuitry to the counter electrode) is substantially proportional to the amount of $H_2O_2$ that diffuses to the working electrode. The output signal is typically a raw data stream that is used to provide a useful value of the measured analyte concentration in a host to the host or doctor, for example. In some alternative embodiments, the sensing mechanism includes electrodes deposited on a planar substrate, wherein the thickness of the implantable portion is less than about 1 mm, see, for example U.S. Pat. Nos. 6,175,752 and 5,779,665.

Some alternative analyte sensors that can benefit from the systems and methods of some embodiments include U.S. Pat. Nos. 5,711,861, 6,642,015, 6,654,625, 6,565,509, 6,514,718, 6,465,066, 6,214,185, 5,310,469, and 5,683,562, 6,579,690, 6,484,046, 6,512,939, and 6,424,847, for example. These patents are not inclusive of all applicable analyte sensors; in general, it should be understood that the disclosed embodiments are applicable to a variety of analyte sensor configurations.

Figure 2A:
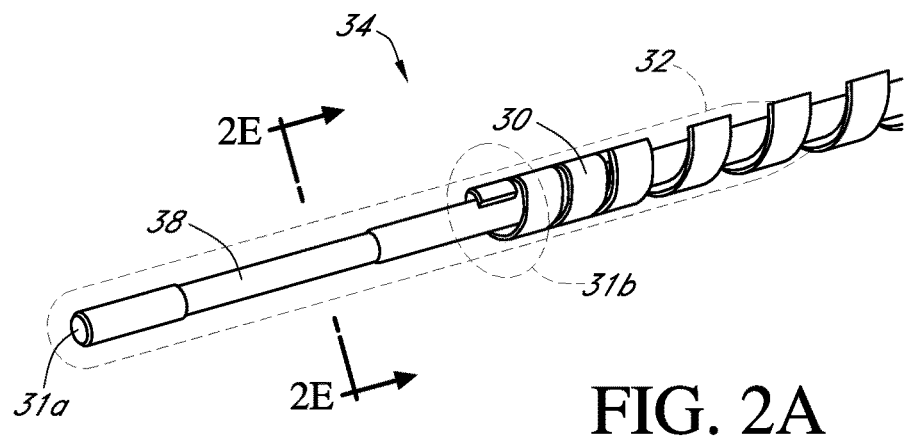
FIG. 2A is a perspective view of an in vivo portion of an analyte sensor, in one embodiment.

FIG. 2A is an expanded view of an exemplary embodiment of a continuous analyte sensor 34, also referred to as a transcutaneous analyte sensor, or needle-type sensor, particularly illustrating the sensing mechanism. Preferably, the sensing mechanism comprises a small structure as defined herein and is adapted for insertion under the host's skin, and the remaining body of the sensor (e.g., electronics, etc.) can reside ex vivo. In the illustrated embodiment, the analyte sensor 34 includes two electrodes, i.e., a working electrode 38 and at least one additional electrode 30, which may function as a counter and/or reference electrode, hereinafter referred to as the reference electrode 30.

In some exemplary embodiments, each electrode is formed from a fine wire with a diameter of from about 0.001 or less to about 0.010 inches or more, for example, and is formed from, e.g., a plated insulator, a plated wire, or bulk electrically conductive material. Although the illustrated electrode configuration and associated text describe one preferred method of forming a transcutaneous sensor, a variety of known transcutaneous sensor configurations can be employed with the transcutaneous analyte sensor system of some embodiments, such as are described in U.S. Pat. No. 6,695,860 to Ward et al., U.S. Pat. No. 6,565,509 to Say et al., U.S. Pat. No. 6,248,067 to Causey III et al., and U.S. Pat. No. 6,514,718 to Heller et al.

In preferred embodiments, the working electrode comprises a wire formed from a conductive material, such as platinum, platinum-iridium, palladium, graphite, gold, carbon, conductive polymer, alloys, or the like. Although the electrodes can by formed by a variety of manufacturing techniques (bulk metal processing, deposition of metal onto a substrate, or the like), it can be advantageous to form the electrodes from plated wire (e.g., platinum on steel wire) or bulk metal (e.g., platinum wire). It is believed that electrodes formed from bulk metal wire provide superior performance (e.g., in contrast to deposited electrodes), including increased stability of assay, simplified manufacturability, resistance to contamination (e.g., which can be introduced in deposition processes), and improved surface reaction (e.g., due to purity of material) without peeling or delamination.

The working electrode 38 is configured to measure the concentration of an analyte, such as but not limited to glucose, uric acid, cholesterol, lactate and the like. In an enzymatic electrochemical sensor for detecting glucose, for example, the working electrode measures the hydrogen peroxide produced by an enzyme catalyzed reaction of the analyte being detected and creates a measurable electronic current. For example, in the detection of glucose wherein glucose oxidase (GOX) produces hydrogen peroxide as a byproduct, $H_2O_2$ reacts with the surface of the working electrode producing two protons ($2H^+$), two electrons ($2e^-$) and one molecule of oxygen ($O_2$), which produces the electronic current being detected.

The working electrode 38 is covered with an insulating material, for example, a non-conductive polymer. Dip-coating, spray-coating, vapor-deposition, or other coating or deposition techniques can be used to deposit the insulating material on the working electrode. In one embodiment, the insulating material comprises parylene, which can be an advantageous polymer coating for its strength, lubricity, and electrical insulation properties. Generally, parylene is produced by vapor deposition and polymerization of para-xylylene (or its substituted derivatives). However, any suitable insulating material can be used, for example, fluorinated polymers, polyethyleneterephthalate, polyurethane, polyimide, other nonconducting polymers, or the like. Glass or ceramic materials can also be employed. Other materials suitable for use include surface energy modified coating systems such as are marketed under the trade names AMC18, AMC148, AMC141, and AMC321 by Advanced Materials Components Express of Bellefonte, Pa. In some alternative embodiments, however, the working electrode may not require a coating of insulator.

Preferably, the reference electrode 30, which may function as a reference electrode alone, or as a dual reference and counter electrode, is formed from silver, silver/silver chloride and the like. Preferably, the electrodes are juxtapositioned and/or twisted with or around each other; however other configurations are also possible. In one example, the reference electrode 30 is helically wound around the working electrode 38 as illustrated in FIG. 2A. The assembly of wires may then be optionally coated together with an insulating material, similar to that described above, in order to provide an insulating attachment (e.g., securing together of the working and reference electrodes).

As described above, conventional transcutaneous devices are believed to suffer from motion artifacts associated with host movement when the host is using the device. For example, when a transcutaneous analyte sensor is inserted into the host, various movements on the sensor (for example, relative movement within and between the subcutaneous space, dermis, skin, and external portions of the sensor) create stresses on the device, which is known to produce artifacts on the sensor signal (e.g., non-constant noise). Accordingly, there are different design considerations (for example, stress considerations) on various sections of the sensor. For example, the in vivo portion of the sensor (e.g., the portion inserted through the host's skin and into the underlying tissue) can benefit in general from greater flexibility as it encounters greater mechanical stresses caused by movement of the tissue within the patient and relative movement between the in vivo and ex vivo portions of the sensor. On the other hand, the ex vivo portion of the sensor (the portion of the sensor that stays outside the body of the host) can benefit in general from a stiffer, more robust design to ensure structural integrity and/or reliable electrical connections. Additionally, in some embodiments wherein a needle is retracted over the ex vivo portion of the device, a stiffer design can minimize crimping of the sensor and/or ease in retraction of the needle from the sensor. Thus, by designing greater flexibility into the in vivo portion, the flexibility is believed to compensate for patient movement, and noise associated therewith. By designing greater stiffness into the ex vivo portion, column strength (for retraction of the needle over the sensor), electrical connections, and integrity can be enhanced. In some alternative embodiments, a stiffer distal end and/or a more flexible proximal end can be advantageous as described in U.S. Patent Publication No. US-2006-0015024-A1 and U.S. Patent Publication No. US-2006-0020187-A1.

Some preferred embodiments provide an in vivo portion of the sensor that is designed to be more flexible than an ex vivo portion of the sensor. The variable stiffness of the sensors of preferred embodiments can be provided by variable pitch of any one or more helically wound wires of the device, variable cross-section of any one or more wires of the device, and/or variable hardening and/or softening of any one or more wires of the device, such as is described in more detail with reference to U.S. Patent Publication No. US-2006-0015024-A1 and U.S. Patent Publication No. US-2006-0020187-A1.

In embodiments wherein an outer insulator is disposed, a portion of the coated assembly structure can be stripped or otherwise removed, for example, by hand, excimer lasing, chemical etching, laser ablation, grit-blasting (e.g., with sodium bicarbonate or other suitable grit), or the like, to expose the electroactive surfaces. Alternatively, a portion of the electrode can be masked prior to depositing the insulator in order to maintain an exposed electroactive surface area. In one exemplary embodiment, grit blasting is implemented to expose the electroactive surfaces, preferably utilizing a grit material that is sufficiently hard to ablate the polymer material, while being sufficiently soft so as to minimize or avoid damage to the underlying metal electrode (e.g., a platinum electrode). Although a variety of "grit" materials can be used (e.g., sand, talc, walnut shell, ground plastic, sea salt, and the like), in some preferred embodiments, sodium bicarbonate is an advantageous grit-material because it is sufficiently hard to ablate, e.g., a parylene coating without damaging, e.g., an underlying platinum conductor. One additional advantage of sodium bicarbonate blasting includes its polishing action on the metal as it strips the polymer layer, thereby eliminating a cleaning step that might otherwise be necessary.

In some embodiments, a radial window is formed through the insulating material to expose a circumferential electroactive surface of the working electrode. Additionally, sections of electroactive surface of the reference electrode are exposed. For example, the sections of electroactive surface can be masked during deposition of an outer insulating layer or etched after deposition of an outer insulating layer. In some applications, cellular attack or migration of cells to the sensor can cause reduced sensitivity and/or function of the device, particularly after the first day of implantation. However, when the exposed electroactive surface is distributed circumferentially about the sensor (e.g., as in a radial window), the available surface area for reaction can be sufficiently distributed so as to minimize the effect of local cellular invasion of the sensor on the sensor signal. Alternatively, a tangential exposed electroactive window can be formed, for example, by stripping only one side of the coated assembly structure. In other alternative embodiments, the window can be provided at the tip of the coated assembly structure such that the electroactive surfaces are exposed at the tip of the sensor. Other methods and configurations for exposing electroactive surfaces can also be employed.

Generally, the sensor electrode(s) can be configured to yield a sensor having a signal-to-noise ratio that is not substantially affected by non-constant noise, such as by systems and methods configured to increase the analyte signal component and/or decrease the non-constant noise component.

In some circumstances, noise can be caused (e.g., during use of an amperometric GOX sensor having a platinum-working electrode) by accumulation of molecular oxygen ($O_2$) on the platinum electrode, which is produced during the electro-oxidation of $H_2O_2$ to water and $O_2$. Platinum black applied to the working electrode can prevent $O_2$ accumulation on a platinum-working electrode, which prevents the occurrence of noise on the sensor. Platinum black is a fine black powder of metallic platinum that can be formed into a paste, ink or paint-like material, which can be applied to a surface (e.g., wire, plastic support) to produce a rough, large surface area coating that is relatively nonpolarizable. Platinum black can be applied to an electrode surface using a platinization process (e.g., to a platinum wire or other platinum surface) or known thin-film techniques, such as dipping, painting or screen-printing, for example. One additional advantage of using platinum black is that a platinum black-coated platinum electrode affords substantive signals from hydrogen peroxide oxidation at a working potential as low as 150 mV, whereas a non-platinum black coated platinum electrode must be operated at a potential of at least 600 mV. Since fewer interferents can be electro-oxidized/reduced at the lower working potential, non-constant noise on the signal will be reduced in sensors operated at a potential lower than 600 mV. Accordingly, in one embodiment, at least the working electrode is coated with platinum black, whereby the non-constant noise component of the signal is reduced and the signal-to-noise ratio is thus adjusted (e.g., increased).

In some embodiments, the signal-to-noise ratio can be rendered substantially unaffected by non-constant noise by distributing the electroactive surface area along a substantial length of the in vivo portion of the sensor. In some embodiments, the electroactive surface area is distributed along 50%, 55%, 60%, 65%, 70%, 75%, 80%, 85%, 90%, 95%, or more of the in vivo portion of the sensor. It is believed that certain interfering electroactive species impinge upon the sensor in a scattered manner (e.g., along the length of the in vivo portion of the sensor). In other words, some transient interferents do not necessarily contact the sensor evenly along the in vivo portion of the sensor. For example, the tissue surrounding an implanted sensor is highly variable. In some circumstances, the electroactive surface may be disposed (when the sensor is implanted) adjacent to a lymph vessel, which can reduce the local concentration of electroactive species that can interfere with the analyte signal and result in a minimal non-constant noise component of the signal. In other circumstances, the electroactive surface may be disposed (when the sensor is implanted) in fat with poor circulation, which may result in build up of electroactive species that can interfere with the sensor's signal adjacent to the electroactive surface, resulting in more non-constant noise on the sensor's signal (e.g., than the surface adjacent to a lymph vessel).

Figure 2B:
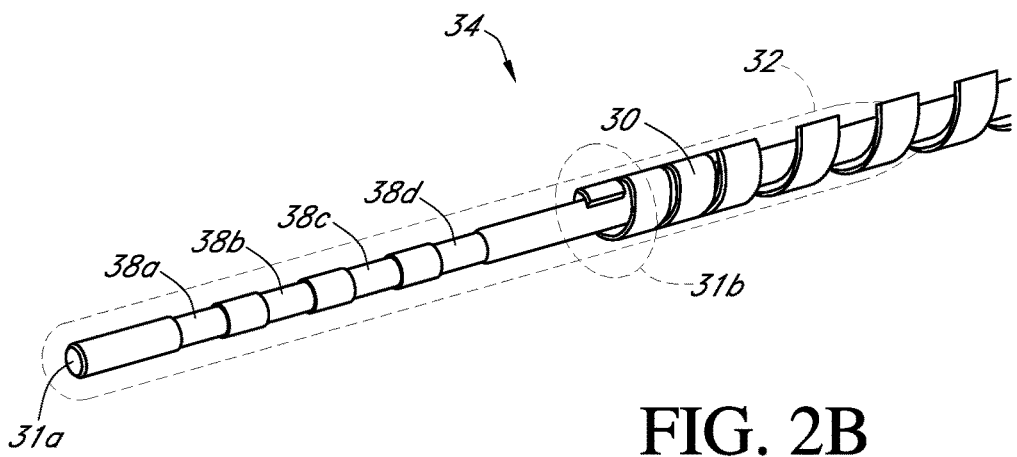
FIG. 2B is a perspective view of an in vivo portion of an analyte sensor, in one embodiment.

FIG. 2B is a perspective view of an in vivo portion of an analyte sensor, in one embodiment, in which the area of electroactive surface has been divided into four equal parts (38a, 38b, 38c, 38d) and distributed along a substantial length of the in vivo portion of the sensor (e.g., spaced apart from each other by a distance such as 1-mm, 2-mm, etc). Accordingly, in some embodiments, the sensor is configured such that the area of the electroactive surface is distributed (e.g., extending, spaced, divided and/or dispersed) along a substantial length of an in vivo portion of the sensor, such that the signal is measured (and can be integrated or averaged) over a more dispersed or distributed portion of the in vivo portion of the sensor (relative to the sensor of FIG. 2A, for example) such that the signal contribution due to the non-constant non-analyte component is less than about 20% of the total signal (e.g., after sensor break-in has been completed). In some embodiments, the area of the electroactive surface can be distributed in a variety of ways, such as but not limited to two or more areas (e.g., 38a, 38b, 38c, 38d, etc.), which cumulatively substantially equal the desired total area of the electroactive surface. The exposed area(s) of the electroactive surface can have any geometric shape, such as circles, dots, rectangles, ovals, stars, and the like. In some embodiments, the exposed surface areas function essentially as microelectrodes along an in vivo portion of the sensor. Microelectrodes can enhance sensor sensitivity, for example by increasing the utilization of the measured electroactive compound due to beneficial edge effects related to a plurality of small surface areas in close proximity to each other. In one exemplary embodiment, a plurality of small spaced electroactive surface areas are able to detect more $H_2O_2$ generated by a glucose oxidase enzyme layer when the plurality of electroactive surfaces are spaced (from each other) within the diffusion distance of $H_2O_2$ (e.g., as compared to one or more electroactive surface areas spaced more than the diffusion distance of $H_2O_2$). Although a wire-type, small-structured sensor is exemplified in the illustrated embodiment, the surface area of a variety of other analyte sensor configurations (e.g., wholly implantable, intravascular, planar-type sensor configured, including implantable continuous sensors and in vitro test strips) can be distributed as described herein. Methods for exposing the sensor's electroactive surface are detailed in U.S. Patent Publication No. US-2006-0020187-A1.

Figure 2C:
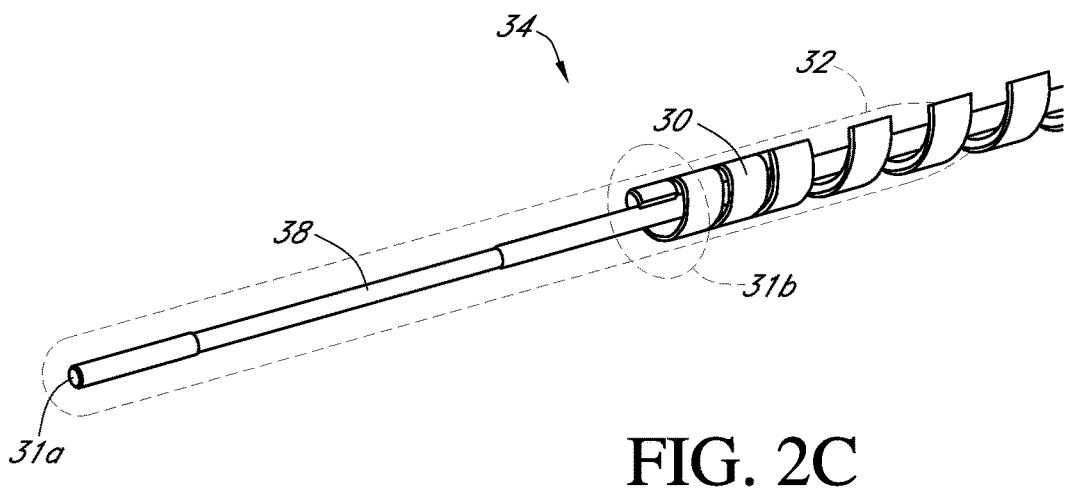
FIG. 2C is a perspective view of an in vivo portion of an analyte sensor, in one embodiment.

FIG. 2C is a perspective view of the in vivo portion of an analyte sensor in one embodiment, wherein the area of the electroactive surface is distributed along a substantial length of the in vivo portion of the analyte sensor. In this embodiment, the area of the electroactive surface 38 is distributed by selecting a working electrode with a preferred width, such that the exposed electroactive surface covers a substantial length of the in vivo portion of the working electrode, while requiring a relatively low current draw. For example, the electroactive surface can be distributed by using a longer, thinner area, such that the electroactive surface covers a substantial length of the in vivo portion of the working electrode, but the total exposed surface area remains unchanged as compared another sensor with a wider, shorter exposed electroactive surface area. For example, in some embodiments, the electrode is formed from a bulk metal wire having a diameter of from about 0.001 to about 0.010 inches. For example, if two sensors are compared, the first sensor having working electrode formed of a 0.001 inch diameter wire with a 1-mm long electroactive surface and the second sensor having a working electrode formed of a 0.010 inch diameter wire with a 0.1-mm long electroactive surface, the two sensors could have the same sensitivity but the signal-to-noise ratio would be rendered substantially unaffected by non-constant noise as compare to that of the second sensor. In some embodiments, the preferred surface area of the working electrode is from about 0.0000839-cm$^2$ or less to about 0.016129-cm$^2$ or more, assuming a diameter of from about 0.001 inches to about 0.010 inches and a length of from about 0.004 inches to about 0.078 inches.

Referring now to FIGS. 2A-2D, some examples of discontinuous surfaces on the sensor are shown, including relatively sharp, abrupt edges, substantially raised surface features or substantial and/or abrupt changes in sensor diameter, such as at the sensor tip 31a and the in vivo termination of the reference electrode 31b. In some circumstances, pockets of a localized, heightened inflammatory response (e.g., an accumulation of inflammatory cells) can form around portions of the sensor having discontinuous surfaces, such as the sensor tip 31a and the in vivo termination 31b of the reference electrode. This phenomenon has been observed, in histological sections of rat tissue explants (after one-day of small-structured sensor implantation), as an accumulation of inflammatory cells around both the sensor tip 31a and the in vivo termination 31b of the reference electrode. In some embodiments, slight diameter changes, such as at the edge of the electroactive surface area of the working electrode, are designed to avoid or minimize a heightened inflammatory response as described above. Such heightened inflammatory responses can be caused by the presence of an increased population of macrophages, lymphocytes, neutrophils, and/or foreign body giant cells, which incites the production of highly diffusible, electroactive noise-causing species in the body, especially free radicals (e.g., reactive oxygen and nitrogen species). Some of the noise-causing compounds produced by the heightened inflammatory response can react at the sensor's working electrode, resulting in noise (e.g., non-constant noise). Accordingly, it is believed that separating the electroactive surface of the working electrode from a discontinuous surface(s), by a distance that is sufficient to minimize or avoid the influence of inflammation at the discontinuous surface (e.g., by a distance substantially farther than the diffusion distance of at least one non-constant noise-causing electroactive species produced by the inflammation), can reduce non-constant noise on the signal to less than about 20% of the total signal. In some preferred embodiments, the electroactive surface of the working electrode is spaced from about 0.020, 0.03, 0.04, or 0.05 inches or less to about 0.06, 0.07, 0.08, 0.09, or 0.100 inches or more from a discontinuous surface, such that non-constant noise is less than about 20% of the total signal and/or the analyte component is at least 80% of the total signal. For example, in one exemplary embodiment, the sensor is configured such that the reference electrode 30 is spaced from the radial window of the working electrode 38 such that the distance (referred to here at the "first distance") between the radial window (e.g., the edge closest to the reference electrode) and the in vivo termination 31*b* of the reference electrode is at least about 0.020-inches, such that the non-constant noise component is less than 20% of the total signal and/or the analyte component is at least 80% of the total signal. In some exemplary embodiments, the first distance is at least 0.030, 0.04, 0.050, 0.060, 0.070, 0.080, 0.090 or 0.100-inches or more. In some exemplary embodiments, the sensor is configured such that the distance between the sensor's tip 31*a* and the nearest edge of the radial window (referred to here as the "second distance") is at least 0.020-inches, such that the non-constant noise component is less than 20% of the total signal and/or the analyte component is at least 80% of the total signal. In some exemplary embodiments, the second distance is at least 0.030, 0.04, 0.050, 0.060, 0.070, 0.080, 0.090 or 0.100-inches or more. In some circumstances, a preferred distance between the electroactive surface of the working electrode and a discontinuous surface to minimize or avoid a heightened inflammatory response can vary, for example, due to factors such as the types/sizes/characteristics of materials used to form the sensor (e.g., electrode material, membrane system components, etc.), differences in tissues into which the sensor is implanted (e.g., type of fat, lean or fat, etc.), the physical state of the host (e.g., illness or injury), the condition of the wound produced during sensor implantation and the like.

Figure 2D:
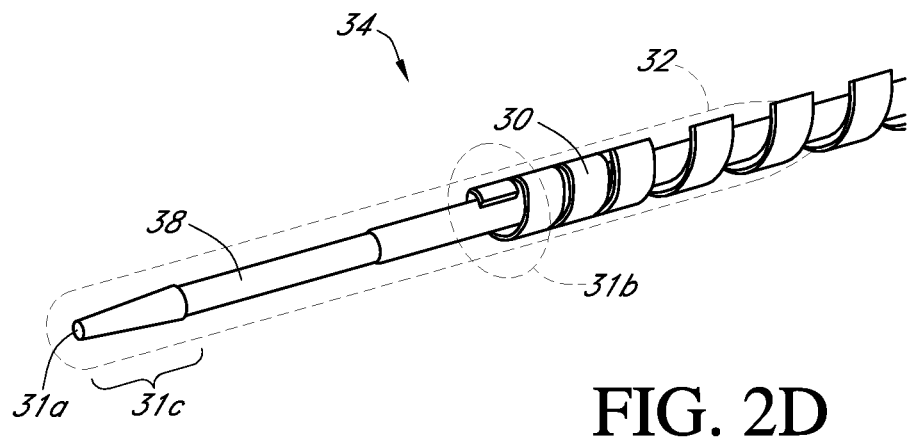
FIG. 2D is a perspective view of an in vivo portion of an analyte sensor, in one embodiment.

FIG. 2D is a perspective view of an in vivo portion of an analyte sensor in one embodiment. In preferred embodiments, the sensor is configured to minimize discontinuous portions and thereby reduce non-constant noise on the signal caused by electroactive species produced from the body's inflammatory response to such discontinuous portions of the sensor. For example, in the embodiment shown in FIG. 2D, the sensor is configured to be substantially non-discontinuous (or substantially continuous) to minimize the inflammatory response, and thus minimize or prevent noise on the signal, such that non-constant noise is less than 20% of the total signal. In one exemplary embodiment, such as shown in FIG. 2D, the tip 31*a* of the sensor is tapered 31*c*. In another exemplary embodiment, a discontinuity at the in vivo termination of the reference electrode 31*b* is reduced (e.g., by minimizing the step difference between at the in vivo termination of the reference electrode), such that the inflammatory response is substantially avoided and non-constant noise is less than about 20% of the total signal and/or the analyte component is at least about 80% of the total signal.

In some embodiments, the sensor is configured to substantially reduce the effect of noise-causing electroactive species caused by inflammation and/or the FBR in response to discontinuous portions of the sensor. In some embodiments, an in vivo portion of the sensor is configured such that the electroactive surface 38 is farther away from the sensor tip 31*a* and/or the end of reference electrode 31*b* than the diffusion distance of at least one noise-causing electroactive species resulting from the host's metabolic processes (e.g., $H_2O_2$ produced outside of the sensor). In some embodiments, some or all discontinuous portions of a sensor are smoothed and/or tapered sufficiently that inflammation and/or a FBR is substantially minimized, such that that noise-causing compounds produced by the inflammation and/or FBR associated with the discontinuous portion do not substantially contribute to the signal. Accordingly, in preferred embodiments, the in vivo portion of the sensor is configured to enable a signal, wherein the non-constant noise component of the total signal is less than about 20%.

In the above-exemplified sensor, an overall diameter of not more than about 0.030 inches is preferred, more preferably not more than about 0.020 inches, and even more preferably not more than about 0.016 inches. In some embodiments, the exposed electroactive surface area has a width of from about 0.001 inches or less to about 0.010 inches or more, preferably from about 0.002 inches to about 0.008 inches, and more preferably from about 0.004 inches to about 0.005 inches. The length of the window can be from about 0.1 mm (about 0.004 inches) or less to about 2 mm (about 0.078 inches) or more, and preferably from about 0.5 mm (about 0.02 inches) to about 0.75 mm (0.03 inches). In such embodiments, the exposed surface area of the working electrode is preferably from about 0.000013 in$^2$ (0.0000839 cm$^2$) or less to about 0.0025 in$^2$ (0.016129 cm$^2$) or more (assuming a diameter of from about 0.001 inches to about 0.010 inches and a length of from about 0.004 inches to about 0.078 inches). In some embodiments, the exposed surface area of the working electrode is selected to produce an analyte signal with a current in the picoAmp range, such as is described in more detail elsewhere herein. However, a current in the picoAmp range can be dependent upon a variety of factors, for example the electronic circuitry design (e.g., sample rate, current draw, A/D converter bit resolution, etc.), the membrane system (e.g., permeability of the analyte through the membrane system), and the exposed surface area of the working electrode. Accordingly, the exposed electroactive working electrode surface area can be selected to have a value greater than or less than the above-described ranges taking into consideration alterations in the membrane system and/or electronic circuitry. In preferred embodiments of a glucose sensor, it can be advantageous to minimize the surface area of the working electrode while maximizing the diffusivity of glucose in order to render the signal-to-noise ratio substantially unaffected by non-constant noise while maintaining sensor performance in both high and low glucose concentration ranges.

In some alternative embodiments, the exposed surface area of the working (and/or other) electrode can be increased by altering the cross-section of the electrode itself. For example, in some embodiments the cross-section of the working electrode can be defined by a cross, star, cloverleaf, ribbed, dimpled, ridged, irregular, or other non-circular configuration; thus, for any predetermined length of electrode, a specific increased surface area can be achieved (as compared to the area achieved by a circular cross-section). Increasing the surface area of the working electrode can be advantageous in providing an increased signal responsive to the analyte concentration, which in turn can be helpful in improving the signal-to-noise ratio, for example.

In some alternative embodiments, additional electrodes can be included within the assembly, for example, a three-electrode system (working, reference, and counter electrodes) and/or an additional working electrode (e.g., an electrode which can be used to generate oxygen, which is configured as a baseline subtracting electrode, or which is configured for measuring additional analytes). U.S. Pat. No. 7,081,195, U.S. Patent Publication No. US-2005-0143635-A1, and U.S. Patent Publication No. US-2007-0027385-A1, each of which are incorporated by reference herein, describe some systems and methods for implementing and using additional working, counter, and/or reference electrodes. In one implementation wherein the sensor comprises two working electrodes, the two working electrodes are juxtapositioned (e.g., extend parallel to each other), around which the reference electrode is disposed (e.g., helically wound). In some embodiments wherein two or more working electrodes are provided, the working electrodes can be formed in a double-, triple-, quad-, etc. helix configuration along the length of the sensor (for example, surrounding a reference electrode, insulated rod, or other support structure). The resulting electrode system can be configured with an appropriate membrane system, wherein the first working electrode is configured to measure a first signal comprising glucose and baseline and the additional working electrode is configured to measure a baseline signal consisting of baseline only (e.g., configured to be substantially similar to the first working electrode without an enzyme disposed thereon). In this way, the baseline signal can be subtracted from the first signal to produce a glucose-only signal that is substantially not subject to fluctuations in the baseline and/or interfering species on the signal. Accordingly, the above-described dimensions can be altered as desired.

In some embodiments, the sensing region may include reference and/or other electrodes associated with the glucose-measuring working electrode and/or separate reference and/or counter electrodes associated with optional auxiliary working electrode(s). In yet another embodiment, the sensing region may include a glucose-measuring working electrode, an auxiliary working electrode, two counter electrodes (one for each working electrode), and one shared reference electrode. In yet another embodiment, the sensing region may include a glucose-measuring working electrode, an auxiliary working electrode, two reference electrodes, and one shared counter electrode. However, a variety of electrode materials and configurations can be used with the implantable analyte sensor of the preferred embodiments.

Co-pending U.S. patent application Ser. No. 11/543,396 filed Oct. 4, 2006 and U.S. Patent Publication No. US-2005-0245799-A1 describe additional configurations for use in different bodily locations. In one exemplary embodiment, the sensor is configured for transcutaneous implantation in the host. In another exemplary embodiment, the sensor is configured for insertion into the circulatory system, such as a peripheral vein or artery. However, in other embodiments, the sensor is configured for insertion into the central circulatory system, such as but not limited to the vena cava. In still other embodiments, the sensor can be configured for insertion into an extracorporeal circulation system, such as but not limited to a shunt (e.g., from an artery to a vein), an extracorporeal blood chemistry analysis device, a dialysis machine or a heart-lung machine (e.g., pumps the blood during heart surgery). In still another embodiment, the sensor can be configured to be wholly implantable, as is described in U.S. Pat. No. 6,001,067.

Although some embodiments illustrate one electrode configuration including one bulk metal wire helically wound around another bulk metal wire, other electrode configurations are also contemplated. In an alternative embodiment, the working electrode comprises a tube with a reference electrode disposed or coiled inside, including an insulator therebetween. Alternatively, the reference electrode comprises a tube with a working electrode disposed or coiled inside, including an insulator therebetween. In another alternative embodiment, a polymer (e.g., insulating) rod is provided, wherein the electrodes are deposited (e.g., electroplated) thereon. In yet another alternative embodiment, a metallic (e.g., steel) rod is provided, coated with an insulating material, onto which the working and reference electrodes are deposited. In yet another alternative embodiment, one or more working electrodes are helically wound around a reference electrode.

Figure 2E:
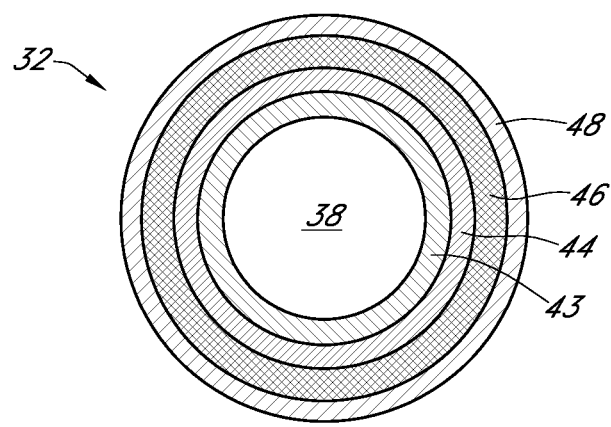
FIG. 2E is a cross-sectional view of the analyte sensor of FIG. 2A, taken along line 2E-2E.

FIG. 2E is a cross-sectional view through the sensor of FIG. 2A on line 2E-2E, illustrating the membrane system 32 in one embodiment. In this embodiment, the membrane system includes an electrode domain 43, an interference domain 44, and enzyme domain 46, and a diffusion resistance domain 48 wrapped around the platinum wire working electrode 38. In some embodiments, this membrane system also includes a cell impermeable domain as described elsewhere herein. In some embodiments, a unitary resistance domain and cell impermeable domain is included in the membrane system (denoted as the resistance domain 48 in this illustration). In some embodiments, the transcutaneous wire sensor is configured for short-term implantation (e.g., from about 1 to 30 days).

Figure 2F:
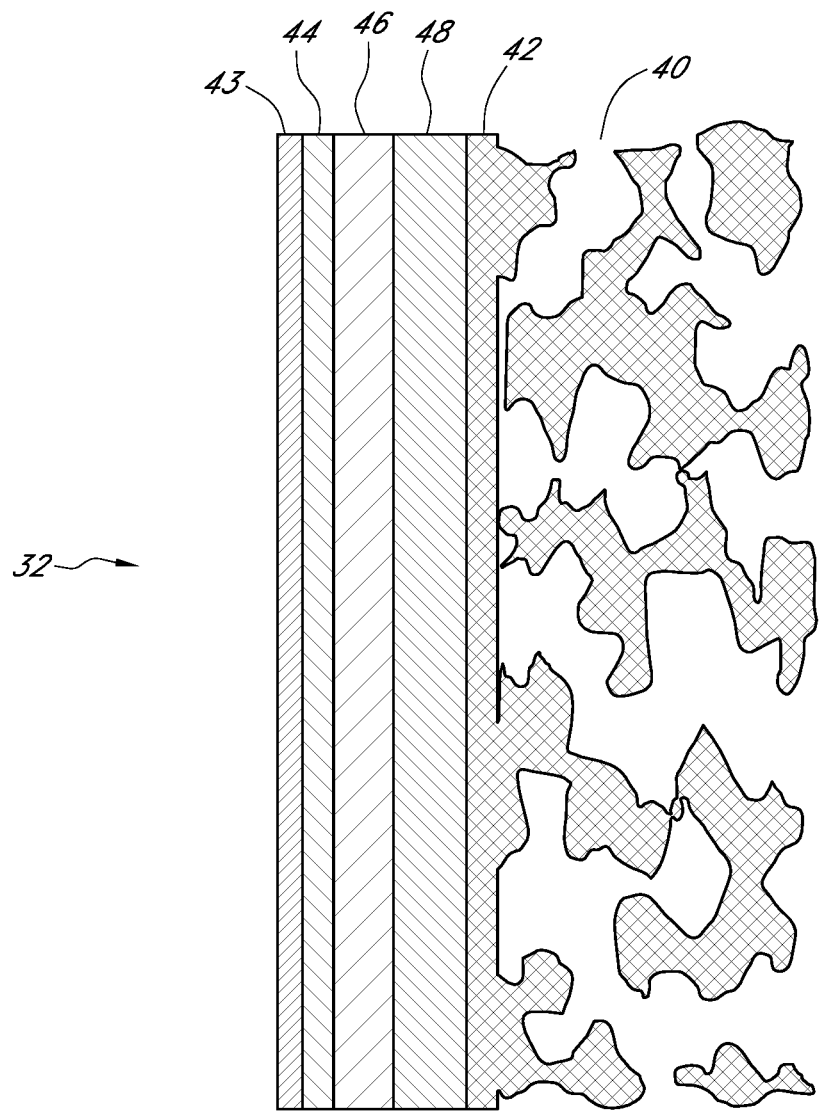
FIG. 2F is a cross-sectional view of a membrane system, in one embodiment.

FIG. 2F is an illustration of a cross-section of a membrane system 32 in an alternative embodiment. The membrane system 32 can be used with a glucose sensor such as those described herein. In this embodiment, the membrane system 32 includes an electrode domain 43 most proximal to the electrochemically reactive surfaces of the working electrode; an (optional) interference domain 44 less proximal to the electrochemically reactive surfaces of the working electrode than the electrode domain; an enzyme domain 46 less proximal to the electrochemically reactive surfaces of the working electrode than the interference domain; a diffusion resistance domain 48 less proximal to the electrochemically reactive surfaces of the working electrode than the enzyme domain; a cell impermeable domain 42 (also referred to as a bioprotective layer) less proximal to the electrochemically reactive surfaces of the working electrode than the diffusion resistance domain; and an optional cell disruptive domain 40 most distal of all domains from the electrochemically reactive surfaces of the working electrode. However, it is understood that the membrane system 32 can be modified for use in other devices, by including only two or more of the layers, or additional layers not recited above.

In general, the sensing membranes 32 of some embodiments include a plurality of domains or layers, for example, an interference domain 44, an enzyme domain 46, and a resistance domain 48, and may include additional domains, such as an electrode domain 43, a cell impermeable domain 42 (also referred to as a bioprotective layer), and/or an oxygen domain (not shown), such as described in more detail in the above-cited U.S. patent publications. However, it is understood that a sensing membrane modified for other sensors, for example, by including fewer or additional domains is within the scope of some embodiments. In some embodiments, one or more domains of the sensing membranes are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones and block copolymers thereof including, for example, di-block, tri-block, alternating, random and graft copolymers. U.S. Patent Publication No. US-2005-024579912-A1 describes biointerface and sensing membrane configurations and materials that may be applied to some embodiments.

In some embodiments, the sensing membrane can be deposited on the electroactive surfaces of the electrode material using known thin or thick film techniques (for example, spraying, electro-depositing, dipping, or the like). It is noted that the sensing membrane that surrounds the working electrode does not have to be the same structure as the sensing membrane that surrounds a reference electrode, etc. For example, the enzyme domain deposited over the working electrode does not necessarily need to be deposited over the reference and/or counter electrodes.

Membrane System

Generally, analyte sensors of the preferred embodiments comprise a membrane system, such as those illustrated in FIGS. 2E and 2F. Preferably, a membrane system is deposited over at least a portion of the electroactive surfaces of the sensor (working electrode(s) and optionally reference electrode) and provides protection of the exposed electrode surface from the biological environment, diffusion resistance (limitation) of the analyte if needed, a catalyst for enabling an enzymatic reaction, limitation or blocking of interferents, and/or hydrophilicity at the electrochemically reactive surfaces of the sensor interface. Some examples of suitable membrane systems are described in U.S. Patent Publication No. US-2005-0245799-A1.

In general, the membrane system 32 includes a plurality of domains, for example, one or more of an electrode domain 43, an interference domain 44, an enzyme domain 46 (for example, including glucose oxidase), and a resistance domain 48, as shown in FIGS. 2B and 2C, and can include a high oxygen solubility domain, a bioprotective domain and/or a cell disruptive domain, such as is described in more detail in U.S. Patent Publication No. US-2005-0245799-A1, and such as are described in more detail below. While the embodiment illustrated in FIGS. 2E and 2F shows the interference domain between the electrode domain and the enzyme domain, the interference domain can be disposed more proximal or more distal to the electroactive surfaces. For example, in some embodiments, the interference domain 44 is more distal to the electroactive surfaces than the enzyme domain. In some embodiments, the interference domain is the most distal layer/domain of the membrane system, relative to the electroactive surfaces. In some embodiments, the interference domain can be the most proximal domain/layer, relative to the electroactive surfaces. In still other embodiments, the interference can be combined with one or more other membrane domains/layers. For example, in some embodiments, the interference domain and the resistance domain are combined into a single domain that provides both interference blocking and control of analyte flux. One skilled in the art appreciates that a wide variety of configurations and combinations encompassed by the preferred embodiments.

The membrane system can be deposited on the exposed electroactive surfaces using known thin film techniques (for example, vapor deposition, spraying, electro-depositing, dipping, or the like). In alternative embodiments, however, other deposition processes (e.g., physical and/or chemical vapor deposition processes) can be useful for providing one or more of the insulating and/or membrane layers, including ultrasonic vapor deposition, electrostatic deposition, evaporative deposition, deposition by sputtering, pulsed laser deposition, high velocity oxygen fuel deposition, thermal evaporator deposition, electron beam evaporator deposition, deposition by reactive sputtering molecular beam epitaxy, atmospheric pressure chemical vapor deposition (CVD), atomic layer CVD, hot wire CVD, low-pressure CVD, microwave plasma-assisted CVD, plasma-enhanced CVD, rapid thermal CVD, remote plasma-enhanced CVD, ultra-high vacuum CVD, and ion implantation for example. However, the membrane system can be disposed over (or deposited on) the electroactive surfaces using any known method, as will be appreciated by one skilled in the art.

In some embodiments, one or more domains of the membrane systems are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers. U.S. Patent Publication No. US-2005-0245799-A1 describes biointerface and membrane system configurations and materials that may be applied to the preferred embodiments.

The function of a membrane system 32 domain is dependent upon a combination of factors, such as but not limited to the domain thickness, the domain composition, the number of layers in the domain (or in the membrane as a whole) and the way the layers are applied (e.g., several thin layers may give better/complete coverage where one thick layer may not completely cover). In preferred embodiments, these factors are configured to provide a membrane system that renders the sensor's signal-to-noise ratio would be rendered substantially unaffected by non-constant noise. The sensor's signal-to-noise ratio can by rendered substantially unaffected by non-constant noise either by substantially increasing the analyte component (e.g., without a corresponding increase in the noise component) or by substantially reducing the noise component (e.g., without substantially reducing the analyte component).

Accordingly, in some preferred embodiments, membrane system 32 is configured to render the sensor's signal-to-noise ratio substantially unaffected by non-constant noise by substantially increasing the diffusion of glucose therein, while diffusion of at least one interferent (e.g., $H_2O_2$ formed outside the membrane system) into the membrane system is substantially unaffected, such that the analyte component is at least 80% of the total signal. Alternatively or additionally, in some preferred embodiments, the membrane system is configured to render the sensor's signal-to-noise ratio to be substantially unaffected by non-constant noise by reducing the noise component (e.g., non-constant noise) of the total signal without a corresponding reduction in the analyte component. In some preferred embodiments, the membrane system is configured to both increase the analyte signal component and reduce the non-constant noise signal component.

In one preferred embodiment, an analyte sensor includes a membrane system disposed over an electrode, such as the working electrode, wherein the membrane system is configured for inactivation of electroactive species that can interfere with the analyte signal. In other preferred embodiments, the membrane system is configured to substantially consume at least one electroactive compound (that interferes with the analyte signal) diffusing therein, such that the compound is substantially prevented from reaching the electroactive surface. The term "consumed" as used herein is a broad term and is used in its ordinary sense, including, without limitation, to render the interferent substantially non-reactive with the electroactive surface and/or the voltage potential of the sensor, such as by oxidation or reduction of the interferent. For example, the membrane system can interact with the interferent such that the interferent's redox potential is changed and the interferent is substantially unable to be oxidized and/or reduced when the interferent contacts the electroactive surface, at the voltage potential at which the sensor operates. In various embodiments, the membrane system is configured to substantially consume at least one interfering species by at least one of the following: a torturous diffusion path, a thickness of from about 2 µm to about 100 µm or more, a peroxidase, oxidase, catalase and/or a Heme compound, and the like, which are described in more detail elsewhere herein. In some preferred embodiments, the membrane thickness is from about 5 µm to about 50 µm.

Electrode Domain

In selected embodiments, the membrane system comprises an electrode domain. The electrode domain 43 is provided to ensure that an electrochemical reaction occurs between the electroactive surfaces of the working electrode and the reference electrode, and thus the electrode domain 43 is preferably situated more proximal to the electroactive surfaces than the interference and/or enzyme domain. Preferably, the electrode domain includes a coating that maintains a layer of water at the electrochemically reactive surfaces of the sensor. In other words, the electrode domain is present to provide an environment between the surfaces of the working electrode and the reference electrode, which facilitates an electrochemical reaction between the electrodes. For example, a humectant in a binder material can be employed as an electrode domain; this allows for the full transport of ions in the aqueous environment. The electrode domain can also assist in stabilizing the operation of the sensor by accelerating electrode start-up and drifting problems caused by inadequate electrolyte. The material that forms the electrode domain can also provide an environment that protects against pH-mediated damage that can result from the formation of a large pH gradient due to the electrochemical activity of the electrodes.

In one embodiment, the electrode domain 43 includes a flexible, water-swellable, hydrogel film having a "dry film" thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 3, 2.5, 2, or 1 microns, or less to about 3.5, 4, 4.5, or 5 microns or more. "Dry film" thickness refers to the thickness of a cured film cast from a coating formulation by standard coating techniques.

In certain embodiments, the electrode domain 43 is formed of a curable mixture of a urethane polymer and a hydrophilic polymer. Particularly preferred coatings are formed of a polyurethane polymer having carboxylate or hydroxyl functional groups and non-ionic hydrophilic polyether segments, wherein the polyurethane polymer is crosslinked with a water-soluble carbodiimide (e.g., 1-ethyl-3-(3-dimethylaminopropyl)carbodiimide (EDC)) in the presence of polyvinylpyrrolidone and cured at a moderate temperature of about 50° C.

In some preferred embodiments, the electrode domain 43 is formed from a hydrophilic polymer (e.g., a polyamide, a polylactone, a polyimide, a polylactam, a functionalized polyamide, a functionalized polylactone, a functionalized polyimide, a functionalized polylactam or a combination thereof) that renders the electrode domain substantially more hydrophilic than an overlying domain, (e.g., interference domain, enzyme domain). In some embodiments, the electrode domain is formed substantially entirely and/or primarily from a hydrophilic polymer. In some embodiments, the electrode domain is formed substantially entirely from PVP. In some embodiments, the electrode domain is formed entirely from a hydrophilic polymer. Useful hydrophilic polymers include but are not limited to poly-N-vinylpyrrolidone (PVP), poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, polyvinylimidazole, poly-N,N-dimethylacrylamide, polyvinyl alcohol (PVA), polyHEME, Poly-methyl methacrylate (PMMA), ethylene vinyl acetate (EVA), PGA-PEG, polyanhydrides, polyacrylic acid, polyethylene oxide, poly-2-ethyl-oxazoline, copolymers thereof and mixtures thereof. A blend of two or more hydrophilic polymers is preferred in some embodiments. In some preferred embodiments, the hydrophilic polymer(s) is not cross-linked. In alternative embodiments, crosslinking is preferred, such as by adding a crosslinking agent, such as but not limited to EDC, or by irradiation at a wavelength sufficient to promote crosslinking between the hydrophilic polymer molecules, which is believed to create a more tortuous diffusion path through the domain.

An electrode domain formed from a hydrophilic and/or conductive polymer (e.g., PVP and buffer) has been shown to substantially reduce break-in time of analyte sensors; for example, a glucose sensor utilizing a cellulosic-based interference domain such as described in more detail elsewhere herein. In some embodiments, a uni-component electrode domain formed from a single hydrophilic polymer (e.g., PVP) has been shown to substantially reduce break-in time of a glucose sensor to less than about 2 hours, less than about 1 hour, less than about 20 minutes and/or substantially immediately. Generally, sensor break-in is the amount of time required (after implantation) for the sensor signal to become substantially representative of the analyte concentration. Sensor break-in includes both membrane break-in and electrochemical break-in, which are described in more detail elsewhere herein. In some embodiments, break-in time is less than about 2 hours. In other embodiments, break-in time is less than about 1 hour. In still other embodiments, break-in time is less than about 30 minutes, less than about 20 minutes, less than about 15 minutes, less than about 10 minutes, or less. In a preferred embodiment, sensor break-in occurs substantially immediately. Advantageously, in embodiments wherein the break-in time is about 0 minutes (substantially immediately), the sensor can be inserted and begin providing substantially accurate analyte (e.g., glucose) concentrations almost immediately post-insertion, for example, wherein membrane break-in does not limit start-up time.

While not wishing to be bound by theory, it is believed that providing an electrode domain that is substantially more hydrophilic than the next more distal membrane layer or domain (e.g., the overlaying domain; the layer more distal to the electroactive surface than the electrode domain, such as an interference domain or an enzyme domain) reduces the break-in time of an implanted sensor, by increasing the rate at which the membrane system is hydrated by the surrounding host tissue. While not wishing to be bound by theory, it is believed that, in general, increasing the amount of hydrophilicity of the electrode domain relative to the overlaying layer (e.g., the distal layer in contact with electrode domain, such as the interference domain, enzyme domain, etc.) increases the rate of water absorption, resulting in reduced sensor break-in time. The hydrophilicity of the electrode domain can be substantially increased by the proper selection of hydrophilic polymers, based on their hydrophilicity relative to each other and relative to the overlaying layer (e.g., cellulosic-based interference domain), with preferred polymers being substantially more hydrophilic than the overlaying layer. In one exemplary embodiment, PVP forms the electrode domain, the interference domain is formed from a blend of cellulosic derivatives, such as but not limited to cellulose acetate butyrate and cellulose acetate; it is believed that since PVP is substantially more hydrophilic than the cellulosic-based interference domain, the PVP rapidly draws water into the membrane to the electrode domain, and enables the sensor to function with a desired sensitivity and accuracy and starting within a substantially reduced time period after implantation. Reductions in sensor break-in time reduce the amount of time a host must wait to obtain sensor readings, which is particularly advantageous not only in ambulatory applications, but particularly in hospital settings where time is critical. In some alternative embodiments, a hydrophilic (e.g., PVP) electrode domain can be formed under a silicone-pluronic polymer blend interference domain, such that the sensor break-in time is substantially reduced.

While not wishing to be bound by theory, it is believed that when the water absorption of the overlaying domain (e.g., the domain overlaying the electrode domain) is less than the water absorption of the electrode domain (e.g., during membrane equilibration), then the difference in water absorption between the two domains will drive membrane equilibration and thus membrane break-in. Namely, increasing the difference in hydrophilicity (e.g., between the two domains) results in an increase in the rate of water absorption, which, in turn, results in a decrease in membrane break-in time and/or sensor break-in time.

Generally, the molecular weight of the analyte is substantially higher than that of many electroactive species that can interfere with the analyte signal, for example, reactive oxygen and nitrogen species. As one example, the molecular weight of glucose is 180 g/mole, while the molecular weight of $H_2O_2$ is 34.02 g/mole. Diffusion of a molecule through the membrane system is substantially regulated by the membrane's porosity (e.g., the size of the pores) and hydrophilicity. Since small molecules, such as $H_2O_2$ and reactive oxygen and nitrogen species, etc., generally diffuse through many membrane systems at substantially their maximum rates (e.g., due to their small size), many membrane system configuration modifications have substantially little affect on their diffusion rates. In contrast, due to its larger size, the diffusion of the analyte (e.g., glucose) through the membrane system is substantially slowed. It is believed that increasing the diffusion rate of the analyte (through the membrane system) does not substantially affect the diffusion rate the above-described small molecules. However, increasing the difference in hydrophilicity (e.g., between the two domains) substantially increases the diffusion rate of the analyte, without an equivalent increase in the diffusion of small molecules, such that the analyte component (e.g., of the total signal) is increased, while the noise component (e.g., of the total signal) remains substantially unchanged, which adjusts (e.g., increases) the signal-to-noise ratio. The adjusted signal-to-noise ratio resulting from inclusion of a hydrophilic electrode domain (e.g., 2×PVP in some embodiments) increases sensor sensitivity and reduces sensor error, which advantageously adjusts the signal to noise ratio of the sensor over which it is located.

As discussed elsewhere herein, the relative hydrophilicity of the electrode domain 43 as compared to the overlying domain(s) can be modulated by the selection of more hydrophilic materials for formation of the electrode domain (and/or more hydrophobic materials for the overlying domain(s)). For example, an electrode domain with hydrophilic polymer capable of absorbing larger amounts of water can be selected instead of a second hydrophilic polymer that is capable of absorbing less water than the first hydrophilic polymer. In some embodiments, the water content difference between the electrode domain and the overlying domain (e.g., during or after membrane equilibration) is from about 1% or less to about 90% or more. In other embodiments, the water content difference between the electrode domain and the overlying domain is from about 10% or less to about 80% or more. In still other embodiments, the water content difference between the electrode domain and the overlying domain is from about 30% or less to about 60% or more. In preferred embodiments, the electrode domain absorbs 5 wt. % or less to 95 wt. % or more water, preferably 5, 10, 15, 20, 25, 30, 35, 40, 45, or 50 wt. % to about 55, 60, 65, 70, 75, 80, 85, 90 or 95 wt. % water than the adjacent (overlying) domain (e.g., the domain that is more distal to the electroactive surface than the electrode domain).

In another example, the rate of water absorption by a polymer can be affected by other factors, such as but not limited to the polymer's molecular weight. For example, the rate of water absorption by PVP is dependent upon its molecular weight, which is typically from about 40-kDa or less to about 360-kDa or more; with a lower molecular weight PVP (e.g., 40-kDa) absorbing water faster than a higher molecular weight PVP. Accordingly, modulating factors, such as molecular weight, that affect the rate of water absorption by a polymer, can promote the proper selection of materials for electrode domain fabrication. In one embodiment, a lower molecular weight PVP is selected, to reduce break-in time.

Preferably, the electrode domain is deposited by known thin film deposition techniques (e.g., spray coating or dip-coating the electroactive surfaces of the sensor). In some embodiments, the electrode domain is formed by dip-coating the electroactive surfaces in an electrode domain solution (e.g., 5, 10, 15, 20, 25 or 30% or more PVP in deionized water) and curing the domain for a time of from about 15 minutes to about 30 minutes at a temperature of from about 40° C. to about 55° C. (and can be accomplished under vacuum (e.g., 20 to 30 mmHg)). In embodiments wherein dip-coating is used to deposit the electrode domain, a preferred insertion rate of from about 1 inch to about 3 inches per minute into the electrode domain solution, with a preferred dwell time of from about 0.5 minutes to about 2 minutes in the electrode domain solution, and a preferred withdrawal rate of from about 0.25 inches to about 2 inches per minute from the electrode domain solution provide a functional coating. However, values outside of those set forth above can be acceptable or even desirable in certain embodiments, for example, depending upon solution viscosity and solution surface tension, as is appreciated by one skilled in the art. In one embodiment, the electroactive surfaces of the electrode system are dip-coated one time (one layer) and cured at 50° C. under vacuum for 20 minutes. In another embodiment, the electroactive surfaces of the electrode system is dip-coated and cured at 50° C. under vacuum for 20 minutes a first time, followed by dip coating and curing at 50° C. under vacuum for 20 minutes a second time (two layers). In still other embodiments, the electroactive surfaces can be dip-coated three or more times (three or more layers). In other embodiments, the 1, 2, 3 or more layers of PVP are applied to the electroactive surfaces by spray coating or vapor deposition. In some embodiments, a crosslinking agent (e.g., EDC) can be added to the electrode domain casting solution to promote crosslinking within the domain (e.g., between electrode domain polymer components, latex, etc.). In some alternative embodiments however, no crosslinking agent is used and the electrode domain is not substantially crosslinked.

In some embodiments, the deposited PVP electrode domain 43 has a "dry film" thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns.

Although an independent electrode domain 43 is described herein, in some embodiments sufficient hydrophilicity can be provided in the interference domain and/or enzyme domain (the domain adjacent to the electroactive surfaces) so as to provide for the full transport of ions in the aqueous environment (e.g. without a distinct electrode domain). In these embodiments, an electrode domain is not necessary.

Interference Domain

In some embodiments, the membrane system 34 comprises an interference domain 44 configured to substantially reduce and/or block diffusion of one or more noise-causing interferents into the membrane system, and thereby increase the signal-to-noise ratio of the sensor. In some embodiments, the interference domain 44 is a component of the membrane system, such as shown in FIGS. 2E and 2F. However, the interference domain can be disposed at any level (e.g., layer or domain) of the membrane system (e.g., more proximal or more distal to the electroactive surfaces than as shown in FIGS. 2E and 2F). In some other embodiments, the interference domain is combined with an additional membrane domain, such as the resistance domain or the enzyme domain.

As discussed elsewhere herein, noise can occur during the first few hours or days after sensor implantation, such as during periods of inactivity (e.g., intermittent, sedentary noise), and is believed to be caused by a local increase in interferants (e.g., electroactive metabolites) that disrupts sensor function, resulting in apparent glucose signals that are generally unrelated to the host's glucose concentration. While not wishing to be bound by theory, it is believed that the noise intensity and/or number of intermittent, sedentary noise occurrences can be reduced or eliminated by reducing the local concentration of interferants, such as by incorporation of an interference domain 44 into the membrane system 34. In general, the term "interference domain" includes any noise-reducing mechanism that substantially blocks, reduces, eliminates, reacts with, or otherwise keeps an interferant from reacting at the working electrode(s). "Noise-reducing mechanisms" as used herein is a broad term, and is to be given its ordinary and customary meaning to a person of ordinary skill in the art (and it is not to be limited to a special or customized meaning), and refers without limitation to any sensor system component or configuration that reduces and/or eliminates noise on the sensor signal. Some noise-reducing mechanisms include but are not limited to electrode configurations (e.g., two or more working electrodes), membrane configurations (e.g., interference domain), algorithmic configurations (e.g., signal processing to remove an identified noise component of the signal), and the like. Additionally, the noise-reducing mechanisms described herein, including structures, membrane materials, bioactive agents, and the like, which can reduce the effect of interfering species (noise) on the sensor signal, can be considered at least a part of an "interference domain." Some examples of interference domain structures are described herein in this section entitled, "Interference Domain." However, other known interference domain structures can be implemented with the sensors described herein. While the embodiments shown in FIGS. 2E and 2F show the interference domain 44 located between the electrode and enzyme domains, the interference domain can be disposed at any level of the membrane system (e.g., more proximal or more distal to the electroactive surfaces). For example, the interference domain can be disposed between the enzyme domain and the resistance domain, between the electroactive surfaces and the electrode domain, as the most exterior membrane domain, etc. In some embodiments, any domain of the membrane system can be configured to function as an interference domain or combined with the interference domain. For example, the enzyme domain and interference domain can be combined into an enzyme-interference domain that performs the functions of an enzyme domain and an interference domain.

In one preferred embodiment, the membrane system includes an interference domain that is configured to substantially reduce noise (e.g., non-constant noise) caused by one or more endogenous or exogenous interferents. In preferred embodiments, the signal-to-noise ratio can be adjusted (e.g., increased) by incorporation of an interference domain of the preferred embodiments onto a sensor. In some preferred embodiments, the interference domain is configured such that the analyte component is at least about 80% of the total signal for a period of at least about one day. In some preferred embodiments, the interference domain is configured such that the non-constant noise component is less than about 20% of the total signal for at least about one day.

As illustrated in FIGS. 2E and 2F, the membrane system 32 of the preferred embodiments includes an interference domain 44. In some preferred embodiments, an interference domain is provided that substantially restricts or blocks the flow of one or more interfering species therethrough. In some embodiments, the interference domain can be configured to reduce noise (and adjust the signal-to-noise ratio) using, one, two or more noise-reducing mechanisms. For example, in some embodiments, the interference domain is configured to substantially block passage of at least one interfering species into the membrane system. In some embodiments, the interference domain is configured to substantially reduce the concentration of at least one interferent. For example, the interferent can be diluted, such as by promoting an increased fluid bulk and/or formation of a fluid pocket around the sensor. Alternatively or additionally, the interferent concentration can be substantially reduced by configuring the interference domain to increase bulk fluid flow (e.g., which carries interferents away via the lymph system). In other embodiments, the interference domain is configured to oxidize and/or reduce an interferent, such that the interferent no longer substantially affects the sensor. In some embodiments, the interference domain is configured to reduce the non-constant noise (and adjust the signal-to-noise ratio) by combining two or more noise-reducing mechanisms, as described below. Some known interfering species for a glucose sensor, as described in more detail herein, include acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid. In some embodiments, the interference domain of the preferred embodiments is less permeable to one or more of the interfering species than to the measured species, e.g., the product of an enzymatic reaction that is measured at the electroactive surface(s), such as but not limited to $H_2O_2$.

Cellulosic Polymer Materials

In one embodiment, the interference domain 44 is formed from one or more cellulosic derivatives. Cellulosic derivatives can include, but are not limited to, cellulose esters and cellulose ethers. In general, cellulosic derivatives include polymers such as cellulose acetate, cellulose acetate butyrate, 2-hydroxyethyl cellulose, cellulose acetate phthalate, cellulose acetate propionate, cellulose acetate trimellitate, and the like, as well as their copolymers and terpolymers with other cellulosic or non-cellulosic monomers. Cellulose is a polysaccharide polymer of β-D-glucose. While cellulosic derivatives are generally preferred, other polymeric polysaccharides having similar properties to cellulosic derivatives can also be employed in the preferred embodiments.

In one preferred embodiment, the interference domain 44 is formed from cellulose acetate butyrate. Cellulose acetate butyrate with a molecular weight of from about 10,000 daltons to about 75,000 daltons, preferably from about 15,000, 20,000, or 25,000 daltons to about 50,000, 55,000, 60,000, 65,000, or 70,000 daltons, and more preferably about 20,000 daltons is employed. In certain embodiments, however, higher or lower molecular weights can be preferred. In some embodiments, a blend of two or more cellulose acetate butyrates having different molecular weights is preferred. While a "blend" as defined herein (a composition of two or more substances that are not substantially chemically combined with each other and are capable of being separated) is generally preferred, in certain embodiments a single polymer incorporating different constituents (e.g., separate constituents as monomeric units and/or substituents on a single polymer chain) can be employed instead. Additionally, a casting solution or dispersion of cellulose acetate butyrate at a weight percent of from about 5% to about 25%, preferably from about 5%, 6%, 7%, 8%, 9%, 10%, 11%, 12%, 13%, 14% or 15% to about 16%, 17%, 18%, 19%, 20%, 21%, 22%, 23%, 24% or 25%, and more preferably from about 5% to about 15% is preferred. Preferably, the casting solution includes a solvent or solvent system, for example an acetone:ethanol solvent system. Higher or lower concentrations can be preferred in certain embodiments. In alternative embodiments, a single solvent (e.g., acetone) is used to form a symmetrical membrane domain. A single solvent is used in casting solutions for forming symmetrical membrane layer(s). A plurality of layers of cellulose acetate butyrate can be advantageously combined to form the interference domain in some embodiments, for example, three layers can be employed. It can be desirable to employ a mixture of cellulose acetate butyrate components with different molecular weights in a single solution, or to deposit multiple layers of cellulose acetate butyrate from different solutions comprising cellulose acetate butyrate of different molecular weights, different concentrations, and/or different chemistries (e.g., functional groups). It can also be desirable to include additional substances in the casting solutions or dispersions, e.g., functionalizing agents, crosslinking agents, other polymeric substances, substances capable of modifying the hydrophilicity/hydrophobicity of the resulting layer, and the like.

In one alternative embodiment, the interference domain 44 is formed from cellulose acetate. Cellulose acetate with a molecular weight of from about 30,000 daltons or less to about 100,000 daltons or more, preferably from about 35,000, 40,000, or 45,000 daltons to about 55,000, 60,000, 65,000, 70,000, 75,000, 80,000, 85,000, 90,000, or 95,000 daltons, and more preferably about 50,000 daltons is preferred. In some embodiments, a blend of two or more cellulose acetates having different molecular weights is preferred. Additionally, a casting solution or dispersion of cellulose acetate at a weight percent of from about 3% to about 10%, preferably from about 3.5%, 4.0%, 4.5%, 5.0%, 5.5%, 6.0%, or 6.5% to about 7.5%, 8.0%, 8.5%, 9.0%, or 9.5%, and more preferably about 8% is preferred. In certain embodiments, however, higher or lower molecular weights and/or cellulose acetate weight percentages can be preferred. It can be desirable to employ a mixture of cellulose acetates with molecular weights in a single solution, or to deposit multiple layers of cellulose acetate from different solutions comprising cellulose acetates of different molecular weights, different concentrations, or different chemistries (e.g., functional groups). It can also be desirable to include additional substances in the casting solutions or dispersions such as described in more detail above.

In addition to forming an interference domain from only cellulose acetate(s) or only cellulose acetate butyrate(s), the interference domain 44 can be formed from combinations or blends of cellulosic derivatives, such as but not limited to cellulose acetate and cellulose acetate butyrate, or combinations of layer(s) of cellulose acetate and layer(s) of cellulose acetate butyrate. In some embodiments, a blend of cellulosic derivatives (for formation of an interference domain) includes up to about 10 wt. % or more of cellulose acetate. For example, about 1, 2, 3, 4, 5, 6, 7, 8, 9 wt. % or more cellulose acetate is preferred, in some embodiments. In some embodiments, the cellulosic derivatives blend includes from about 90 wt. % or less to about 100 wt. % cellulose acetate butyrate. For example, in some embodiments, the blend includes about 91, 92, 93, 94, 95, 96, 97, 98 or 99 wt. % cellulose acetate butyrate. In some embodiments, the cellulosic derivative blend includes from about 1.5, 2.0, 2.5, 3.0 or 3.5 wt. % cellulose acetate to about 98.5, 98.0, 97.5, 97.0 or 96.5 wt. % cellulose acetate butyrate. In other embodiments, the blend includes from about 4, 4.5, 5, 5.5, 6, 6.5, 7, 7.5 or 8 wt. % cellulose acetate to about 96, 95.5, 95, 94.5, 94, 93.3, 93, 92.5 or 92 wt. % cellulose acetate butyrate. In still other embodiments, the blend includes from about 8.5, 9.0, 9.5, 10.0, 10.5 or 11.0 wt. % cellulose acetate to about 91.5, 91.0, 90.5, 90, 89.5 or 89 wt. % cellulose acetate butyrate.

In some embodiments, preferred blends of cellulose acetate and cellulose acetate butyrate contain from about 1.5 parts or less to about 60 parts or more cellulose acetate butyrate to one part of cellulose acetate. In some embodiments, a blend contains from about 2 parts to about 40 parts cellulose acetate butyrate to one part cellulose acetate. In other embodiments, about 4, 6, 8, 10, 12, 14, 16, 18 or 20 parts cellulose acetate butyrate to one part cellulose acetate is preferred for formation of the interference domain 26. In still other embodiments, a blend having from 22, 24, 26, 28, 30, 32, 34, 36 or 38 parts cellulose acetate butyrate to one part cellulose acetate is preferred. As is discussed elsewhere herein, cellulose acetate butyrate is relatively more hydrophobic than cellulose acetate. Accordingly, the cellulose acetate/cellulose acetate butyrate blend contains substantially more hydrophobic than hydrophilic components.

Cellulose acetate butyrate is a cellulosic polymer having both acetyl and butyl groups, in addition to hydroxyl groups. Acetyl groups are more hydrophilic than butyl groups, and hydroxyl groups are more hydrophilic than both acetyl and butyl groups. Accordingly, the relative amounts of acetyl, butyl and hydroxyl groups can be used to modulate the hydrophilicity/hydrophobicity of the cellulose acetate butyrate of the cellulose acetate/cellulose acetate butyrate blend. A cellulose acetate butyrate can be selected based on the compound's relative amounts of acetate, butyrate and hydroxyl groups; and a cellulose acetate can be selected based on the compounds relative amounts of acetate and hydroxyl groups. For example, in some embodiments, a cellulose acetate butyrate having about 35% or less acetyl groups, about 10% to about 25% butyl groups, and hydroxyl groups making up the remainder is preferred for formation of the interference domain 44. In other embodiments a cellulose acetate butyrate having from about 25% to about 34% acetyl groups and from about 15 to about 20% butyl groups is preferred. In still other embodiments, the preferred cellulose acetate butyrate contains from about 28% to about 30% acetyl groups and from about 16 to about 18% butyl groups. In yet another embodiment, the cellulose acetate butyrate can have no acetate groups and from about 20% to about 60% butyrate groups. In yet another embodiment, the cellulose acetate butyrate has about 55% butyrate groups and no acetate groups.

While an asymmetric interference domain can be used in some alternative embodiments, a symmetrical interference domain 44 (e.g., of cellulosic-derivative blends, such as but not limited to blends of cellulose acetate components and cellulose acetate butyrate components) is preferred in some embodiments. Symmetrical membranes are uniform throughout their entire structure, without gradients of pore densities or sizes, or a skin on one side but not the other, for example. In various embodiments, a symmetrical interference domain can be formed by the appropriate selection of a solvent (e.g., no anti-solvent is used), for making the casting solution. Appropriate solvents include solvents belonging to the ketone family that are able to solvate the cellulose acetate and cellulose acetate butyrate. The solvents include but are not limited to acetone, methyl ethyl ketone, methyl n-propyl ketone, cyclohexanone, and diacetone alcohol. Other solvents, such as furans (e.g., tetra-hydro-furan and 1,4-dioxane), may be preferred in some embodiments. In one exemplary embodiment, from about 7 wt. % to about 9 wt. % solids (e.g., a blend of cellulosic derivatives, such as cellulose acetate and cellulose acetate butyrate) are blended with a single solvent (e.g., acetone), to form the casting solution for a symmetrical interference domain. In another embodiment, from about 10% to about 15% solids are blended with acetone to form the casting solution. In yet another embodiment, from about 16 to about 18% solids are blended with acetone to form the casting solution. A relatively lower or greater weight percent of solids is preferred to form the casting solution, in some embodiments.

The casting solution can be applied either directly to the electroactive surface(s) of the sensor or on top of an electrode domain layer (if included in the membrane system). The casting solution can be applied using any known thin film technique, as discussed elsewhere herein. Additionally, in various embodiments, a symmetrical interference domain 44 includes at least one layer; and in some embodiments, two, three or more layers are formed by the sequential application and curing of the casting solution.

The concentration of solids in the casting solution can be adjusted to deposit a sufficient amount of solids on the electrode in one layer (e.g., in one dip or spray) to form a membrane layer with sufficient blocking ability, such that the equivalent glucose signal of an interferent (e.g., compounds with an oxidation or reduction potential that overlaps with that of the measured species (e.g., $H_2O_2$)), measured by the sensor, is about 60 mg/dL or less. For example, in some embodiments, the casting solution's percentage of solids is adjusted such that only a single layer (e.g., dip one time) is required to deposit a sufficient amount of the cellulose acetate/cellulose acetate butyrate blend to form a functional symmetric interference domain that substantially blocks passage therethrough of at least one interferent, such as but not limited to acetaminophen, ascorbic acid, dopamine, ibuprofen, salicylic acid, tolbutamide, tetracycline, creatinine, uric acid, ephedrine, L-dopa, methyl dopa and tolazamide. In some embodiments, the amount of interference domain material deposited by as single dip is sufficient to reduce the equivalent glucose signal of the interferant (e.g., measured by the sensor) to about 60 mg/dl or less. In preferred embodiments, the interferent's equivalent glucose signal response (measured by the sensor) is 50 mg/dl or less. In more preferred embodiments, the interferent produces an equivalent glucose signal response of 40 mg/dl or less. In still more preferred embodiments, the interferent produces an equivalent glucose signal response of less than about 30, 20 or 10 mg/dl. In one exemplary embodiment, the interference domain is configured to substantially block acetaminophen passage therethrough, wherein the equivalent glucose signal response of the acetaminophen is less than about 30 mg/dl.

In alternative embodiments, the interference domain is configured to substantially block a therapeutic dose of acetaminophen. The term "therapeutic dose" as used herein is a broad term, and is to be given its ordinary and customary meaning to a person of ordinary skill in the art (and is not to be limited to a special or customized meaning), and refers without limitation to the quantity of any substance required to effect the cure of a disease, to relieve pain, or that will correct the manifestations of a deficiency of a particular factor in the diet, such as the effective dose used with therapeutically applied compounds, such as drugs. For example, a therapeutic dose of acetaminophen can be an amount of acetaminophen required to relieve headache pain or reduce a fever. As a further example, 1,000 mg of acetaminophen taken orally, such as by swallowing two 500 mg tablets of acetaminophen, is the therapeutic dose frequently taken for headaches. In some embodiments, the interference membrane is configured to block a therapeutic dose of acetaminophen, wherein the equivalent glucose signal response of the acetaminophen is less than about 60 mg/dl. In a preferred embodiment, the interference membrane is configured to block a therapeutic dose of acetaminophen, wherein the equivalent glucose signal response of the acetaminophen is less than about 40 mg/dl. In a more preferred embodiment, the interference membrane is configured to block a therapeutic dose of acetaminophen, wherein the equivalent glucose signal response of the acetaminophen is less than about 30 mg/dl.

While not wishing to be bound by theory, it is believed that, with respect to symmetrical cellulosic-based membranes, there is an inversely proportional balance between interferent blocking and analyte sensitivity. Namely, changes to the interference domain configuration that increase interferent blocking can result in a corresponding decrease in sensor sensitivity in some embodiments. Sensor sensitivity is discussed in more detail elsewhere herein. It is believed that the balance between interferent blocking and sensor sensitivity is dependent upon the relative proportions of hydrophobic and hydrophilic components of the membrane layer (e.g., the interference domain), with sensors having more hydrophobic interference domains having increased interferent blocking but reduced sensitivity; and sensors having more hydrophilic interference domains having reduced interferent blocking but increased sensitivity. It is believed that the hydrophobic and hydrophilic components of the interference domain can be balanced, to promote a desired level of interferent blocking while at the same time maintaining a desired level of analyte sensitivity. The interference domain hydrophobe-hydrophile balance can be manipulated and/or maintained by the proper selection and blending of the hydrophilic and hydrophobic interference domain components (e.g., cellulosic derivatives having acetyl, butyryl, propionyl, methoxy, ethoxy, propoxy, hydroxyl, carboxymethyl, and/or carboxyethyl groups). For example, cellulose acetate is relatively more hydrophilic than cellulose acetate butyrate. In some embodiments, increasing the percentage of cellulose acetate (or reducing the percentage of cellulose acetate butyrate) can increase the hydrophilicity of the cellulose acetate/cellulose acetate butyrate blend, which promotes increased permeability to hydrophilic species, such as but not limited to glucose, $H_2O_2$ and some interferents (e.g., acetaminophen). In another embodiment, the percentage of cellulose acetate butyrate is increased to increase blocking of interferants, but less permeability to some desired molecules, such as $H_2O_2$ and glucose, is also reduced.

One method, of manipulating the hydrophobe-hydrophile balance of the interference domain, is to select the appropriate percentages of acetyl groups (relatively more hydrophilic than butyl groups), butyl groups (relatively more hydrophobic than acetyl groups) and hydroxyl groups of the cellulose acetate butyrate used to form the interference domain 44. For example, increasing the percentage of acetate groups on the cellulose acetate butyrate will make the cellulose acetate butyrate more hydrophilic. In another example, increasing the percentage of butyl groups on the cellulose acetate butyrate will make the cellulose acetate butyrate more hydrophobic. In yet another example, increasing the percentage of hydroxyl groups will increase the hydrophilicity of the cellulose acetate butyrate. Accordingly, the selection of a cellulose acetate butyrate that is more or less hydrophilic (or more or less hydrophobic) can modulate the over-all hydrophilicity of the cellulose acetate/cellulose acetate butyrate blend. In one exemplary embodiment, an interference domain can be configured to be relatively more hydrophobic (and therefore block interferants more strongly) by reducing the percentage of acetyl or hydroxyl groups or by increasing the percentage of butyl groups on the cellulose acetate butyrate used in the casting solution (while maintaining the relative ratio of cellulose acetate to cellulose acetate butyrate).

In some alternative embodiments, the interference domain is formed of a blend of cellulosic derivatives, wherein the hydrophilic and hydrophobic components of the interference domain are balanced, such that the glucose sensitivity is from about 1 pA/mg/dL to about 100 pA/mg/dL, and at least one interferent is sufficiently blocked from passage through the interference domain such that the equivalent glucose signal response of the at least one interferent is less than about 60 mg/dL. In a preferred embodiment, the glucose sensitivity is from about 5 pA/mg/dL to about 25 pA/mg/dL. In a more preferred embodiments, the glucose sensitivity is from about 5 pA/mg/dL to about 25 pA/mg/dL and the equivalent glucose signal response of the at least one interferent is less than about 40 mg/dL. In a still more preferred embodiments, the glucose sensitivity is from about 5 pA/mg/dL to about 25 pA/mg/dL and the equivalent glucose signal response of the at least one interferent is less than about 30 mg/dL. In some embodiments, the balance between hydrophilic and hydrophobic components of the interference domain can be achieved by adjusting the amounts of hydrophilic and hydrophobic components, relative to each other, as well as adjusting the hydrophilic and hydrophobic groups (e.g., acetyl, butyryl, propionyl, methoxy, ethoxy, propoxy, hydroxyl, carboxymethyl, and/or carboxyethyl groups) of the components themselves (e.g., cellulosic derivatives, such as but not limited to cellulose acetate and cellulose acetate butyrate).

In some alternative embodiments, additional polymers, such as Nafion®, can be used in combination with cellulosic derivatives to provide equivalent and/or enhanced function of the interference domain 44. As one example, a layer of a 5 wt. % Nafion® casting solution was applied over a previously applied (e.g., and cured) layer of 8 wt. % cellulose acetate, e.g., by dip coating at least one layer of cellulose acetate and subsequently dip coating at least one layer Nafion® onto a needle-type sensor such as described with reference to the preferred embodiments. Any number of coatings or layers formed in any order may be suitable for forming the interference domain of the preferred embodiments.

In some alternative embodiments, more than one cellulosic derivative can be used to form the interference domain 44 of the preferred embodiments. In general, the formation of the interference domain on a surface utilizes a solvent or solvent system, in order to solvate the cellulosic derivative (s) (or other polymer) prior to film formation thereon. In preferred embodiments, acetone and ethanol are used as solvents for cellulose acetate; however one skilled in the art appreciates the numerous solvents that are suitable for use with cellulosic derivatives (and other polymers). Additionally, one skilled in the art appreciates that the preferred relative amounts of solvent can be dependent upon the cellulosic derivative (or other polymer) used, its molecular weight, its method of deposition, its desired thickness, and the like. However, a percent solute of from about 1 wt. % to about 25 wt. % is preferably used to form the interference domain solution so as to yield an interference domain having the desired properties. The cellulosic derivative (or other polymer) used, its molecular weight, method of deposition, and desired thickness can be adjusted, depending upon one or more other of the parameters, and can be varied accordingly as is appreciated by one skilled in the art.

In some alternative embodiments, other polymer types that can be utilized for the interference domain 44 including polyurethanes, polymers having pendant ionic groups, and polymers having controlled pore size, for example. In one such alternative embodiment, the interference domain includes a thin, hydrophobic membrane that is non-swellable and restricts diffusion of high molecular weight species. The interference domain is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system of the preferred embodiments are described in U.S. Pat. No. 7,074, 307, U.S. Patent Publication No. US-2005-0176136-A1, U.S. Pat. No. 7,081,195, and U.S. Patent Publication No. US-2005-0143635-A1. In some alternative embodiments, a distinct interference domain is not included.

In some embodiments, the interference domain 44 is deposited either directly onto the electroactive surfaces of the sensor or onto the distal surface of the electrode domain, for a domain thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 1, 1.5 or 2 microns to about 2.5 or 3 microns. Thicker membranes can also be desirable in certain embodiments, but thinner membranes are generally preferred because they have a lower impact on the rate of diffusion of hydrogen peroxide from the enzyme membrane to the electrodes. In some embodiments, the interference domain can be deposited either more proximal or more distal than the electrode domain, relative to the electroactive surfaces, depending upon the interference domain composition and membrane system configuration.

In general, the membrane systems of the preferred embodiments can be formed and/or deposited on the exposed electroactive surfaces (e.g., one or more of the working and reference electrodes) using known thin film techniques (for example, casting, spray coating, drawing down, electro-depositing, dip coating, and the like), however casting or other known application techniques can also be utilized. Preferably, the interference domain is deposited by spray or dip coating. In one exemplary embodiment of a needle-type (transcutaneous) sensor such as described herein, the interference domain is formed by dip coating the sensor into an interference domain solution using an insertion rate of from about 0.5 inch/min to about 60 inches/min, preferably 1 inch/min, a dwell time of from about 0 minute to about 2 minutes, preferably about 1 minute, and a withdrawal rate of from about 0.5 inch/minute to about 60 inches/minute, preferably 1 inch/minute, and curing (drying) the domain from about 1 minute to about 30 minutes, preferably from about 3 minutes to about 15 minutes (and can be accomplished at room temperature or under vacuum (e.g., 20 to 30 mmHg)). In one exemplary embodiment including cellulose acetate butyrate interference domain, a 3 minute cure (i.e., dry) time is preferred between each layer applied. In another exemplary embodiment employing a cellulose acetate interference domain, a 15 minute cure (i.e., dry) time is preferred between each layer applied.

In some embodiments, the dip process can be repeated at least one time and up to 10 times or more. In other embodiments, only one dip is preferred. The preferred number of repeated dip processes depends upon the cellulosic derivative(s) used, their concentration, conditions during deposition (e.g., dipping) and the desired thickness (e.g., sufficient thickness to provide functional blocking of certain interferents), and the like. In some embodiments, 1 to 3 microns may be preferred for the interference domain thickness; however, values outside of these can be acceptable or even desirable in certain embodiments, for example, depending upon viscosity and surface tension, as is appreciated by one skilled in the art. In one exemplary embodiment, an interference domain is formed from three layers of cellulose acetate butyrate. In another exemplary embodiment, an interference domain is formed from 10 layers of cellulose acetate. In another embodiment, an interference domain is formed from 1 layer of a blend of cellulose acetate and cellulose acetate butyrate. In alternative embodiments, the interference domain can be formed using any known method and combination of cellulose acetate and cellulose acetate butyrate, as will be appreciated by one skilled in the art.

In some embodiments, the electroactive surface can be cleaned prior to application of the interference domain 44. In some embodiments, the interference domain of the preferred embodiments can be useful as a bioprotective or biocompatible domain, namely, a domain that interfaces with host tissue when implanted in an animal (e.g., a human) due to its stability and biocompatibility.

In some embodiments, the interference domain is formed of a silicone-hydrophilic/hydrophobic polymer blend, such as but not limited to a silicone-Pluronic polymer blend, such as described in the section entitled "Silicone/Hydrophilic Polymer Blend Materials."

Enzyme Domain

In preferred embodiments, the membrane system further includes an enzyme domain 46 disposed more distally from the electroactive surfaces than the interference domain; however other configurations can be desirable (FIGS. 2E-2F). In the preferred embodiments, the enzyme domain provides an enzyme to catalyze the reaction of the analyte and its co-reactant, as described in more detail below. In the preferred embodiments of a glucose sensor, the enzyme domain includes glucose oxidase; however other oxidases, for example, galactose oxidase or uricase oxidase, can also be used.

For an enzyme-based electrochemical glucose sensor to perform well, the sensor's response is preferably limited by neither enzyme activity nor co-reactant concentration. Because enzymes, including glucose oxidase (GOX), are subject to deactivation as a function of time even in ambient conditions, this behavior is compensated for in forming the enzyme domain. Preferably, the enzyme domain is constructed of aqueous dispersions of colloidal polyurethane polymers including the enzyme. However, in alternative embodiments the enzyme domain is constructed from an oxygen enhancing material, for example, silicone, or fluorocarbon, in order to provide a supply of excess oxygen during transient ischemia. Preferably, the enzyme is immobilized within the domain. See, e.g., U.S. Patent Publication No. US-2005-0054909-A1.

In preferred embodiments, the enzyme domain 46 is deposited onto the interference domain 44 for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. However in some embodiments, the enzyme domain can be deposited directly onto the electroactive surfaces. Preferably, the enzyme domain is deposited by spray or dip coating. In one embodiment of needle-type (transcutaneous) sensor such as described herein, the enzyme domain is formed by dip coating the interference domain coated sensor into an enzyme domain solution and curing the domain for from about 15 minutes to about 30 minutes at a temperature of from about 40° C. to about 55° C. (and can be accomplished under vacuum (e.g., 20 to 30 mmHg)). In embodiments wherein dip coating is used to deposit the enzyme domain at room temperature, a preferred insertion rate of from about 0.25 inches per minute to about 3 inches per minute, with a preferred dwell time of from about 0.5 minutes to about 2 minutes, and a preferred withdrawal rate of from about 0.25 inch per minute to about 2 inches per minute provides a functional coating. However, values outside of those set forth above can be acceptable or even desirable in certain embodiments, for example, depending upon viscosity and surface tension, as is appreciated by one skilled in the art. In one embodiment, the enzyme domain is formed by dip coating two times (namely, forming two layers) in an enzyme domain solution and curing at 50° C. under vacuum for 20 minutes. However, in some embodiments, the enzyme domain can be formed by dip coating and/or spray coating one or more layers at a predetermined concentration of the coating solution, insertion rate, dwell time, withdrawal rate, and/or desired thickness.

Figure 3A:
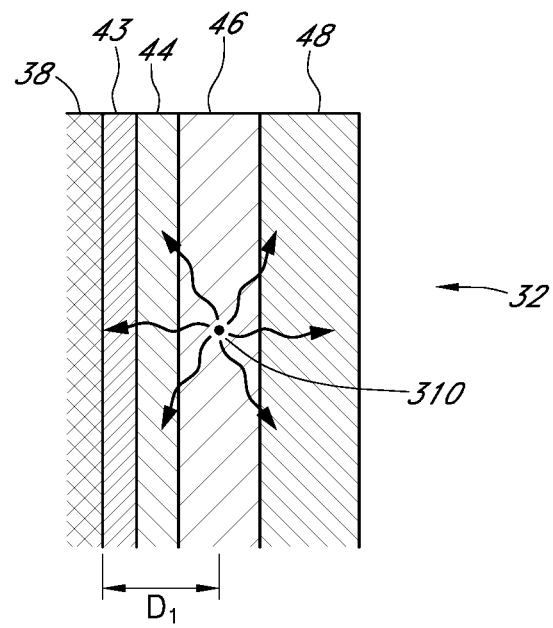
FIG. 3A is a cross-sectional view of a membrane system, in one embodiment, illustrating the diffusion distance $D_1$ between $H_2O_2$ generated within the enzyme domain and the electroactive surface.

FIG. 3A is a cross-sectional view of a membrane system, in one embodiment, illustrating the diffusion distance $D_1$ between $H_2O_2$ generated in the enzyme domain and the electroactive surface of the electrode 38. Generally, when $H_2O_2$ 310 is generated by the metabolism of glucose by GOX (in the enzyme domain 46), the generated $H_2O_2$ can diffuse in all directions (e.g., from the location within the enzyme domain where the $H_2O_2$ was generated). A portion of the generated $H_2O_2$ diffuses a distance $D_1$ to the electroactive surface and generates a signal related to the analyte (e.g., FIG. 3A).

Figure 3B:
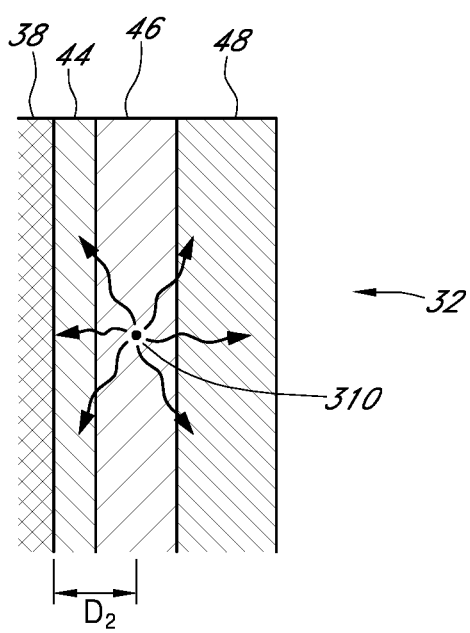
FIG. 3B is a cross-sectional view of a membrane system, in another embodiment, illustrating the diffusion distance $D_2$ between $H_2O_2$ generated within the enzyme domain and the electroactive surface.

FIG. 3B is a cross-sectional view of a membrane system, in another embodiment, illustrating the diffusion distance $D_2$ between $H_2O_2$ generated in the enzyme domain and the electroactive surface. In this embodiment, the distance $D_2$ between the location of $H_2O_2$ generation and the electroactive surface is reduced (relative to $D_1$). Thus more of the $H_2O_2$ will reach the electroactive surface and be detected in the embodiment of FIG. 3B relative to the embodiment of FIG. 3A.

Figure 3C:
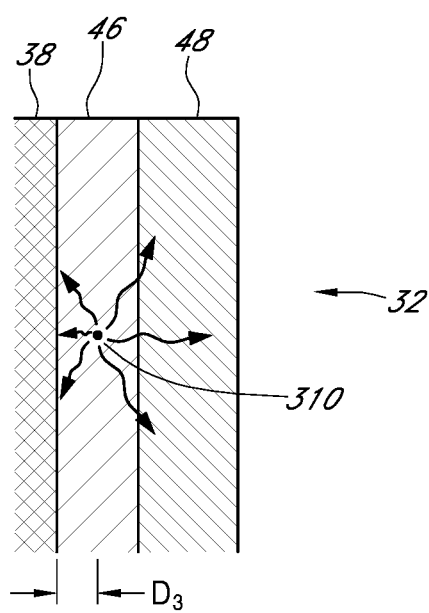
FIG. 3C is a cross-sectional view of a membrane system, in another embodiment, illustrating the diffusion distance $D_3$ between $H_2O_2$ generated within the enzyme domain and the electroactive surface.

FIG. 3C is a cross-sectional view of a membrane system, in yet another embodiment, illustrating the diffusion distance $D_3$ between $H_2O_2$ generated in the enzyme domain and the electroactive surface. Namely, in the embodiment shown in FIG. 3C, the distance $D_3$ between the location of $H_2O_2$ generation and the electroactive surface is reduced (relative to $D_1$ and $D_2$). Thus even more of the $H_2O_2$ (relative to the embodiments of FIGS. 3A and 3B) will contact the electroactive surface and be detected in the embodiment of FIG. 3C. Accordingly, in preferred embodiments, the system is configured such that the analyte component of the signal is at least 80% of the total signal, at least in part, due to a preferred $H_2O_2$ diffusion distance. In some embodiments, the preferred diffusion distance is achieved by including GOX in the layer adjacent to the electrode (i.e., in an $H_2O_2$ diffusion-based sensors). In some embodiments, the preferred diffusion distance is less than about 20 µm. In some preferred embodiments, the preferred diffusion distance is less than about 10 µm. In some preferred embodiments, the preferred diffusion distance is less than about 5 µm. In still other preferred embodiments, the preferred diffusion distance is less than about 1 µm. In preferred embodiments, the analyte component is at least 80% of the total signal for a period of at least one day.

In some embodiments, the enzyme domain 46 is located adjacent to the electroactive surfaces (e.g., by eliminating or combining the functions of the electrode and/or interference domains). In some embodiments, the enzyme (e.g., GOX) can be contained within the electrode domain, for example, using a coupling agent. Suitable coupling agents include but are not limited to disulfosuccinimidyl tartarate (sulfo-DST), bis(sulfosuccinimidyl) suberate (BS3), ethylene glycol bis(sulfosuccinimidyl succinate (Sulfo-EGS), 3,3'-Dithiobis (sulfosuccinimidyl propionate) (DTSSP), N,N'1,3-phenylenedimaleimide (mPDM), N,N'-1,2-phenylenedimaleimide (oPDM), N,N'-1,4-phenylenedimaleimide (pPDM), N,N'-(methylene-4-1-phenylene)bismaleimide (BM), naphthalene-1,5-dimaleimide (NDM), bismaleimidoethane (BMOE), 1,4-bismaleimidobutane (BMB), 1,4-bis-maleimidyl-2,3-dihydroxybutane (BMDB), dithio-bis-maleimdoethane (DTME), 1,6-bismaleimidohexane (BMH), 1,8-bismaleimidotriethyleneglycol (BM[PEO]3), 1,11-bis-maleimidotetraethyleneglycol (BM[PEO]4), dimethyl adipimidate (DMA), dimethyl pimelimidiate (DMP), dimethyl suberimidate (DMS), dimethyl 3,3'-dithiobis-propionimidate (DTBP), disuccimimidyl tartarate (DST), disuccinimidyl glutarate (DSG), dithiobis(succinimidylpropionate) (DSP), disuccinimidyl suberate (DSS), bis(2-[succinimidooxycarbonyloxy]ethyl)sulfone (BSOCOES), ethyleneglycol bis-(succinimidylsuccinate) (EGS), 1,5-difluro-2,4dinitrobenzene (DFDNB), 4,4'-difluoro3,3'-dinitrodiphenylsulfone (DFDNPS), dibromobimane (bBBr) and the like. In some embodiments, the enzyme, e.g., GOX) can be absorbed to the electroactive surface (using techniques known in the art), such as by dipping the electrode into an enzyme solution and allowing the electrode to dry, followed by application of at least one membrane domain. In still other embodiments, the enzyme can be mixed with the electrode domain material (e.g., a PVP or other hydrophilic polymer) and applied to the electroactive surface to form the electrode domain. Additionally, the thickness of the enzyme domain, itself, can be adjusted to increase the analyte component of the signal. In some embodiments, the enzyme domain has a thickness of about 10 µm or less. In some preferred embodiments, the enzyme domain has a thickness of about 5 µm or less. In a more preferred embodiment, the enzyme domain has a thickness of about 2 µm or less.

In some embodiments, the enzyme domain is configured to adjust $H_2O_2$ utilization and/or production, such as by including a coenzyme in the enzyme domain, or in membrane domains more proximal to the electroactive surface than the enzyme domain. In some circumstances, coenzymes can stabilize enzyme reactions products (e.g., $H_2O_2$ from the metabolization of glucose by GOX) and/or increase the enzyme's reaction efficiency. For example, NADPH colocalized with other enzyme systems dramatically increases the enzyme's effectiveness. Suitable coenzymes include but are not limited to superoxide dismutase (SOD), hydrogenases, reductases, oxidases, peroxidases, flavoenzymes and NADPH. For example, the reaction product (e.g., $H_2O_2$) can be stabilized by compounds such as SOD, which eliminate more reactive oxygen radical species and can enhance the life of the reaction product ($H_2O_2$). Stabilization of the reaction product and/or adjustment of the enzyme reaction rate can produce a corresponding increase in the analyte signal. Accordingly, in some embodiments, the sensor is configured such that (after complete sensor break-in) the analyte signal is at least 80% of the total signal for a period of at least one day. In some preferred embodiments, the analyte signal is at least 90% of the total signal for a period of at least two days.

In some embodiments, an enzymatic, electrochemical analyte sensor includes at least one working electrode (that includes an electroactive surface) and a membrane system (including an enzyme domain) configured such that the enzyme domain is substantially adjacent to the electroactive surface. Additionally, the sensor is configured to detect $H_2O_2$ that diffuses from its location of synthesis (e.g., within the enzyme domain) to the electroactive surface (after sensor break-in is complete), such that the analyte component is at least 80% of the total signal, for a period of at least one day. In preferred embodiments, the sensor is configured such that the non-constant noise component does not substantially contribute to the total signal. For example, in some preferred embodiments, the non-constant noise component is less than 20% of the total signal over period of one or more days.

Resistance Domain

In preferred embodiments, the membrane system 32 includes a resistance domain 48 disposed more distal from the electroactive surfaces than the enzyme domain 46 (e.g., FIGS. 2E-2F). Although the following description is directed to a resistance domain for a glucose sensor, the resistance domain can be modified for other analytes and co-reactants as well.

There exists a molar excess of glucose relative to the amount of oxygen in blood; that is, for every free oxygen molecule in extracellular fluid, there are typically more than 100 glucose molecules present (see Updike et al., Diabetes Care 5:207-21 (1982)). However, an immobilized enzyme-based glucose sensor employing oxygen as co-reactant is preferably supplied with oxygen in non-rate-limiting excess in order for the sensor to respond linearly to changes in glucose concentration, while not responding to changes in oxygen concentration. Specifically, when a glucose-monitoring reaction is oxygen limited, linearity is not achieved above minimal concentrations of glucose. Without a semipermeable membrane situated over the enzyme domain to control the flux of glucose and oxygen, a linear response to glucose levels can be obtained only for glucose concentrations of up to about 40 mg/dL. However, in a clinical setting, a linear response to glucose levels is desirable up to at least about 400 mg/dL.

The resistance domain 48 includes a semipermeable membrane that controls the flux of oxygen and glucose to the underlying enzyme domain 46, preferably rendering oxygen in a non-rate-limiting excess. As a result, the upper limit of linearity of glucose measurement is extended to a much higher value than that which is achieved without the resistance domain. In one embodiment, the resistance domain exhibits an oxygen to glucose permeability ratio of from about 50:1 or less to about 400:1 or more, preferably about 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)).

In alternative embodiments, a lower ratio of oxygen-to-glucose can be sufficient to provide excess oxygen by using a high oxygen solubility domain (for example, a silicone or fluorocarbon-based material or domain) to enhance the supply/transport of oxygen to the enzyme domain. If more oxygen is supplied to the enzyme, then more glucose can also be supplied to the enzyme without creating an oxygen rate-limiting excess. In alternative embodiments, the resistance domain is formed from a silicone composition, such as is described in U.S. Patent Publication No. US-2005-0090607-A1.

Polyurethane Polymer Materials

In a preferred embodiment, the resistance domain includes a polyurethane membrane with both hydrophilic and hydrophobic regions to control the diffusion of glucose and oxygen to an analyte sensor, the membrane being fabricated easily and reproducibly from commercially available materials. A suitable hydrophobic polymer component is a polyurethane, or polyetherurethaneurea. Polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Preferred diisocyanates include aliphatic diisocyanates containing from about 4 to about 8 methylene units. Diisocyanates containing cycloaliphatic moieties can also be useful in the preparation of the polymer and copolymer components of the membranes of preferred embodiments. The material that forms the basis of the hydrophobic matrix of the resistance domain can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In a preferred embodiment, the hydrophilic polymer component is polyethylene oxide. For example, one useful hydrophobic-hydrophilic copolymer component is a polyurethane polymer that includes about 5% hydrophilic polyethylene oxide. The polyethylene oxide portions of the copolymer are thermodynamically driven to separate from the hydrophobic portions of the copolymer and the hydrophobic polymer component. The 5% polyethylene oxide-based soft segment portion of the copolymer used to form the final blend affects the water pick-up and subsequent glucose permeability of the membrane.

In some embodiments, alternative polyurethanes, which include urethane groups and the polyurethane ureas (which also include urea groups), can be used to configure the resistance domain to regulate the flux of the analyte (e.g., glucose) therethrough, and preferably to increase the signal-to-noise ratio. For example, the polyurethanes and the polyurethane ureas selected to form the resistance domain can be based on poly(oxyalkylene) glycols including poly(oxyethylene) glycol. In accordance with conventional usage, both types of polymers will be referred to herein as polyurethanes. Membranes of polyurethanes based on poly(oxyalkylene) glycol display no predictable relationship between molecular weight and permeability. The unique separation observed with the present membranes may be explained on the basis of substance-membrane or solute-membrane interactions which tend to affect the partitioning is not due only to the hydrophilic poly(oxyalkylene) glycol or "soft" segment, but the hydrophobic or "hard" segment of the block copolymer also contributes to the overall selectivity. Thus, by changing the structure of the hydrophobic segment of the block copolymer and/or increasing or decreasing the molecular weight of the poly(oxyalkylene) glycol, the selectivity of the membrane system can be modified. In the membrane system of some embodiments, for example, the use of two different membranes of block copolyether urethanes based on poly(oxyalkylene) glycol produces the desired selectivity for glucose and hydrogen peroxide. Additional description of polyurethane resistance domains can be found in PCT International Publication No. WO1992/013271.

In preferred embodiments, the resistance domain is deposited onto the enzyme domain to yield a domain thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. Preferably, the resistance domain is deposited onto the enzyme domain by vapor deposition, spray coating, or dip coating. In one preferred embodiment, spray coating is the preferred deposition technique. The spraying process atomizes and mists the solution, and therefore most or all of the solvent is evaporated prior to the coating material settling on the underlying domain, thereby minimizing contact of the solvent with the enzyme.

In a preferred embodiment, the resistance domain is deposited on the enzyme domain by spray coating a solution of from about 1 wt. % to about 5 wt. % polymer and from about 95 wt. % to about 99 wt. % solvent. In spraying a solution of resistance domain material, including a solvent, onto the enzyme domain, it is desirable to mitigate or substantially reduce any contact with enzyme of any solvent in the spray solution that can deactivate the underlying enzyme of the enzyme domain. Tetrahydrofuran (THF) is one solvent that minimally or negligibly affects the enzyme of the enzyme domain upon spraying. Other solvents can also be suitable for use, as is appreciated by one skilled in the art.

Silicone/Hydrophilic Polymer Blend Materials

It is believed that incorporation of a silicone-hydrophilic polymer blend into the membrane system can render the signal-to-noise ratio of the sensor substantially unaffected by non-constant noise by substantially reducing and/or eliminating noise, such as by substantially blocking and/or slowing (e.g., reducing the diffusion rate) the passage of an interferent therethrough. In preferred embodiments, a sensor having one or more working electrodes includes a membrane system 34 wherein the resistance domain 48 includes a blend of a silicone polymer with a hydrophilic polymer configured to reduce noise-causing species, such as non-constant noise-causing species. In some embodiments, the membrane domains/layers include a blend of a silicone polymer with a hydrophilic polymer configured to reduce noise-causing species. In some preferred embodiments, the sensor includes a silicone-hydrophilic polymer blend membrane domain and/or layer (e.g., an interference domain) that has a micellar jacket structure (described elsewhere herein). While not wishing to be bound by theory, it is believed that membrane domains that include a silicone-hydrophilic polymer blend can reduce noise by blocking and/or suppressing passage of at least one interfering species into the membrane system, while at the same time allowing for and/or promoting the transport of the analyte (e.g., glucose or other such water-soluble molecules, such as drugs).

By "hydrophilic polymer," it is meant that the polymer has an affinity for water, due to the presence of one or more hydrophilic substituents, and generally is primarily soluble in water or has a tendency to absorb water. In one example, the hydrophilic component of a hydrophilic polymer promotes the movement of water and/or compounds in the water (e.g., by diffusion or other means) through a membrane formed of the hydrophilic polymer, such as by lowering the thermodynamic barrier to movement of compounds in the water into the membrane.

In some embodiments, hydrophilic polymers include hydrophilic-hydrophobic polymers. Generally, the terms "hydrophilic-hydrophobic" and "hydrophobic-hydrophilic" are used interchangeably herein (are not meant to imply that either the hydrophilic or the hydrophobic substituents are the major component of the polymer) and refer to the property of having both hydrophilic and hydrophobic substituents and/or characteristics in a single molecule, such as, for example, a polymer.

The hydrophilic and hydrophobic substituents of a polymer can affect the polymer's behavior in certain circumstances, such as but not limited to silicone/hydrophilic-hydrophobic blend materials and micellar jackets, which are discussed elsewhere herein. Using PEO-PPO-PEO as an exemplary polymer, the polymer's major component (PEO) is hydrophilic and can provide an overall hydrophilic character to the molecule (e.g., the molecule generally behaves in a hydrophilic manner). However, the hydrophobic component (PPO) of the polymer makes it possible for the polymer to have some hydrophobic character (e.g., for portions of the molecule to behave in the manner of a hydrophobic molecule), in some situations. In some circumstances, such as formation of micellar jackets in a silicone/hydrophilic-hydrophobic blend material, the polymer self-organizes, relative to the silicone (e.g., silicone globule(s)) such that the hydrophobic PPO is adjacent to the silicone (which is hydrophobic) and the two PEO groups project away from the silicone (e.g., due to thermodynamic forces). Depending upon the circumstance (e.g., the polymer selected), variations of the micellar jacket structure described above (e.g., opposite orientations) are possible. For example, it is believed that in a mixture of PPO-PEO-PPO and silicone, the PPO groups self-orient toward the silicone and the PEO center is oriented away from the silicone.

In one embodiment, the hydrophilic polymer has a molecular weight of at least about 1000 g/mol, 5,000 g/mol, 8,000 g/mol, 10,000 g/mol, or 15,000 g/mol or more. In one embodiment, the hydrophilic polymer comprises both a hydrophilic domain and a partially hydrophobic domain (e.g., a copolymer, also referred to herein as a hydrophobic-hydrophilic polymer). The hydrophobic domain(s) facilitate the blending of the hydrophilic polymer with the hydrophobic silicone polymer, such as but not limited to formation of micellar jackets within and/or around the silicone. In one embodiment, the hydrophobic domain is itself a polymer (i.e., a polymeric hydrophobic domain). For example, in one embodiment, the hydrophobic domain is not a simple molecular head group but is rather polymeric. In various embodiments, the molecular weight of any covalently continuous hydrophobic domain within the hydrophilic polymer is at least about 500 g/mol, 700 g/mol, 1000 g/mol, 2000 g/mol, 5000 g/mol, or 8,000 g/mol or more. In various embodiments, the molecular weight of any covalently continuous hydrophilic domain within the hydrophilic polymer is at least about 500 g/mol, 700 g/mol, 1000 g/mol, 2000 g/mol, 5000 g/mol, or 8,000 g/mol or more.

In some embodiments, within a particular layer, the ratio of the silicone polymer to hydrophilic polymer is selected to provide an amount of oxygen and water-soluble molecule solubility such that oxygen and water-soluble molecule transport through a domain is adjusted according to the desired function of that particular layer. Furthermore, in some embodiments, the ratio of silicone polymer to hydrophilic polymer, as well as the polymeric compositions, is selected such that a layer constructed from the material has interference characteristics that inhibit transport of one or more interfering species through the layer. Some known interfering species for a glucose sensor include, but are not limited to, acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid. Accordingly, in some embodiments, a silicone polymer/hydrophilic polymer layer as disclosed herein is less permeable to one or more of these interfering species than to the analyte, e.g., glucose.

In some of these embodiments, the ratio of silicone polymer to hydrophilic polymer (in the layers incorporating the blends) varies according to the desired functionality of each layer. The relative amounts of silicone polymer and hydrophilic polymer described below are based on the respective amounts found in the cured polymeric blend. Upon introduction into an aqueous environment, some of the polymeric components may leach out, thereby changing the relative amounts of silicone polymer and hydrophilic polymer. For example, substantial amounts of the portions of the hydrophilic polymer that are not cross-linked may leach out, for example, depending on the hydrophilic polymer's molecular weight and how tortuous it the diffusion path out of the membrane.

In some embodiments, the silicone and hydrophilic polymers form a substantial blend. Namely, the amount of any cross-linking between the silicone polymer and the hydrophilic polymer is substantially limited. In various embodiments, at least about 75%, 85%, 95%, or 99% or more of the silicone polymer is not covalently linked to the hydrophilic polymer. In some embodiments, the silicone polymer and the hydrophilic polymer do not cross-link at all unless a cross-linking agent is used (e.g., such as described below). Similarly, in some embodiments, the amount of any entanglement (e.g., blending on a molecular level) between the silicone polymer and the hydrophilic polymer is substantially limited. In one embodiment, the silicone polymer and hydrophilic polymers form microdomains. For example, in one embodiment, the silicone polymer forms micellar jacket structures surrounded by a network of hydrophilic polymer.

The silicone polymer for use in the silicone/hydrophilic polymer blend may be any suitable silicone polymer. In some embodiments, the silicone polymer is a liquid silicone rubber that may be vulcanized using a metal- (e.g., platinum), peroxide-, heat-, ultraviolet-, or other radiation-catalyzed process. In some embodiments, the silicone polymer is a dimethyl- and methylhydrogen-siloxane copolymer. In some embodiments, the copolymer has vinyl substituents. In some embodiments, commercially available silicone polymers may be used. For example, commercially available silicone polymer precursor compositions may be used to prepare the blends, such as described below. In one embodiment, MED-4840 available from NUSIL® Technology LLC is used as a precursor to the silicone polymer used in the blend. MED-4840 consists of a 2-part silicone elastomer precursor including vinyl-functionalized dimethyl- and methylhydrogen-siloxane copolymers, amorphous silica, a platinum catalyst, a crosslinker, and an inhibitor. The two components may be mixed together and heated to initiate vulcanization, thereby forming an elastomeric solid material. Other suitable silicone polymer precursor systems include, but are not limited to, MED-2174 peroxide-cured liquid silicone rubber available from NUSIL® Technology LLC, SILASTIC® MDX4-4210 platinum-cured biomedical grade elastomer available from DOW CORNING®, and Implant Grade Liquid Silicone Polymer (durometers 10-50) available from Applied Silicone Corporation.

The hydrophilic polymer for use in the blend may be any suitable hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. Nos. 4,803,243 and 4,686,044, which are incorporated herein by reference). In one embodiment, the hydrophilic polymer is a copolymer of poly(ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. Some PLURONIC® polymers are triblock copolymers of poly(ethylene oxide)-poly(propylene oxide)-poly(ethylene oxide) having the general molecular structure:

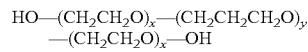

wherein the repeat units x and y differ amongst various PLURONIC® products. The poly(ethylene oxide) blocks act as a hydrophilic domain allowing the dissolution of aqueous agents in the polymer. The poly(propylene oxide) block acts as a hydrophobic domain facilitating the blending of the PLURONIC® polymer with a silicone polymer. In one embodiment, PLURONIC® F-127 is used having x of approximately 100 and y of approximately 65. The molecular weight of PLURONIC® F-127 is approximately 12,600 g/mol as reported by the manufacture. Other PLURONIC® polymers include PPO-PEO-PPO triblock copolymers (e.g., PLURONIC® R products) and PEO-PDMS-PEO triblock copolymers (e.g., PEO-polydimethylsiloxane-PEO, SILSURF® from BASF, USA) Other suitable commercial polymers include, but are not limited to, SYNPERONICS® products available from UNIQEMA®.

The polyether structure of PLURONIC® polymers is relatively inert. Accordingly, without being bound by any particular theory, it is believed that the PLURONIC® polymers do not substantially react with the components in MED-4840 or other silicone polymer precursors.

Those of skill in the art will appreciate that other copolymers having hydrophilic and hydrophobic domains may be used. For example, in one alternative embodiment, a triblock copolymer having the structure hydrophobic-hydrophilic-hydrophobic may be used. In another alternative embodiment, a diblock copolymer having the structure hydrophilic-hydrophobic is used. Additional devices, methods and compositions are described in U.S. Patent Publication No. US-2006-0270923-A1 and U.S. patent application Ser. No. 11/404,417 filed on Apr. 14, 2006.

Layers and/or domains that include a silicone polymer-hydrophilic polymer blend can be made using any of the methods of forming polymer blends known in the art. In one embodiment, a silicone polymer precursor (e.g., MED-4840) is mixed with a solution of a hydrophilic polymer (e.g., PLURONIC® F-127 dissolved in a suitable solvent such as acetone, ethyl alcohol, xylene or 2-butanone). The mixture may then be drawn into a film or applied in a multi-layer membrane structure using any method known in the art (e.g., spraying, painting, dip coating, vapor depositing, molding, 3-D printing, lithographic techniques (e.g., photolithograph), micro- and nano-pipetting printing techniques, etc.). The mixture may then be cured under high temperature (e.g., 50° C. to 150° C.). Other suitable curing methods include ultraviolet or gamma radiation, for example. During curing, the silicone polymer precursor will vulcanize and the solvent will evaporate. In one embodiment, after the mixture is drawn into a film, another preformed layer of the membrane system is placed on the film. Curing of the film then provides bonding between the film and the other preformed layer. In one embodiment, the preformed layer is the cell disruptive layer. In one embodiment, the cell disruptive domain comprises a preformed porous silicone membrane. In other embodiments, the cell disruptive domain is also formed from a silicone polymer/hydrophilic polymer blend. In some embodiments, multiple films are applied on top of the preformed layer. Each film may posses a finite interface with adjacent films or may together form a physically continuous structure having a gradient in chemical composition.

Some amount of cross-linking agent may also be included in the mixture to induce cross-linking between hydrophilic polymer molecules. For example, when using a PLURONIC® polymer, a cross-linking system that reacts with pendant or terminal hydroxy groups or methylene, ethylene, or propylene hydrogen atoms may be used to induce cross linking. Non-limiting examples of suitable cross-linking agents include ethylene glycol diglycidyl ether (EGDE), poly(ethylene glycol) diglycidyl ether (PEGDE), or dicumyl peroxide (DCP). While not being bound by any particular theory, at low concentrations, these cross-linking agents are believed to react primarily with the PLURONIC® polymer with some amount possibly inducing cross-linking in the silicone polymer or between the PLURONIC® polymer and the silicone polymer. In one embodiment, enough cross-linking agent is added such that the ratio of cross-linking agent molecules to hydrophilic polymer molecules added when synthesizing the blend is from about 10 to about 30 (e.g., about 15 to about 20). In one embodiment, from about 0.5% to about 15% w/w of cross-linking agent is added relative to the total dry weights of cross-linking agent, silicone polymer, and hydrophilic polymer added when blending the ingredients (in one example, from about 1% to about 10%). In one embodiment, from about 5% to about 30% of the dry ingredient weight is the PLURONIC® polymer.

In some embodiments, other agents may be added to the mixture to facilitate formation of the blend. For example, a small amount of butylhydroxy toluene (BHT) (e.g., about 0.01% w/w) or other suitable antioxidant may be mixed with a PLURONIC® to stabilize it.

In some alternative embodiments, precursors of both the silicone polymer and hydrophilic polymer may be mixed prior to curing such that polymerization of both the silicone polymer and the hydrophilic polymer occur during curing. In another embodiment, already polymerized silicone polymer is mixed with a hydrophilic polymer such that no significant polymerization occurs during curing.

While not wishing to be bound by theory, it is believed that a micelle-like structure, referred to herein as a micellar jacket structure, can be formed by combining certain hydrophobic polymers (e.g., silicone) with certain amphipathic polymers (e.g., hydrophilic polymers such as PLURONIC® polymers), which, when substantially blended, create a mechanism by which glucose and other analytes are transported at a limited rate. One example of a limited rate is diffusion of oxygen and glucose into the membrane at a ratio of 50:1 (50 oxygen molecules for every one glucose molecule). In a preferred embodiment, oxygen and glucose diffuse into the membrane at the limited rate of 100:1. In a more preferred embodiment, oxygen and glucose diffuse into the membrane at the limited rate of 200:1.

In a first mechanism of limited analyte transport, it is believed that the PLURONIC® hydrophilic and hydrophobic constituents can promote self-organization of the PLURONIC® molecules, in conjunction with the silicone, into micellar jackets. The micellar jackets provide a contiguous channel (e.g., a tortuous path) though the silicone, through which the analyte travels. For example, at a first side of a membrane/domain, glucose dissolves into the hydrophilic component of the micellar jackets (e.g., within the membrane/domain) and diffuses through the hydrophilic portion of adjacent micellar jackets, to reach the opposite side of the membrane/domain.

In a second mechanism of limited analyte transport, it is believed that micellar jackets can provide a hydrophilic phase within the silicone membrane/domain structure. There is an energetic barrier to diffusion of the analyte (e.g., glucose) into the silicone. However, an energetic, thermodynamic force (e.g., an analyte concentration gradient) drives the analyte to pass across/through the membrane by "jumping" from one micellar jacket to another. For example, a glucose concentration gradient can provide the energy for a glucose molecule to pass into the membrane domain or layer (e.g., the cell impermeable domain formed of a substantial blend of silicone and PLURONIC®), to the first micellar jacket, then to "jump" to the next micellar jacket, and so on, until the molecule reaches the opposite side of the membrane domain/layer.

In one exemplary embodiment, a silicone-hydrophilic polymer (e.g., wherein the hydrophilic polymer is an amphipathic polymer, such as but not limited to PLURONIC®) blend is believed to promote the macromolecular self-organization of micellar jackets that clothe colloidal silicone globules (e.g., silicone granules that form a three-dimensional contiguous macromolecular structure having silicone-to-silicone contacts between the silicone granules, coated with the hydrophilic polymer), within the membrane domain. The hydrophilic groups of the micellar jackets orient toward the silicone, with the hydrophobic portions of the polymer oriented away from the silicone core of the structure. For example, in the case of silicone globules clothed with PLURONIC® (PEO-PPO-PEO), it is believed that it is thermodynamically favorable for a PLURONIC® molecule to orient itself such that the PPO "lies against" the silicone and the PEO to bends away from the silicone, for example, in a U-like shape. Inverse micellar jackets are also possible, for example, inverted micellar jackets (e.g., with the hydrophobic PPO facing outward toward the silicone and the hydrophilic PEO facing inward) within the silicone. Additionally, the micellar jackets may not be in direct, physical contact with each other, which would provide a thermodynamic barrier to molecules entering the membrane layer and traveling through/across the layer by energetically "jumping" from one micellar jacket to the next.

In addition to facilitating analyte passage through the membrane domain, it has been found that the micellar jacket structure blocks diffusion of small, reactive oxygen and nitrogen interferents (e.g., $H_2O_2$, oxygen radicals, peroxynitrates, etc.) that can cause non-constant noise. While not wishing to be bound by theory, it is believed that the micellar jacket structure sufficiently slows the diffusion of the reactive oxygen and nitrogen interferents such that these molecules self-annihilate before reaching the electroactive surface(s). In contrast, it is believed that large molecular weight interferents (e.g., acetaminophen and ascorbate) are sterically and/or thermodynamically blocked and/or trapped by the micellar jackets, and thus do not reach the electroactive surface(s). Accordingly, in preferred embodiments, the non-constant noise produced by both small and large molecular weight interferents is substantially attenuated, such that the non-constant noise component of the signal is less than 20% of the total signal for a period of at least one day.

In one exemplary embodiment, an enzyme-based electrochemical sensor is configured to block non-constant, non-analyte-related noise-producing compounds and includes at least one working electrode and a membrane system (e.g., FIGS. 2E and 2F) that includes at least one domain formed of a silicone-hydrophilic polymer blend with a micellar jacket structure. In some embodiments, the membrane system includes at least one additional domain, such as but not limited to an electrode domain, an interference domain, an enzyme domain, a resistance domain and a cell disruptive domain. In one preferred embodiment, the sensor includes a membrane system with a combined resistance-interference domain formed of the silicone-hydrophilic polymer blend (with a micellar jacket structure) is configured to modulate the flux of the analyte into the membrane system and reduce non-constant noise by blocking the passage of at least one interferent (e.g., acetaminophen) into the membrane system.

In some preferred embodiments, the analyte sensor (e.g., an enzyme-based electrochemical analyte sensor) includes at least one working electrode and a membrane system with a resistance domain configured to substantially consume and/or block at least one intermittent non-constant noise-causing species produced by the host's metabolic processes (e.g., $H_2O_2$ from sources outside the sensor), such that the signal contribution due to the non-constant non-analyte component is less than about 20% over a period of about one or more days. In more preferred embodiments, the non-constant non-analyte component is less than about 20% over a period of about 1, 2, 3, 4, 5, 6 or 7 days, or longer. In some preferred embodiments, the non-constant noise is less than about 18%, 16%, 14%, 12%, 10%, 8%, 6%, 5%, 4%, 3%, 2%, or 1% or less of the total signal for at least about one day.

In preferred embodiments, the resistance domain is configured to consume and/or block small molecule interferents caused by the host's metabolic processes, such as but not limited to externally generated $H_2O_2$, reactive oxygen and nitrogen species, such as by rendering the interferents electrochemically inactive at the sensor's applied voltage. For example, reactive oxygen and nitrogen species (e.g., oxygen and nitrogen radicals) and externally generated $H_2O_2$ (e.g., derived from local immune cells that have invaded the sensor locality as part of the wound healing process) are highly reactive and spontaneously react with anything that they contact, such as the materials of the membrane system. Thus, as these small molecule interferents diffuse through the membrane system, only a portion of the them diffuse all of the way to the sensor's electroactive surface. The remaining small molecule interferents, generally, bump into and react with the matrix of the membrane system. When these interferents react with the matrix, they are generally oxidized/reduced, such that they are no longer substantially reactive with the sensor's electroactive surface at the applied voltage. For example, the reactive oxygen species $O_2^{2-}$ can be oxidized to $O_2$. Accordingly, reducing the number of interferent molecules reaching the electroactive surface can decrease the noise component and increase the signal-to-noise ratio. Thus the systems of the preferred embodiments are enabled to provide a signal, wherein the substantially non-constant non-analyte-related component does not substantially contribute to the signal. For example, in some embodiments, the non-constant noise is less than about 20% of the total signal for at least about one day.

In some embodiments, the resistance domain is configured to provide a tortuous pathway for noise causing compounds, such that the reactive electroactive species, which can interfere with the analyte signal, contact the tortuous diffusion path and are thereby consumed (e.g., rendered electrochemically inactive at the electroactive surface at the applied voltage). In some embodiments, a resistance domain and/or membrane system thickness is configured, such that the non-constant noise component of the signal is less than about 20% of the total signal over a period of at least about 1, 2 or 3 days, or longer due to self-annihilation of some relatively unstable electroactive compounds as they diffuse there through. In some embodiments, the thickness of the resistance domain is from about 1 µm to about 25 µm or more. In some embodiments, the thickness of the membrane system is from about 5 µm to about 10 µm or more. In alternative embodiments, the resistance domain is configured to consume at least one interferent (e.g., reactive oxygen or nitrogen species, externally derived $H_2O_2$) by inclusion of a compound that binds and/or metabolizes the interferent, such that the interferent is rendered substantially electrochemically unreactive with the electroactive surface (at the applied voltage). In some embodiments, an enzyme, such as but not limited to a peroxidase (e.g., catalase, horseradish peroxidase, cytochrome c peroxidase, glutathione peroxidase, and the like) is incorporated into the resistance domain. In one exemplary embodiment, a peroxidase disposed in the resistance domain can metabolize externally generated $H_2O_2$ (diffusing into the membrane system) to water and molecular oxygen, which do not substantially interact with the sensor's electroactive surfaces. Thus, substantially only $H_2O_2$ produced within the enzyme domain (e.g., from the metabolism of glucose by GOX) diffuses to the sensor electroactive surface and produces a signal; accordingly, a desired thickness of the resistance domain and/or membrane system can be achieved by a variety of known techniques, such as applying one or more additional layers of resistance domain material during membrane system construction (e.g., 2-layers instead of 1-layer).

In some embodiments, the resistance domain includes one or more Heme compounds, which are well known antioxidants that react with reactive interfering species (which renders the interferent unreactive with the electroactive surface), such that the non-constant noise component is less than about 20% of the total signal for about one or more days. Suitable Heme compounds include but are not limited to hemin, metmyoglobin, hemoglobin, methemoglobin, and cytochrome c, desferroxamine, or synthesized by partial denaturing and crosslinking to a polymer backbone.

Interferent Scavenging

In some embodiments, the signal-to-noise ratio can be increased by including an interferent scavenger in one or more layers of the membrane system. Depending upon the nature of the interferent, the interferent scavenger can be incorporated into a membrane domain either more distal or proximal to the electroactive surfaces than the enzyme domain; in some embodiments, the scavenger can be incorporated into the membrane's enzyme domain. For example, some interferents are ionic and bind to ionic interferents. Accordingly, incorporating interferent-scavenging ionic components, such as Nation®, into one or more layers of the membrane system can substantially block and/or slow diffusion of an interferent having the same charge as the ionic component through the membrane system, in some embodiments. Thus, less interferent reaches the electroactive surfaces and noise is reduced.

An interferent-scavenging enzyme can be incorporated into one or more layers of the membrane system. Useful enzymes include but are not limited to peroxidases and/or oxidases. In general, a peroxidase catalyzes the reduction of a compound using $H_2O_2$. Exemplary peroxidases include horseradish peroxidase, glutathione peroxidase, cytochrome C peroxidase, myeloperoxidase, and the like. Horseradish peroxidase is a preferred peroxidase because interferents present in biological fluids, such as ascorbate, urate, acetaminophen, bilirubin and cysteine, are rapidly oxidized by hydrogen peroxide in the presence of horseradish peroxidase. In general, an oxidase catalyzes the oxidation/reduction of a compound using molecular $O_2$. Exemplary oxidases include glucose oxidase, monoamine oxidase, cytochrome P450 oxidase, NADPH oxidase, cytochrome C oxidase, Xanthine oxidase, L-gulonolactone oxidase, lactate oxidase, lysyl oxidase, catalase and the like. In some embodiments, the peroxidase can be crosslinked to one or more membrane domains using known protein cross-linking techniques, such as but not limited to glutaraldehyde cross-linking, $NaIO_4$, oxidation of enzyme oligosaccharide groups followed by coupling to the matrix. Some useful coupling methods are described in U.S. Pat. Nos. 5,262,305 and 5,356,786.

In one exemplary embodiment, a peroxidase is incorporated into a distal membrane domain (e.g., above the enzyme domain) to remove $H_2O_2$ derived from external sources (e.g., from macrophages during wound healing). In one exemplary embodiment, a distal membrane domain includes horseradish-peroxidase. Additional scavenging techniques are described in U.S. Pat. Nos. 5,356,786, 6,284,478, and 7,003,341.

In some embodiments, non-constant noise can be decreased by including one or more membrane domains with an interferent-blocking compound. A variety of interferent-blocking compounds can be used, such as but not limited to sulfonated polyether sulfone, polyamino-phenol or polypyrrole. In one embodiment, the membrane system includes 3-amino-phenol, which allows the diffusion of $H_2O_2$ while blocking the transport of acetaminophen. Interferent-blocking compounds can be applied to the electrodes using any method know in the art, such as but not limited to dipping, spraying, electro-polymerization, spin coating and the like, as are discussed elsewhere herein. In one exemplary embodiment, the sensor is a glucose sensor comprising two working electrodes, wherein a solution of 3-amino-phenol is sprayed onto the working electrodes and dried prior to the application of the membrane enzyme domain. In a further embodiment, the sensor includes additional membrane layers. Additional methods and devices can be found in U.S. Pat. No. 7,120,483, to Russell, which is incorporated herein by reference in its entirety.

Other systems and methods for reducing or eliminating interference species that can be applied to the membrane system of the preferred embodiments are described in U.S. Patent Publication No. US-2005-0115832-A1, U.S. Patent Publication No. US-2005-0176136-A1, U.S. Patent Publication No. US-2005-0161346-A1, and U.S. Patent Publication No. US-2005-0143635-A1. In some alternative embodiments, a distinct interference domain is not included.

Outer Hydrophilic Surface

In some embodiments, the membrane system is configured with a hydrophilic outer surface (and/or domain) that is at least discontinuously hydrophilic, and can be continuously hydrophilic in some embodiments, configured to contact the host's tissue. The term "discontinuous(ly) hydrophilic surface (domain)" as used herein is a broad phrase, and is to be given its ordinary and customary meaning to a person of ordinary skill in the art (and it is not to be limited to a special or customized meaning), and refers without limitation to a surface including some hydrophilic and some hydrophobic domains located thereon. While not wishing to be bound by theory, it is believed that the outer surface of the resistance domain is responsible for a substantial portion of the domain's analyte resistance capability. It is believed that the signal-to-noise ratio can be rendered substantially unaffected by non-constant noise by providing an at least discontinuous hydrophilic outer surface, such as by surface-treatment with a polymer having a sufficient hydrophilic component so as to provide an outer surface with at least discontinuous hydrophilic characteristics and/or by application of a distal discontinuous hydrophilic layer or domain formed of a polymer having a substantial hydrophilic component. Such a surface treatment and/or discontinuously hydrophilic domain outer surface enables a sensor system with an analyte component of at least about 80% of the total signal.

In some embodiments, a discontinuously hydrophilic outer domain having a surface with discontinuous hydrophilic components (e.g., either the resistance domain itself or applied in addition to the resistance domain in the exemplary embodiments), configured such that the analyte component of the sensor's signal is at least about 80% of the total signal for at least about one day. In some embodiments, a discontinuously hydrophilic outer domain includes a silicone/hydrophilic polymer blend. For example, in some embodiments, the hydrophilic component of the silicone/hydrophilic polymer blend is at least about 5 wt. %. In some preferred embodiments, the hydrophilic component of the silicone/hydrophilic polymer blend is at least about 10 wt. %. In some preferred embodiments, the hydrophilic component of the silicone/hydrophilic polymer blend is at least about 15 wt. %. In even more preferred embodiments, the hydrophilic component of the silicone/hydrophilic polymer blend is at least about 20 wt. %. In still other more preferred embodiments, the hydrophilic component of the silicone/hydrophilic polymer blend is at least about 25 wt. %.

In some embodiments, the discontinuously hydrophilic outer domain includes a surface-treated resistance domain, wherein the outer surface of the resistance domain has been configured, such that the hydrophilicity of the resistance domain's surface is increased to such an extent that the analyte component is at least 80% of the total signal for at least about one day. In some embodiments, the discontinuously hydrophilic outer domain includes a polyurethane-based resistance domain that has been surface-treated with a polymer containing hydrophilic moieties (e.g., PEG compounds, Pluronic compounds or a substantially hydrophilic polyurethane compound). In some embodiments, the applied polymer solution, which is applied over the polyurethane-based resistance domain 48 (which was substantially cured), forms a cell impermeable domain 42, as described elsewhere herein. In some embodiments, the applied solution is composed of PEG in acetone, such as but not limited to a 1%, 5%, 10%, 20%, 30%, 40% or more solution of PEG in acetone, is applied. For example, in experiments using small-structured sensors (e.g., transcutaneous) dipped one time in a 30% solution of PEG in acetone, sensitivity of the treated sensors increased from about 20% to about 75% when compared with non-treated sensors.

In some embodiments, the discontinuously hydrophilic outer domain (e.g., having a discontinuously hydrophilic outer surface) is formed from polyurethane. To adjust the glucose permeability through a polyurethane-based outer hydrophilic domain, the amount of hydrophilic component can be adjusted, such that the analyte component of the total signal is at least about 80%. For example, in some embodiments, an analyte sensor includes an outer discontinuously hydrophilic domain formed of a blend of polyurethanes, wherein the percentage of the more hydrophilic polyurethane is selected such that the analyte component of the total signal is at least 80% or more. In some embodiments of the analyte sensor, the discontinuously hydrophilic outer domain is a resistance domain, which is formed of a polyurethane blend that includes a sufficient percentage of a hydrophilic polyurethane (e.g., a polyurethane having hydrophilic groups, such as but not limited to PEG, PEO, PVP) to provide a signal in which the analyte component is at least 80% of the total signal, such as for a period of at least about one day. In some preferred embodiments, the hydrophilic component is at least about 5% or more of the intermittently hydrophilic outer domain. In some embodiments, the hydrophilic component of the outer intermittently hydrophilic outer domain is at least about 1%, 2%, 5%, 7%, 10%, 15%, 20% or 25% or more of the polyurethane blend.

In still other embodiments, a surface of the resistance domain surface is treated (e.g., coated) with a polymer having a sufficient number of hydrophilic moieties, such that the analyte component is at least 80% of the total signal. In one exemplary embodiment, a resistance domain of a polyurethane blend is treated with a hydrophilic polymer such as but not limited to Pluronic® (available from BASF Corp., Florham Park, N.J., USA) or a sufficiently hydrophilic polyurethane-based polymer. In another exemplary embodiment, the sensor is dipped into PEG or PVP to increase the glucose-permeability of the resistance domain. Other known hydrophiles, such as those described in the sections entitled "Silicone/Hydrophilic Polymer Materials," can be used to increase the glucose permeability of the resistance domain without substantially affecting the permeability of interferents. In some embodiments, in which the surface of the resistance domain is treated with a hydrophilic polymer, the analyte component of the signal is at least 90% of the total signal. In preferred embodiments, the analyte component of the signal is at least 99% of the total signal. In preferred embodiments, the analyte component of the signal is at least 80% of the total signal for at least about one or more days.

These principles and/or resistance domain configurations find use with a variety of other analyte sensors, such as but not limited to those sensors described in U.S. Pat. Nos. 6,721,587; 4,484,987; 4,671,288; 5,322,063; 6,654,625; 6,689,265; and U.S. Patent Publication No. US-2003-0031699-A1.

Fluid Pocket Formation

While not wishing to be bound by theory, it is believed that non-constant, non-analyte-related noise can be decreased by diluting and/or removing transient electroactive species that can interfere with the analyte signal, such as by increasing fluid bulk (e.g., a fluid pocket), increasing bulk fluid flow and/or increasing diffusion rate around at least a portion of the sensor, such as the sensing portion of the sensor. Furthermore, a physical spacer can reduce the effect of lymph pooling (e.g., build-up of interfering electroactive species in the tissue surrounding an implanted sensor) due to local compression (described elsewhere herein) by mechanically maintaining a fluid pocket. Since a spacer can maintain the fluid bulk around the sensor during local compression, the affect of interferant concentration increases can be suppressed or reduced, thereby reducing noise and promoting heightened sensor function. One preferred embodiment provides a device having an architecture that allows and/or promotes increased fluid bulk and/or increased bulk fluid flow in the area surrounding at least a portion of an implanted sensor in vivo, which is believed to enable a sensor signal, wherein the non-constant noise component is at least less than about 20% of the total signal over a time period of at least one day.

A variety of structures can be incorporated into the sensor configuration to allow and/or promote (e.g., to stimulate or to promote) fluid bulk, bulk fluid flow, and/or diffusion rate, such as by forming a fluid pocket, which can enable a sensor signal in which the non-constant noise component is less than about 20% of the total signal (for about one or more days). These structures can include but are not limited to spacers, meshes, shedding layers, roughened surfaces, machineable materials, nanoporous materials, shape-memory materials, porous memory materials, self-assembly materials, collapsible materials, biodegradable materials, combinations thereof, and the like. Structures that promote increased fluid bulk and/or increased bulk fluid flow can also include but are not limited to structures that promote fluid influx or efflux (e.g., fluid influx-promoting architecture, fluid efflux-promoting architecture), that promote vasodilation (e.g., vasodilating architecture), that promote inflammation (e.g., inflammatory architecture), that promote wound healing or perpetuate wounding (e.g., wound-healing architecture and wounding architecture, respectively), that promote angiogenesis (e.g., angiogenic architecture), that suppress inflammation (e.g., an anti-inflammatory architecture) or combinations thereof.

In some embodiments, the sensor includes a physical spacer that is disposed between the sensor and the surrounding tissue; the spacer allows for a liquid sheath to form around at least a portion of the sensor, such as the area surrounding the electrodes, for example. A fluid sheath can provide a fluid bulk that dilutes or buffers interferants while promoting glucose and oxygen transport to the sensor. In some embodiments, the spacer is a mesh or optionally a fibrous structure. Suitable mesh materials are known in the art and include open-weave meshes fabricated of biocompatible materials such as but not limited to PLA, PGA, PP, nylon and the like. Mesh spacers can be applied directly to the sensing mechanism or over a biointerface membrane, such as a porous biointerface membrane disclosed elsewhere herein. Mesh spacers can act as a fluid influx- or efflux-promoting structure and provides the advantage of relatively more rapid fluid movement, mixing and/or diffusion within the mesh to reduce local interferant concentrations and increasing glucose and oxygen concentrations. The increased fluid volume within the mesh can also promote increased fluid movement in and out of the area, which brings in glucose and oxygen while removing or diluting interferants.

In one exemplary embodiment, the sensor is wrapped with a single layer of open weave polypropylene (PP) biocompatible mesh. When the sensor is inserted, the mesh holds the surrounding tissue away from the sensor surface and allows an influx of extracellular fluid to enter the spaces within the mesh, thereby creating a fluid pocket around the sensor. Within the fluid pocket, fluid can mix substantially rapidly as extracellular fluid enters and leaves the fluid pocket or due to host movement. Interferants are carried by the fluid and therefore can be mixed and/or diluted. Since the host can wear the sensor for a plurality of days, sedentary periods will inevitably occur. During these periods interferants can accumulate. However, the increased fluid volume provided by the mesh can substantially buffer accumulated interferants until the sedentary period ends. When the sedentary period is over, any accumulated interferants can be diluted or carried away by an influx or efflux of fluid.

In some embodiments, a mesh can be applied to a sensor either symmetrically or asymmetrically. For example, the mesh can be tightly wrapped around the sensor. In another example, a strip of mesh can be applied to only one side of the sensor. In yet another example, the mesh can form a flat envelope about a few millimeters to about a centimeter wide, with the sensor sandwiched within the envelope. In some embodiments, the mesh can cover only a portion of the sensor, such as the portion containing the electrochemically reactive surface(s). In other embodiments, the mesh can cover the entire sensor.

In another alternative embodiment, noise can be reduced by inclusion of a hydrogel on the surface of at least a portion of the sensor, such as the sensing region. A hydrogel is a network of super absorbent (they can contain from about 20 wt. % to about 99 wt. % water, preferably 80 wt. % to over 99 wt. % water) natural or synthetic polymer chains. Hydrogels are sometimes found as a colloidal gel in which water is the dispersion medium. Since hydrogels are nonporous, fluid and interferants within the hydrogel move by diffusion. Accordingly, the movement of molecules within hydrogels is relatively slower than that possible within mesh-based fluid pockets as described above. Optionally, the hydrogel can be biodegradable. A biodegradable hydrogel can provide a fluid pocket that gradually diminishes and is eventually eliminated by the surrounding tissue.

In a further embodiment, a hydrogel includes a flexible, water-swellable, film (as disclosed elsewhere herein) having a "dry film" thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. "Dry film" thickness refers to the thickness of a cured film cast from a coating formulation by standard coating techniques. The hydrogel material can be applied to the entire sensor or a portion of it, using any method known in the art, such as but not limited to dipping, painting, spraying, wrapping, and the like.

In some embodiments, scavenging agents (e.g., bioactive agents that can scavenge, bind-up or substantially inactivate interferants) can be incorporated into the hydrogel or other aspect of the device (e.g., membrane system). Scavenging agents can suppress prolonged wounding and inflammation by removing signal associated with irritating substances from the locality of the sensor and/or internally generated hydrogen peroxide. One exemplary scavenging agent embodiment incorporates an $H_2O_2$-degrading enzyme, such as but not limited to glutathione peroxidase (GSH peroxidase), catalase, heme-containing peroxidases, eosinophil peroxidase, thyroid peroxidase or horseradish peroxidase (HRP) into the hydrogel to degrade the available $H_2O_2$ and produce oxygen. The scavenging agent can act within the hydrogel or can be released into the local environment to act outside the hydrogel.

In some embodiments, a mesh and a hydrogel can be used in combination to provide greater mechanical support (to hold the surrounding tissue away from the sensor) while slowing down the diffusion rate within the mesh-hydrogel layer. For example, a PP mesh can be applied to the sensor followed by spraying a dry hydrogel material onto the PP-wrapped sensor. Alternatively, the hydrogel can be dried within the mesh before application to the sensor. Upon sensor implantation, the hydrogel can absorb fluid from the surrounding tissue, expand and fill the mesh pores. In a further example, the hydrogel can be biodegradable. In this example, the hydrogel can initially slow fluid movement. But as the hydrogel is biodegraded, the pores of the mesh are opened up and fluid movement can speed up or increase.

A variety of alternative materials can be used to create architectures that create a fluid pocket. For example, shape-memory materials can be used as an alternative to a mesh, to form a fluid pocket around the sensor. Shape-memory materials are metals or polymers that "remember" their geometries. Shape-memory metals (e.g., memory metals or smart wire) include copper-zinc-aluminum, copper-aluminum-nickel, and nickel-titanium (NiTi) alloys. Shape-memory polymers include materials such as polynorbornene, segmented poly(epsilon-caprolactone) polyurethanes, poly(ethylene glycol)-poly(epsilon-caprolactone) diblock copolymers, and the like, for example. A shape-memory material can be deformed from its "original" conformation and regains its original geometry by itself in response to a force, such as temperature or pressure.

In some embodiments, a porous memory material that has been collapsed into a flat, nonporous sheet can be applied to the exterior of the sensor as a flat film. After insertion into the body, increased temperature or moisture exposure can stimulate the memory material to transform to a 3-dimensional, porous architecture that promotes fluid pocket formation, for example.

In some embodiments, nanoporous materials, which act as molecular sieves, can be used to exclude interferants surrounding the sensor. In another alternative embodiment, a swellable material (e.g., a material having an initial volume that absorbs fluid, such as water, when it contacts the fluid to become a second volume that is greater than the initial volume) or collapsible material (e.g., a material having an initial volume that collapse to a second volume that is smaller than the initial volume) can produce or maintain a fluid pocket.

In some embodiments, materials with differing characteristics can be applied in combination, such as alternating bands or layers, to suppress uniform capsule formation. For example, alternating bands of collapsible and non-collapsible swellable material can be applied around a portion of the sensor. Upon implantation, both materials swell with fluid from the surrounding tissue. However, only the segments of collapsible material can deform. Since the material surrounding the sensor will be irregular, it can disrupt formation of a continuous cell layer, thereby reducing noise and extending sensor life.

In addition to providing a physical spacer, mesh, porous material or the like, irritating sensor configurations can reduce noise by promoting fluid pocket formation and/or increased bulk fluid flow. Accordingly, one embodiment of an irritating biointerface includes a structure having a roughened surface, which can rub or poke adjacent cells in vivo. The sensor surface can be roughened by coating the sensor with a machineable material that is or can be etched to form ridges, bristles, spikes, grids, grooves, circles, spirals, dots, bumps, pits or the like, for example. The material can be any convenient, biocompatible material, such as machined porous structures that are overlaid on the sensor, such as but not limited to machineable metal matrix composites, bone substrates such as hydroxyapatite, coral hydroxyapatite and β-tricalcium phosphate (TCP), porous titanium (Ti) mixtures made by sintering of elemental powders, bioglasses (calcium and silicon-based porous glass), ceramics and the like. The material can be "machined" by any convenient means, such as but not limited to scraping, etching, lathing or lasering, for example.

Micro-motion of the sensor can increase the irritating effect of a roughened surface. Micro-motion is an inherent property of any implanted device, such as an implanted glucose sensor. Micro-motion of the device (e.g., minute movements of the device within the host) is caused by host movements, ranging from breathing and small local muscle movements to gross motor movements, such as walking, running or even getting up and sitting down. External forces, such as external pressure application, can also cause micro-motion. Micro-motion includes movement of the sensor back and forth, rotation, twisting and/or turning. Accordingly, as the sensor is moved by micro-motion, the sensor's rough surface can rub more vigorously against the surrounding tissue, causing increased or extended wounding, resulting in additional stimulation of the wound healing process and increases in fluid bulk, bulk fluid flow and/or fluid pocket formation, with a concomitant reduction in noise.

In some embodiments, an irritating architecture is formed from self-assembly materials. Self-assembly biomaterials comprise specific polypeptides that are designed a priori to self-assemble into targeted nano- and microscopic structures. Intramolecular self-assembling molecules are often complex polymers with the ability to assemble from the random coil conformation into a well-defined stable structure (secondary and tertiary structure). A variety of self-assembly materials known in the art can find use in the present embodiment. For example, PuraMatrix™ (3DM Inc., Cambridge, Mass., USA) can be used to create synthetic self-assembling peptide nanofiber scaffolds and defined 3-D microenvironments.

In an exemplary embodiment of an irritating biointerface, an irritating superstructure is applied to the working electrode or the completed sensor. A "superstructure," as used herein is a broad term and used in its ordinary sense, including, without limitation, to refer to any structure built on something else, such as but not limited to the overlying portion of a structure. An irritating superstructure can include any substantial structure that prevents cell attachment and is irritating to the surrounding tissue in vivo. In one example, an irritating superstructure can include large spaces, such as at least about 50 μm wide and at least about 50 μm deep. Cells surrounding the sensor can be prevented from attachment in the spaces within the superstructure, allowing fluid to fill these spaces. In some exemplary embodiments, an irritating superstructure takes advantage of sensor micromotion, to prevent cell attachment and stimulate fluid pocket formation.

In one exemplary embodiment, an irritating superstructure is comprised of ridges at least about 0.25 μm to 0.50 μm in diameter and about 50 μm high, and separated by at least about 0.25 μm to 0.50 μm. In another exemplary embodiment, an exposed silver wire, at least about 0.25 μm to 0.50 μm in diameter, is applied to the sensor exterior to form grooves about 50 μm wide and about 50 μm deep. Since silver is pro-inflammatory and stimulates fluid influx from the surrounding tissues, the combination of an irritating superstructure and a chemical irritant could promote an increased rate of fluid influx or prolong irritation and fluid influx. In yet another exemplary embodiment, with reference to the embodiment shown in FIG. 2A, the configuration (e.g., diameter) of the reference electrode 30 can be changed (e.g., increased in size and/or coil spacing) such that the reference electrode, itself, becomes an irritating superstructure.

Porous Membrane

In addition to the devices described above, fluid bulk and or bulk fluid flow at and/or adjacent to the sensor can be increased by incorporating a porous membrane into the sensor system, such that noise is substantially reduced and sensor accuracy and/or sensitivity are improved. A porous membrane can be referred to as a "bioprotective domain" or a "cell disruptive domain." In some embodiments, the sensor includes a porous material disposed over some portion thereof, which modifies the host's tissue response to the sensor and thereby reduces noise (e.g., due to a local build up of electroactive species that can interfere with the analyte signal). For example, in some embodiments, the porous material surrounding the sensor advantageously enhances and extends sensor performance and lifetime in the short-term by slowing or reducing cellular migration to the sensor and associated degradation that would otherwise be caused by cellular invasion if the sensor were directly exposed to the in vivo environment. Alternatively, the porous material can provide stabilization of the sensor via tissue ingrowth into the porous material in the long-term. Suitable porous materials include silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, poly(ethylene oxide), poly(propylene oxide) and copolymers and blends thereof, polysulfones and block copolymers thereof including, for example, di-block, tri-block, alternating, random and graft copolymers, as well as metals, ceramics, cellulose, hydrogel polymers, poly (2-hydroxyethyl methacrylate, pHEMA), hydroxyethyl methacrylate, (HEMA), polyacrylonitrile-polyvinyl chloride (PAN-PVC), high density polyethylene, acrylic copolymers, nylon, polyvinyl difluoride, polyanhydrides, poly(l-lysine), poly (L-lactic acid), hydroxyethylmethacrylate, hydroxyapeptite, alumina, zirconia, carbon fiber, aluminum, calcium phosphate, titanium, titanium alloy, nintinol, stainless steel, and CoCr alloy, or the like, such as are described in U.S. Patent Publication No. US-2005-0031689-A1 and U.S. Patent Publication No. US-2005-0112169-A1.

In some embodiments, the porous material surrounding the sensor provides unique advantages in the short-term (e.g., one to 14 days) that can be used to enhance and extend sensor performance and lifetime. However, such materials can also provide advantages in the long-term too (e.g., greater than 14 days). Particularly, the in vivo portion of the sensor (the portion of the sensor that is implanted into the host's tissue) is encased (partially or fully) in a porous material. The porous material can be wrapped around the sensor (for example, by wrapping the porous material around the sensor or by inserting the sensor into a section of porous material sized to receive the sensor). Alternately, the porous material can be deposited on the sensor (for example, by electrospinning of a polymer directly thereon). In yet other alternative embodiments, the sensor is inserted into a selected section of porous biomaterial. Other methods for surrounding the in vivo portion of the sensor with a porous material can also be used as is appreciated by one skilled in the art.

The porous material surrounding the sensor advantageously slows or reduces cellular migration to the sensor and associated degradation that would otherwise be caused by cellular invasion if the sensor were directly exposed to the in vivo environment. Namely, the porous material provides a barrier that makes the migration of cells towards the sensor more tortuous and therefore slower (providing short-term advantages). It is believed that this reduces or slows the sensitivity loss normally observed in a short-term sensor over time.

In an embodiment wherein the porous material is a high oxygen solubility material, such as porous silicone, the high oxygen solubility porous material surrounds some of or the entire in vivo portion of the sensor. In some embodiments, a lower ratio of oxygen-to-glucose can be sufficient to provide excess oxygen by using a high oxygen soluble domain (for example, a silicone- or fluorocarbon-based material) to enhance the supply/transport of oxygen to the enzyme membrane and/or electroactive surfaces. It is believed that some signal noise normally seen by a conventional sensor can be attributed to an oxygen deficit. Silicone has high oxygen permeability, thus promoting oxygen transport to the enzyme layer. By enhancing the oxygen supply through the use of a silicone composition, for example, glucose concentration can be less of a limiting factor. In other words, if more oxygen is supplied to the enzyme and/or electroactive surfaces, then more glucose can also be supplied to the enzyme without creating an oxygen rate-limiting excess. While not being bound by any particular theory, it is believed that silicone materials provide enhanced bio-stability when compared to other polymeric materials such as polyurethane.

In certain aspects, including a biointerface structure, material, matrix, and/or membrane that creates a space appropriate for filling with fluid in vivo on a sensor can enhance sensor performance. In some embodiments, a sensor includes a porous biointerface material, which allows fluid from the surrounding tissues to form a fluid-filled pocket around at least a portion of the sensor. It is believed that the fluid-filled pocket provides a sufficient source of analyte-containing fluid for accurate sensor measurement in the short-term. Additionally or alternatively, inclusion of bioactive agents can modify the host's tissue response, for example to reduce or eliminate tissue ingrowth or other cellular responses into the biointerface.

In some aspects, modifying a sensor with a structure, material, and/or membrane/matrix that allows tissue ingrowth without barrier cell formation can enhance sensor performance. For example, a vascularized bed of tissue for long-term analyte sensor measurement. In some embodiments, a porous biointerface membrane, including a plurality of interconnected cavities and a solid portion, covering at least the sensing portion of a sensor allows vascularized tissue ingrowth therein. Vascularized tissue ingrowth provides a sufficient source of analyte-containing tissue in the long-term. Additionally or alternatively, inclusion of bioactive agents can modify the host's tissue response, for example to reduce or eliminate barrier cell layer formation within the membrane.

When used herein, the terms "membrane" and "matrix" are meant to be interchangeable. In these embodiments first domain is provided that includes an architecture, including cavity size, configuration, and/or overall thickness, that modifies the host's tissue response, for example, by creating a fluid pocket, encouraging vascularized tissue ingrowth, disrupting downward tissue contracture, resisting fibrous tissue growth adjacent to the device, and/or discouraging barrier cell formation. The biointerface preferably covers at least the sensing mechanism of the sensor and can be of any shape or size, including uniform, asymmetrically, or axisymmetrically covering or surrounding a sensing mechanism or sensor.

In some embodiments, a second domain is optionally provided that is impermeable to cells and/or cell processes. A bioactive agent is optionally provided that is incorporated into the at least one of the first domain, the second domain, the sensing membrane, or other part of the implantable device, wherein the bioactive agent is configured to modify a host tissue response.

In one embodiment, a porous material that results in increased fluid bulk, bulk fluid flow and/or diffusion rate, as well as formation of close vascular structures, is a porous polymer membrane, such as but not limited to polytetrafluoroethylene (PTFE), polysulfone, polyvinylidene difluoride, polyacrylonitrile, silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, poly(ethylene oxide), poly(propylene oxide) and copolymers and blends thereof, polysulfones and block copolymers thereof including, for example, di-block, tri-block, alternating, random and graft copolymers, as well as metals, ceramics, cellulose, hydrogel polymers, poly (2-hydroxyethyl methacrylate, pHEMA), hydroxyethyl methacrylate, (HEMA), polyacrylonitrile-polyvinyl chloride (PAN-PVC), high density polyethylene, acrylic copolymers, nylon, polyvinyl difluoride, polyanhydrides, poly(l-lysine), poly (L-lactic acid), and hydroxyethylmethacrylate, having an average nominal pore size of at least about 0.6 µm to 20 µm, using conventional methods for determination of pore size in the trade. In one embodiment, at least approximately 50% of the pores of the membrane have an average size of approximately 0.6 µm to about 20 µm, such as described in U.S. Pat. No. 5,882,354. In this exemplary embodiment, the structural elements, which provide the three-dimensional conformation, can include fibers, strands, globules, cones or rods of amorphous or uniform geometry that is smooth or rough. These elements, hereafter referred to as "strands," have in general one dimension larger than the other two and the smaller dimensions do not exceed five microns.

In another further embodiment, the porous polymer membrane material, as described above, consists of strands that define "apertures" formed by a frame of the interconnected strands. The apertures have an average size of no more than about 20 µm in any but the longest dimension. The apertures of the material form a framework of interconnected apertures, defining "cavities" that are no greater than an average of about 20 µm in any but the longest dimension. In another embodiment the porous polymer membrane material has at least some apertures having a sufficient size to allow at least some vascular structures to be created within the cavities. At least some of these apertures, while allowing vascular structures to form within the cavities, prevent connective tissue from forming therein because of size restrictions.

In a further embodiment, the porous membrane has frames of elongated strands of material that are less than 5 microns in all but the longest dimension and the frames define apertures which interconnect to form three-dimensional cavities which permit substantially all inflammatory cells migrating into the cavities to maintain a rounded morphology. Additionally, the porous material promotes vascularization adjacent but not substantially into the porous material upon implantation into a host. Exemplary materials include but are not limited to polyethylene, polypropylene, polytetrafluoroethylene (PTFE), cellulose acetate, cellulose nitrate, polycarbonate, polyester, nylon, polysulfone, mixed esters of cellulose, polyvinylidene difluoride, silicone, polyacrylonitrile, and the like.

In some embodiments, a short-term sensor is provided with a spacer adapted to provide a fluid pocket between the sensor and the host's tissue. It is believed that this spacer, for example a biointerface material, matrix, mesh, hydrogel and like structures and the resultant fluid pocket provide for oxygen and/or glucose transport to the sensor.

In one exemplary embodiment, the sensor includes a biointerface membrane configured to prevent adipose cell contact with an inserted transcutaneous sensor or an implanted sensor. Preferably, a porous biointerface membrane surrounds the sensor, covering the sensing mechanism (e.g., at least a working electrode) and is configured to fill with fluid in vivo, thereby creating a fluid pocket surrounding the sensor. Accordingly, the adipose cells surrounding the sensor are held a distance away (such as the thickness of the porous biointerface membrane, for example) from the sensor surface. Accordingly, as the porous biointerface membrane fills with fluid (e.g., creates a fluid pocket), oxygen and glucose are transported to the sensing mechanism in quantities sufficient to maintain accurate sensor function. Additionally, as discussed elsewhere herein, interferants are diluted, suppressing or reducing interference with sensor function.

In another exemplary embodiment, a short-term sensor (or short-term function of a long-term sensor) including a biointerface, including but not limited to, for example, porous biointerface materials, mesh cages, and the like, all of which are described in more detail elsewhere herein, can be employed to improve sensor function in the short-term (e.g., first few hours to days), such as by reducing noise on the sensor signal. Porous biointerface membranes need not necessarily include interconnected cavities for creating a fluid pocket in the short-term.

Bioactive Agents

A variety of bioactive agents are known to promote fluid influx or efflux. Accordingly, incorporation of bioactive agents into the membrane can increasing fluid bulk, bulk fluid flow and/or diffusion rates (and promoting glucose and oxygen influx), thereby decrease non-constant noise. In some embodiments, fluid bulk and/or bulk fluid flow are increased at (e.g., adjacent to the sensor exterior surface) the sensor by incorporation of one or more bioactive agents. In some embodiments, the sensor is configured to include a bioactive agent that irritates the wound and stimulates the release of soluble mediators that are known to cause a local fluid influx at the wound site. In some embodiments, the sensor is configured to include a vasodilating bioactive agent, which can cause a local influx of fluid from the vasculature.

A variety of bioactive agents can be found useful in preferred embodiments. Exemplary bioactive agents include but are not limited to blood-brain barrier disruptive agents and vasodilating agents, vasodilating agents, angiogenic factors, and the like. Useful bioactive agents include but are not limited to mannitol, sodium thiosulfate, VEGF/VPF, NO, NO-donors, leptin, bradykinin, histamines, blood components, platelet rich plasma (PRP), matrix metalloproteinases (MMP), Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-Beta), Transforming Growth Factor Alpha (TGF-Alpha), Hepatocyte Growth Factor, Tumor Necrosis Factor-Alpha (TNF-Alpha), Placental Growth Factor (PLGF), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, Leptin, Copper Sulphate, Estradiol, prostaglandins, cox inhibitors, endothelial cell binding agents (for example, decorin or vimentin), glenipin, hydrogen peroxide, nicotine, and Growth Hormone. Still other useful bioactive agents include enzymes, cytotoxic or necrosing agents (e.g., pactataxyl, actinomycin, doxorubicin, daunorubicin, epirubicin, bleomycin, plicamycin, mitomycin), cyclophosphamide, chlorambucil, uramustine, melphalan, bryostatins, inflammatory bacterial cell wall components, histamines, proinflammatory factors and the like.

Bioactive agents can be added during manufacture of the sensor by incorporating the desired bioactive agent in the manufacturing material for one or more sensor layers or into an exterior biomaterial, such as a porous silicone membrane. For example, bioactive agents can be mixed with a solution during membrane formation, which is subsequently applied onto the sensor during manufacture. Alternatively, the completed sensor can be dipped into or sprayed with a solution of a bioactive agent, for example. The amount of bioactive agent can be controlled by varying its concentration, varying the indwell time during dipping, applying multiple layers until a desired thickness is reached, and the like, as disclosed elsewhere herein. In an alternative embodiment, the bioactive agent is microencapsulated before application to the sensor. For example, microencapsulated bioactive agent can be sprayed onto a completed sensor or incorporated into a structure, such as an outer mesh layer or a shedding layer. Microencapsulation can offer increased flexibility in controlling bioactive agent release rate, time of release occurrence and/or release duration.

Chemical systems/methods of irritation can be incorporated into an exterior sensor structure, such as the biointerface membrane (described elsewhere herein) or a shedding layer that releases the irritating agent into the local environment. For example, in some embodiments, a "shedding layer" releases (e.g., sheds or leaches) molecules into the local vicinity of the sensor and can speed up osmotic fluid shifts. In some embodiments, a shedding layer can provide a mild irritation and encourage a mild inflammatory/foreign body response, thereby preventing cells from stabilizing and building up an ordered, fibrous capsule and promoting fluid pocket formation.

A shedding layer can be constructed of any convenient, biocompatible material, include but not limited to hydrophilic, degradable materials such as polyvinylalcohol (PVA), PGC, Polyethylene oxide (PEO), polyethylene glycol-polyvinylpyrrolidone (PEG-PVP) blends, PEG-sucrose blends, hydrogels such as polyhydroxyethyl methacrylate (pHEMA), polymethyl methacrylate (PMMA) or other polymers with quickly degrading ester linkages. In certain embodiment, absorbable suture materials, which degrade to compounds with acid residues, can be used. The acid residues are chemical irritants that stimulate inflammation and wound healing. In certain embodiments, these compounds include glycolic acid and lactic acid based polymers, polyglactin, polydioxone, polydyconate, poly(dioxanone), poly (trimethylene carbonate) copolymers, and poly (caprolactone) homopolymers and copolymers, and the like.

In other exemplary embodiments, the shedding layer can be a layer of materials listed elsewhere herein for the first domain, including copolymers or blends with hydrophilic polymers such as polyvinylpyrrolidone (PVP), polyhydroxyethyl methacrylate, polyvinylalcohol, polyacrylic acid, polyethers, such as polyethylene glycol, and block copolymers thereof including, for example, di-block, tri-block, alternating, random and graft copolymers (block copolymers are discussed in U.S. Pat. No. 4,803,243 and U.S. Patent). In one preferred embodiment, the shedding layer is comprised of polyurethane and a hydrophilic polymer. For example, the hydrophilic polymer can be polyvinylpyrrolidone. In one preferred embodiment, the shedding layer is polyurethane comprising not less than 5 weight percent polyvinylpyrrolidone and not more than 45 weight percent polyvinylpyrrolidone. Preferably, the shedding layer comprises not less than 20 weight percent polyvinylpyrrolidone and not more than 35 weight percent polyvinylpyrrolidone and, most preferably, polyurethane comprising about 27 weight percent polyvinylpyrrolidone.

In other exemplary embodiments, the shedding layer can include a silicone elastomer, such as a silicone elastomer and a poly(ethylene oxide) and poly(propylene oxide) co-polymer blend, as disclosed in copending U.S. patent application Ser. No. 11/404,417 filed Apr. 14, 2006. In one embodiment, the silicone elastomer is a dimethyl- and methylhydrogensiloxane copolymer. In one embodiment, the silicone elastomer comprises vinyl substituents. In one embodiment, the silicone elastomer is an elastomer produced by curing a MED-4840 mixture. In one embodiment, the copolymer comprises hydroxy substituents. In one embodiment, the co-polymer is a triblock poly(ethylene oxide)-poly(propylene oxide)-poly(ethylene oxide) polymer. In one embodiment, the co-polymer is a triblock poly(propylene oxide)-poly(ethylene oxide)-poly(propylene oxide) polymer. In one embodiment, the co-polymer is a PLURONIC® polymer. In one embodiment, the co-polymer is PLURONIC® F-127. In one embodiment, at least a portion of the co-polymer is cross-linked. In one embodiment, from about 5% w/w to about 30% w/w of the membrane is the co-polymer.

A shedding layer can take any shape or geometry, symmetrical or asymmetrical, to promote fluid influx in a desired location of the sensor, such as the sensor head or the electrochemically reactive surfaces, for example. Shedding layers can be located on one side of sensor or both sides. In another example, the shedding layer can be applied to only a small portion of the sensor or the entire sensor.

In one exemplary embodiment, a shedding layer comprising polyethylene oxide (PEO) is applied to the exterior of the sensor, where the tissue surrounding the sensor can directly access the shedding layer. PEO leaches out of the shedding layer and is ingested by local cells that release pro-inflammatory factors. The pro-inflammatory factors diffuse through the surrounding tissue and stimulate an inflammation response that includes an influx of fluid. Accordingly, early noise can be reduced or eliminated and sensor function can be improved.

In another exemplary embodiment, the shedding layer is applied to the sensor in combination with an outer porous layer, such as a mesh or a porous biointerface as disclosed elsewhere herein. In one embodiment, local cells access the shedding layer through the through pores of a porous silicone biointerface. In one example, the shedding layer material is applied to the sensor prior to application of the porous silicone. In another example, the shedding layer material can be absorbed into the lower portion of the porous silicone (e.g., the portion of the porous silicone that will be proximal to the sensor after the porous silicone has been applied to the sensor) prior to application of the porous silicone to the sensor.

Wound Suppression

Non-constant noise can be decreased by wound suppression (e.g., during sensor insertion), in some embodiments. Wound suppression includes any systems or methods by which an amount of wounding that occurs upon sensor insertion is reduced and/or eliminated. While not wishing to be bound by theory, it is believed that if wounding is suppressed or at least significantly reduced, the sensor will be surrounded by substantially normal tissue (e.g., tissue that is substantially similar to the tissue prior to sensor insertion). Substantially normal tissue is believed to have a lower metabolism than wounded tissue, producing fewer interferants and reducing early noise.

Wounds can be suppressed or minimized by adaptation of the sensor's architecture to one that either suppresses wounding or promotes rapid healing, such as an architecture that does not cause substantial wounding (e.g., an architecture configured to prevent wounding), an architecture that promotes wound healing, an anti-inflammatory architecture, and the like. In one exemplary embodiment, the sensor is configured to have a low profile, a zero-footprint or a smooth surface. For example, the sensor can be formed of substantially thin wires, such as wires from about 50 µm to about 150 µm in diameter, for example. Preferably, the sensor is small enough to fit within a very small gauge needle, such as a 30, 31, 32, 33, 34, or 35 gauge needle (or smaller) on the Stubs scale, for example. In general, a smaller needle, the more reduces the amount of wounding during insertion. For example, a very small needle can reduce the amount of tissue disruption and thereby reduce the subsequent wound healing response. In an alternative embodiment, the sensor's surface is smoothed with a lubricious coating, to reduce wounding upon sensor insertion.

Wounding can also be reduced by inclusion of wound-suppressive agents (bioactive agents) that either reduce the amount of initial wounding or suppress the wound healing process. While not wishing to be bound by theory, it is believed that application of a wound-suppressing agent, such as an anti-inflammatory, an immunosuppressive agent, an anti-infective agent, or a scavenging agent, to the sensor can create a locally quiescent environment and suppress wound healing. In a quiescent environment, bodily processes, such as the increased cellular metabolism associated with wound healing, can minimally affect the sensor. If the tissue surrounding the sensor is undisturbed, it can continue its normal metabolism and promote sensor function.

In some embodiment, useful compounds and/or factors for suppressing wounding include but are not limited to first-generation $H_1$-receptor antagonists: ethylenediamines (e.g., mepyramine (pyrilamine), antazoline), ethanolamines (e.g., diphenhydramine, carbinoxamine, doxylamine, clemastine, and dimenhydrinate), alkylamines (pheniramine, chlorphenamine (chlorpheniramine), dexchlorphenamine, brompheniramine, and triprolidine), piperazines (cyclizine, hydroxyzine, and meclizine), and tricyclics (promethazine, alimemazine (trimeprazine), cyproheptadine, and azatadine); second-generation $H_1$-receptor antagonists such as acrivastine, astemizole, cetirizine, loratadine, mizolastine, azelastine, levocabastine, and olopatadine; mast cell stabilizers such as cromoglicate (cromolyn) and nedocromil;

anti-inflammatory agents, such as acetometaphen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (e.g., L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone; immunosuppressive and/or immunomodulatory agents such as anti-proliferative, cell-cycle inhibitors (e.g., paclitaxel, cytochalasin D, infiximab), taxol, actinomycin, mitomycin, thospromote VEGF, estradiols, NO donors, QP-2, tacrolimus, tranilast, actinomycin, everolimus, methothrexate, mycophenolic acid, angiopeptin, vincristing, mitomycine, statins, C MYC antisense, sirolimus (and analogs), RestenASE, 2-chloro-deoxyadenosine, PCNA Ribozyme, batimstat, prolyl hydroxylase inhibitors, PPARγ ligands (for example troglitazone, rosiglitazone, pioglitazone), halofuginone, C-proteinase inhibitors, probucol, BCP671, EPC antibodies, catchins, glycating agents, endothelin inhibitors (for example, Ambrisentan, Tesosentan, Bosentan), Statins (for example, Cerivastatin), *E. coli* heat-labile enterotoxin, and advanced coatings; anti-infective agents, such as anthelmintics (mebendazole); antibiotics such as aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum *Crystallinum*; gatifloxacin; and sulfamethoxazole/trimethoprim; interferant scavengers, such as superoxide dismutase (SOD), thioredoxin, glutathione peroxidase and catalase, anti-oxidants, such as uric acid and vitamin C, iron compounds, Heme compounds, and some heavy metals; artificial protective coating components, such as albumin, fibrin, collagen, endothelial cells, wound closure chemicals, blood products, platelet-rich plasma, growth factors and the like.

While not wishing to be bound by theory, it is believed that, in addition to the analyte sensor configurations described elsewhere herein, application of a lubricious coating to the sensor can substantially reduce and/or suppress noise occurrence by substantially preventing injury to the host. Accordingly, in some embodiments, a lubricious coating can be applied to the in vivo portion of the sensor to reduce the foreign body response to the implanted sensor. The term "lubricous coating" as used herein is a broad term and is used in its ordinary sense, including without limitation, a surface treatment that provides a reduced surface friction. A variety of polymers are suitable for use as a lubricious sensor coating, such as but not limited to Teflon, polyethylene, polycarbonate, polyurethane, poly(ethylene oxide), poly(ethylene oxide)-poly(propylene oxide) copolymers, and the like. In one exemplary embodiment, one or more layers of HydroMed™, a polyether-polyurethane manufactured by CardioTech International, Inc. (Wilmington, Mass., USA) is applied to the sensor (e.g., over the resistance domain). A more detailed description can be found in Example 1, below.

In some embodiments, wounding can be suppressed by inclusion of a silicone coating (e.g., silicon-hydrophilic polymer blend) or a hydrophilic shedding layer can be applied to the sensor. While not wishing to be bound by theory, it is believed that a silicone bioprotective coating or shedding layer can promote formation and maintenance of a fluid pocket around the sensor, to enhance glucose and fluid transport as well as clearance of interferants. A silicone bioprotective coating can create a local environment with enhanced vascular permeability and/or vascularization. Such a coating is believed to speed up the inflammatory response to achieve a substantially consistent wound environment more quickly than without the coating. Furthermore, a silicone bioprotective coating is believed to be able to subdue the inflammatory response to reduce production of cellular byproducts that are believed to be electrochemical interferants.

In one embodiment, a silicone bioprotective coating can consist of one or more layer(s) formed from a composition that, in addition to providing high oxygen solubility, allows for the transport of glucose or other such water-soluble molecules (for example, drugs). In one embodiment, these layers comprise a blend of a silicone polymer with a hydrophilic polymer. For additional description, see the section entitled "Silicon/Hydrophilic Polymer Blend Materials" herein and co-pending U.S. patent application Ser. No. 11/404,417, filed Apr. 14, 2006, co-pending U.S. patent application Ser. No. 11/675,063, U.S. Patent Publication No. US-2005-0090607-A1, U.S. Patent Publication No. US-2006-0270923-A1, and U.S. Patent Publication No. US-2007-0027370-A1.

Many of the above disclosed methods and structures for forming a fluid pocket, diluting interferants, reducing noise and the like can be used in combination to facilitate a desired effect or outcome. For example, in one embodiment, a shedding layer composed of a hydrophilic silicone film and a necrosing agent can be applied in combination to at least a portion of the sensor. The silicone film can suppress protein adherence to the sensor surface while the necrosing agent can devitalize a small portion of tissue adjacent to the sensor, stimulating formation of a fluid pocket around the hydrophilic silicone film. Preferably, the increased volume of fluid surrounding the sensor dilutes interferants while the shedding layer provides a physical separation between the sensor and the surrounding tissue.

In another exemplary embodiment, a mesh sprayed with dexamethasone is wrapped around the exterior of the sensor. The mesh can provide a physical spacer for a fluid pocket while the dexamethasone inhibits inflammation. Preferably, fluid can fill the mesh and the dexamethasone can promote normal tissue metabolism around the sensor by inhibiting an influx of inflammatory cells. Consequently, glucose and oxygen can travel freely between the tissue and the sensor through the fluid filled mesh without a buildup of interferants, even during periods of tissue compression, thereby promoting sensor sensitivity and thereby reducing noise.

Additional description of increasing fluid bulk, by adapting the sensor's configuration can be found in co-pending U.S. Patent Publication No. US-2006-0229512-A1 and co-pending U.S. patent application Ser. No. 11/654,140 filed on Jan. 17, 2007.

Auxiliary Electrode

In some circumstances, non-constant noise can be reduced by incorporating into the sensor system an auxiliary electrode configured to electrochemically modify (for example, oxidize or reduce) electrochemical interferants to render them substantially non-electroactively reactive at the electroactive sensing surface(s) in order to overcome the effects of interferants on the working electrode. It is known that many electrochemical interferants can be reduced at a potential of from about +0.1V to about +1.2V or more; for example, acetaminophen is reduced at a potential of about +0.4 V. It is noted that one challenge to generating oxygen electrochemically in this way is that while an auxiliary electrode does produce excess oxygen, the placement of the auxiliary electrode in proximity to the analyte-measuring working electrode can cause oxidation of hydrogen peroxide at the auxiliary electrode, resulting in reduced signals at the working electrode. Accordingly, the sensors of preferred embodiments place an auxiliary electrode above the electrode system, or other electroactive sensing surface, thereby reducing or eliminating the problem of inaccurate signals as described above.

Preferably, the auxiliary electrode is located within or adjacent to the membrane system, for example, between the enzyme and other domains, although the auxiliary electrode can be placed anywhere between the electroactive sensing surface and the outside fluid. The auxiliary electrode is formed from known working electrode materials (for example, platinum, palladium, graphite, gold, carbon, conductive polymer, or the like) and has a voltage setting that produces oxygen (for example, from about +0.6 V to about +1.2 V or more) and/or that electrochemically modifies (for example, reduces) electrochemical interferants to render them substantially non-reactive at the electroactive sensing surface(s) (for example, from about +0.1 V to about +1.2 V or more). The auxiliary electrode can be a mesh, grid, plurality of spaced wires or conductive polymers, or other configurations designed to allow analytes to penetrate therethrough.

In another aspect of the preferred embodiments, the auxiliary electrode is configured to electrochemically modify (for example, oxidize or reduce) electrochemical interferants to render them substantially non-reactive at the electroactive sensing surface(s). In these embodiments, which can be in addition to or alternative to the above-described oxygen-generating embodiments, a polymer coating is chosen to selectively allow interferants (for example, urate, ascorbate, and/or acetaminophen such as described in U.S. Pat. No. 6,579,690) to pass through the coating and electrochemically react with the auxiliary electrode, which effectively pre-oxidizes the interferants, rendering them substantially non-reactive at the working electrode. In one exemplary embodiment, silicone materials can be synthesized to allow the transport of oxygen, acetaminophen and other interferants, but not allow the transport of glucose. In some embodiments, the polymer coating material can be chosen with a molecular weight that blocks glucose and allows the transport of oxygen, urate, ascorbate, and acetaminophen. In another exemplary embodiment, silicone materials can be synthesized to allow the transport of oxygen, glucose, acetaminophen, and other interferants. In some embodiments, the polymer coating material is chosen with a molecular weight that allows the transport of oxygen, glucose, urate, ascorbate, and acetaminophen. The voltage setting necessary to react with interfering species depends on the target electrochemical interferants, for example, from about +0.1 V to about +1.2 V. In some embodiments, wherein the auxiliary electrode is set at a potential of from about +0.6 to about +1.2 V, both oxygen-generation and electrochemical interferant modification can be achieved. In some embodiments, wherein the auxiliary electrode is set at a potential below about +0.6 V, the auxiliary electrode will function mainly to electrochemically modify interferants, for example. Additional description can be found in U.S. Pat. No. 7,074,307.

Sensor Electronics

The following description of sensor electronics associated with the electronics unit is applicable to a variety of continuous analyte sensors, such as non-invasive, minimally invasive, and/or invasive (e.g., transcutaneous and wholly implantable) sensors. For example, the sensor electronics and data processing as well as the receiver electronics and data processing described below can be incorporated into the wholly implantable glucose sensor disclosed in U.S. Patent Publication No. 2005-0245799-A1 and U.S. Patent Publication No. US-2006-0015020-A1. Additional description of sensor electronics can be found in co-pending U.S. patent application Ser. No. 11/734,184, filed on Apr. 11, 2007.

Figure 4:
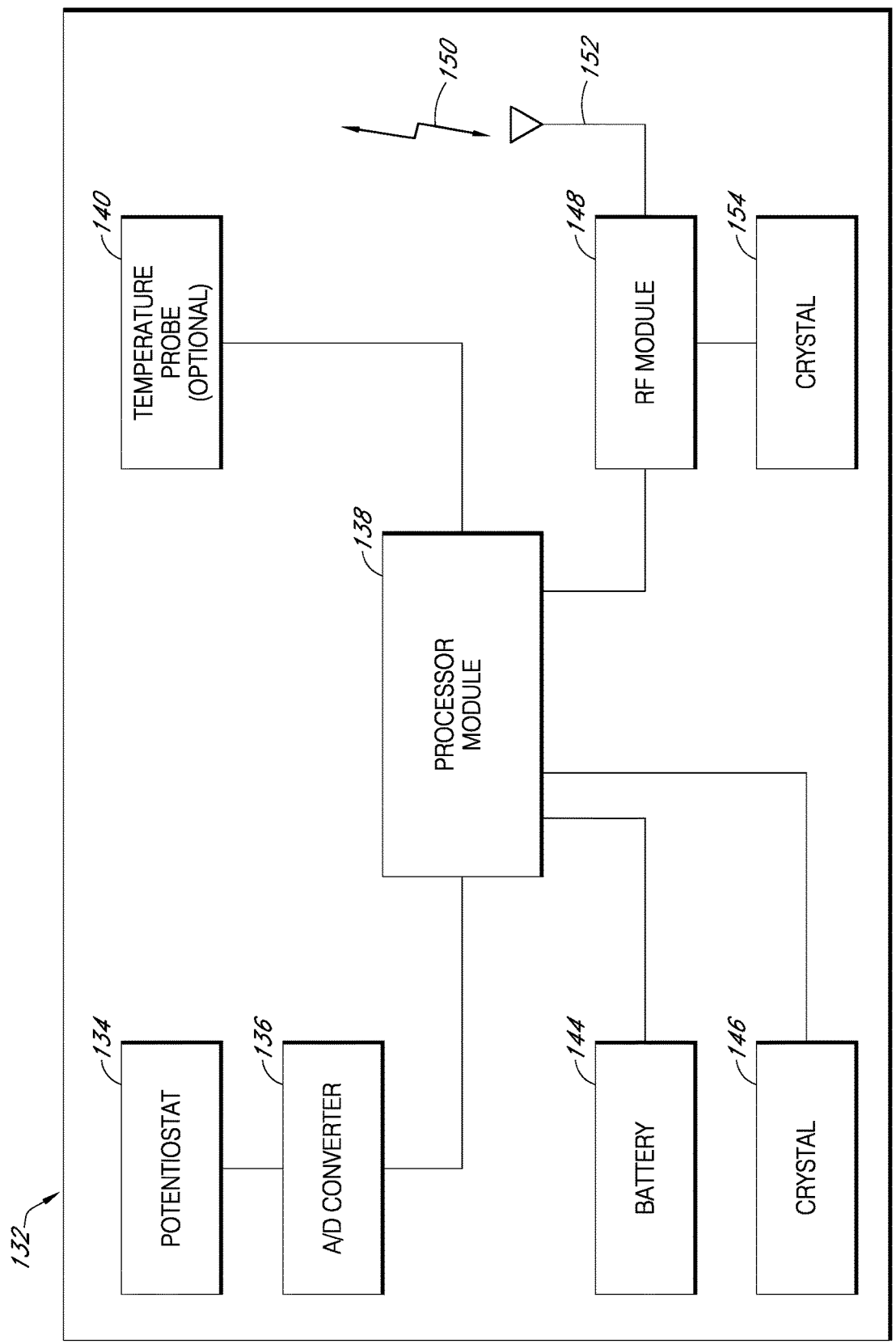
FIG. 4 is a block diagram that illustrates electronics associated with a sensor system, in one embodiment.

FIG. 4 is a block diagram that illustrates the electronics 132 associated with the sensor system, in one embodiment. In this embodiment, a potentiostat 134 is shown, which is operably connected to an electrode system (such as described above) and provides a voltage to the electrodes, which biases the sensor to enable measurement of an current signal indicative of the analyte concentration in the host (also referred to as the analog portion). In some embodiments, the potentiostat includes a resistor (not shown) that translates the current into voltage. In some alternative embodiments, a current to frequency converter is provided that is configured to continuously integrate the measured current, for example, using a charge counting device.

An A/D converter 136 digitizes the analog signal into a digital signal, also referred to as "counts" for processing. Accordingly, the resulting raw data stream in counts, also referred to as raw sensor data, is directly related to the current measured by the potentiostat 134.

A processor module 138 includes the central control unit that controls the processing of the sensor electronics 132. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing and/or replacement of signal artifacts such as is described in U.S. Patent Publication No. US-2005-0043598-A1. The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, or the like.

In some embodiments, the processor module comprises a digital filter, for example, an infinite impulse response (IIR)

or finite impulse response (FIR) filter, configured to smooth the raw data stream from the A/D converter. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter as described above, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter. In preferred embodiments, the processor module is configured with a programmable acquisition time, namely, the predetermined time interval for requesting the digital value from the A/D converter is programmable by a user within the digital circuitry of the processor module. An acquisition time of from about 2 seconds to about 512 seconds is preferred; however any acquisition time can be programmed into the processor module. A programmable acquisition time is advantageous in improving noise filtration, time lag, and processing/battery power.

Preferably, the processor module is configured to build the data packet for transmission to an outside source, for example, an RF transmission to a receiver as described in more detail below. Generally, the data packet comprises a plurality of bits that can include a sensor ID code, raw data, filtered data, and/or error detection or correction. The processor module can be configured to transmit any combination of raw and/or filtered data.

In some embodiments, the processor module further comprises a transmitter portion that determines the transmission interval of the sensor data to a receiver, or the like. In some embodiments, the transmitter portion, which determines the interval of transmission, is configured to be programmable. In one such embodiment, a coefficient can be chosen (e.g., a number of from about 1 to about 100, or more), wherein the coefficient is multiplied by the acquisition time (or sampling rate), such as described above, to define the transmission interval of the data packet. Thus, in some embodiments, the transmission interval is programmable from about 2 seconds to about 850 minutes, more preferably from about 30 second to 5 minutes; however, any transmission interval can be programmable or programmed into the processor module. However, a variety of alternative systems and methods for providing a programmable transmission interval can also be employed. By providing a programmable transmission interval, data transmission can be customized to meet a variety of design criteria (e.g., reduced battery consumption, timeliness of reporting sensor values, etc.)

Conventional glucose sensors measure current in the nanoAmp range. In contrast to conventional glucose sensors, the preferred embodiments are configured to measure the current flow in the picoAmp range, and in some embodiments, femtoAmps. Namely, for every unit (mg/dL) of glucose measured, at least one picoAmp of current is measured. In some embodiments, from about 1, 2, 3, 4, or 5 picoAmps to about 25, 50, 100, 250, or 500 picoAmps of current is measured for every unit (mg/dl) of glucose measured. Preferably, the analog portion of the A/D converter 136 is configured to continuously measure the current flowing at the working electrode and to convert the current measurement to digital values representative of the current. In one embodiment, the current flow is measured by a charge counting device (e.g., a capacitor). Thus, a signal is provided, whereby a high sensitivity maximizes the signal received by a minimal amount of measured hydrogen peroxide (e.g., minimal glucose requirements without sacrificing accuracy even in low glucose ranges), reducing the sensitivity to oxygen limitations in vivo (e.g., in oxygen-dependent glucose sensors).

A battery 144 is operably connected to the sensor electronics 132 and provides the power for the sensor. In one embodiment, the battery is a lithium manganese dioxide battery; however, any appropriately sized and powered battery can be used (for example, AAA, nickel-cadmium, zinc-carbon, alkaline, lithium, nickel-metal hydride, lithium-ion, zinc-air, zinc-mercury oxide, silver-zinc, and/or hermetically-sealed). In some embodiments, the battery is rechargeable, and/or a plurality of batteries can be used to power the system. The sensor can be transcutaneously powered via an inductive coupling, for example. In some embodiments, a quartz crystal 146 is operably connected to the processor 138 and maintains system time for the computer system as a whole, for example for the programmable acquisition time within the processor module.

Optional temperature probe 140 is shown, wherein the temperature probe is located on the electronics assembly or the glucose sensor itself. The temperature probe can be used to measure ambient temperature in the vicinity of the glucose sensor. This temperature measurement can be used to add temperature compensation to the calculated glucose value.

An RF module 148 is operably connected to the processor 138 and transmits the sensor data from the sensor to a receiver within a wireless transmission 150 via antenna 152. In some embodiments, a second quartz crystal 154 provides the time base for the RF carrier frequency used for data transmissions from the RF transceiver. In some alternative embodiments, however, other mechanisms, such as optical, infrared radiation (IR), ultrasonic, or the like, can be used to transmit and/or receive data.

In the RF telemetry module of the preferred embodiments, the hardware and software are designed for low power requirements to increase the longevity of the device (for example, to enable a life of from about 3 to about 24 months, or more) with maximum RF transmittance from the in vivo environment to the ex vivo environment for wholly implantable sensors (for example, a distance of from about one to ten meters or more). Preferably, a high frequency carrier signal of from about 402 MHz to about 433 MHz is employed in order to maintain lower power requirements. Additionally, in wholly implantable devices, the carrier frequency is adapted for physiological attenuation levels, which is accomplished by tuning the RF module in a simulated in vivo environment to ensure RF functionality after implantation; accordingly, the preferred glucose sensor can sustain sensor function for 3 months, 6 months, 12 months, or 24 months or more.

Preferably, the electronics unit indicates to the receiver (FIG. 5) that calibration is to be initialized (or re-initialized). The electronics unit transmits a series of bits within a transmitted data packet wherein a sensor code can be included in the periodic transmission of the device. The status code is used to communicate sensor status to the receiving device. The status code can be inserted into any location in the transmitted data packet, with or without other sensor information. In one embodiment, the status code is designed to be unique or near unique to an individual sensor, which can be accomplished using a value that increments, decrements, or changes in some way after the transmitter detects that a sensor has been removed and/or attached to the transmitter. In an alternative embodiment, the status code can be configured to follow a specific progression, such as a BCD interpretation of a Gray code.

In some embodiments, the sensor electronics 132 are configured to detect a current drop to zero in the working electrode 38 associated with removal of a sensor 34 from the host, which can be configured to trigger an increment of the status code. If the incremented value reaches a maximum, it can be designed to roll over to 0. In some embodiments, the sensor electronics are configured to detect a voltage change cycle associated with removal and/or re-insertion of the sensor, which can be sensed in the counter electrode (e.g., of a three-electrode sensor), which can be configured to trigger an increment of the status code.

In some embodiments, the sensor electronics 132 can be configured to send a special value (for example, 0) that indicates that the electronics unit is not attached when removal of the sensor (or electronics unit) is detected. This special value can be used to trigger a variety of events, for example, to halt display of analyte values. Incrementing or decrementing routines can be used to skip this special value.

In some embodiments, the electronics unit is configured to include additional contacts, which are designed to sense a specific resistance, or passive value, in the sensor system while the electronics unit is attached to the mounting unit. Preferably, these additional contacts are configured to detect information about a sensor, for example, whether the sensor is operatively connected to the mounting unit, the sensor's ID, a calibration code, or the like. For example, subsequent to sensing the passive value, the sensor electronics can be configured to change the sensor ID code by either mapping the value to a specific code, or internally detecting that the code is different and adjusting the sensor ID code in a predictable manner. As another example, the passive value can include information on parameters specific to a sensor (such as in vitro sensitivity information as described elsewhere herein).

In some situations, it can be desirable to wait an amount of time after insertion of the sensor to allow the sensor to equilibrate in vivo, also referred to as "break-in." Accordingly, the sensor electronics can be configured to aid in decreasing the break-in time of the sensor by applying different voltage settings (for example, starting with a higher voltage setting and then reducing the voltage setting) to speed the equilibration process.

In some situations, the sensor may not properly deploy, connect to, or otherwise operate as intended. Accordingly, the sensor electronics can be configured such that if the current obtained from the working electrode, or the subsequent conversion of the current into digital counts, for example, is outside of an acceptable threshold, then the sensor is marked with an error flag, or the like. The error flag can be transmitted to the receiver to instruct the user to reinsert a new sensor, or to implement some other error correction.

The above-described detection and transmission methods can be advantageously employed to minimize or eliminate human interaction with the sensor, thereby minimizing human error and/or inconvenience. Additionally, the sensors of preferred embodiments do not require that the receiver be in proximity to the transmitter during sensor insertion. Any one or more of the above described methods of detecting and transmitting insertion of a sensor and/or electronics unit can be combined or modified, as is appreciated by one skilled in the art.

Receiver

Figure 5:
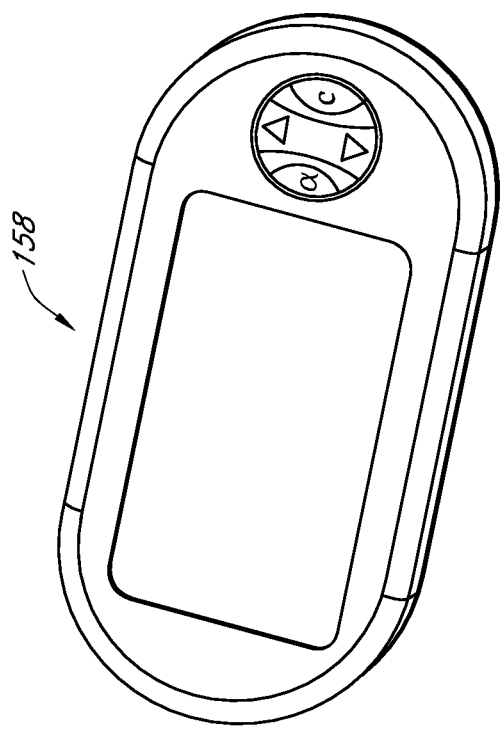
FIG. 5 is perspective view of a receiver, in one embodiment.

FIG. 5 is a perspective view of a receiver 158, in one embodiment. Preferably the electronics unit is wirelessly connected to a receiver 158 via one- or two-way RF transmissions or the like. However, a wired connection is also contemplated. The receiver 158 provides much of the processing and display of the sensor data, and can be selectively worn and/or removed at the host's convenience. Thus, the sensor system can be discreetly worn, and the receiver, which provides much of the processing and display of the sensor data, can be selectively worn and/or removed at the host's convenience. Particularly, the receiver 158 includes programming for retrospectively and/or prospectively initiating a calibration, converting sensor data, updating the calibration, evaluating received reference and sensor data, and evaluating the calibration for the analyte sensor, such as described in more detail with reference to U.S. Patent Publication No. US-2005-0027463-A1 and co-pending U.S. patent application Ser. No. 11/734,184 filed on Apr. 11, 2007.

Figure 6:
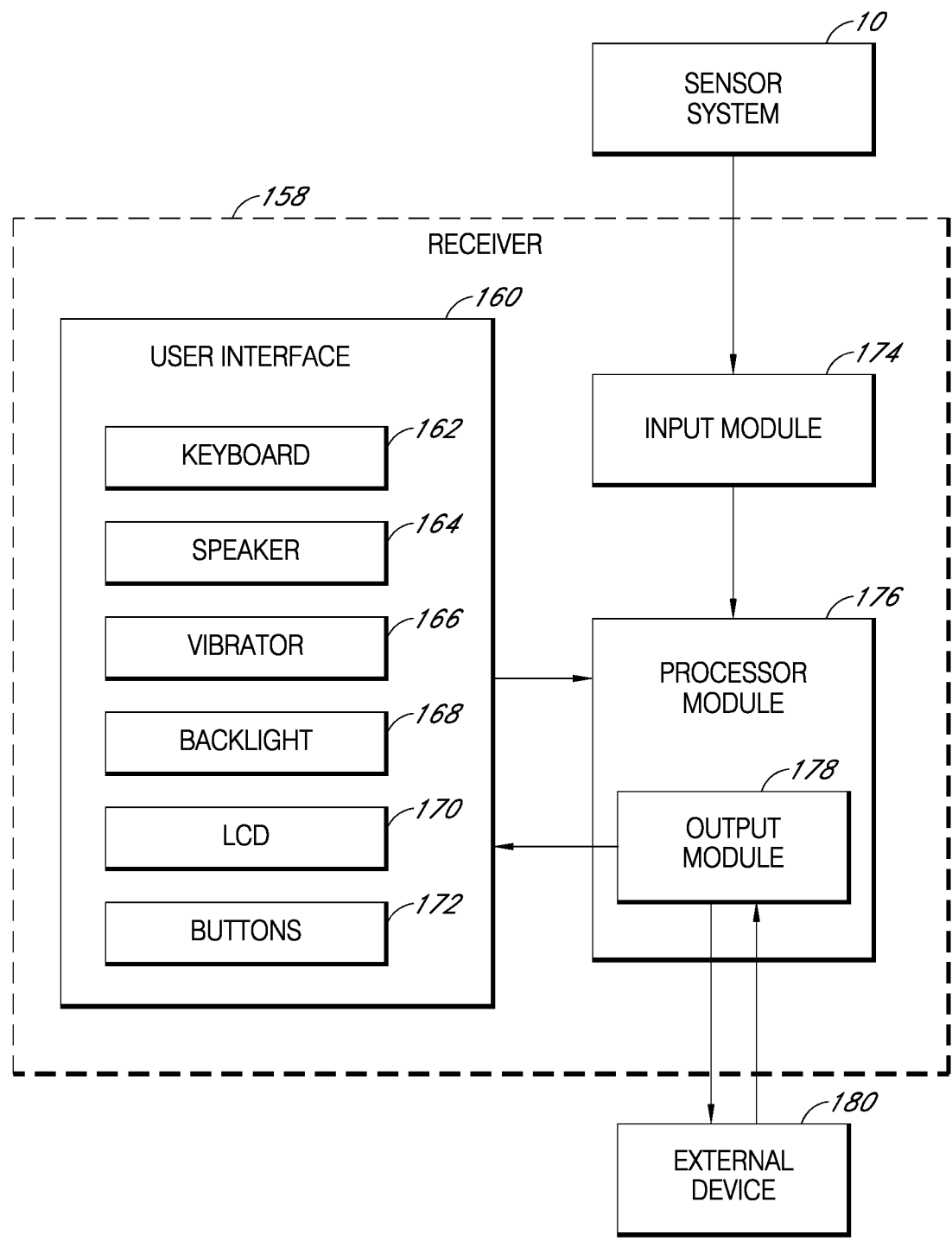
FIG. 6 is a block diagram that illustrates a configuration of a medical device including a continuous analyte sensor, a receiver, and an external device, in one embodiment.

FIG. 6 is a block diagram that illustrates the configuration of the medical device in one embodiment, including a continuous analyte sensor, a receiver 158, and an optional external device 180. In general, the analyte sensor system is any sensor configuration that provides an output signal indicative of a concentration of an analyte (e.g., invasive, minimally-invasive, and/or non-invasive sensors as described above). The output signal is sent to a receiver 158 and received by an input module 174, which is described in more detail below. The output signal is typically a raw data stream that is used to provide a useful value of the measured analyte concentration to a patient or a doctor, for example. In some embodiments, the raw data stream can be continuously or periodically algorithmically smoothed or otherwise modified to diminish outlying points that do not accurately represent the analyte concentration, for example due to signal noise or other signal artifacts, such as described in U.S. Pat. No. 6,931,327.

Referring again to FIG. 6, the receiver 158, which is operatively linked to the sensor system 10, receives a data stream from the sensor system 10 via the input module 174. In one embodiment, the input module includes a quartz crystal operably connected to an RF transceiver (not shown) that together function to receive and synchronize data streams from the sensor system 10. However, the input module 174 can be configured in any manner that is capable of receiving data from the sensor. Once received, the input module 174 sends the data stream to a processor 176 that processes the data stream, such as is described in more detail below.

The processor 176 is the central control unit that performs the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, or the like. The processor includes hardware and software that performs the processing described herein, for example flash memory provides permanent or semi-permanent storage of data, storing data such as sensor ID, receiver ID, and programming to process data streams (for example, programming for performing estimation and other algorithms described elsewhere herein) and random access memory (RAM) stores the system's cache memory and is helpful in data processing.

Preferably, the input module 174 or processor module 176 performs a Cyclic Redundancy Check (CRC) to verify data integrity, with or without a method of recovering the data if there is an error. In some embodiments, error correction techniques such as those that use Hamming codes or Reed-Solomon encoding/decoding methods are employed to correct for errors in the data stream. In one alternative embodiment, an iterative decoding technique is employed, wherein the decoding is processed iteratively (e.g., in a closed loop) to determine the most likely decoded signal. This type of decoding can allow for recovery of a signal that is as low as 0.5 dB above the noise floor, which is in contrast to conventional non-iterative decoding techniques (such as Reed-Solomon), which requires approximately 3 dB or about twice the signal power to recover the same signal (e.g., a turbo code).

An output module 178, which is integral with and/or operatively connected with the processor 176, includes programming for generating output based on the data stream received from the sensor system 10 and its processing incurred in the processor 176. In some embodiments, output is generated via a user interface 160.

The user interface 160 comprises a keyboard 162, speaker 164, vibrator 166, backlight 168, liquid crystal display (LCD) screen 170, and one or more buttons 172. The components that comprise the user interface 160 include controls to allow interaction of the user with the receiver. The keyboard 162 can allow, for example, input of user information about himself/herself, such as mealtime, exercise, insulin administration, customized therapy recommendations, and reference analyte values. The speaker 164 can produce, for example, audible signals or alerts for conditions such as present and/or estimated (e.g., predicted) hyperglycemic or hypoglycemic conditions in a person with diabetes. The vibrator 166 can provide, for example, tactile signals or alerts for reasons such as described with reference to the speaker, above. The backlight 168 can be provided, for example, to aid the user in reading the LCD 170 in low light conditions. The LCD 170 can be provided, for example, to provide the user with visual data output, such as is described in U.S. Patent Publication No. US-2005-0203360-A1. FIGS. 17B to 17D illustrate some additional visual displays that can be provided on the screen 170. In some embodiments, the LCD is a touch-activated screen, enabling each selection by a user, for example, from a menu on the screen. The buttons 172 can provide for toggle, menu selection, option selection, mode selection, and reset, for example. In some alternative embodiments, a microphone can be provided to allow for voice-activated control.

In some embodiments, prompts or messages can be displayed on the user interface to convey information to the user, such as reference outlier values, requests for reference analyte values, therapy recommendations, deviation of the measured analyte values from the estimated analyte values, or the like. Additionally, prompts can be displayed to guide the user through calibration or trouble-shooting of the calibration.

Additionally, data output from the output module 178 can provide wired or wireless, one- or two-way communication between the receiver 158 and an optional external device 180. The external device 180 can be any device that wherein interfaces or communicates with the receiver 158. In some embodiments, the external device 180 is a computer, and the receiver 158 is able to download historical data for retrospective analysis by the patient or physician, for example. In some embodiments, the external device 180 is a modem or other telecommunications station, and the receiver 158 is able to send alerts, warnings, emergency messages, or the like, via telecommunication lines to another party, such as a doctor or family member. In some embodiments, the external device 180 is an insulin pen, and the receiver 158 is able to communicate therapy recommendations, such as insulin amount and time to the insulin pen. In some embodiments, the external device 180 is an insulin pump, and the receiver 158 is able to communicate therapy recommendations, such as insulin amount and time to the insulin pump. The external device 180 can include other technology or medical devices, for example pacemakers, implanted analyte sensor patches, other infusion devices, telemetry devices, or the like.

The user interface 160, including keyboard 162, buttons 172, a microphone (not shown), and the external device 180, can be configured to allow input of data. Data input can be helpful in obtaining information about the patient (for example, meal time, exercise, or the like), receiving instructions from a physician (for example, customized therapy recommendations, targets, or the like), and downloading software updates, for example. Keyboard, buttons, touch-screen, and microphone are all examples of mechanisms by which a user can input data directly into the receiver. A server, personal computer, personal digital assistant, insulin pump, and insulin pen are examples of external devices that can provide useful information to the receiver. Other devices internal or external to the sensor that measure other aspects of a patient's body (for example, temperature sensor, accelerometer, heart rate monitor, oxygen monitor, or the like) can be used to provide input helpful in data processing. In one embodiment, the user interface can prompt the patient to select an activity most closely related to their present activity, which can be helpful in linking to an individual's physiological patterns, or other data processing. In another embodiment, a temperature sensor and/or heart rate monitor can provide information helpful in linking activity, metabolism, and glucose excursions of an individual. While a few examples of data input have been provided here, a variety of information can be input, which can be helpful in data processing.

Algorithms

Figure 7:
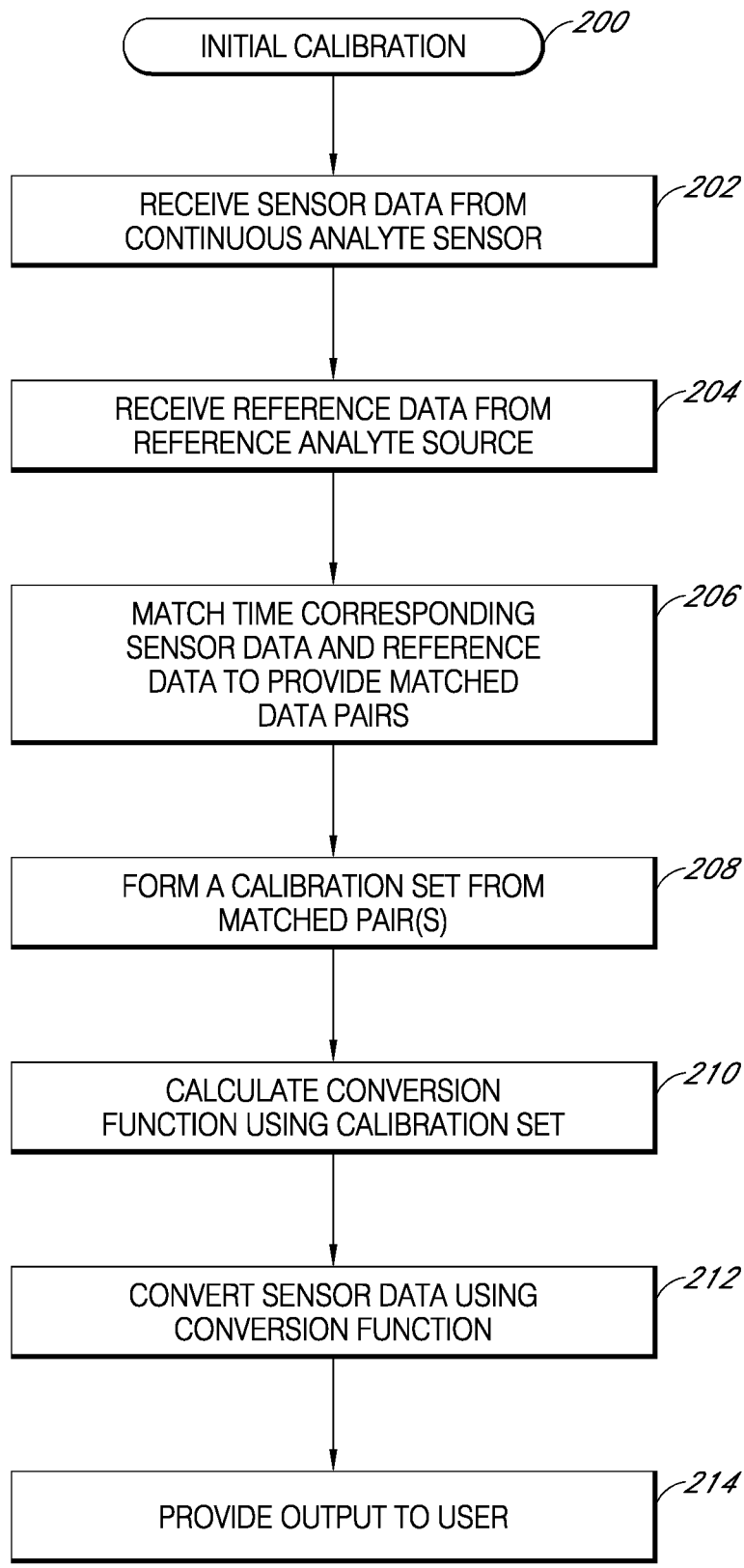
FIG. 7 is a flow chart that illustrates the initial calibration and data output of sensor data, in one embodiment.

FIG. 7 provides a flow chart 200 that illustrates the initial calibration and data output of the sensor data in one embodiment, wherein calibration is responsive to reference analyte data. Initial calibration, also referred to as start-up mode, occurs at the initialization of a sensor, for example, the first time an electronics unit is used with a particular sensor. In certain embodiments, start-up calibration is triggered when the system determines that it can no longer remain in normal or suspended mode, which is described in more detail in co-pending U.S. patent application Ser. No. 11/734,184 filed on Apr. 11, 2007.

Calibration of an analyte sensor comprises data processing that converts sensor data signal into an estimated analyte measurement that is meaningful to a user. Accordingly, a reference analyte value is used to calibrate the data signal from the analyte sensor.

At block 202, a sensor data receiving module, also referred to as the sensor data module, receives sensor data (e.g., a data stream), including one or more time-spaced sensor data points, from the sensor 34 via the receiver 158, which can be in wired or wireless communication with the sensor. The sensor data point(s) can be smoothed (filtered) in certain embodiments using a filter, for example, a finite impulse response (FIR) or infinite impulse response (IIR) filter. During the initialization of the sensor, prior to initial calibration, the receiver receives and stores the sensor data, however it can be configured to not display any data to the user until initial calibration and, optionally, stabilization of the sensor has been established. In some embodiments, the data stream can be evaluated to determine sensor break-in (equilibration of the sensor in vitro or in vivo).

At block 204, a reference data receiving module, also referred to as the reference input module, receives reference data from a reference analyte monitor, including one or more reference data points. In one embodiment, the reference analyte points can comprise results from a self-monitored blood analyte test (e.g., finger stick test). For example, the user can administer a self-monitored blood analyte test to obtain an analyte value (e.g., point) using any known analyte sensor, and then enter the numeric analyte value into the computer system. Alternatively, a self-monitored blood analyte test is transferred into the computer system through a wired or wireless connection to the receiver (e.g. computer system) so that the user simply initiates a connection between the two devices, and the reference analyte data is passed or downloaded between the self-monitored blood analyte test and the receiver.

In yet another embodiment, the self-monitored analyte monitor (e.g., SMBG) is integral with the receiver so that the user simply provides a blood sample to the receiver, and the receiver runs the analyte test to determine a reference analyte value, such as is described in more detail herein and with reference to U.S. Patent Publication No. US-2005-0154271-A1, which is incorporated herein by reference in its entirety and which describes some systems and methods for integrating a reference analyte monitor into a receiver for a continuous analyte sensor.

In some embodiments, the integrated receiver comprises a microprocessor, which can be programmed to process sensor data to perform the calibration. Such programming, which can be stored in a computer readable memory, can also comprise data acceptability testing using criteria such as that discussed above with reference to FIG. 7. For example the microprocessor can be programmed so as to determine the rate of change of glucose concentration based on the continuous sensor data, and perform calibration only if the rate of change is below a predetermined threshold, such as 2 mg/dL/min. In some embodiments the receiver can also comprise modules to perform a calibration procedure such as is described herein. Such modules include, but are not limited to an input module, a data matching module, a calibration module, a conversion function module, a sensor data transformation module, a calibration evaluation module, a clinical module, a stability module, and a user interface, each of which have been described herein.

The monitor can be of any suitable configuration. For example, in one embodiment, the reference analyte points can comprise results from a self-monitored blood analyte test (e.g., from a finger stick test), such as those described in U.S. Pat. Nos. 6,045,567; 6,156,051; 6,197,040; 6,284,125; 6,413,410; and 6,733,655. In one such embodiment, the user can administer a self-monitored blood analyte test to obtain an analyte value (e.g., point) using any suitable analyte sensor, and then enter the numeric analyte value into the computer system (e.g., the receiver). In another such embodiment, a self-monitored blood analyte test comprises a wired or wireless connection to the receiver (e.g. computer system) so that the user simply initiates a connection between the two devices, and the reference analyte data is passed or downloaded between the self-monitored blood analyte test and the receiver. In yet another such embodiment, the self-monitored analyte test is integral with the receiver so that the user simply provides a blood sample to the receiver, and the receiver runs the analyte test to determine a reference analyte value.

Other suitable monitor configurations include, for example, those described in U.S. Pat. Nos. 4,994,167, 4,757,022, and 6,551,494. In alternative embodiments, the single point glucose monitor of this particular embodiment can be configured as described with reference to U.S. Patent Publication No. US-2005-0154271-A1. In other alternative embodiments, the monitor can be configured using other glucose meter configurations. Numerous advantages associated with the integrated receiver, such as ensuring accurate time stamping of the single point glucose test at the receiver and other advantages described herein, can be provided by an integrated continuous glucose receiver and single point glucose monitor, such as described herein.

In some embodiments, the reference data is based on sensor data from another substantially continuous analyte sensor, e.g., a transcutaneous analyte sensor described herein, or another type of suitable continuous analyte sensor. In an embodiment employing a series of two or more transcutaneous (or other continuous) sensors, the sensors can be employed so that they provide sensor data in discrete or overlapping periods. In such embodiments, the sensor data from one continuous sensor can be used to calibrate another continuous sensor, or be used to confirm the validity of a subsequently employed continuous sensor.

In some embodiments, reference data can be subjected to "outlier detection" wherein the accuracy of a received reference analyte data is evaluated as compared to time-corresponding sensor data. In one embodiment, the reference data is compared to the sensor data on a modified Clarke Error Grid (e.g., a test similar to the Clarke Error Grid except the boundaries between the different regions are modified slightly) to determine if the data falls within a predetermined threshold. If the data is not within the predetermined threshold, then the receiver can be configured to request additional reference analyte data. If the additional reference analyte data confirms (e.g., closely correlates to) the first reference analyte data, then the first and second reference values are assumed to be accurate and calibration of the sensor is adjusted or re-initialized. Alternatively, if the second reference analyte value falls within the predetermined threshold, then the first reference analyte value is assumed to be an outlier and the second reference analyte value is used by the algorithm(s) instead. In one alternative embodiments of outlier detection, projection is used to estimate an expected analyte value, which is compared with the actual value and a delta evaluated for substantial correspondence. However, other methods of outlier detection are possible.

Certain acceptability parameters can be set for reference values received from the user. In some embodiments, the calibration process monitors the continuous analyte sensor data stream to determine a preferred time for capturing reference analyte concentration values for calibration of the continuous sensor data stream. In an example wherein the analyte sensor is a continuous glucose sensor, when data (for example, observed from the data stream) changes too rapidly, the reference glucose value may not be sufficiently reliable for calibration due to unstable glucose changes in the host. In contrast, when sensor glucose data are relatively stable (for example, relatively low rate of change), a reference glucose value can be taken for a reliable calibration. For example, in one embodiment, the receiver can be configured to only accept reference analyte values of from about 40 mg/dL to about 400 mg/dL. As another example, the receiver can be configured to only accept reference analyte values when the rate of change is less than a predetermined maximum, such as 1, 1.5, 2, 2.5, 3, or 3.5, mg/dL/min. As yet another example, the receiver can be configured to only accept reference analyte values when the rate of acceleration (or deceleration) is less than a predetermined maximum, such as 0.01 mg/dL/min$^2$, 0.02 mg/dL/min$^2$, 0.03 mg/dL/min$^2$, 0.04 mg/dL/min$^2$, or 0.05 mg/dL/min$^2$ or more.

In some embodiments, the reference data is pre-screened according to environmental and/or physiological issues, such as time of day, oxygen concentration, postural effects, and patient-entered environmental data. In one example embodiment, wherein the sensor comprises an implantable glucose sensor, an oxygen sensor within the glucose sensor is used to determine if sufficient oxygen is being provided to successfully complete the necessary enzyme and electrochemical reactions for glucose sensing. In another example wherein the sensor comprises an implantable glucose sensor, the counter electrode could be monitored for a "rail-effect," that is, when insufficient oxygen is provided at the counter electrode causing the counter electrode to reach operational (e.g., circuitry) limits. In some embodiments the receiver is configured such that when conditions for accepting reference analyte values are not met, the user is notified. Such notice can include an indication as to the cause of the unacceptability, such as low oxygen or high rate of analyte value change. In some embodiments the indication can also include an indication of suggested corrective action, such as moderately increasing muscular activity so as to increase oxygen levels or to wait until the rate of analyte value change reduces to an acceptable value.

In one embodiment, the calibration process can prompt the user via the user interface to "calibrate now" when the reference analyte values are considered acceptable. In some embodiments, the calibration process can prompt the user via the user interface to obtain a reference analyte value for calibration at intervals, for example when analyte concentrations are at high and/or low values. In some additional embodiments, the user interface can prompt the user to obtain a reference analyte value for calibration based at least in part upon certain events, such as meals, exercise, large excursions in analyte levels, faulty or interrupted data readings, or the like. In some embodiments, the algorithms can provide information useful in determining when to request a reference analyte value. For example, when analyte values indicate approaching clinical risk, the user interface can prompt the user to obtain a reference analyte value.

In yet another example embodiment, the patient is prompted to enter data into the user interface, such as meal times and/or amount of exercise, which can be used to determine likelihood of acceptable reference data. Evaluation data, such as described in the paragraphs above, can be used to evaluate a preferred time for reference analyte measurement. Correspondingly, the user interface can then prompt the user to provide a reference data point for calibration within a given time period. Consequently, because the receiver proactively prompts the user during preferred calibration times, the likelihood of error due to environmental and physiological limitations may decrease and consistency and acceptability of the calibration may increase.

In some embodiments, the calibration process monitors the continuous analyte sensor data stream to determine a preferred time for capturing reference analyte concentration values for calibration of the continuous sensor data stream. In an example wherein the analyte sensor is a continuous glucose sensor, when data (for example, observed from the data stream) changes too rapidly, the reference glucose value may not be sufficiently reliable for calibration due to unstable glucose changes in the host. In contrast, when sensor glucose data are relatively stable (for example, relatively low rate of change), a reference glucose value can be taken for a reliable calibration. In one embodiment, the calibration process can prompt the user via the user interface to "calibrate now" when the analyte sensor is considered stable.

Referring again to FIG. 7, at block 206, a data matching module, also referred to as the processor module, matches reference data (e.g., one or more reference analyte data points) with substantially time corresponding sensor data (e.g., one or more sensor data points) to provide one or more matched data pairs. One reference data point can be matched to one time corresponding sensor data point to form a matched data pair. Alternatively, a plurality of reference data points can be averaged (e.g., equally or non-equally weighted average, mean-value, median, or the like) and matched to one time corresponding sensor data point to form a matched data pair, one reference data point can be matched to a plurality of time corresponding sensor data points averaged to form a matched data pair, or a plurality of reference data points can be averaged and matched to a plurality of time corresponding sensor data points averaged to form a matched data pair.

In one embodiment, time corresponding sensor data comprises one or more sensor data points that occur from about 0 minutes to about 20 minutes after the reference analyte data time stamp (e.g., the time that the reference analyte data is obtained). In one embodiment, a 5 minute time delay is chosen to compensate for a system time-lag (e.g., the time necessary for the analyte to diffusion through a membrane(s) of an analyte sensor). In alternative embodiments, the time corresponding sensor value can be greater than or less than that of the above-described embodiment, for example ±60 minutes. Variability in time correspondence of sensor and reference data can be attributed to, for example, a longer or shorter time delay introduced by the data smoothing filter, or if the configuration of the analyte sensor incurs a greater or lesser physiological time lag.

In some implementations of the sensor, the reference analyte data is obtained at a time that is different from the time that the data is input into the receiver. Accordingly, the "time stamp" of the reference analyte (e.g., the time at which the reference analyte value was obtained) is not the same as the time at which the receiver obtained the reference analyte data. Therefore, some embodiments include a time stamp requirement that ensures that the receiver stores the accurate time stamp for each reference analyte value, that is, the time at which the reference value was actually obtained from the user.

In certain embodiments, tests are used to evaluate the best-matched pair using a reference data point against individual sensor values over a predetermined time period (e.g., about 30 minutes). In one such embodiment, the reference data point is matched with sensor data points at 5 minute intervals and each matched pair is evaluated. The matched pair with the best correlation can be selected as the matched pair for data processing. In some alternative embodiments, matching a reference data point with an average of a plurality of sensor data points over a predetermined time period can be used to form a matched pair.

In certain embodiments, the data matching module only forms matched pairs when a certain analyte value condition is satisfied. Such a condition can include any of the conditions discussed above with reference to embodiments pre-screening or conditionally accepting reference analyte value data at block 204.

At block 208, a calibration set module, also referred to as the calibration module or processor module, forms an initial calibration set from a set of one or more matched data pairs, which are used to determine the relationship between the reference analyte data and the sensor analyte data. The matched data pairs, which make up the initial calibration set, can be selected according to predetermined criteria. The criteria for the initial calibration set can be the same as, or different from, the criteria for the updated calibration sets. In certain embodiments, the number (n) of data pair(s) selected for the initial calibration set is one. In other embodiments, n data pairs are selected for the initial calibration set wherein n is a function of the frequency of the received reference data points. In various embodiments, two data pairs make up the initial calibration set or six data pairs make up the initial calibration set. In an embodiment wherein a substantially continuous analyte sensor provides reference data, numerous data points are used to provide reference data from more than 6 data pairs (e.g., dozens or even hundreds of data pairs). In one exemplary embodiment, a substantially continuous analyte sensor provides 288 reference data points per day (every five minutes for twenty-four hours), thereby providing an opportunity for a matched data pair 288 times per day, for example. While specific numbers of matched data pairs are referred to in the preferred embodiments, any suitable number of matched data pairs per a given time period can be employed.

In certain embodiments, the data pairs are selected only when a certain analyte value condition is satisfied. Such a condition can include any of the conditions discussed above with reference to embodiments pre-screening or conditionally accepting reference analyte value data at block 204. In certain embodiments, the data pairs that form the initial calibration set are selected according to their time stamp, for example, by waiting a predetermined "break-in" time period after implantation, the stability of the sensor data can be increased. In certain embodiments, the data pairs that form the initial calibration set are spread out over a predetermined time period, for example, a period of two hours or more. In certain embodiments, the data pairs that form the initial calibration set are spread out over a predetermined glucose range, for example, spread out over a range of at least 90 mg/dL or more.

At block 210, a conversion function module, also referred to as the conversion module or processor module, uses the calibration set to create a conversion function. The conversion function substantially defines the relationship between the reference analyte data and the analyte sensor data.

A variety of known methods can be used with the preferred embodiments to create the conversion function from the calibration set. In one embodiment, wherein a plurality of matched data points form the calibration set, a linear least squares regression is used to calculate the conversion function; for example, this regression calculates a slope and an offset using the equation y=mx+b. A variety of regression or other conversion schemes can be implemented herein.

In certain embodiments, the conversion function module only creates a conversion function when a certain analyte value condition is satisfied. Such a condition can include any of the conditions discussed above with reference to embodiments pre-screening or conditionally accepting reference analyte value data at block 204 or with reference to selecting data pairs at block 208.

In some alternative embodiments, the sensor is calibrated with a single-point through the use of a dual-electrode system to simplify sensor calibration. In one such dual-electrode system, a first electrode functions as a hydrogen peroxide sensor including a membrane system containing glucose-oxidase disposed thereon, which operates as described herein. A second electrode is a hydrogen peroxide sensor that is configured similar to the first electrode, but with a modified membrane system (with the enzyme domain removed, for example). This second electrode provides a signal composed mostly of the baseline signal, b.

In some dual-electrode systems, the baseline signal is (electronically or digitally) subtracted from the glucose signal to obtain a glucose signal substantially without baseline. Accordingly, calibration of the resultant difference signal can be performed by solving the equation y=mx+b with a single paired measurement. Calibration of the implanted sensor in this alternative embodiment can be made less dependent on the values/range of the paired measurements, less sensitive to error in manual blood glucose measurements, and can facilitate the sensor's use as a primary source of glucose information for the user. U.S. Patent Publication No. US-2005-0143635-A1 describes systems and methods for subtracting the baseline from a sensor signal.

In some alternative dual-electrode system embodiments, the analyte sensor is configured to transmit signals obtained from each electrode separately (e.g., without subtraction of the baseline signal). In this way, the receiver can process these signals to determine additional information about the sensor and/or analyte concentration. For example, by comparing the signals from the first and second electrodes, changes in baseline and/or sensitivity can be detected and/or measured and used to update calibration (e.g., without the use of a reference analyte value). In one such example, by monitoring the corresponding first and second signals over time, an amount of signal contributed by baseline can be measured. In another such example, by comparing fluctuations in the correlating signals over time, changes in sensitivity can be detected and/or measured.

In some alternative embodiments, a regression equation y=mx+b is used to calculate the conversion function; however, prior information can be provided for m and/or b, thereby enabling calibration to occur with fewer paired measurements. In one calibration technique, prior information (e.g., obtained from in vivo or in vitro tests) determines a sensitivity of the sensor and/or the baseline signal of the sensor by analyzing sensor data from measurements taken by the sensor (e.g., prior to inserting the sensor). For example, if there exists a predictive relationship between in vitro sensor parameters and in vivo parameters, then this information can be used by the calibration procedure. For example, if a predictive relationship exists between in vitro sensitivity and in vivo sensitivity, $m \approx f(m_{in\ vitro})$, then the predicted m can be used, along with a single matched pair, to solve for b (b=y−mx). If, in addition, b can be assumed=0, for example with a dual-electrode configuration that enables subtraction of the baseline from the signal such as described above, then both m and b are known a priori, matched pairs are not needed for calibration, and the sensor can be completely calibrated e.g. without the need for reference analyte values (e.g. values obtained after implantation in vivo.)

In another alternative embodiment, prior information can be provided to guide or validate the baseline (b) and/or sensitivity (m) determined from the regression analysis. In this embodiment, boundaries can be set for the regression line that defines the conversion function such that working sensors are calibrated accurately and easily (with two points), and non-working sensors are prevented from being calibrated. If the boundaries are drawn too tightly, a working sensor may not enter into calibration. Likewise, if the boundaries are drawn too loosely, the scheme can result in inaccurate calibration or can permit non-working sensors to enter into calibration. For example, subsequent to performing regression, the resulting slope and/or baseline are tested to determine whether they fall within a predetermined acceptable threshold (boundaries). These predetermined acceptable boundaries can be obtained from in vivo or in vitro tests (e.g., by a retrospective analysis of sensor sensitivities and/or baselines collected from a set of sensors/patients, assuming that the set is representative of future data).

If the slope and/or baseline fall within the predetermined acceptable boundaries, then the regression is considered acceptable and processing continues to the next step (e.g., block 212). Alternatively, if the slope and/or baseline fall outside the predetermined acceptable boundaries, steps can be taken to either correct the regression or fail-safe such that a system will not process or display errant data. This can be useful in situations wherein regression results in errant slope or baseline values. For example, when points (matched pairs) used for regression are too close in value, the resulting regression statistically is less accurate than when the values are spread farther apart. As another example, a sensor that is not properly deployed or is damaged during deployment can yield a skewed or errant baseline signal.

In some alternative embodiments, the sensor system does not require initial and/or update calibration by the host; in these alternative embodiments, also referred to as "zero-point calibration" embodiments, use of the sensor system without requiring a reference analyte measurement for initial and/or update calibration is enabled. In general, the systems and methods of the preferred embodiments provide for stable and repeatable sensor manufacture, particularly when tightly controlled manufacturing processes are utilized. Namely, a batch of sensors of the preferred embodiments can be designed with substantially the same baseline (b) and/or sensitivity (m) (+1-10%) when tested in vitro. Additionally, the sensor of the preferred embodiments can be designed for repeatable m and b in vivo. Thus, an initial calibration factor (conversion function) can be programmed into the sensor (sensor electronics and/or receiver electronics) that enables conversion of raw sensor data into calibrated sensor data solely using information obtained prior to implantation (namely, initial calibration does not require a reference analyte value). Additionally, to obviate the need for recalibration (update calibration) during the life of the sensor, the sensor is designed to minimize drift of the sensitivity and/or baseline over time in vivo. Accordingly, the preferred embodiments can be manufactured for zero point calibration.

At block 212, a sensor data transformation module, also referred to as the calibration module, conversion module, or processor module, uses the conversion function to transform sensor data into substantially real-time analyte value estimates, also referred to as calibrated data, or converted sensor data, as sensor data is continuously (or intermittently) received from the sensor. For example, the sensor data, which can be provided to the receiver in "counts," is translated in to estimate analyte value(s) in mg/dL. In other words, the offset value at any given point in time can be subtracted from the raw value (e.g., in counts) and divided by the slope to obtain the estimate analyte value:

$$mg/dL = \frac{(rawvalue - \text{offset})}{\text{slope}}$$

In one embodiment, the conversion function can be used to estimate analyte values for a future time period by forward projection. In alternative preferred embodiments, the processor can provide intelligent estimation, including dynamic determination of an algorithm, physiological boundaries, evaluation of the estimative algorithm, analysis of variations associated with the estimation, and comparison of measured analyte values with time corresponding estimated analyte values.

In some alternative embodiments, the sensor and/or reference analyte values are stored in a database for retrospective analysis.

In certain embodiments, the sensor data transformation module only converts sensor data points into calibrated data points when a certain analyte value condition is satisfied. Such a condition can include any of the conditions discussed above with reference to embodiments pre-screening or conditionally accepting reference analyte value data at block 204, with reference to selecting data pairs at block 208, or with reference to creating a conversion function at block 210.

At block 214, an output module provides output to the user via the user interface. The output is representative of the estimated analyte value, which is determined by converting the sensor data into a meaningful analyte value. User output can be in the form of a numeric estimated analyte value, an indication of directional trend of analyte concentration, and/or a graphical representation of the estimated analyte data over a period of time, for example. Other representations of the estimated analyte values are also possible, for example audio and tactile.

In one exemplary embodiment, the estimated analyte value is represented by a numeric value. In other exemplary embodiments, the user interface graphically represents the estimated analyte data trend over predetermined a time period (e.g., one, three, and nine hours, respectively). In alternative embodiments, other time periods can be represented.

In some embodiments, the user interface begins displaying data to the user after the sensor's stability has been affirmed. In some alternative embodiments, however, the user interface displays data that is somewhat unstable (e.g., does not have sufficient stability and/or accuracy); in these embodiments, the receiver may also include an indication of instability of the sensor data (e.g., flashing, faded, or another indication of sensor instability displayed on the user interface). In some embodiments, the user interface informs the user of the status of the stability of the sensor data.

Accordingly, after initial calibration of the sensor, and optionally determination of stability of the sensor data, real-time continuous analyte information can be displayed on the user interface so that the user can regularly and proactively care for his/her diabetic condition within the bounds set by his/her physician.

In alternative embodiments, the conversion function is used to predict analyte values at future points in time. These predicted values can be used to alert the user of upcoming hypoglycemic or hyperglycemic events. Additionally, predicted values can be used to compensate for the time lag (e.g., 15 minute time lag such as described elsewhere herein), so that an estimated analyte value displayed to the user represents the instant time, rather than a time delayed estimated value.

In some embodiments, the substantially real time estimated analyte value, a predicted future estimate analyte value, a rate of change, and/or a directional trend of the analyte concentration is used to control the administration of a constituent to the user, including an appropriate amount and time, in order to control an aspect of the user's biological system. One such example is a closed loop glucose sensor and insulin pump, wherein the analyte data (e.g., estimated glucose value, rate of change, and/or directional trend) from the glucose sensor is used to determine the amount of insulin, and time of administration, that may be given to a diabetic user to evade hyper- and hypoglycemic conditions.

In some embodiments, annotations are provided on the graph; for example, bitmap images are displayed thereon, which represent events experienced by the host. For example, information about meals, insulin, exercise, sensor insertion, sleep, and the like, can be obtained by the receiver (by user input or receipt of a transmission from another device) and displayed on the graphical representation of the host's glucose over time. It is believed that illustrating a host's life events matched with a host's glucose concentration over time can be helpful in educating the host to his or her metabolic response to the various events.

In yet another alternative embodiment, the sensor utilizes one or more additional electrodes to measure an additional analyte. Such measurements can provide a baseline or sensitivity measurement for use in calibrating the sensor. Furthermore, baseline and/or sensitivity measurements can be used to trigger events such as digital filtering of data or suspending display of data, all of which are described in more detail in U.S. Patent Publication No. US-2005-0143635-A1.

Accordingly, after initial calibration of the sensor, continuous analyte values can be displayed on the user interface so that the user can regularly and proactively care for his/her diabetic condition within the bounds set by his/her physician. Both the reference analyte data and the sensor analyte data from the continuous analyte sensor can be displayed to the user. In an embodiment wherein the continuous analyte sensor functions as an adjunctive device to a reference analyte monitor, the user interface can display numeric reference analyte data, while showing the sensor analyte data only in a graphical representation so that the user can see the historical and present sensor trend information as well as the most recent reference analyte data value. In an embodiment wherein the continuous analyte sensor functions as a non-adjunctive device to the reference analyte monitor, the user interface can display the reference analyte data and/or the sensor analyte data. The user can toggle through menus and screens using the buttons in order to view alternate data and/or screen formats, for example.

In some embodiments, the measured analyte value, an estimated future analyte value, a rate of change, and/or a directional trend of the analyte concentration is used to control the administration of a constituent to the user, including an appropriate amount and time, in order to control an aspect of the user's biological system. One such example is a closed loop glucose sensor and insulin pump, wherein the glucose data (for example, estimated glucose value, rate of change, and/or directional trend) from the glucose sensor is used to determine the amount of insulin, and time of administration, that can be given to a person with diabetes to evade hyperglycemic and hypoglycemic conditions.

Electronic Identification and Removal of Non-Constant Noise

In addition blocking and/or diluting interfering species before they can cause noise on the sensor signal, a non-constant noise signal component can be electronically identified, such that the identified noise component can be removed from the signal by algorithmic/mathematical means, in some embodiments. For example, in a glucose sensor (e.g., as described herein) that catalyzes the conversion of oxygen and glucose to hydrogen peroxide and gluconate (e.g., by GOX incorporated into the membrane system), for each glucose molecule metabolized there is an equivalent change in molecular concentration in the co-reactant $O_2$ and the product $H_2O_2$. Consequently, one can use an electrode (for example, working electrode 16) to monitor the concentration-induced current change in either the co-reactant or the product (for example, $H_2O_2$) to determine glucose concentration. However, if an interfering species exists with an oxidation or reduction potential that overlaps with the co-reactant or the product (for example, $H_2O_2$), then the current change does not accurately reflect glucose concentration. Additionally, if an oxygen deficiency exists, such that insufficient oxygen is present to react with an analyte at the enzyme for example, then the current change similarly does not accurately reflect glucose concentration.

It is noted that a glucose sensor signal obtained from glucose when the bias potential is set from about +0.35V to about +0.75V is substantially constant under standard physiologic conditions. In contrast, a glucose sensor signal obtained from interfering species when the same bias potentials are set (from about +0.35V to about +0.75V) is not substantially constant under standard physiologic conditions. Current-voltage curves are known for various analytes and are available in the literature (for example, such as described by Lerner et al. *Ann NY Acad Sci* 1984, 428, 263-278). Additional description can be found in U.S. Pat. No. 7,081,195.

EXAMPLES

Example 1

Resistance Domain Configurations to Increased the Analyte Signal Reduce Non-Constant Noise Transcutaneous sensors, with electrode, interference, enzyme and resistance (polyurethane blend) domains, were built and tested in non-diabetic hosts. The control and test sensors were built as described in U.S. Publication No. 2006-0020187, which is incorporated herein by reference in its entirety, with the following exception: the resistance domain of the test sensors was formed of 3 layers of a 60% ChronoThane® H (CardioTech International, Wilmington, Mass., USA; the PEO concentration of ChronoThane® H is about 25%) polyurethane blend solution, as compared to a single layer of a 45% ChronoThane® H polyurethane blend solution in the control sensors. Test and control sensors were implanted bilaterally in the abdomens of non-diabetic host volunteers, for a period of about 7 days.

Figure 8:
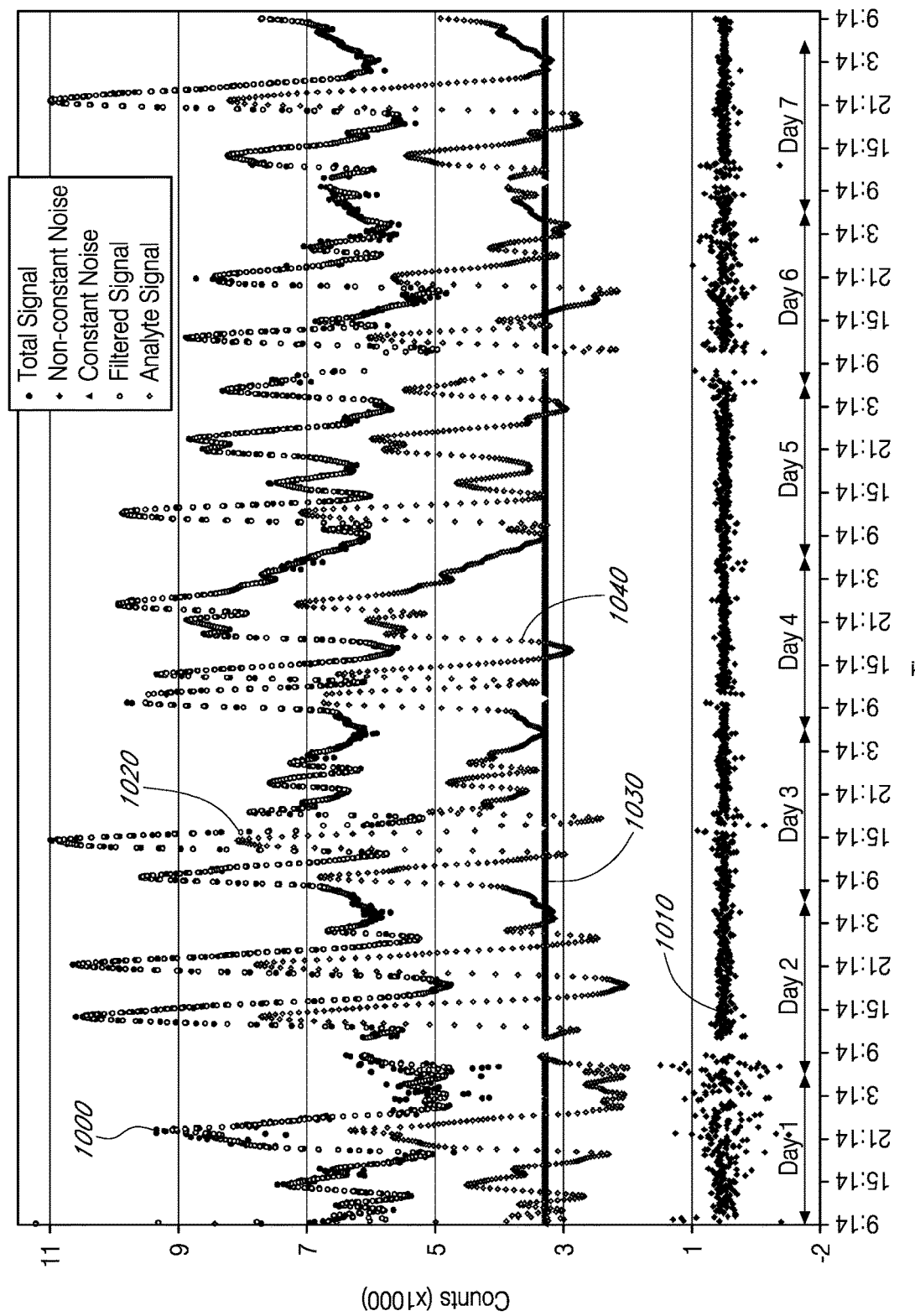
FIG. 8 is a graph illustrating the signal components of a total signal from an analyte sensor, in one embodiment, collected from a volunteer human host over a period of 7 days.

FIG. 8 illustrates exemplary test results from one test sensor, over a period of about 7 days, after sensor break-in. The Y-axis represents signal intensity (in counts). The X-axis represents time. Double-headed arrows approximately indicate the days of the study. The total signal detected by the test glucose sensor is shown as dotted line 1000. To determine the signal components, the total signal 1000 was analyzed in the following manner. First, the total signal 1000 was filtered using an IIR filter to obtain the filtered signal 1020 . . . . The non-constant noise component 1010 was obtained by subtracting the filtered signal 1020 from the total signal 1000. Next, the filtered signal 1020 was calibrated using glucose values obtained from a finger-stick glucose meter (SMBG), as described as described in more detail elsewhere herein, to obtain the constant noise signal component 1030 (e.g., from the baseline of the calibration equation). Finally, the analyte component 1040 (e.g., glucose concentration) of the total signal 1000 was obtained by subtracting the constant noise signal component 1030 from the filtered signal 1020.

During the seven days the sensor was tested, the glucose signal varied widely, depending upon the host's activity and calorie consumption. Using the Root Mean Square (RMS) method, it was determined that the non-constant noise signal component was no more than about 4.2% of the total signal during the 7 days of the trial. Additionally, during about days two through five of the trial, the non-constant noise was no more than about 2.9% of the total signal.

Accordingly, it was shown that the non-constant noise component can be reduced to less than about 20% of the total signal over a period of about 7 days by increasing the resistance domain thickness, as described in more detail elsewhere herein.

Example 2

A Lubricious Coating Configured to Reduce Non-Constant Noise

Control and test sensors, with electrode, enzyme and resistance domains, were built as described in U.S. Patent Publication No. US-2006-0020187-A1, including a resistance domain formed using a polyurethane polymer blend having about 8 wt. % PEO, as described in the section entitled "Polyurethane Polymer Material" above. A lubricious coating was applied to the test sensors by dipping them one time into a solution of HydroMed™ (CardioTech International, Inc., Wilmington, Mass., USA) and drying. The control and test sensors were tested in vitro (see Table 1, below). The test sensors (with the lubricious coating) had a substantially increased sensitivity (m) but with no corresponding increase in constant noise (b), when compared to control sensors (no lubricious coating). Accordingly, it was shown that application of a lubricious coating over a polyurethane blend resistance domain of a glucose sensor can (in vitro) substantially increase the analyte component of the total signal, while having little affect on constant noise (e.g., baseline).

TABLE 1

| Sensor Type | Average Sensitivity (pA/mg/dl) | Average Constant Noise |
| --- | --- | --- |
| Test (with lubricious coating) | 20.68 | 1.36 |
| Control (no lubricious coating) | 8.33 | 1.36 |

Figure 9:
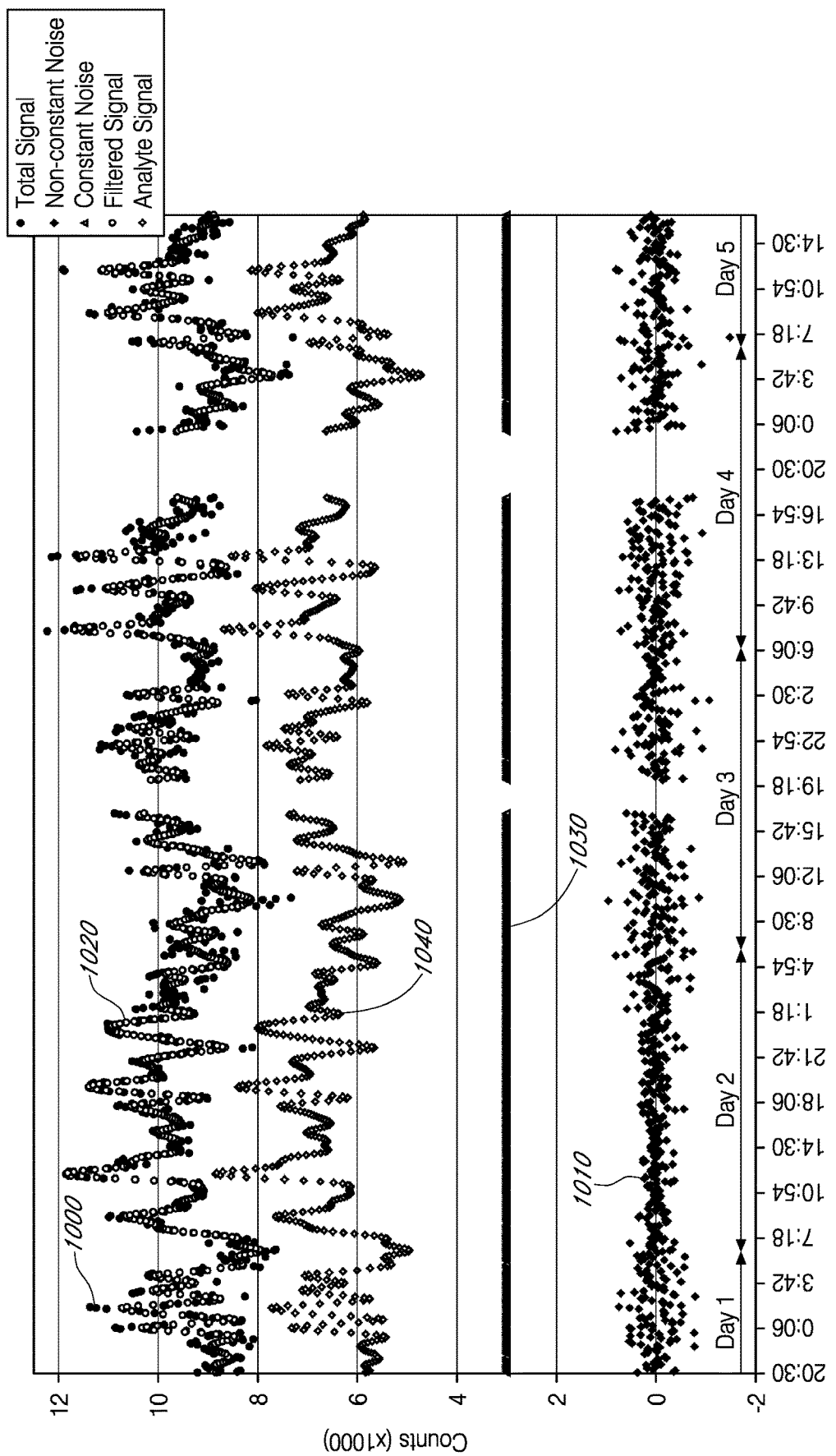
FIG. 9 is a graph illustrating the signal components of a total signal from an analyte sensor including a lubricious coating, in one embodiment.

FIG. 9 is a graph showing exemplary test results when a test sensor as described above, including a lubricious coating, was implanted in a non-diabetic human host. Components of the Total Signal 1000 were determined, as described in Example 1. The Y-axis represents signal intensity (in counts). The X-axis represents time. FIG. 9 shows the non-constant noise component 1010, the filtered signal 1020, the constant noise component 1030 and the analyte signal 1040. Using the RMS method, it was determined that, for the test sensor including a lubricious coating, the analyte component of the total signal was at least about 96% for about four days, after sensor break-in. Additionally, the non-constant noise component was no more than about 5% for about four days, after sensor break-in. Accordingly, it was shown that, in ambulatory humans, application of a lubricious coating to a sensor over a resistance domain provides a sensor that, in vivo, has a substantially non-constant non-analyte related signal component does not substantially contribute to the signal after sensor break-in.

Example 3

Figure 10:
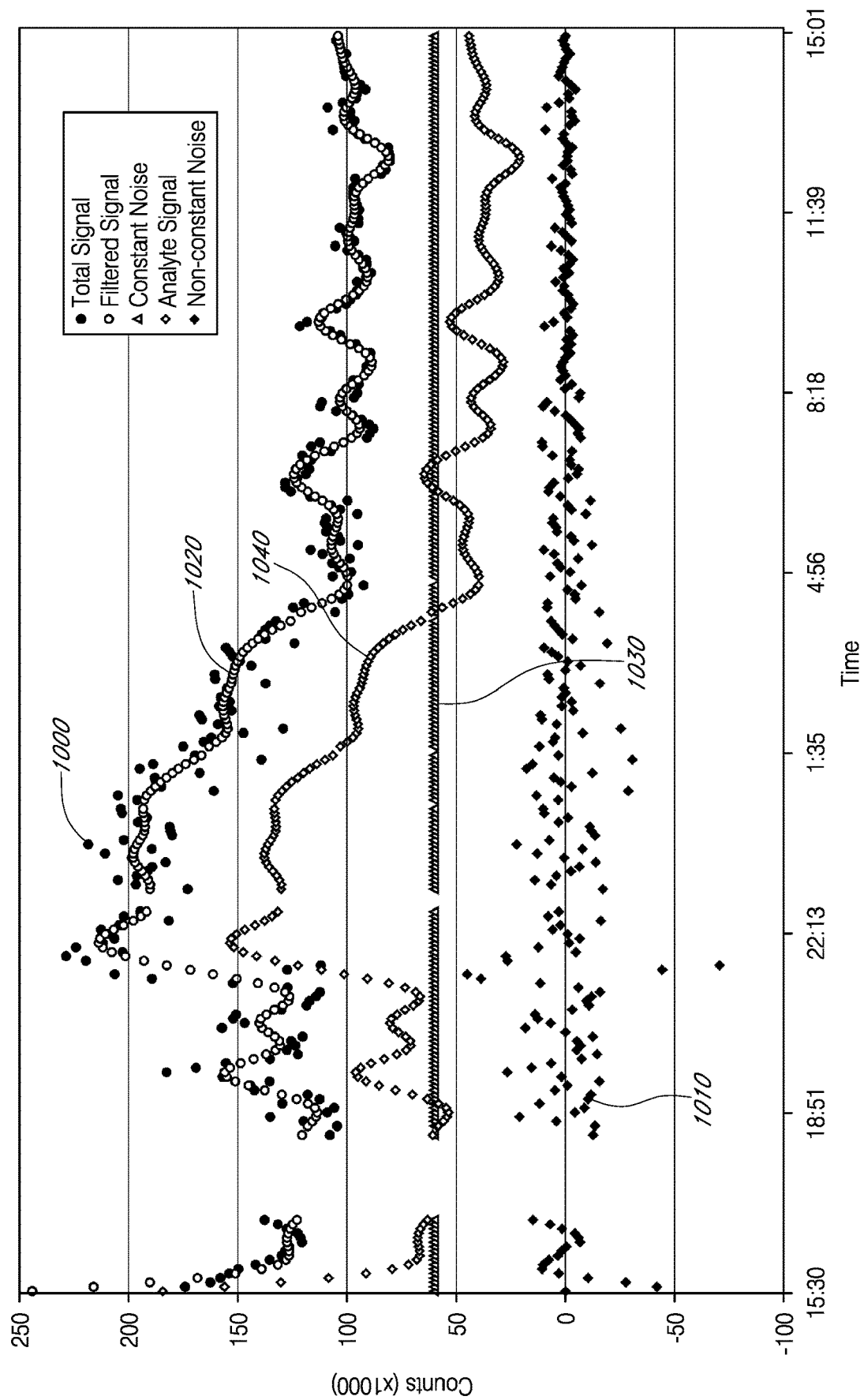
FIG. 10 is a graph illustrating the signal components of a total signal from an analyte sensor including a hydrophilic surface treatment, in one embodiment.

Discontinuous Hydrophilic Overcoat on Resistance Domain Configured to Reduce Non-constant Noise To determine if a hydrophilic overcoat on the resistance layer can increase the analyte signal component and/or reduce the non-constant noise component, test and control sensors were build and tested in volunteer human hosts, over a period of 3 days. Both the test and control sensors included an electrode layer, an enzyme layer and a polyurethane blend resistance domain. The polyurethane blend used to form the resistance domain included 8% hydrophile (i.e., PEO). After fabrication, the test sensors were sprayed (one time) in a solution of 5% ChronoThane® H (about 25% PEO; CardioTech International, Wilmington, Mass., USA) and cured. Test and control sensors were implanted bilaterally in the abdomens of the volunteer human hosts. FIG. 10 is a graph showing test results from one exemplary sensor. Components of the Total Signal 1000 were determined, as described in Example 1. The Y-axis represents signal intensity (in counts). The X-axis represents time. FIG. 10 shows the non-constant noise component 1010, the filtered signal 1020, the constant noise component 1030 and the analyte signal 1040. Using the RMS method, it was determined that, for sensor having a hydrophilic coating, the non-constant noise component of the total signal was no more than about 3% during the study.

While not wishing to be bound by theory, it is believed that application of a hydrophilic overcoat to the sensor can provide a sensor that has a non-constant noise component that is less than about 20% of the total signal.

Methods and devices that are suitable for use in conjunction with aspects of the preferred embodiments are disclosed in U.S. Pat. Nos. 4,994,167; 4,757,022; 6,001,067; 6,741,877; 6,702,857; 6,558,321; 6,931,327; 6,862,465; 7,074,307; 7,081,195; 7,108,778; 7,110,803; and 7,192,450.

Methods and devices that are suitable for use in conjunction with aspects of the preferred embodiments are disclosed in U.S. Patent Publication No. US-2005-0176136-A1; U.S. Patent Publication No. US-2005-0251083-A1; U.S. Patent Publication No. US-2005-0143635-A1; U.S. Patent Publication No. US-2005-0181012-A1; U.S. Patent Publication No. US-2005-0177036-A1; U.S. Patent Publication No. US-2005-0124873-A1; U.S. Patent Publication No. US-2005-0115832-A1; U.S. Patent Publication No. US-2005-0245799-A1; U.S. Patent Publication No. US-2005-0245795-A1; U.S. Patent Publication No. US-2005-0242479-A1; U.S. Patent Publication No. US-2005-0182451-A1; U.S. Patent Publication No. US-2005-0056552-A1; U.S. Patent Publication No. US-2005-0192557-A1; U.S. Patent Publication No. US-2005-0154271-A1; U.S. Patent Publication No. US-2004-0199059-A1; U.S. Patent Publication No.

US-2005-0054909-A1; U.S. Patent Publication No. US-2005-0051427-A1; U.S. Patent Publication No. US-2003-0032874-A1; U.S. Patent Publication No. US-2005-0103625-A1; U.S. Patent Publication No. US-2005-0203360-A1; U.S. Patent Publication No. US-2005-0090607-A1; U.S. Patent Publication No. US-2005-0187720-A1; U.S. Patent Publication No. US-2005-0161346-A1; U.S. Patent Publication No. US-2006-0015020-A1; U.S. Patent Publication No. US-2005-0043598-A1; U.S. Patent Publication No. US-2003-0217966-A1; U.S. Patent Publication No. US-2005-0033132-A1; U.S. Patent Publication No. US-2005-0031689-A1; U.S. Patent Publication No. US-2004-0186362-A1; U.S. Patent Publication No. US-2005-0027463-A1; U.S. Patent Publication No. US-2005-0027181-A1; U.S. Patent Publication No. US-2005-0027180-A1; U.S. Patent Publication No. US-2006-0020187-A1; U.S. Patent Publication No. US-2006-0036142-A1; U.S. Patent Publication No. US-2006-0020192-A1; U.S. Patent Publication No. US-2006-0036143-A1; U.S. Patent Publication No. US-2006-0036140-A1; U.S. Patent Publication No. US-2006-0019327-A1; U.S. Patent Publication No. US-2006-0020186-A1; U.S. Patent Publication No. US-2006-0020189-A1; U.S. Patent Publication No. US-2006-0036139-A1; U.S. Patent Publication No. US-2006-0020191-A1; U.S. Patent Publication No. US-2006-0020188-A1; U.S. Patent Publication No. US-2006-0036141-A1; U.S. Patent Publication No. US-2006-0020190-A1; U.S. Patent Publication No. US-2006-0036145-A1; U.S. Patent Publication No. US-2006-0036144-A1; U.S. Patent Publication No. US-2006-0016700-A1; U.S. Patent Publication No. US-2006-0142651-A1; U.S. Patent Publication No. US-2006-0086624-A1; U.S. Patent Publication No. US-2006-0068208-A1; U.S. Patent Publication No. US-2006-0040402-A1; U.S. Patent Publication No. US-2006-0036142-A1; U.S. Patent Publication No. US-2006-0036141-A1; U.S. Patent Publication No. US-2006-0036143-A1; U.S. Patent Publication No. US-2006-0036140-A1; U.S. Patent Publication No. US-2006-0036139-A1; U.S. Patent Publication No. US-2006-0142651-A1; U.S. Patent Publication No. US-2006-0036145-A1; U.S. Patent Publication No. US-2006-0036144-A1; U.S. Patent Publication No. US-2006-0200022-A1; U.S. Patent Publication No. US-2006-0198864-A1; U.S. Patent Publication No. US-2006-0200019-A1; U.S. Patent Publication No. US-2006-0189856-A1; U.S. Patent Publication No. US-2006-0200020-A1; U.S. Patent Publication No. US-2006-0200970-A1; U.S. Patent Publication No. US-2006-0183984-A1; U.S. Patent Publication No. US-2006-0183985-A1; U.S. Patent Publication No. US-2006-0195029-A1; U.S. Patent Publication No. US-2006-0229512-A1; U.S. Patent Publication No. US-2006-0222566-A1; U.S. Patent Publication No. US-2007-0032706-A1; U.S. Patent Publication No. US-2007-0016381-A1; U.S. Patent Publication No. US-2007-0027370-A1; U.S. Patent Publication No. US-2007-0027384-A1; U.S. Patent Publication No. US-2007-0032717-A1; U.S. Patent Publication No. US-2007-0032718 A1; U.S. Patent Publication No. US-2007-0059196-A1; and U.S. Patent Publication No. US-2007-0066873-A1.

Methods and devices that are suitable for use in conjunction with aspects of the preferred embodiments are disclosed in U.S. application Ser. No. 09/447,227 filed Nov. 22, 1999 and entitled "DEVICE AND METHOD FOR DETERMINING ANALYTE LEVELS"; U.S. application Ser. No. 11/654,135 filed Jan. 17, 2007 and entitled "POROUS MEMBRANES FOR USE WITH IMPLANTABLE DEVICES"; U.S. application Ser. No. 11/675,063 filed Feb. 14, 2007 and entitled "ANALYTE SENSOR"; U.S. application Ser. No. 11/543,734 filed Oct. 4, 2006 and entitled "DUAL ELECTRODE SYSTEM FOR A CONTINUOUS ANALYTE SENSOR"; U.S. application Ser. No. 11/654,140 filed Jan. 17, 2007 and entitled "MEMBRANES FOR AN ANALYTE SENSOR"; U.S. application Ser. No. 11/654,327 filed Jan. 17, 2007 and entitled "MEMBRANES FOR AN ANALYTE SENSOR"; U.S. application Ser. No. 11/543,396 filed Oct. 4, 2006 and entitled "ANALYTE SENSOR"; U.S. application Ser. No. 11/543,490 filed Oct. 4, 2006 and entitled "ANALYTE SENSOR"; U.S. application Ser. No. 11/543,404 filed Oct. 4, 2006 and entitled "ANALYTE SENSOR"; U.S. application Ser. No. 11/681,145 filed Mar. 1, 2007 and entitled "ANALYTE SENSOR"; U.S. application Ser. No. 11/690,752 filed Mar. 23, 2007 and entitled "TRANSCUTANEOUS ANALYTE SENSOR"; U.S. application Ser. No. 11/691,426 filed Mar. 26, 2007 and entitled "ANALYTE SENSOR"; U.S. application Ser. No. 11/691,432 filed Mar. 26, 2007 and entitled "ANALYTE SENSOR"; U.S. application Ser. No. 11/691,424 filed Mar. 26, 2007 and entitled "ANALYTE SENSOR"; U.S. application Ser. No. 11/691,466 filed Mar. 26, 2007 and entitled "ANALYTE SENSOR"; and U.S. application Ser. No. 11/692,154 filed Mar. 27, 2007 and entitled "DUAL ELECTRODE SYSTEM FOR A CONTINUOUS ANALYTE SENSOR".

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A transcutaneous electrochemical glucose sensor configured for implantation in a host, the transcutaneous electrochemical glucose sensor comprising:

a first portion configured to remain outside a body of the host during sensor use, wherein the first portion is configured to operably connect with sensor electronics; and a second portion configured to be inserted inside the body of the host during sensor use, wherein the second portion comprises:

a working electrode configured for use in measuring a signal indicative of a glucose concentration of the host, wherein the working electrode comprises a first sensing area, a second sensing area, a third sensing area, and a fourth sensing area;

wherein each of the sensing areas comprises a surface that is shaped like a circle, a dot, or an oval;

wherein the sensing areas are spaced along a length of the second portion of the transcutaneous electrochemical glucose sensor;

wherein the second portion of the transcutaneous electrochemical glucose sensor comprises a distal end;

wherein the first sensing area is located closer to the distal end of the second portion of the transcutaneous electrochemical glucose sensor than the second sensing area, the third sensing area, and the fourth sensing area; wherein the second sensing area is located closer to the distal end of the second portion of the transcutaneous electrochemical glucose sensor than the third sensing area and the fourth sensing area; wherein the third sensing area is located closer to the distal end of the second portion of the transcutaneous electrochemical glucose sensor than the fourth sensing area;

a membrane covering at least a portion of the working electrode; and a reference electrode disposed at least in part on the second portion of the transcutaneous electrochemical glucose sensor;

wherein the first sensing area, the second sensing area, the third sensing area, and the fourth sensing area are disposed along a common axis of insertion of the second portion of the transcutaneous electrochemical glucose sensor into the host;

wherein the first sensing area, the second sensing area, the third sensing area, and the fourth sensing area are located closer to the distal end of the second portion of the electrochemical transcutaneous sensor than the reference electrode; and wherein the transcutaneous electrochemical glucose sensor has a planar shape.

2. The transcutaneous electrochemical glucose sensor of claim 1, wherein the membrane comprises a layer configured to control a diffusion of glucose therethrough.

3. The transcutaneous electrochemical glucose sensor of claim 2, wherein the layer comprises polyurethane.

4. The transcutaneous electrochemical glucose sensor of claim 1, wherein the reference electrode comprises silver and silver chloride.

5. The transcutaneous electrochemical glucose sensor of claim 1, further comprising a counter electrode disposed at least in part on the second portion of the transcutaneous electrochemical glucose sensor.

6. The transcutaneous electrochemical glucose sensor of claim 1, wherein sensing areas are arranged such that a distance from the first sensing area to the second sensing area is substantially equal to a distance from the second sensing area to the third sensing area.

7. The transcutaneous electrochemical glucose sensor of claim 1, wherein the membrane is a membrane system.

8. The transcutaneous electrochemical glucose sensor of claim 1, wherein the membrane is a membrane layer.

9. The transcutaneous electrochemical glucose sensor of claim 1, wherein each of the sensing areas comprises an enzyme.

* * * * *

UNITED STATES PATENT AND TRADEMARK OFFICE
CERTIFICATE OF CORRECTION

PATENT NO. : 10,791,928 B2  
APPLICATION NO. : 16/796830  
DATED : October 6, 2020  
INVENTOR(S) : Simpson et al.

Page 1 of 4

It is certified that error appears in the above-identified patent and that said Letters Patent is hereby corrected as shown below:

On the Title Page

On page 7, in Column 1, item (56), Other Publications, Line 21, delete "Biosenors" and insert --Biosensors--.

On page 7, in Column 2, item (56), Other Publications, Line 55, delete "SurFACTS" and insert --Surfaces--.

On page 8, in Column 1, item (56), Other Publications, Line 63, delete "Biosonsors" and insert --Biosensors--.

On page 8, in Column 2, item (56), Other Publications, Line 34, delete "Sensivity" and insert --Sensitivity--.

On page 9, in Column 1, item (56), Other Publications, Line 18, delete "Aniodic" and insert --Anionic--.

On page 9, in Column 1, item (56), Other Publications, Line 20, delete "Commence" and insert --Commerce--.

On page 10, in Column 1, item (56), Other Publications, Line 36, delete "Glucoseoxidase" and insert --Glucose oxidase--.

On page 11, in Column 1, item (56), Other Publications, Line 9, delete "Hypogylcemia" and insert --Hypoglycemia--.

On page 11, in Column 1, item (56), Other Publications, Line 9, delete "Glucowatch" and insert --GlucoWatch--.

On page 11, in Column 1, item (56), Other Publications, Line 42, delete "Subcutaenous" and insert Signed and Sealed this  
Twenty-second Day of December, 2020

Andrei Iancu  
*Director of the United States Patent and Trademark Office*

--Subcutaneous--.

On page 12, in Column 1, item (56), Other Publications, Line 37, delete "Gluco Watch" and insert --GlucoWatch--.

On page 12, in Column 2, item (56), Other Publications, Line 2, delete "Tranducers" and insert --Transducers--.

In the Specification

In Column 3, Line 29, delete "host" and insert --host.--.

In Column 5, Line 32, delete "andrenostenedione" and insert --androstenedione--.

In Column 5, Line 47, delete "diptheria" and insert --diphtheria--.

In Column 5, Line 54, delete "perioxidase" and insert --peroxidase--.

In Column 5, Line 64, delete "(adenovirus" and insert --adenovirus--.

In Column 5, Line 67 and Column 6, Line 1, delete "duodenalisa," and insert --duodenalis,--.

In Column 6, Line 8, delete "Trepenoma pallidium" and insert --Treponema pallidum--.

In Column 6, Line 9, delete "stomatis" and insert --stomatitis--.

In Column 6, Line 10 (approx.), delete "virus)" and insert --virus--.

In Column 6, Line 30, delete "PreState" and insert --ProState--.

In Column 6, Line 31, delete "barbituates" and insert --barbiturates--.

In Column 6, Line 47, delete "FHIAA)." and insert --5-HIAA).--.

In Column 24, Line 62, delete "A1" and insert --A1.--.

In Column 26, Line 24, delete "by" and insert --be--.

In Column 26, Line 59, delete "polyethyleneterephthalate" and insert --polyethylene terephthalate--.

In Column 32, Line 10, delete "that that" and insert --that--.

In Column 36, Line 42, delete "by" and insert --be--.

In Column 52, Line 6, delete "(mPDM)," and insert --(PDM),--.

CERTIFICATE OF CORRECTION (continued)
U.S. Pat. No. 10,791,928 B2

In Column 52, Line 16, delete "pimelimidiate" and insert --pimelimidate--.

In Column 52, Line 18, delete "disuccimimidyl tartarate" and insert --disuccinimidyl tartrate--.

In Column 52, Line 22, delete "difluro" and insert --difluoro--.

In Column 57, Line 51, delete "NUSIL" and insert --NuSil--.

In Column 57, Line 61, delete "NUSIL" and insert --NuSil--.

In Column 58, Line 2, delete "polyvinylalcohol" and insert --polyvinyl alcohol--.

In Column 59, Line 48, delete "butylhydroxy toluene" and insert --butylhydroxytoluene--.

In Column 70, Lines 5-6, delete "and or" and insert --and/or--.

In Column 70, Line 45, delete "nintinol" and insert --nitinol--.

In Column 74, Line 6, delete "PDEGF" and insert --PDGF--.

In Column 74, Line 16, delete "glenipin" and insert --genipin--.

In Column 74, Line 58, delete "polyvinylalcohol" and insert --polyvinyl alcohol--.

In Column 75, Line 9, delete "polyvinylalcohol" and insert --polyvinyl alcohol--.

In Column 76, Line 60, delete "dexchlorphenamine" and insert --chlorpheniramine--.

In Column 77, Line 1, delete "acetometaphen" and insert --acetaminophen--.

In Column 77, Line 7, delete "melenamic" and insert --mefenamic--.

In Column 77, Lines 11-12, delete "betamethesone" and insert --betamethasone--.

In Column 77, Line 21, delete "infiximab)," and insert --infliximab),--.

In Column 77, Line 22, delete "estradiols," and insert --estradiol,--.

In Column 77, Lines 23-24, delete "methothrexate" and insert --methotrexate--.

In Column 77, Line 24, delete "vincristing" and insert --vincristine--.

In Column 77, Line 27, delete "batimstat" and insert --batimastat--.

In Column 77, Line 31, delete "Tesosentan" and insert --Tezosentan--.

CERTIFICATE OF CORRECTION (continued)
U.S. Pat. No. 10,791,928 B2

In Column 77, Line 34, delete "aminoclycosides" and insert --aminoglycosides--.

In Column 81, Line 57, delete "etc.)" and insert --etc.).--.

In Column 92, Line 62, delete "vivo.)" and insert --vivo.).--.

In Column 93, Line 42, delete "+1-10%" and insert --+/-10%--.

In Column 96, Line 47, delete "Increased" and insert --Increase--.